United States Patent [19]
Blanch et al.

[11] Patent Number: 6,032,343
[45] Date of Patent: Mar. 7, 2000

[54] AUTOMATED SWAGE WIND AND PACKAGING MACHINE

[75] Inventors: John F. Blanch, Tinton Falls; David D. Demarest, Parsippany; Robert A. Daniele, Flemington; Anthony Esteves, Somerville; William F. Smith, Ringoes; Michael G. Hodulik, Dunellen; Teresa M. Shaw, Lawrenceville, all of N.J.; George Horst Reinemuth, Glen Mills; Richard Paul Branco, Collegeville, both of Pa.; Matthew Cafone, Edgewater Park, N.J.

[73] Assignee: Ethicon, Inc., Somerville, N.J.

[21] Appl. No.: 09/020,085

[22] Filed: Feb. 6, 1998

Related U.S. Application Data

[63] Continuation-in-part of application No. 08/804,039, Feb. 24, 1997, application No. 08/871,568, Jun. 4, 1997, abandoned, and application No. 08/848,927, Apr. 30, 1997.

[51] Int. Cl.$^7$ .............................. B23P 11/00; B21D 39/00; B65B 63/04
[52] U.S. Cl. ............................... 29/33 R; 29/712; 29/788; 53/118
[58] Field of Search ..................................... 29/33 R, 712, 29/715, 783, 720, 788; 83/153, 950, 151; 53/118, 116; 250/202, 560, 561; 356/376

[56] References Cited

U.S. PATENT DOCUMENTS

| | | |
|---|---|---|
| 2,736,194 | 2/1956 | Dilts . |
| 3,857,313 | 12/1974 | Endo . |
| 4,011,155 | 3/1977 | Feurstein et al. . |
| 4,187,051 | 2/1980 | Kirsch et al. . |
| 4,358,976 | 11/1982 | Alviti . |
| 4,412,293 | 10/1983 | Kelley et al. . |
| 4,437,114 | 3/1984 | LaRussa . |
| 4,475,404 | 10/1984 | Rutledge, Jr. et al. . |
| 4,652,738 | 3/1987 | Nishihara et al. ........................ 250/202 |
| 4,652,765 | 3/1987 | Nishihara et al. ........................ 250/560 |
| 4,653,104 | 3/1987 | Tamura ................................. 356/376 X |
| 4,672,871 | 6/1987 | Gudmestad . |
| 4,744,035 | 5/1988 | Hashim . |
| 4,806,737 | 2/1989 | Coates . |
| 4,835,450 | 5/1989 | Suzuki . |
| 4,909,376 | 3/1990 | Herndon et al. . |
| 4,929,843 | 5/1990 | Chmielewski et al. .................. 250/561 |
| 4,942,796 | 7/1990 | Dom et al. . |
| 5,065,237 | 11/1991 | Tsikos et al. . |
| 5,131,533 | 7/1992 | Alpern . |
| 5,150,307 | 9/1992 | McCourt et al. . |
| 5,156,788 | 10/1992 | Chesterfield et al. . |
| 5,195,234 | 3/1993 | Pine et al. ................................... 29/720 |
| 5,370,216 | 12/1994 | Tsuruyama et al. ..................... 198/395 |
| 5,473,810 | 12/1995 | Demarest et al. .......................... 29/712 |
| 5,608,962 | 3/1997 | Colligan et al. ....................... 29/788 Y |
| 5,660,024 | 8/1997 | Ivanov et al. .............................. 53/430 |
| 5,661,954 | 9/1997 | Ivanov et al. .......................... 53/116 X |

FOREIGN PATENT DOCUMENTS

| | | |
|---|---|---|
| 63 299 834 | 12/1988 | Japan . |
| 2 167 211 | 5/1986 | United Kingdom . |
| 92/03364 | 3/1992 | WIPO . |

*Primary Examiner*—William Briggs

[57] ABSTRACT

The present invention is directed to improvements in an Automated Swage Wind and Packaging Machine that is particularly adapted to assist in the automated singulation of surgical needles to enable subsequent automated handling of the needle, automatic swaging of the suture into a receiving end of the needle, automatic pull testing of the combined needle and suture, and automated packaging of the pull tested combined needle and suture into a tray having a cover.

84 Claims, 74 Drawing Sheets

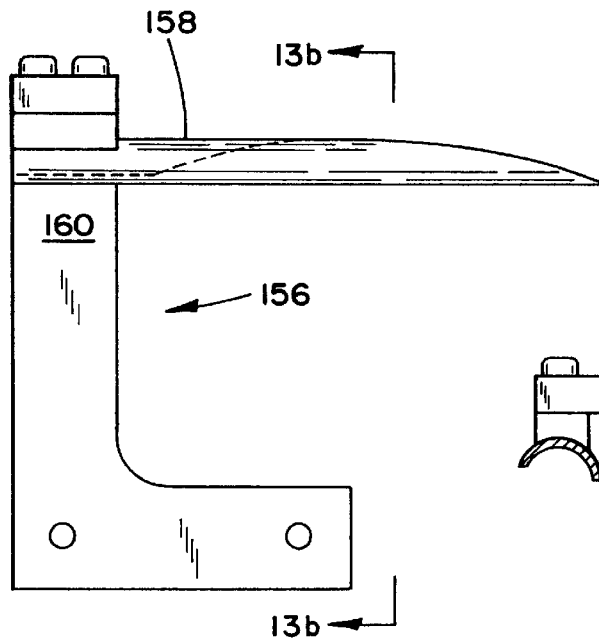
FIG.13(a)
FIG.13(b)
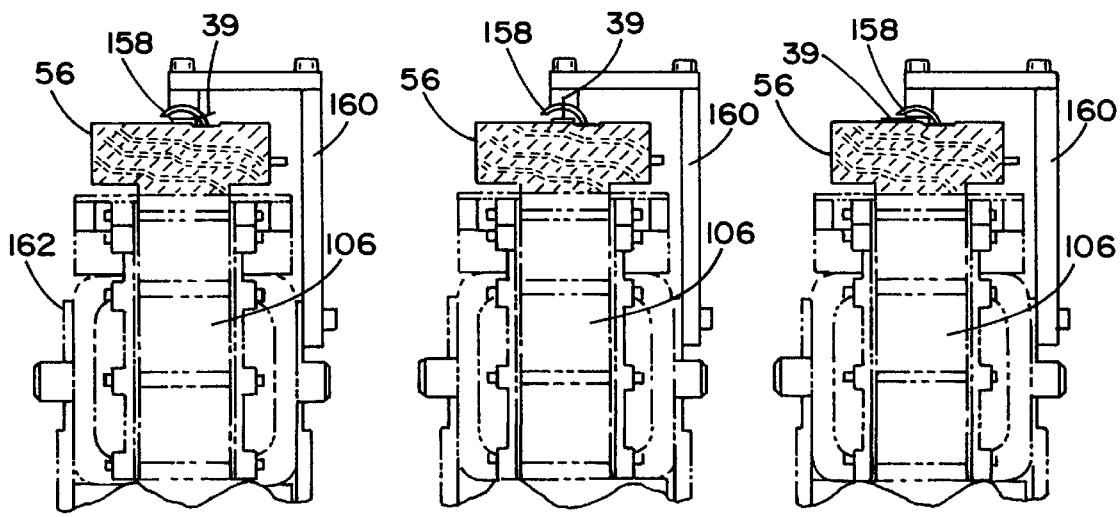
FIG.13(c)    FIG.13(d)    FIG.13(e)

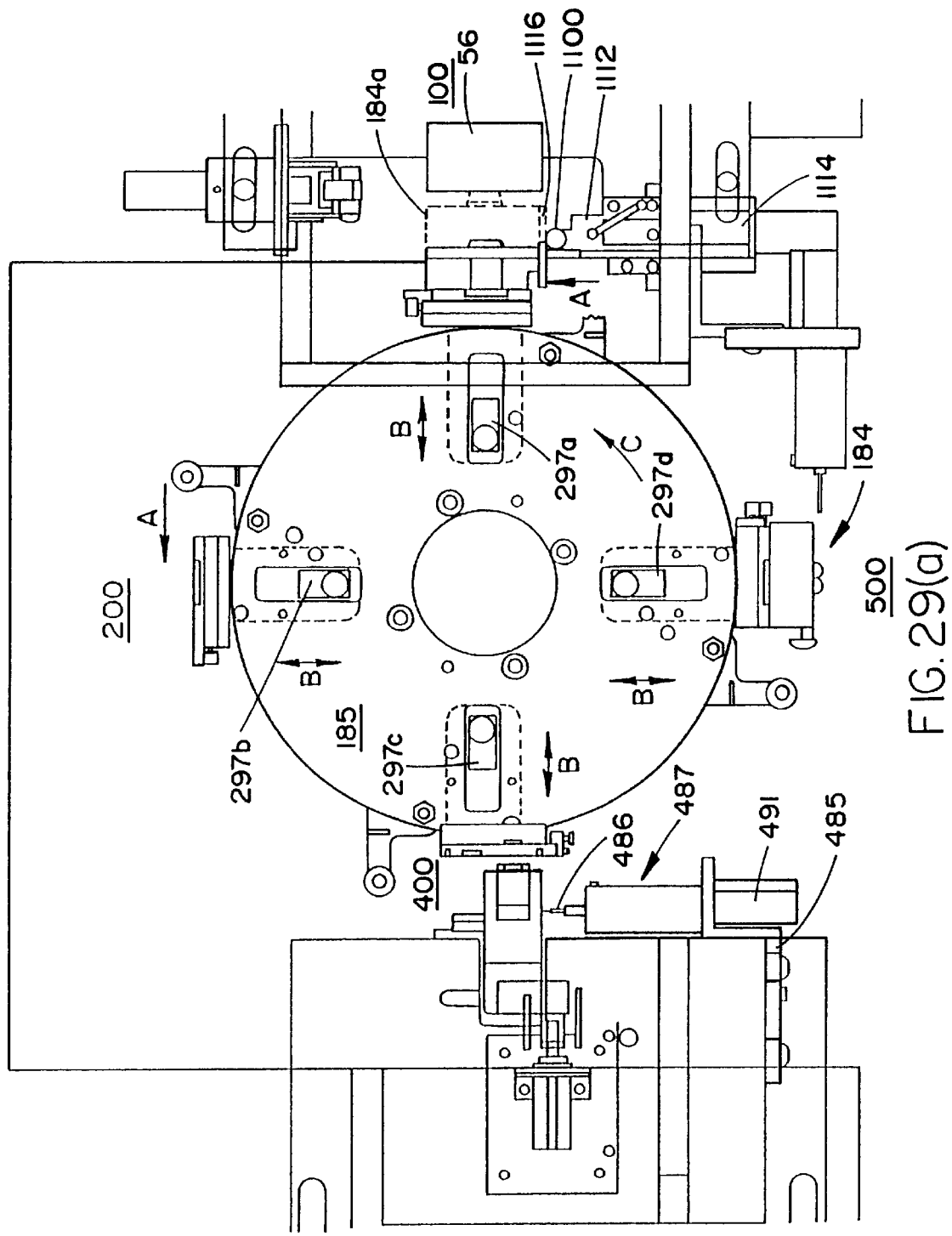

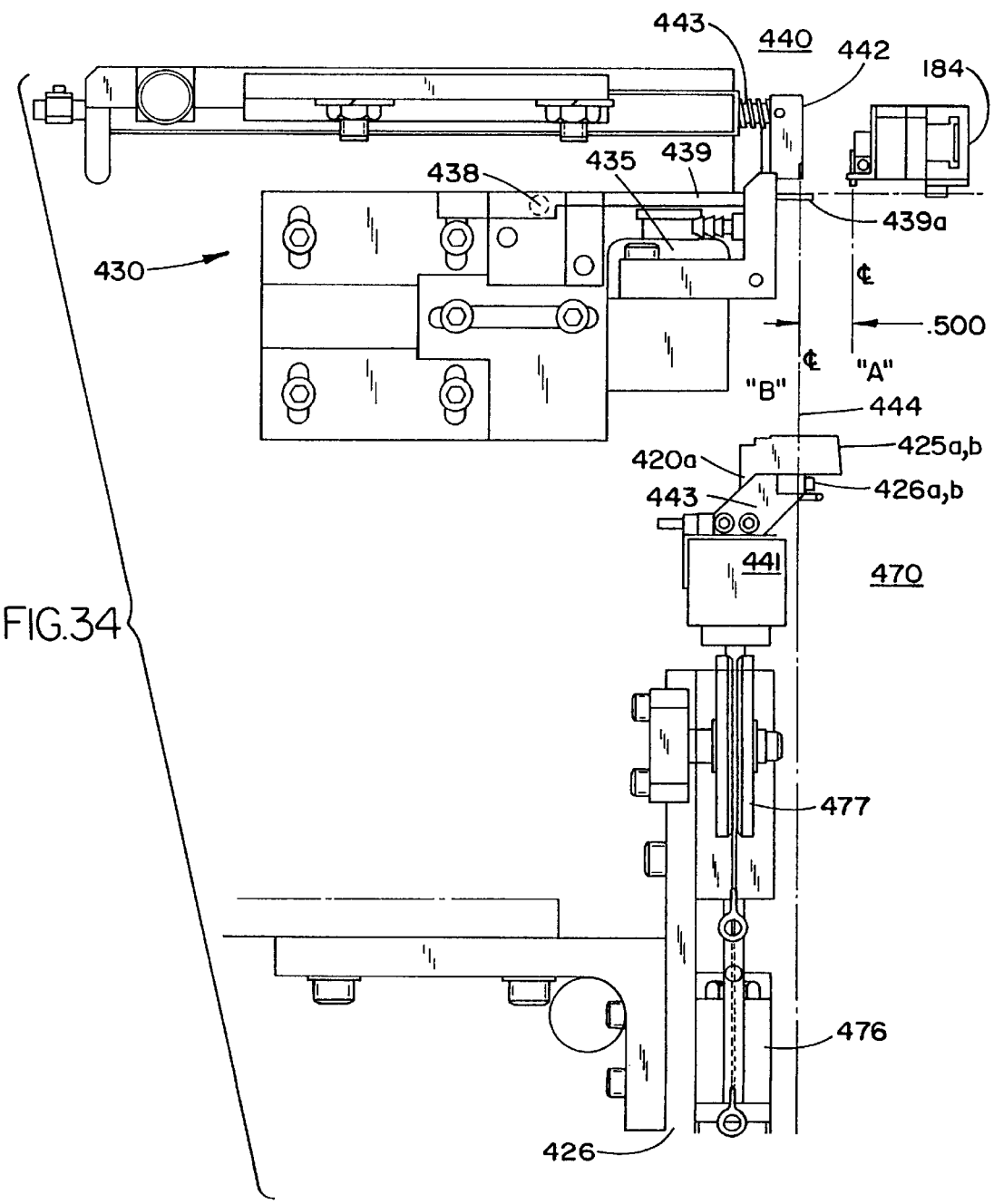

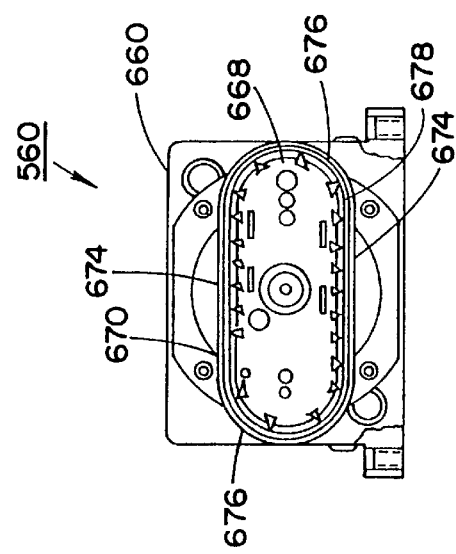
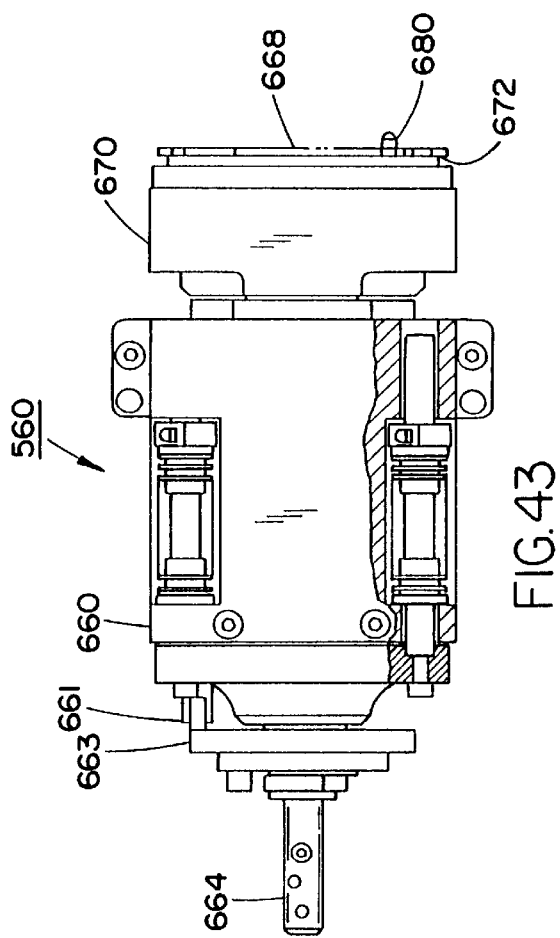
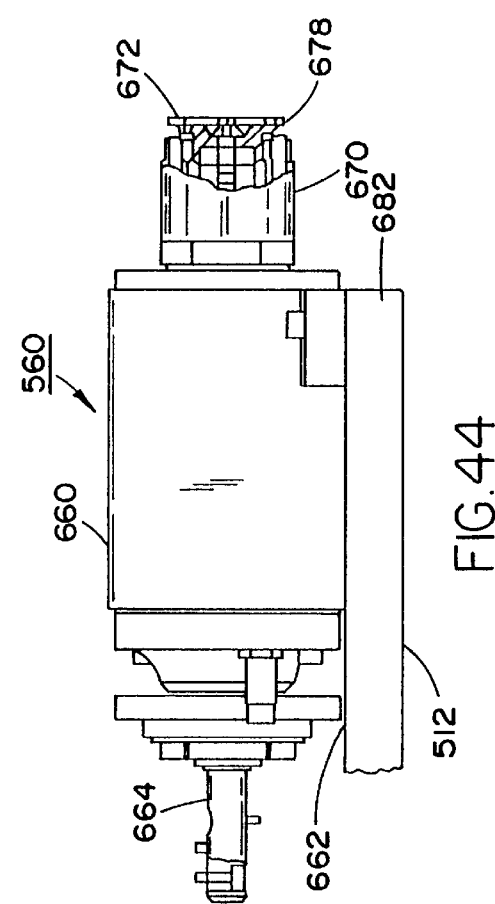

AUTOMATED SWAGE WIND AND PACKAGING MACHINE

CROSS REFERENCE TO RELATED APPLICATIONS

This application is a continuation-in-part of U.S. Ser. Nos. 08/804,039 filed Feb. 24, 1997 entitled "Needle Sorting Assembly," 08/871,568 filed Jun. 4, 1997 entitled "Suture Cutting System, now abandoned" and 08/848,927 filed Apr. 30, 1997 entitled "Stand Alone Swage Method and Apparatus."

BACKGROUND OF THE INVENTION

1. Field of the Invention

The present invention relates generally to machines for automatically swaging needles, such as surgical needles to a suture, and more specifically, to an apparatus that automatically singulates unsorted needles and automatically swages them to a suture, tests the needle-suture bond, and then automatically packages an individual needle suture assembly.

2. Description of the Prior Art

This application describes in detail improvements to the machines disclosed in U.S. Pat. No. 5,473,810 entitled "Needle-Suture Assembly and Packaging System" and U.S. Ser. No. 08/848,927 entitled "Stand Alone Swage Method and Apparatus," both of which are assigned to the assignee of the present invention.

The automatic needle and suture threading machines described in the above referenced U.S. patent and application are highly automated machines intended for high volume production and packaging of needles and sutures wherein approximately 60 needles and sutures are to be produced and packaged per minute.

Previous to these machines, the introduction of needles with attached sutures into suture packages or molded plastic trays was being implemented in a substantially manual manner. In that instance, the needles were manually placed into the tray so as to be clampingly engaged by means of suitable needle-gripping structure, and thereafter the attached sutures wound or positioned within the confines of the tray. Subsequently, a suitable cover was superimposed upon and fastened to the filled tray, and the resultant armed suture package conveyed to a suitable arrangement for possible sterilizing or further over wrapping.

These automated machines, as well as previous generation machines, are substantially adapted, in a highly efficient and extremely rapid mode, to continually fill successive trays of the type described hereinabove with pluralities of surgical needles and attached sutures, and subsequently causing the sutures to be wound into the confines of the tray, such as into a peripheral channel extending about the tray. Thereafter, the packaging machine was designed to implement the automated positioning and fastening of covers to the needle and suture-filled trays to produce completed suture packages of the type described hereinabove, which were then adapted to be transported to a suitable locale for selective further processing, such as sterilizing, and/or over wrapping, as is required by this technology.

In particular, the automated packaging machine was designed to provide the packages with each housing a plurality of needles and attached sutures. For example, the packaging machine for accomplishing the foregoing, which is commonly assigned to the assignee of the present application, is described in U.S. Pat. Nos. 5,487,212; 5,473, 854; 5,469,689; 5,473,810; 5,511,670; 5,452,636; 5,438, 746; 5,500,991; 5,477,609; 5,485,668; and 5,487,216.

The flat, tray-shaped suture package produced by the packaging machine set forth in the above-mentioned patents provides for the storage therein of multiple surgical needles and attached sutures, while concurrently recognizing the need to facilitate the smooth and unobstructed withdrawal of individual needles and attached sutures from the suture package. For instance, such a suture package is disclosed in applicants' U.S. Pat. No. 5,230,424, which is commonly assigned to the assignee of the present application; and wherein the suture package is referred to as an RSO package (Reduced Size Organizer).

In the specific design of the flat tray-shaped plastic container having a peripheral channel as disclosed in the above-mentioned patent, the suture package is basically constituted of a rectangular round-cornered and flat-bottomed injection-molded plastic tray having a flat central surface area including a raised needle clamping structure formed thereon for engaging and "parking" a plurality of needles in a predetermined spaced array. Sutures each have one end thereof attached to each of the respective needles so as to form so-called "armed sutures". The sutures extend from each of the needles into a channel extending about the perimeter or periphery of the suture tray and are conducted into the channel so as to be essentially wound within the circumferential confines of the suture tray. The plurality of sutures which are positioned within the suture tray channel are protected against inadvertent outward displacement therefrom through the presence of a multiplicity of contiguously positioned resilient fingers which are integrally molded with the suture tray, and which project outwardly above the confines of the channel along a major portion of the length of the channel and, collectively, form a so-called "zipper structure" in which the inherently resilient nature of the fingers facilitates their temporary raising up to enable the introduction of the sutures into the suture tray channel by means of a suitable suture winding apparatus.

Although the machine pursuant to the foregoing U.S. patents provide for the packaging of armed sutures; in effect, needles with attached sutures, in a rapid and fully automated manner, such as by supplying the tray-shaped packages; thereafter parking the plurality of armed sutures in the packages, applying covers and removing the completed suture packages from the machine in a sequential station-to-station procedure, the machine was designed to primarily produce suture packages each containing a plurality of armed sutures.

SUMMARY OF THE INVENTION

The present invention is an improved automatic needle singulation, swage dial, and packaging assembly for the swaging and packaging of individual needles to sutures fed and cut to length by the apparatus, together with improvements in the operation of the apparatus.

The present invention is directed to improvements for an Automated swage wind and packaging machine that is particularly adapted to assist in the automated singulation of surgical needles to enable subsequent automated handling of the needle, automatic swaging, automatic pull testing of the combined needle and suture (armed sutures), and automated packaging of the armed sutures.

It is an object of the present invention to provide a machine which will efficiently singulate, swage, test, and package armed surgical needles.

It is another object of the present invention to provide a machine which is flexible in operation and enables quick changeovers between production lots and which minimizes the number of change parts required to migrate from one size needle or suture to another.

It is yet another and basic object of the present invention to provide a novel automated swage wind and packaging machine including operative structure for sequentially feeding individual package trays to successive tool nests on a rotary dial having a plurality of circumferentially spaced tool nests mounted thereon, so as to facilitate the trays to be subsequently supplied with armed sutures and tray covers or labels and thereafter transported in a rapid sequence from the machine.

Accordingly, an automated swage wind and packaging machine is provided. The machine includes a needle singulating apparatus for automatically singulating needles for an automatic swaging machine wherein the apparatus comprises vibratory bowls and tracks which singulate a bulk supply of surgical needles for transport to a precise positioning apparatus. The precise positioning apparatus then positions the needle at a first predetermined position for hand-off to an automatic swaging apparatus. The precise positioning apparatus precisely positions the needle during the hand-off to a precision multi-axis gripper that will grip the needle and hold it during suture insertion. High precision is necessary in the precise positioning stages of the present invention, or the sutures can not be automatically inserted into the needle barrel in the subsequent swage operation.

In addition, a plurality of multi-axis grippers mounted on a rotating swage dial are provided for successively receiving an individual one of a plurality of precisely positioned needles at a first predetermined location and indexing each of said individual successive needles in a predetermined orientation from said first predetermined location through successive locations for sequential processing at subsequent predetermined locations, each of said multi-axis grippers having a cam follower which cooperates with a cam dial to provide radial reciprocation of the multi-axis grippers with respect to said swage dial in response to rotation of said cam dial. The machine includes a swage dial and a cam dial mounted for rotation about a common first axis of rotation, with the swage dial supported by and mounted for rotation on a first drive shaft which rotates about this single first axis of rotation. This first drive shaft is driven by said first intermittent drive to provide intermittent advancement of the swage dial.

An automatic swage apparatus with an improved swage dial is also provided, the swage dial having an off-set motion for the multi-axis grippers that enables the multi-axis grippers to place and retrieve needles held in a swage device having a swage die opening formed in a fixed swage die and to provide multi-axis grippers which are rotated by said swage dial to each of said predetermined locations and reciprocated in and out of an operative position by said cam dial at each of said plurality of predetermined locations while simultaneously being off-set so as to be able to place and retrieve needles held in a swage device having a swage die opening formed in a fixed swage die for swaging a suture to the needles.

The swage apparatus is provided with an automatic pull-test system that can automatically perform minimum pull-testing of the needle-suture assembly in a cost-effective manner and without manual intervention. The automatic pull-test system is operated in combination with the automatic swage apparatus, wherein the needle-suture assembly is automatically indexed to an automatic pull-test station after the suture has been cut and swaged to the surgical needle wherein the pull-test apparatus includes a first gripping means for use in non-destructive testing and a second gripping means for use in destructive testing of the needle-suture assembly.

The automatic pull-test system can perform a destructive pull-test of a needle-suture assembly and retain the maximum pull-test values thereof for statistical analysis thereof and for statistical process control and that can provide automatic adjustment of the upstream swaging dies used to produce the armed needle in accordance with statistical process control values.

Finally, an automated packaging station is provided for automated packaging of individual needles with an attached suture. The automated packaging station includes operative structure for sequentially feeding individual package trays to successive tool nests on a rotary dial having a plurality of circumferentially spaced tool nests mounted thereon, so as to facilitate the trays to be subsequently supplied with armed sutures and tray covers or labels and thereafter transported in a rapid sequence from the machine for further processing.

Pursuant to the present inventive concept, the above-mentioned automated machine is further improved upon in a novel and unique manner in that the machine is adapted to produce suture packages each containing a single armed suture, such packages being frequently in demand rather than packages containing a plurality of needles and sutures. Thus, in order to provide for high production rates which are essentially compatible with those employed in the manufacture of suture packages each containing a plurality of armed sutures, the present invention contemplates the provision of a fully automated packaging machine with a considerably increased rate of operating speed and production capability so as to render the packaging machines economically viable in comparison with the previously described automated packaging machines, while maintaining structural and functional reliability and ease of construction and maintenance.

In order to attain the essentially automated packaging of singly-packaged or individual surgical needles with attached sutures, the automated packaging machine pursuant to the invention sets forth the provision of a rotary turret or dial-like turntable having a plurality of tool nests each possessing a suture tray supporting surface, with each tool next being circumferentially spaced about the turntable so as to be uniformly distributed about the periphery thereof. The rotary turret is rotated to cause the tool nests supporting packaging trays to be indexed forwardly so as to advance through a plurality of successive work stations which are adapted to, respectively, effectuate the supplying of each of the trays located on the tool nests or support surfaces with a single or individual surgical needle and attached suture, winding the suture into the confines of each needle and suture-containing tray, forming a latching engagement between a tray cover and the tray; and thereafter conveying each completed suture package to a station for removal from the machine and transfer to stacking bins or the like.

Operatively communicating in synchronism with the indexing rotation of the rotary turret is a carousel device housing stacks of trays, which is adapted to supply empty trays sliced or separated from the bottom of a respective stack of the trays to a rotatable platform, and includes operative robotic pivot arm structure to successively remove the trays from the rotatable platform and mount the empty trays on successive tool nests so as to be oriented in a vertical plane facing radially outwardly of the rotary turret. Thereafter, each tray is indexed sequentially forwardly by the rotary turret to a workstation which will impart movement to a portion of the tool nest having the tray supported thereon, whereby the tray remains oriented essentially vertically it is rotated angularly relative to the horizontal plane of rotation of the rotary turret. This movement enables a transfer device with a needle and suture swaging mechanism to cause needle grippers to insert and position a surgical needle with its attached suture into a therewith aligned tray for retentive engagement with needle-engaging structure formed in the tray so as to grip and park the needle therein, with the suture extending from the needle and depending downwardly therefrom outwardly of the tray. The needle and suture-containing tray is then advanced forwardly on its respective tool nest to successive workstations responsive to indexed advance of the rotary turret wherein, at a first suture winding station, structure operatively cooperating with the tray and the tool nest supporting the tray imparts an initial rotational movement to the tray about an axis perpendicular to the plane of the tray while maintaining the depending suture under tension, and at a second subsequent winding station imparts a rapid winding motion to the tray over multiple predetermined rotations so as to fully wind the downwardly depending suture into a peripheral tray channel extending within the perimeter of the tray.

Thereafter, the tool nest mounting the tray with the needle parked therein and the attached suture which has been wound into the peripheral channel of the tray is advanced to a further workstation responsive to indexed rotation of the rotary turret; at which workstation an operating mechanism causes a bottommost cover to be sliced or separated from a stack of covers and transferred to a rotatable platform. The cover is then engaged by a robotically-controlled pivot arm which, under the action of a vacuum, pivots the cover into a vertical orientation and applies the cover onto the tray while concurrently imparting pressure to the cover to cause cooperating latching structure to clampingly fasten the cover to the needle and suture-containing tray. Upon completion of the cover-attaching sequence, the resultingly completed suture package is indexed to a further workstation at which suitable vacuum grippers on a pivot arm mechanism engages the suture package, and the suture package is disengaged from the tool nest on which it is supported and transferred to and stacked in repository or receiving units to be readied for further processing, such as sterilizing, overwrapping or the like, as may be required.

The foregoing sequence of operative steps is continually repeated for each successive tool nest on the rotary turret or turntable sequentially receiving empty trays from the carousel, while preceding tool nests each mounting a tray are conveyed through the above-mentioned packaging cycle. Thus, a successive tray is always placed into a position of readiness at a following or subsequent workstation and processed in a similar manner as before described during the forward indexing motion of the rotary turret or turntable. This ensures a continuously repetitive packaging cycle for successive suture packages in a highly efficient and high-speed operation without the need for any manual intervention in the operation of the packaging machine.

Intermediate various of the workstations as set forth hereinbefore; there may be arranged other workstations incorporating sensors adapted to enable ascertaining the presence of empty trays at the initial workstation, for a verification of a needle having been inserted into the trays and for inspection of the trays subsequent to the winding of the sutures into the tray channels; checking for the application of the covers to the trays, and facilitating the possible ejection of incomplete trays or the removal from the machine of defective packages.

BRIEF DESCRIPTION OF THE DRAWINGS

These and other features, and advantages of the instruments and methods of the present invention will become better understood with regard to the following description, appended claims, and accompanying drawings where:

FIG. 11(b) is a detailed elevation view of the precision conveyor boat taken along line 11b—11b of the boat illustrated in FIG. 11a;

FIG. 13(a) is a side view of the needle rollover (plow) which ensures uniform orientation of the needle on the conveyor boat prior to automatic swaging;

FIG. 13(b) is a front view of the plow taken along line 13—13 of FIG. 13(a).

FIGS. 13(c)–13(e) are front views illustrating the plow orienting a needle in one direction upon a boat of the precision conveyor.

FIG. 18(b) is a partial sectional view of the multi-axis gripper of FIG. 18a;

FIG. 29(a) is a top view of the swage dial assembly comprising a swage dial plate having four multi-axis gripper stations mounted thereon;

FIG. 34 is a diagrammatic side elevation view of the pull test apparatus of the present invention illustrating a load-cell assembly, the gripper assembly and a pull test assembly, and their relationship to the multi-axis gripper;

FIGS. 43, 44 and 45 illustrate, respectively, partially-sectional side and top plan views and a front end view of a tool nest utilized in the machine of FIG. 40;

DETAILED DESCRIPTION OF THE PREFERRED EMBODIMENT

Figure 1:
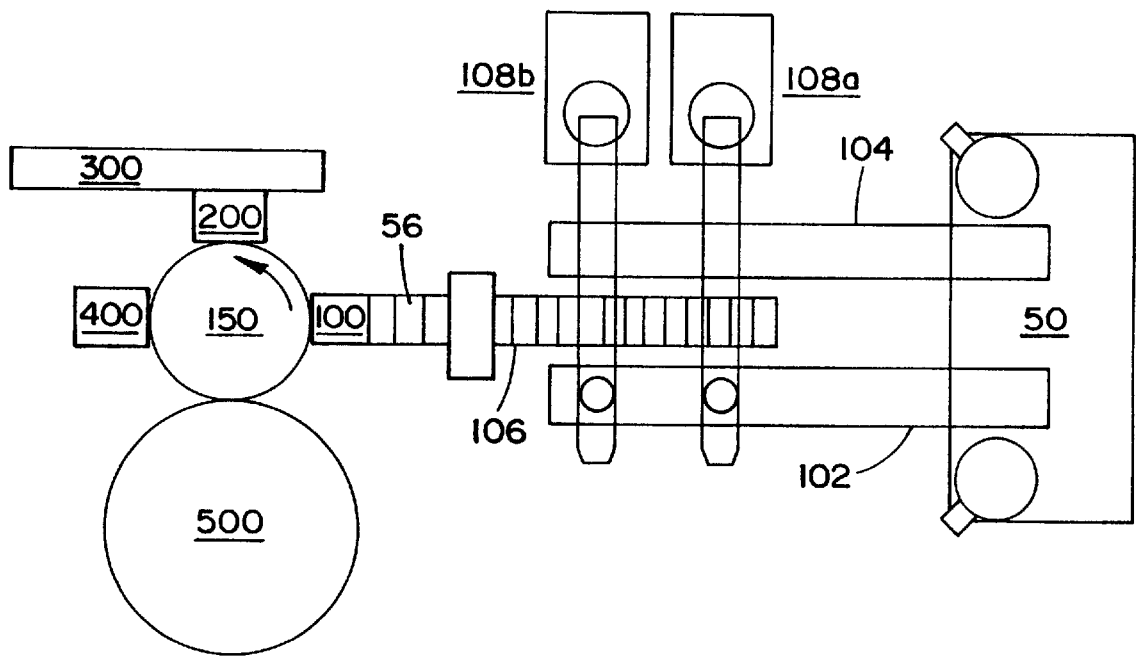
FIG. 1 is a diagrammatic top view of the Automatic Swage Winding and Packaging Machine incorporating an automatic needle sorting and singulating station for feeding individual needles to a multi-axis gripper mounted on a rotary swage dial, an automatic swaging station, an automatic pull-test station, and an automatic packaging station.

The present invention is directed to improvements in a Automated Swage Wind and Packaging Machine that is particularly adapted to assist in the automated singulation of surgical needles to enable subsequent automated handling of the needle, automatic swaging, automatic pull testing of the combined needle and suture, and automated packaging of the pull tested combined needle and suture.

The present application describes improvements in the automated singulation, swaging, and packaging assemblies that singulates, swages, and packages needles to sutures, together with improvements in the operation of the apparatus. The present invention enables the swaging of needles in symmetric dies, even when one of the dies is fixed in position.

This application describes in detail improvements to the machines disclosed in U.S. Pat. No. 5,473,810 entitled "Needle-Suture Assembly and Packaging System" and U.S. application Ser. No. 08/848,927 entitled "Stand Alone Swage Method and Apparatus," both of which are assigned to the assignee of the present invention.

The automatic needle and suture threading machine described in U.S. Pat. No. 5,473,810 is a highly automated machine intended for high volume production and packaging of needles and sutures wherein 20,000 to 40,000 needles and sutures are to be produced in a single run.

The machine described in U.S. application Ser. No. 08/848,927 is also a highly automated machine intended to efficiently handle small batches or production runs on needles and to efficiently handle premium needles and super sharp cutting edge needles in an efficient manner. It was intended to provide flexibility in operation and a quick changeover between production lots and to minimize the number of change parts required to migrate from one size needle or suture to another. It was also intended to handle odd runs or "doctors' specials" as referred to in the trade, where a particular surgeon expresses a preference for an unusual combination of needle type or size and suture material.

The automated swage wind and packaging machine of the present invention combines automated needle singulation, automated swaging, suture cutting, pull testing, and automated packaging of single armed sutures at a rate of approximately one package per second. Unlike the previous machines which packaged eight needles into a package in approximately eight seconds, the present machine has been improved to account for the higher packaging speeds. Thus, in order to provide for high production rates which are essentially compatible with those employed in the manufacture of suture packages each containing a plurality of armed sutures, the present invention contemplates the provision of a fully automated machine with a considerably increased rate of operating speed and production capability so as to render the machines economically viable in comparison with the previously described automated machines, while maintaining structural and functional reliability, quick change configurability, and ease of maintenance.

Figure 2:
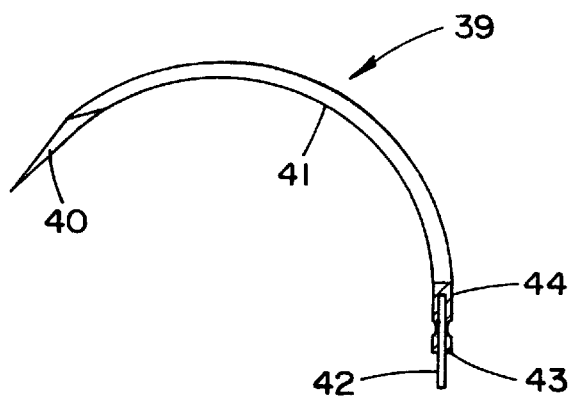
FIG. 2 is a diagrammatic view of a needle that is typical of the needles to be singulated, swaged, and packages according to the present invention.

As illustrated in FIG. 2, a needle 39 includes a arcuate blade portion 40 and a barrel portion 41 and is illustrated with an attached suture 42 which has been attached by swaging as indicated at 44 at the suture receiving end (or butt end) 43 of the needle 39. The suture 42 may be of any predefined length, but is commonly provided in lengths that are multiples of nine inches (18, 27 and 36 inch suture sizes are particularly common).

Generally, in the needle threading and swaging system of the present invention, parallel operations take place simultaneously at a plurality of different stations to ensure that approximately sixty (60) armed surgical needles are assembled and discharged per minute. For instance, as shown in FIG. 1, an automatic needle sorting and singulating station 50 sorts and singulates individual needles to a pair of translucent indexing conveyors 102, 104 where the singulated needles are imaged by a vision system, selected by a computer, and transferred from the translucent indexing conveyors 102, 104 to a precision indexing conveyor 106 by at least one robotic gripper 108. The precision indexing conveyor 106 conveys precisely oriented surgical needles to a precise positioning station 100 to be sequentially received by a plurality of grippers mounted on the rotary swage dial 150. The rotary swage dial then rotates counter-clockwise as shown by the arrow in FIG. 1, to index each needle to the automatic swaging station 200 where the suture material is cut, inserted into the needle 39, and automatically swaged thereto. A suture drawing and cutting station 300 pulls, tips, cuts and inserts the suture into the needle to be swaged. The needle is swaged and then, the rotary swage dial 150 rotates to index the armed suture to the automatic pull-test station 400 where each armed needle is pull-tested to ensure that the minimum and/or destructive pull-test requirements of the medical profession, are met. Finally, the rotary swage dial indexes the pull-tested armed needle to the automated packaging station 500 where the surgical needle 39 and suture assemblies are packaged.

FIGS. 3(a) through 3(e) are block diagrams which illustrate the automatic needle threading and swaging process of the instant invention. For instance, at the needle singulating station 50, needles are first loaded into vibratory bowls or hoppers at step 10, automatically singulated, and then automatically and individually fed at step 11 to one of the translucent indexing conveyors 102, 104. The needles are imaged at step 12 and then evaluated with respect to orientation and position by a vision tracking system at step 13, picked up by a robot apparatus at step 14, transferred to a precision conveyor 106 for positioning by the robot apparatus 108 at step 15, and finally conveyed to a load station 100 where the needles are precisely positioned at step 16 and transferred to a multi-axis gripper located on a rotary swage dial 150 for subsequent transfer to the swaging station 200 indicated at step 25. A detailed explanation of the apparatus used to carry out each step will be explained in further detail hereinbelow.

Figure 3A:
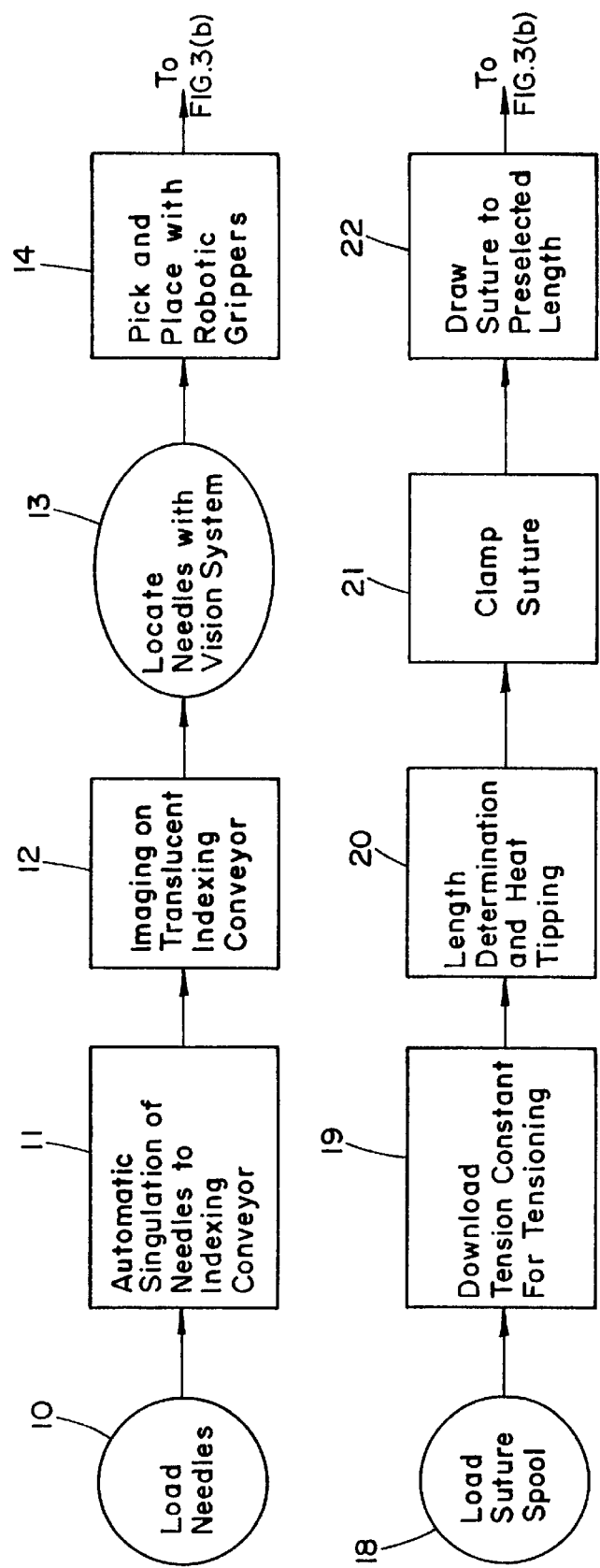
FIGS. 3(a)–3(e) together form a flow diagram illustrating the process for the automated swage winding and packaging system of the present invention.
Figure 3B:
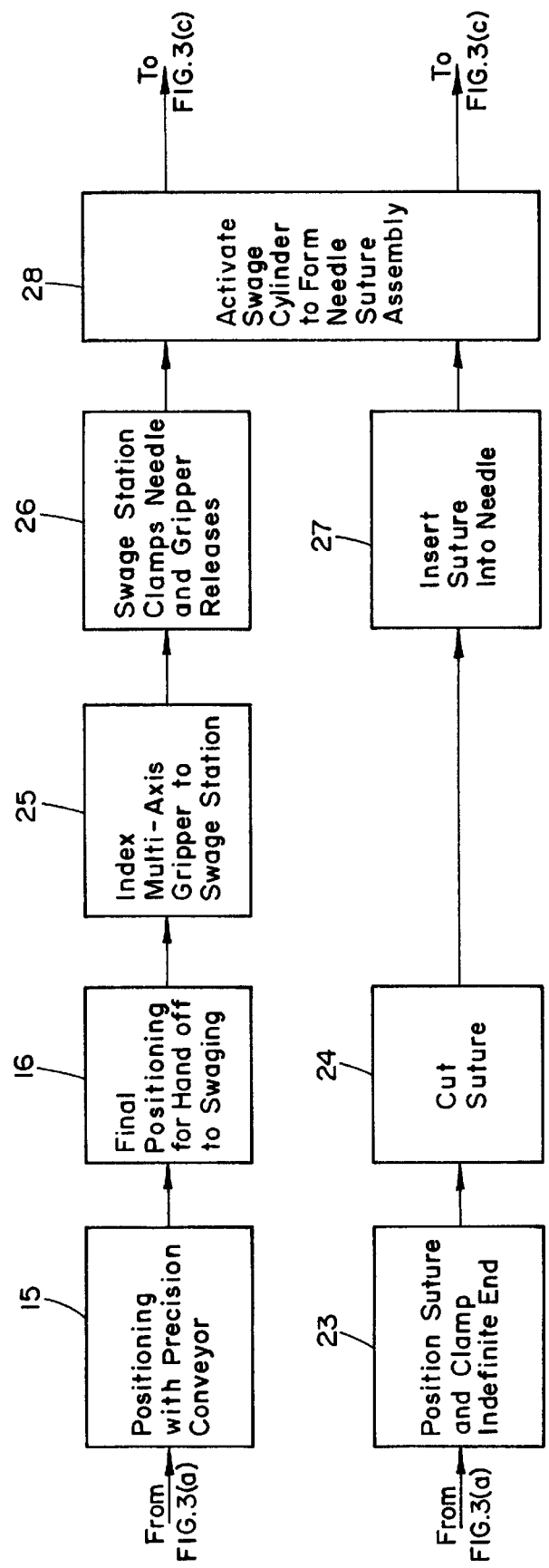

Simultaneous with the needle sorting process described above with respect to steps 10 through 25, an automatic suture cutting process takes place at the suture station 300 as shown in FIGS. 3(a) and 3(b) with respect to steps 18 through 28. Indefinite length suture material is supplied in various spools and configurations that may carry up to 5000 yards of material. This is indicated at step 18 in FIG. 3(a), where the suture material is loaded into a payoff assembly. A tension constant for the suture to be drawn is downloaded as indicated at step 19. A drawing tower apparatus includes grippers that alternately draw lengths of the suture material from the spool to enable cutting thereof which lengths are predetermined at step 20.

While the material is being drawn, it may require extra treatment or processing. For instance, as described in detail below, it may be desirable to heat the suture material under tension at the area which will become the suture tip in order to stiffen the material to facilitate the positioning thereof within the suture receiving opening of a surgical needle. Thus, at step 20, heat may be applied to a portion of suture material. In the preferred embodiment of the invention the heating step is performed upstream of the drawing and cutting apparatus to enable the suture to partially cool and harden before cutting. At step 21 of the block diagram of FIG. 3(a), the suture material is clamped and gripped by the servo grippers, and at step 22, the suture strand is drawn to a predetermined length and positioned for insertion within the suture receiving opening of the needle for swaging. As the suture is positioned for insertion, a second suture clamp, clamps the suture at a position which will hold the indefinite length end at step 23, and the suture is cut at step 24 to separate the suture of predetermined length from the indefinite length suture.

Figure 3C:
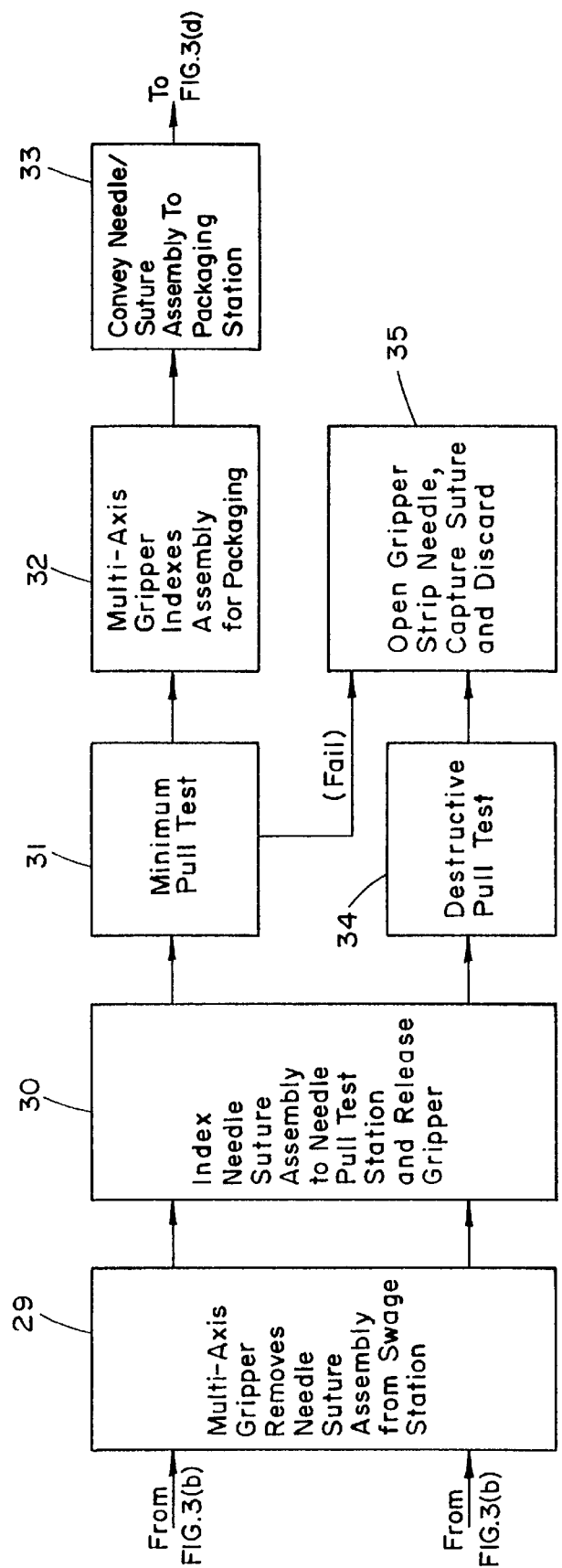

After a surgical needle is indexed to the swaging station 200 at step 25, as described above, the multi-axis gripper positions the needle in a precisely oriented position at the swage die opening formed at the ends of two swaging dies of a swage assembly as indicated as step 26 in FIG. 3(b). Simultaneously, the suture strand is drawn along a suture axis to register a tip thereof for insertion within the suture receiving end of the needle. Next, at step 27, the gripper assembly at the drawing tower inserts the tip of the suture strand within a lower funnel guide for accurate positioning within the suture receiving opening of the needle that is aligned with the suture drawing axis. At step 28, the swage cylinder is activated to automatically swage the suture to the needle. Referring now to FIG. 3(c), the multi-axis gripper is actuated to grip the needle, and then retracted on the rotary swage dial as shown as step 29 and indexed to a pull-test station 400 at step 30 so that minimum pull-testing at step 31 or destructive pull-testing at step 34 may be performed.

Depending upon the results of the minimum pull-test, the needle and suture assembly will either be indexed by the rotary swage dial to the packaging station 500 where the armed needle will be packaged if the pull-test requirements are met (as shown as step 32 in FIG. 3(c)), or, will be discharged at the pull-test station if the needle fails the minimum pull-test (as shown as step 35 in FIG. 3(c)). The destructive pull-test always renders the needle incapable of further processing so the needle is automatically discharged at the pull-test station 400 as indicated at step 35 in FIG. 3(c).

The needle and suture assemblies passing the minimum pull test are conveyed to the packaging station 500 at step 33 in FIG. 3(c) where the individual armed sutures are packaged for subsequent sterilization.

Figure 3D:
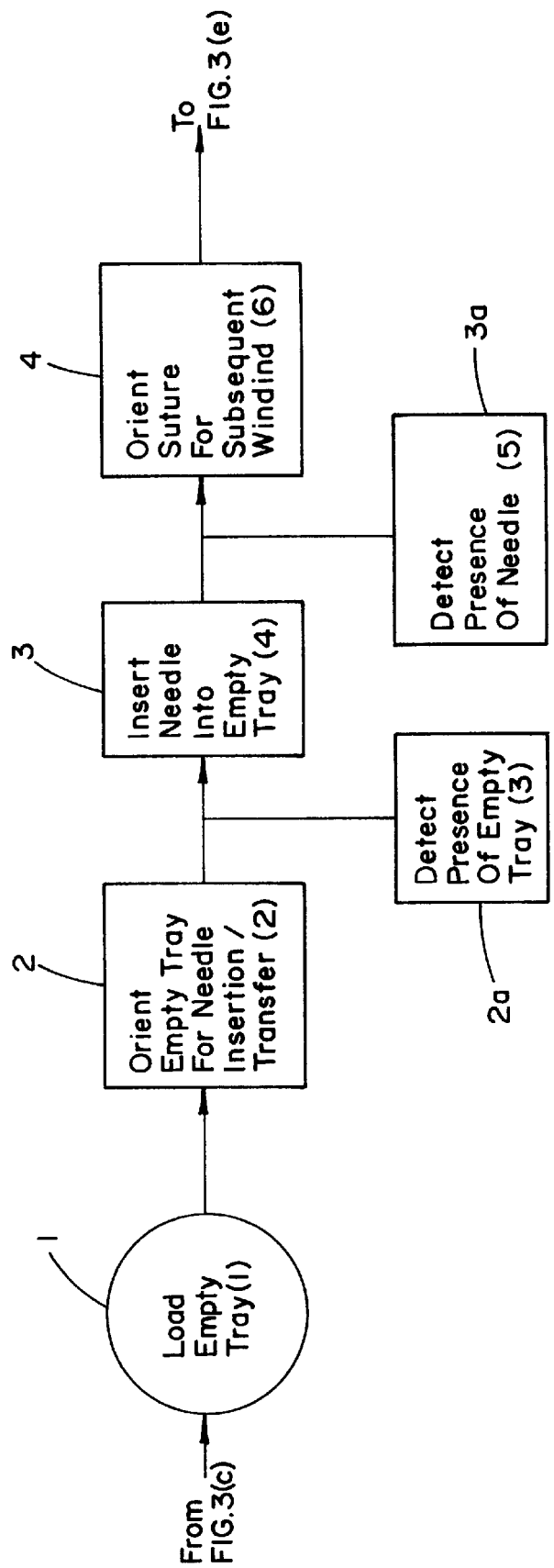
Figure 3E:
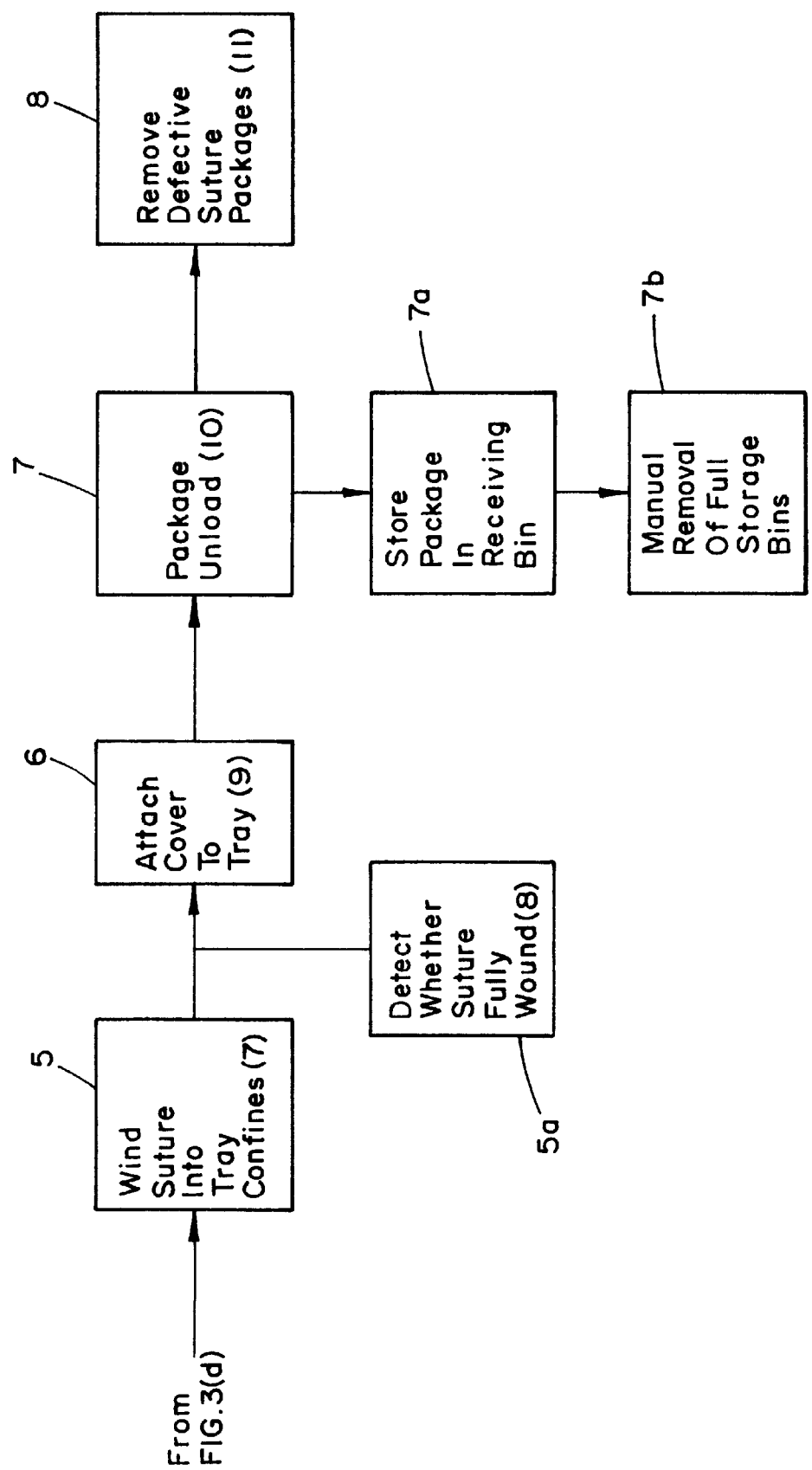

FIGS. 3(c) and 3(d) are block diagrams illustrating the automatic packaging of the armed needle/suture assembly of the present invention. At step 1 an empty tray is loaded onto a first sub-station of the packaging station. The empty package is incremented to a second sub-station where the empty tray is oriented at step 2 for subsequent needle insertion. At step 2a, the optional step of detecting the presence of the empty tray is performed at a third substation.

The oriented empty tray is then incremented to a fourth sub-station at step 3 at which an armed needle/suture assembly is inserted into the empty tray. At step 3a the optional step of detecting the presence of the needle in the tray is performed at a fifth sub-station. At step 4, the tray is incremented to a sixth sub-station at which the suture is oriented and tensioned for subsequent winding which takes place at step 5 at a seventh sub-station. Optionally, at step 5a and sub-station eight, a sensor detects whether or not the suture is fully wound within the tray.

At step 6, the wound needle/suture assembly is incremented to a ninth sub-station where a cover or label is attached to the tray forming a complete suture package. The completed suture package is then incremented to a tenth sub-station at step 7 for unloading. The suture package is then stored into a receiving bin at step 7a and the bins subsequently manually removed at step 7b for further processing, such as sterilization. Lastly, any defective packages not unloaded at step 7 are incremented to an eleventh sub-station and removed at step 8. Defective packages are not unloaded at step 7 because of one or more defective conditions, such as a missing cover, missing needle, or a suture which is not fully wound.

A detailed explanation of the apparatus used to carry out each step in the suture cutting and packaging processes will be explained in further detail hereinbelow.

Overview of the Apparatus

Figure 4:
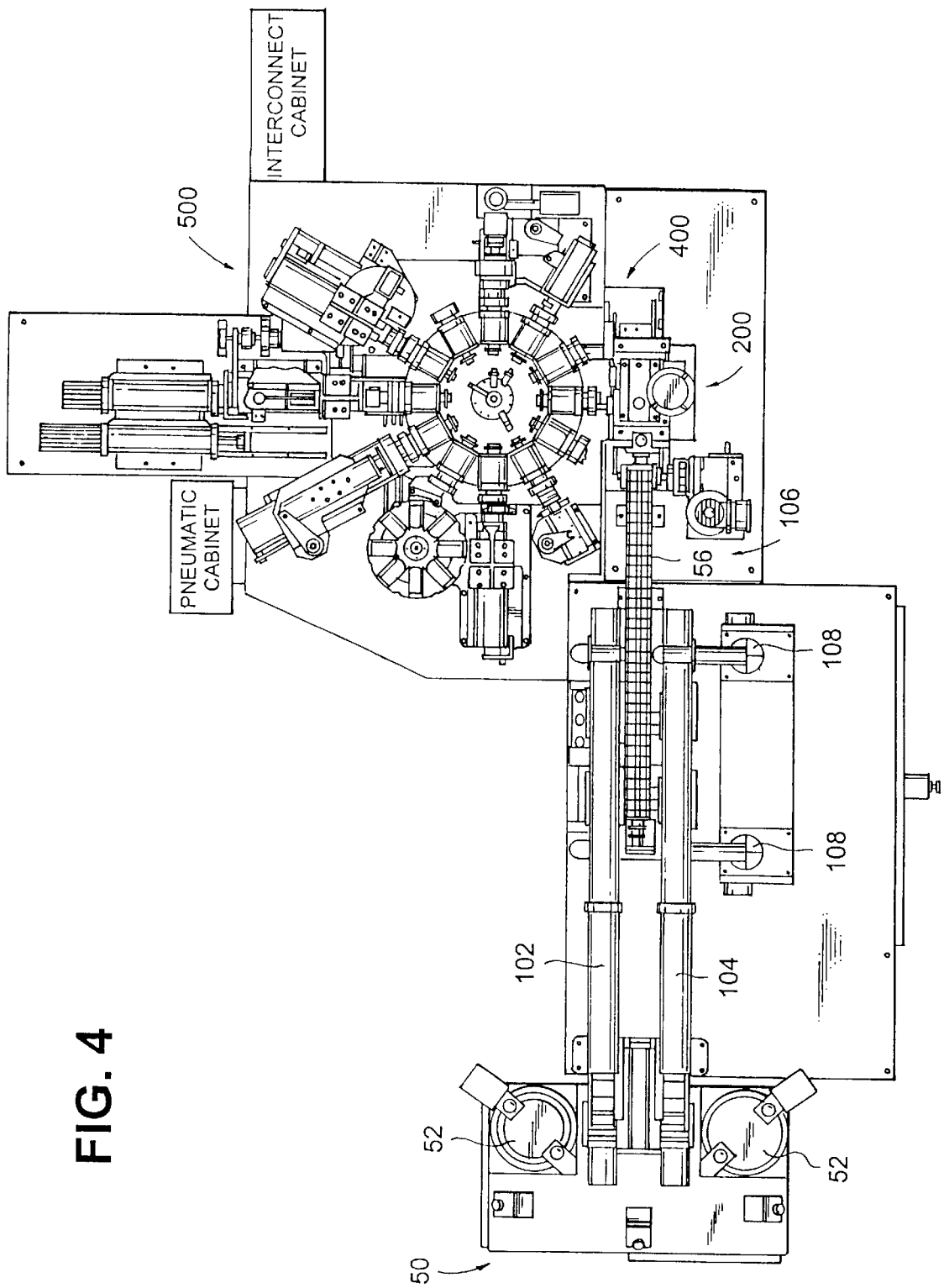
FIG. 4 is an plan view of the present invention illustrating a needle singulation station, portions of the robotic handling device, the swage dial of the present invention, and the packaging station.

FIG. 4 is a top plan view of the automated swage wind and packaging machine. FIG. 4 is used in the following descriptive overview of the apparatus.

This apparatus includes an automatic needle singulation and transfer station 50 for automatically sorting needles and preparing them for automatic swaging and packaging. The needle sorting device 50 comprises at least one, preferably two, receptacle means 52 for holding a plurality of needles, the receptacle means 52 being provided with a means for singulating the needles into a single file of individual needles, and then depositing individual needles on at least one translucent indexing conveyor 102 to provide a moving line of singulated needles for further imaging, manipulation and handling. A first set of remotely located video cameras obtains images of the individual needles upon the translucent conveyor 102 and the images are subsequently digitized to enable processing by a control system computer. The digitized signals are processed to obtain both positional and orientation data for individual selected needles on the conveyor 102. Inasmuch as the curved needle 39 has a sharp point 40 on one end thereof and a butt end 43 on the other end thereof for receiving a suture, it is necessary to determine not only the needles position, but also its orientation.

A robot assembly is provided for transferring individual selected and imaged needles from the translucent indexing conveyor 102 to a precision conveyor 106 for conveying the needles to an automatic swaging machine 200.

The control system computer additionally generates instructions for use by the robot assembly based upon the positional and orientation data of the selected unoriented needle. The robot assembly receives the instructions from the control system so that a robot gripper 108 may grasp each selected needle and position it in an engagement boat 56 located upon the precision conveyor 106.

One or more orientation devices are provided to ensure that the needles are all uniformly oriented up to within 0.001 of its specified position upon the precision conveyor 106, so that a transfer for subsequent swaging can effectively take place.

The needle sorting system may also be provided with a second video camera means and a second robot assembly means that operate in the manner as described above on a second translucent indexing conveyor 104. The redundancy is designed in the system to ensure that a continuous and uninterrupted flow of about 60 needles/minute is supplied to the automatic swaging station.

The rotary swage dial 150 includes a drive motor and first and second indexing transmissions which are used to drive the swage dial in a manner as will be hereinafter explained in detail.

The needles transferred by the robotic apparatus 108 are transferred so that the butt end of the needle 43 is engaged by gripping jaws on the conveyor boats 56 of the precision conveyor 106. While the butt end is located and gripped by the robotic apparatus 108, at the point of pickup it may be oriented in either direction of curvature. For particularly small needles a fixed post may be provided for the robotic apparatus to use in correcting the orientation of curvature. For larger needles, a needle plow is used so that the direction of curvature for each of the needles is uniform. The apparatus also includes a prepositioner which is adapted to approximately locate the butt end of the needle and a moveable hard stop assembly at station 100 that precisely registers the butt end of the needle to an accuracy of 0.001 inches.

After the needle has been received at the precise positioning station 100, it is gripped by one of the multi-axis grippers located on the swage dial mechanism 150 to be indexed through a plurality of stations including a swage station 200 wherein a suture of definite length is cut from a suture spool of indefinite length at station 300 and inserted into the needle at swage station 200 for permanent assembly thereto. After swaging, the needle is advanced to the pull-test station 400 for testing of the needle suture bond, and then indexed to an automated packaging station 500 wherein armed needles are individually packaged for subsequent processing.

Figure 19:
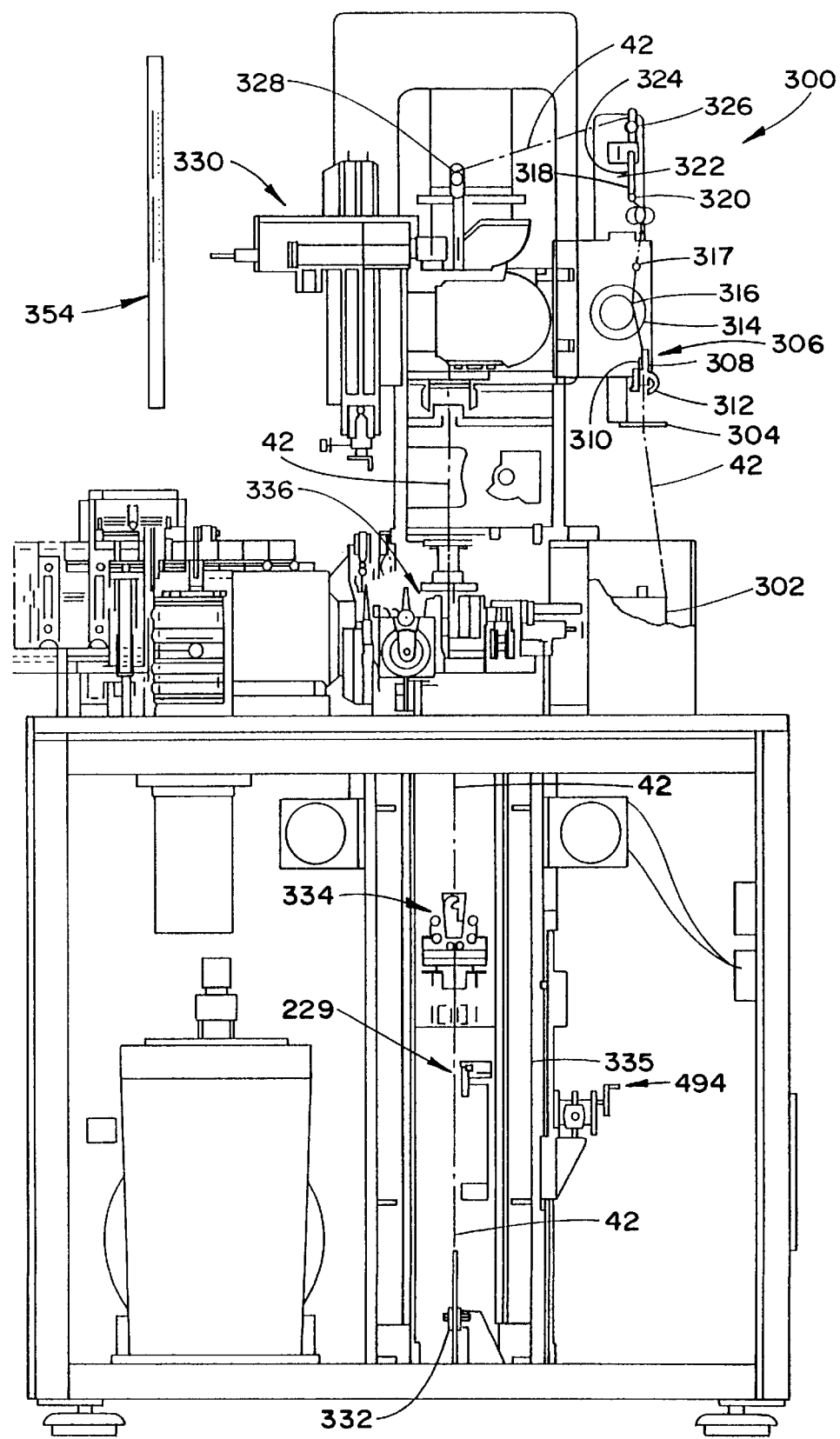
FIG. 19 illustrates a front elevational view of the servo tower showing the suture path therethrough and the locations of the major assemblies thereof.
Figure 38:
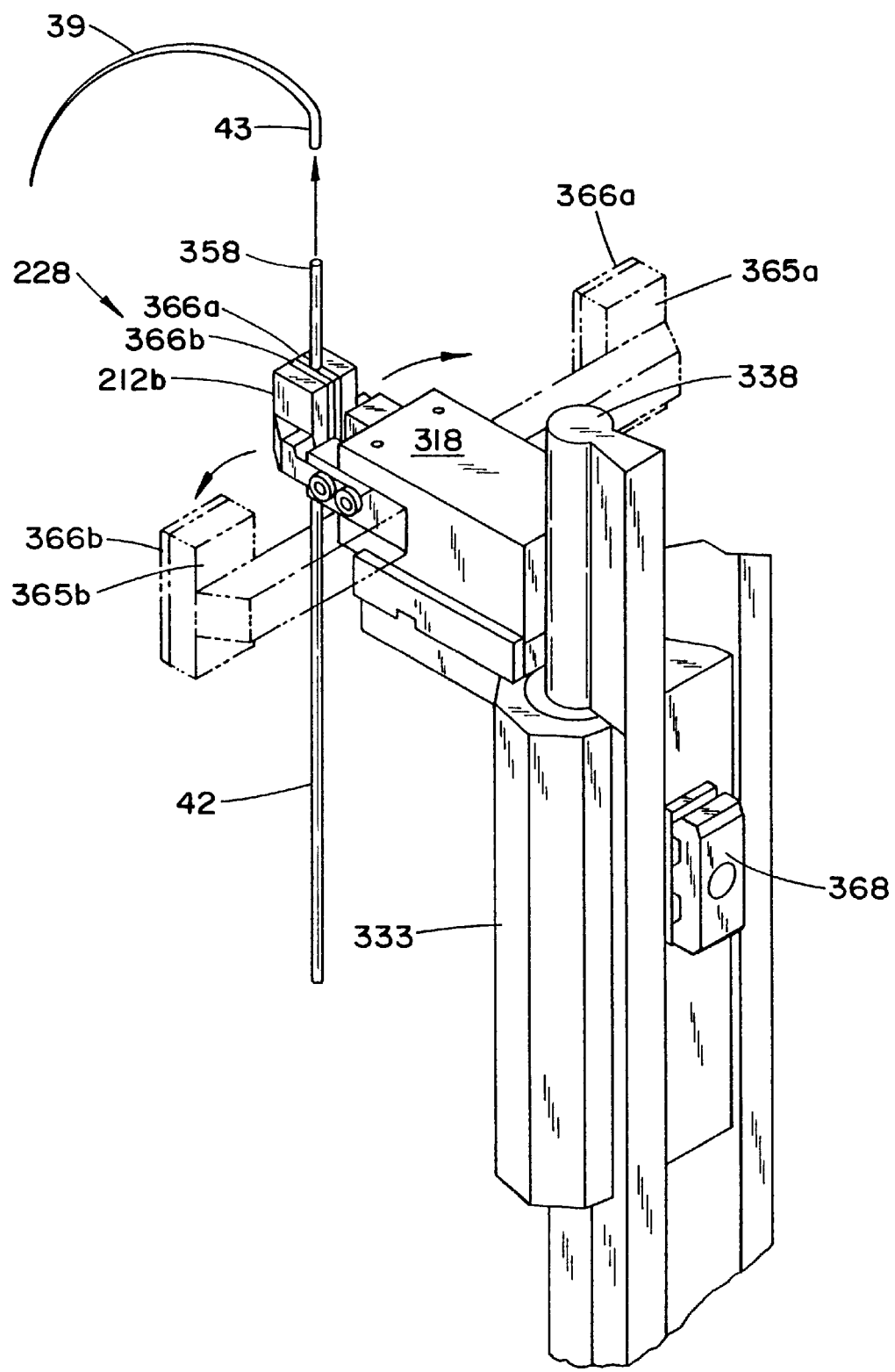
FIG. 38 is an enlarged isometric view of a suture gripper assembly having gripper arms shown in their open (dotted lines) and closed (suture gripping) positions.

An overview of the precision conveyor apparatus and the suture drawing and cutting station 300 will now be discussed. As illustrated in FIG. 19, a spool of suture material 302 is mounted on a convenient location and the indefinite length suture material is fed to the suture drawing station through a pretensioning apparatus, a tensioning roller having a computer controlled tension constant which may be selectively downloaded from the computer control means to match the suture material being handled, and a knot detector which may be used to provide a knot presence signal to the control computer to reject that length of suture after swaging to a needle. From the knot detector the suture strand is fed through a tipping station which heats the suture strand to a predetermined temperature to assist in tipping and cutting the suture for insertion into the surgical needle. From the heating and tipping station, the suture material is passed to the bottom of the machine to a turnaround roller where it is grasped by first and second suture clamps which advance the suture material in a hand over hand manner. As illustrated in FIG. 38, clamp 232 includes a traveling carriage 333 which reciprocates up and down frame member 338 by means of a timing belt which is secured to the carriage at 368. A pneumatic actuator 318 includes first and second clamps 212a, 212b and first and second gripping surfaces 366a, 366b which clamp the suture material therebetween.

In a first cycle of operation, clamp 232 draws the suture of indefinite length to a suture insertion point immediately adjacent the swage plates of the swaging station and then dwells while a second suture clamp clamps the indefinite suture length below the suture cutter 334 (illustrated in FIG.

Figure 22:
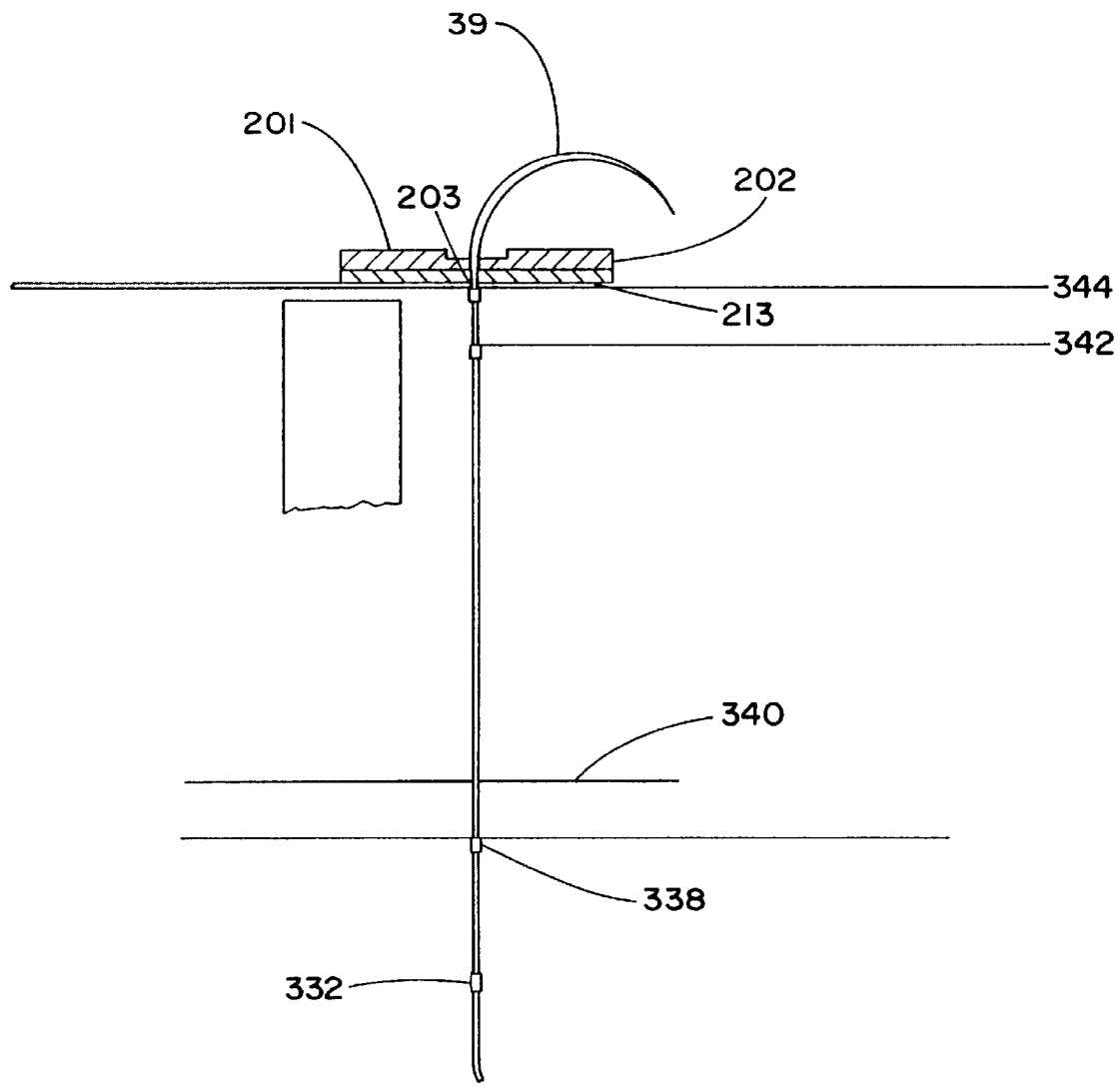
FIG. 22 is a schematic illustration of the different positions in the servo tower including from the bottom, the large idler roller, the bottom servo gripper position, the cut blade position, the home position of the servo gripper, and the final insertion position of the servo gripper.

19). After the second suture clamp has engaged the suture, the cutter 334 is actuated to cut the suture and the tip end of the suture 42, illustrated in FIG. 19 is inserted into the needle as illustrated in FIG. 22. The tip end of the suture 42a is positioned below a funnel dye formed in suture alignment plates 211, 213 which reciprocate immediately below swage plates 201, 202. After the suture tip end 42a has been inserted into the barrel end 43 of needle 39, the swage station is actuated driving the swage plate 202 against swage plate 201 to swage the suture tip 42a in the surgical needle 39.

The armed needles are then indexed to the pull-test station 400 and then to the packaging station 500 by the multi-axis grippers of the swage dial apparatus 150. The automated packaging station 500 comprises a rotary turret or dial-like turntable having a plurality of tool nests each possessing a suture tray supporting surface, with each tool next being spaced about the turntable. The rotary turret is rotated to advance the tool nests successive work stations which are adapted to, respectively, effectuate the supplying of each of the trays (illustrated in FIG. 6 as reference numeral 45) located on the tool nests or support surfaces with a single or individual surgical needle and attached suture, winding the suture into the confines of each needle and suture-containing tray, forming a latching engagement between a tray cover (reference numeral 46 in FIG. 6) and the tray; and thereafter conveying each completed suture package (reference numeral 47 in FIG. 6) to a station for removal from the machine and transfer to stacking bins or the like, such as final packaging and sterilization.

Intermediate the workstations there may be arranged other workstations incorporating sensors adapted to enable ascertaining the presence of empty trays at the initial workstation, for a verification of a needle having been inserted into the trays and for inspection of the trays subsequent to the winding of the sutures into the tray channels; checking for dangling sutures and the application of the covers to the trays, and facilitating the possible ejection of incomplete trays or the removal from the machine of defective packages.

A detailed explanation of the apparatus used to carry out each step will be explained hereinbelow. A further explanation of the computer control system will also be explained in further detail hereinbelow and in detail in copending U.S. application Ser. No. 09/019,138, entitled "Control System for an Automatic Needle-Suture Assembly and Packaging Machine" and assigned to the same assignee of the present invention, the disclosure of which is incorporated herein by reference thereto.

Each station and aspect of the Automated Swage Wind and Packaging Machine will now be described in detail.

Automatic Needle Singulation and Transfer

The automatic needle singulation and transfer station 50 is a needle infeed apparatus that is designed to automatically singulate, convey and align surgical needles of various sizes to the automatic swaging station 200 where sutures are attached to individual needles.

Figure 5:
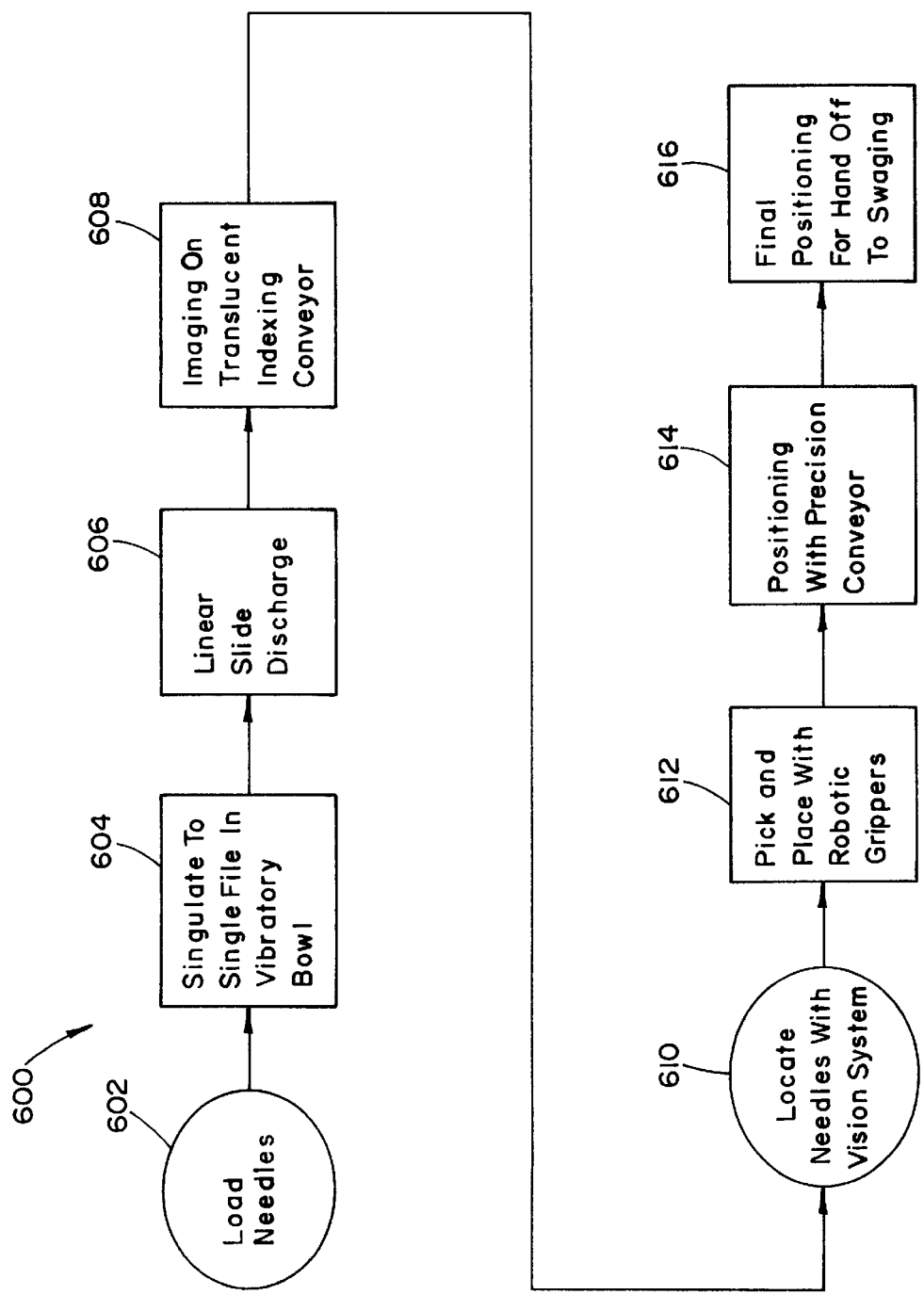
FIG. 5 is a block diagram showing the process flow for the needle sorting and precise positioning apparatus of the present invention.

FIG. 5 is a block diagram generally illustrating the process 600 used to sort, singulate, and convey surgeons' needles of various sizes prior to automatically swaging sutures thereto and prior to packaging them.

Figure 6:
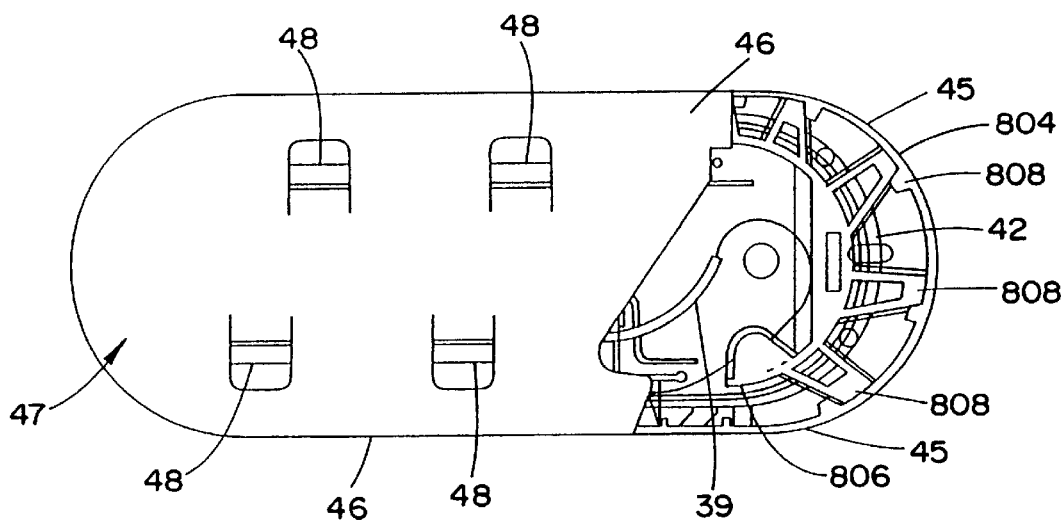
FIG. 6 illustrates a completed suture package with the cover applied thereto.

FIG. 6 illustrates a needle to be singulated and positioned for swaging by the present invention, shown packaged. Each package 47 comprises a tray 45 and tray cover 46 and holds a surgical needle 39 having a suture receiving end or opening 43 for swaging a suture 42 thereto.

While the automatic needle singulation and transfer station 50 serves the purpose of singulating needles from a bulk manufacturing operation, it also provides a method and means for precise positioning of the needle during the hand-off to a precision multi-axis gripper that will grip the needle and hold it during suture insertion which occurs at the precise position station 100. Thus high precision is necessary in the later stages of the station, or the sutures cannot be automatically inserted into the needle barrel in the subsequent swage operation.

Generally, in the automatic needle sorting process 600 shown in FIG. 5, needles are first loaded into a vibratory bowl at step 602, automatically singulated into single file at step 604, and individually fed in a spaced relationship at step 606 to a translucent indexing conveyor. The translucent indexing conveyor allows imaging of the needles 39 at step 608, which images are converted to digital data, and evaluated with respect to orientation and position by a vision tracking system which is part of a computer control system at step 610. After determining position and orientation, the needles are picked up by a robot apparatus at step 612, and transferred to a precision conveyor by the robot apparatus at step 614. At the final step the needles are pre-positioned and then precisely positioned where they are transferred to a multi-axis indexing means for conveyance to subsequent swaging workstation at step 616.

Figure 7A:
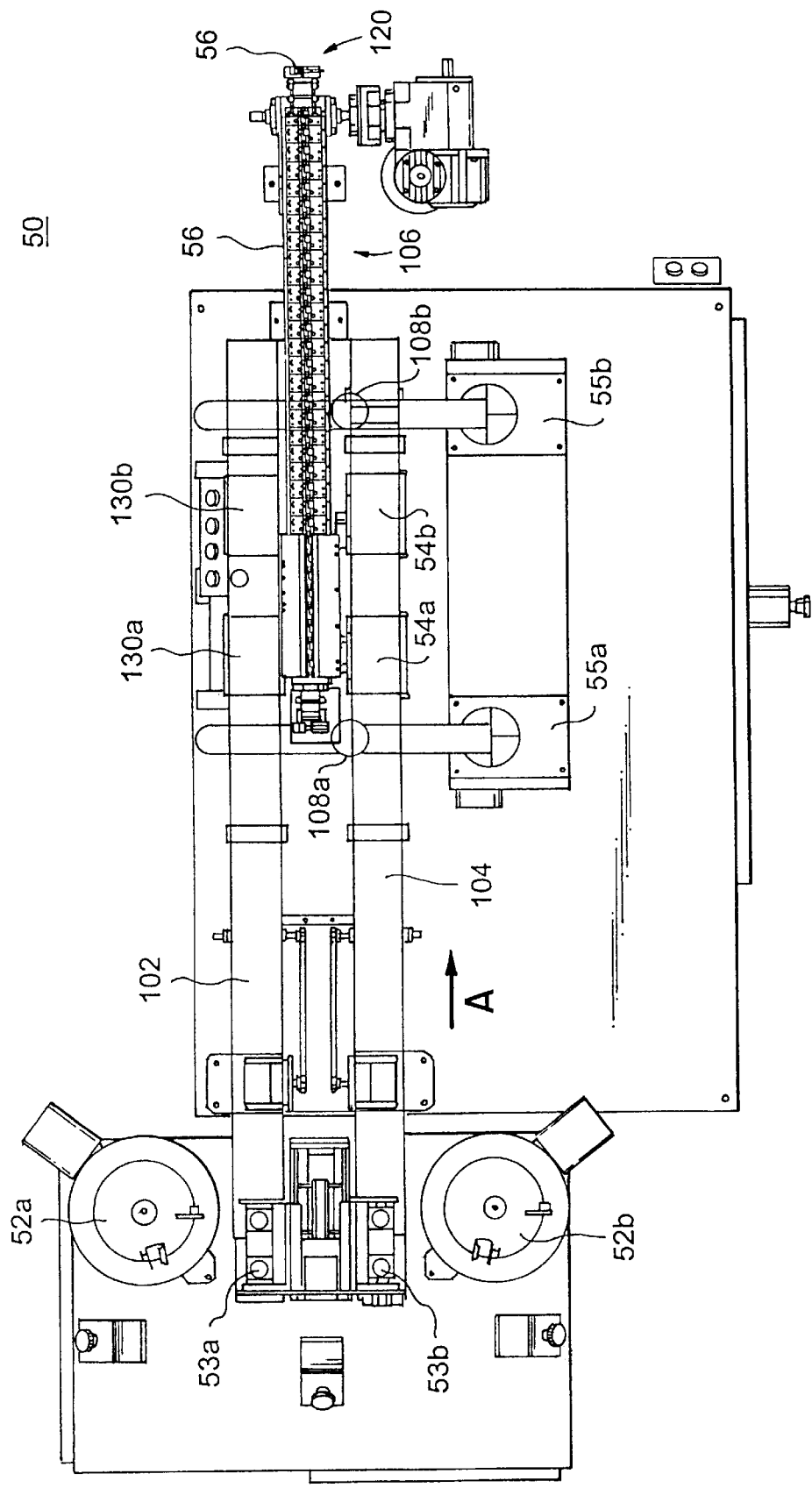
FIG. 7(a) is a top view of the needle sorting device of the instant invention illustrating the initial vibratory bowl parts feeders which singulate the needles, the linear slide discharge mechanisms, the first and second translucent indexing conveyors, the robotic assemblies and the precision conveyor.
Figure 7B:
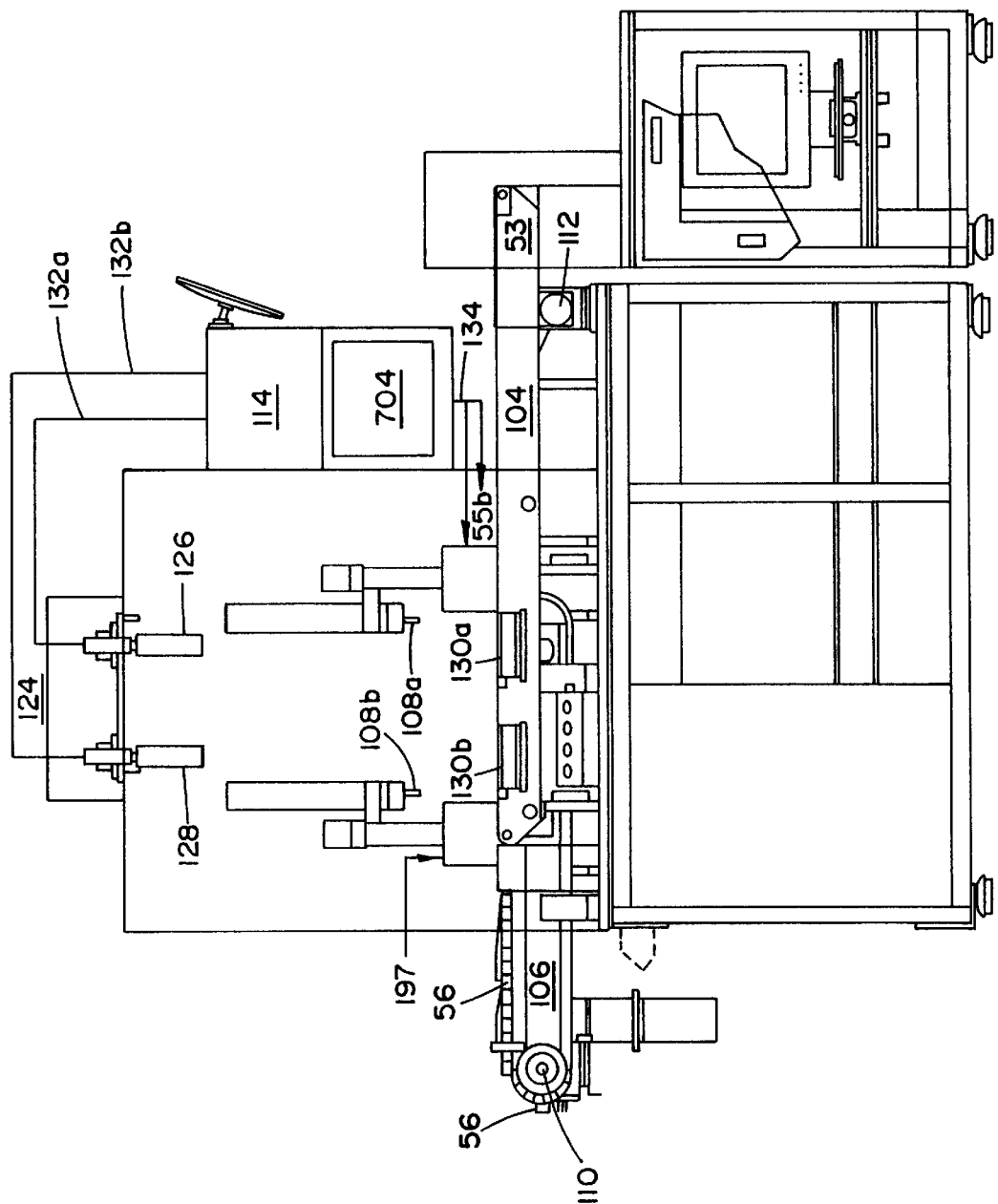
FIG. 7(b) is a side elevational view of the needle sorting device of FIG. 3(a) showing the robot assembly above the first conveyor means and the vision tracking means comprising two video cameras for obtaining images of the needles and the control system means for processing the image data.

The preferred embodiment of the needle sorting and transfer station 50 is illustrated in the top view of the system in FIG. 7(a) and the side view of FIG. 7(b). As shown therein, needles 39 are delivered in bulk to each of two vibratory bowls or hoppers 52a, b where they are singulated by the vibratory bowls into a single file of needles, and intermittently fed to the linear slide discharge assemblies 53a, b where they are individually deposited upon each of two translucent conveyors 102, 104. The two translucent conveyors 102, 104 carry the singulated and deposited needles 39 in the direction indicated by the arrow A in FIG. 7(a) where their position and orientation are evaluated by a remotely located vision tracking system that will be discussed in detail below with respect to FIG. 7(b).

The tracking system evaluates the position and orientation of each available needle on the translucent conveyors 102, 104 as it forwardly conveys the needles over illuminated (backlit) platforms 54a and 54b and further evaluates the position and orientation of the each available needle upon translucent conveyor 104 as it forwardly conveys the needles over illuminated (backlit) platforms 54a and 54b.

The orientation and positional information obtained from the vision tracking system is processed and converted to coordinates usable by each of two robot assemblies 55a, b for instructing respective robot grippers 108 to pick up and transfer identified needles from one of the translucent conveyors to individual engagement boats 56, located on a precision conveyor 106 that is also being indexed in the same direction as the translucent conveyors as shown in FIG. 7(a).

The control system computer instructs a robot gripper, for e.g., gripper 108a of the robot assembly 55a, to grab the tracked needle from one of the two conveyors 102, 104 for a dwell cycle of the system, i.e., when the respective conveyor has paused. If the singulated needles 39 are oriented such that neither of the robot grippers 108a, b are able to pick one of them up or place a needle onto the precision conveyor 106 because of its limited range of motion, a recovery procedure will be executed to ensure that there are no shortages of needles 39 to be fed by the precision conveyor 106 to the automatic high-speed swaging workstation 200 which can achieve up to 80 needle swages per minute.

In the preferred embodiment, the timing of each conveyor 102, 104 is identical, but the dwell periods are out of phase. Because of the phased timing, the vision tracking system will be identifying needles on one indexing conveyor, for e.g., 102, while both robots are picking needles from the other indexing conveyor 104 and placing each needle in an individual engagement boat 56 of the precision conveyor 106. Similarly, while both robots are picking needles from the indexing conveyor 102, the vision tracking system will be identifying needles on the other indexing conveyor 104.

The first step of the automatic needle singulating and transfer process 600 involves introducing a predetermined amount of needles 39 from an infeed device, such as a vibratory bowl or hopper 52a, b, which serves as the first component in the needle singulating station 50.

This first step in singulating needles for the automatic swage/wind station 200 involves singulating individual needles from a bulk supply of needles for introduction to the vision inspection system.

The improvement of the automatic needle singulation and transfer station from previous generation machines such as those disclosed in U.S. Ser. Nos. 08/567,264 and 08/181,600 include an improved vibrating hopper assembly which singulates the needles into a single file, and a linear discharge slide mechanism which provides for timed and positioned placement of individual needles on the translucent indexing conveyor.

As illustrated in FIG. 7A, a pair of vibrating bowls 52a and 52b are illustrated. In the preferred embodiment, both bowls 52a and 52b are provided with a singulating track for singulating the needles into single file, as illustrated in greater detail in FIG. 8(d). A pair of linear slide discharge mechanisms 53a, b are also provided to transport and align individual needles from the vibrating bowls assembly 52a, b to the translucent conveyors 102, 104 for imaging by the inspection system.

The function of the improved feed mechanism, including a vibrating bowl and a linear slide discharge mechanism, is to deposit individual needles in a spaced relationship on the translucent conveyor 102, 104 for imaging by the vision system and subsequent handling by the robotic assemblies 55a, b.

Figure 8A:
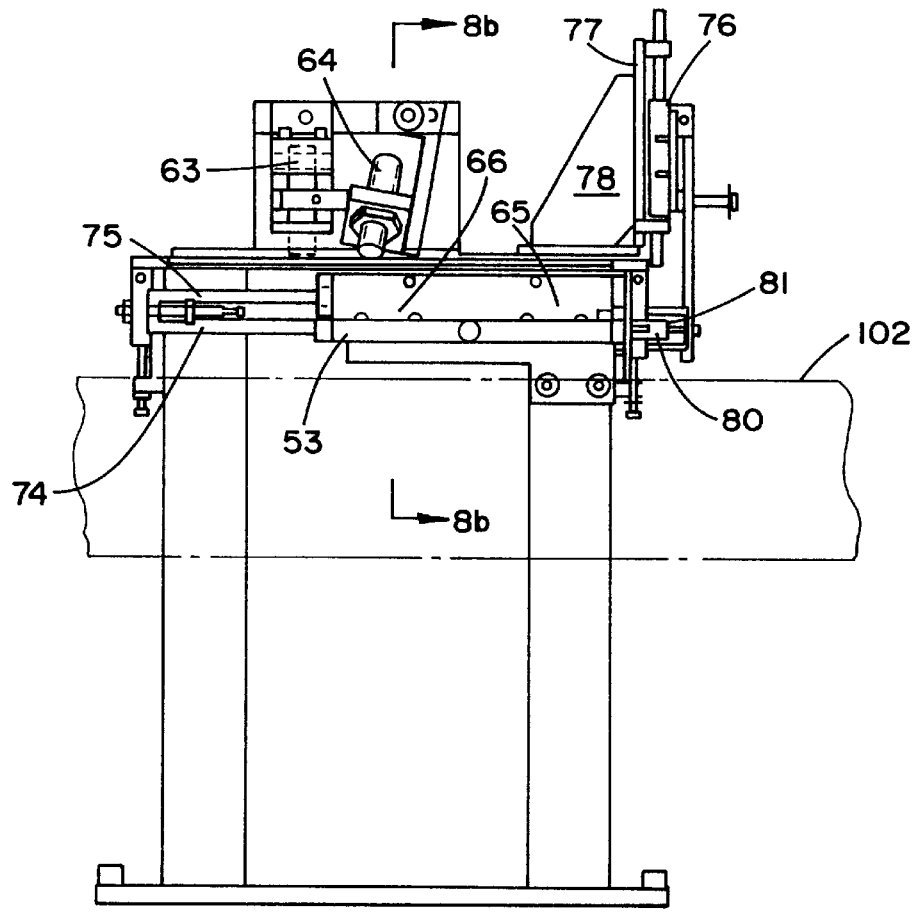
FIG. 8(a) is a detailed side elevation view of the linear slide mechanism used to singulate and deposit individual needles onto the translucent conveyors.
Figure 8B:
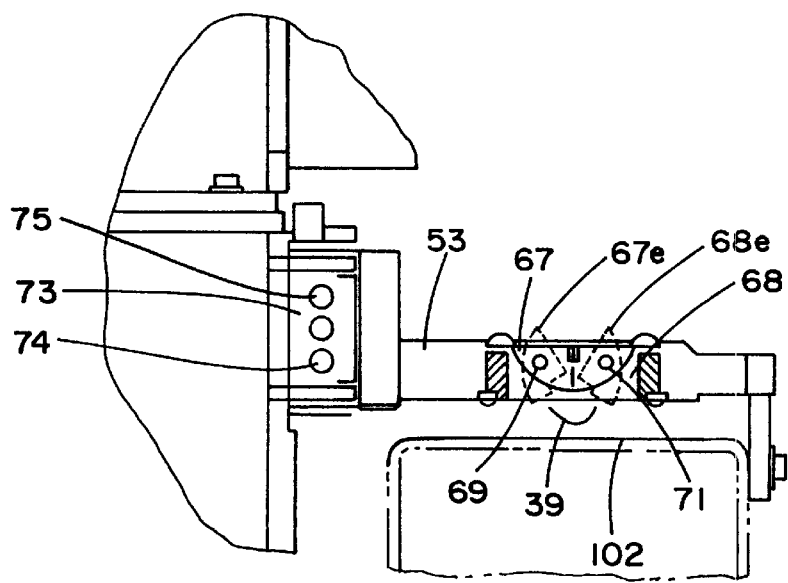
FIG. 8(b) is a detail cross-sectioned view of the linear slide device of FIG. 8(a) taken along section line B-B' showing the slide above one of the translucent conveyors.
Figure 8C:
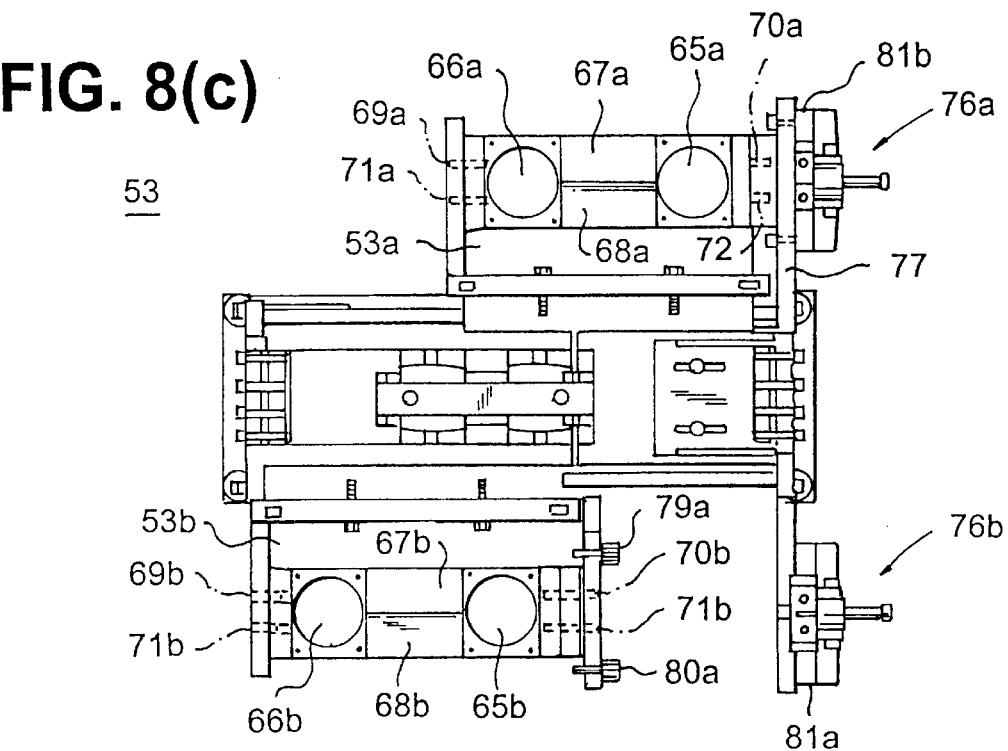
FIG. 8(c) is a detailed plan view of the linear slide mechanism illustrated in FIG. 8(a)

Two separate needle feed mechanisms are illustrated in FIG. 7(a) to feed two separate translucent indexing conveyors. In FIGS. 8(a)–8(c), the linear slide mechanisms 53a, b are illustrated in greater detail, and the vibrating bowl assembly is illustrated in greater detail in FIG. 8(d). Parts that are substantially identical in the two separate feed mechanisms are identified with the same reference numeral with an (a) or (b) suffix, depending on which feed mechanism they are associated with. When a part is referred to without the suffix, it is understood the description applies equally to both needle feed mechanisms.

Figure 8D:
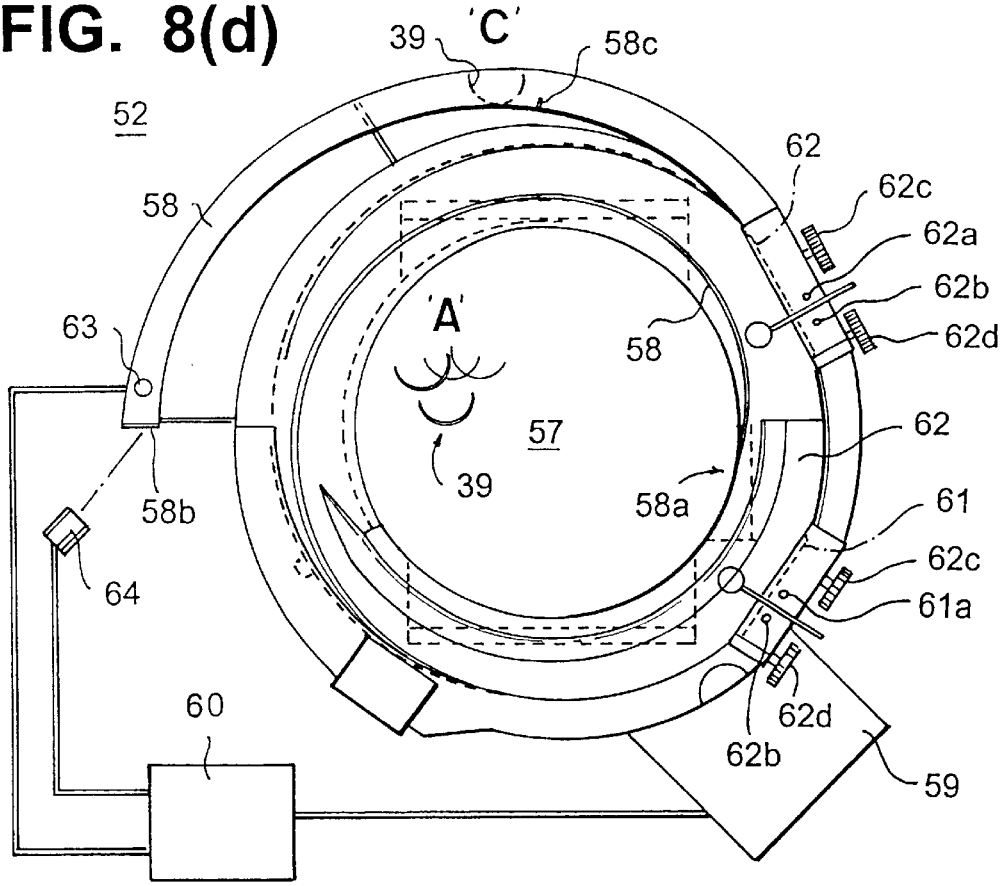
FIG. 8(d) is a detailed top plan view of one of the vibratory conveyor bowls and the needle trackway used to feed the linear slide mechanisms.

As illustrated in FIG. 8(d), a vibrating bowl assembly receives a plurality of needles in bulk on a central floor area 57. The vibrating bowl is a modified vibrating parts feed device manufactured by FMC Corp. to provide between 60 and 100 parts per minute. The bowl is fabricated of surgical stainless steel with a polyurethane lining in the bowl and all riding surfaces of the track assembly are also coated to prevent damage to the needle points. The track assembly 58 is a continuous spiral track which begins at the bottom of the bowl at 58(a) and ends at the linear discharge point 58(b).

The track includes along virtually all of its entirety a vertical rib 58(c) which supports the needle during the vibratory transport as illustrated by the needle 39 at position C. The needles are transported from the floor 57 at position A to the discharge point 58(b) by pulsed vibration from vibratory unit 59 controlled by a control means 60. The vibrations supplied by the unit 59 are both vertical and horizontal and are timed to coincide to provide a maximum rate of movement for the needles 39. Track member 58 begins at the floor of the unit 57 and winds upwardly to the top of the vibrating bowl wherein the vertical portion 58c is interrupted for a pair of vertical gates 61 and 62 which redirect overlapping needles and nested needles back into the vibrating bowl 52. A secondary track and dam 62 is used to catch overlapping needles screened by the first dam 61 and return them to the floor of the hopper 57 with minimal damage to the points of the needle. Each of the vertical dams 61, 62 include adjustable knock off screws 61a, b and 62a, b which are used to provide precise adjustment of dams 61 and 62 for various needle sizes. Thumb screws 61c, d and 62c, d provide coarse adjustment of the gates 61, 62 while knock off screws 61a, b and 62a, b provide for fine adjustment thereof.

As stated earlier, the entire raceway track 58 and the vibrating bowl 52 are coated in polyurethane to minimize any damage to the needle points. The polyurethane coating on the stainless steel bowls and a silicone coating on the needles tend to create during operation of the device a static charge which can effectively inhibit movement of the needles along trackway 58. This static buildup may be countered in one of two ways, first by providing a stream of ionized air over the trackway or second by coating the polyurethane racetrack 58 with a Teflon spray lubricant available commercially. It has been found that an application of the Teflon spray lubricant will remain effective for approximately 500,000 needles.

The pulsed vibration of vibrating unit 59 provides a single file stream of needles oriented on trackway 58 as illustrated at position A and C by needles 39. As they reach the end of the track 58b, they are first detected by an optical sensor 63 which is activated by the reflection of the needle on the trackway 58. When the needle has fallen from the trackway at 58(b), a second detector signal is generated by a second optical detector 64. The electrical signals from optical detectors 63, 64 are provided to control means 60 for use in controlling the vibratory motor 59 as will be hereinafter described in greater detail.

Vibrating bowls 52a, b provide a serial single line output of needles, dispensed one at a time to the needle feed stations 53a, b which are more fully illustrated and described with respect to FIGS. 8(a)–8(c).

As illustrated in FIG. 8c, the needle feed stations include a first linear slide 53a and a second linear slide 53b which are reciprocated between the two positions illustrated in FIGS. 8(c) by slides 53a and 53b. In a first position, as illustrated by the linear discharge slide 53b, a first needle pocket 65 is arranged under the drop point 58b of the trackway 58 leading from the vibrating bowl members 52a, b. After sensor means 64 has detected a falling needle from the end of trackway 58, the linear slide is reciprocated to its second position illustrated by slide 53a in FIG. 8c. In this position, the second needle cup 66a is now positioned below the end of a trackway 58b formed on the vibrator bowl assembly 52a. The pulsing vibrator unit 59 is then energized until a second needle is detected by optical sensor 64 as it falls into needle pocket 66a.

The needle pockets 65 and 66 are formed in a pair of pivoting blocks 67, 68 which are mounted for pivotal movement on the slide mechanism 53a, b. As illustrated in FIG. 8(c), block member 67a pivots on pins 69, 70 while block member 68 pivots on pins 71, 72.

The pivotal movement is illustrated in FIG. 8(b) wherein block members 67, 68 pivot around pivot points 69, 71 to the position illustrated at 67(e) and 68(e). As the block members 67, 68 pivot, the needle pockets are opened as illustrated in FIG. 8(b) to deposit the needle 39 on the translucent indexing conveyor 102. An air slide mechanism 73 and guide rails 74, 75 which provide the reciprocal movement of the slide mechanisms 53a, b are also illustrated in cross-section in FIG. 8(b).

Referring to FIG. 8(c), the block members 67, 68 are pivoted by means of a second pair of air slides 76a, b which are mounted on a vertical plate 77 which is suspended above translucent conveyors 102, 104 by means of a support base 78. Each of the blocks 67, 68 is also equipped with rollers 79, 80 which engage a rectangular raceway 81 when the linear slide mechanism is reciprocated to its forward position as illustrated by slide 53a in FIG. 8(c). When the rollers 79(b), 80(b) are received within rectangular raceway 81(b) the air slide 76b is actuated to raise the rectangular raceway 81(b) vertically. Since block members 67, 68 are mounted for pivotal movement with pins 69, 71 on the inbound side of the blocks, a lifting motion on the rollers 79, 146 on the outbound side of the blocks will cause pivotal movement about pins 69, 71 as the rollers 79, 80 come together within the rectangular raceway 81. After the needles have been deposited on the translucent conveyor 102, the air slide 76 is then lowered which returns block members 67, 68 to the position illustrated in FIG. 8(c).

In the sequence of operation, the control means 60 energizes the vibratory motor 59 to vibrate the bowl in a pulsed manner, with the amplitude of the pulses controlled by an adjustable rheostat. The adjustable amplitude setting varies depending upon the size and mass of the needle to be transported along the trackway 58. The needles are then singulated in single file along the entire length of the track 58 from the floor of the vibratory bowl 57 to the discharge point 58b. When optical sensor 63 senses the presence of a needle at the end of the trackway, vibrating motor 59 is stopped until the reciprocating slide 58 is reciprocated to its most rearward position as illustrated by slide 53b in FIG. 8(c). After linear slide 53b is in position, control means 60 energizes the motor 59 and the needle is vibrated from trackway 58 into needle pocket 65b. As the needle falls from the trackway to the pocket, its presence is detected by optical sensor 64. Control circuit 60 keeps motor 59 vibrating until another needle is sensed on track 58 by sensor 63. After receiving a needle, the linear slide 53b is then advanced to the forward position as illustrated by slide 53a in FIG. 8(c). In the event a second needle is detected by optical detector 63 before slide member 53b has reached its forward position, the drive motor 59 is stopped until slide member 53b is in position to receive the second needle. Thus there are two control situations for the deposit of a needle into the second pocket 66b. If a needle was detected at sensor 63, then the vibrating motor 59 is re-energized to vibrate that needle off the end of track 58 and into needle pocket 66b. If a needle has not been detected by optical sensor 63, the control means will keep vibrator 59 running following the first drop, and the vibrator will continue to run until sensor 64 detects a dropping needle. After each drop, the control means 60 keeps the vibrating motor 59 running until a needle is detected at optical sensor 63. After both needle pockets 65b, 66b have received a single needle, the air slide 76 is actuated opening the needle cups and depositing the needles therein in a singulated and spaced relationship on the translucent conveyor 102 for imaging by the optical system and further handling by the robotic tracking system.

It should be understood that while the needles 39 deposited on translucent conveyor 102, 104 are singulated and spaced apart, they will be randomly positioned and unoriented. In the preferred embodiment, each translucent conveyor 102, 104 is an endless loop conveyor that is driven at a rate of four inches per sec (4 in./sec) and runs parallel to a precision conveyor 106 as shown in FIGS. 7(a).

As described above, and in view of FIG. 7(a), the robot assembly comprises two robots 55a, b located downstream from each needle singulating assembly 53a, b and proximate both the precision and translucent indexing conveyors. In the preferred embodiment described herein, each robot assembly 55a, b is an Adept® 604-S robot capable of accomplishing needle transfers at a rate of approximately 40 transfers per minute as controlled by each robot's corresponding Adept® CC controller. Each robot is a four-axis SCARA (Selective Compliance Assembly Robot Arm) robot comprising four Joints: Joint 1, being the shoulder joint having a rotational range of motion of +/−100°; Joint 2, the elbow joint, having a rotational range of motion of +/−140°; Joint 3 providing translational motion for a robot quill for up to 150 mm in an up down motion; and, Joint 4, being the wrist joint, providing +/−360° rotational motion of the quill. Robot grippers 108a, b are attached to the quill of each respective robot assembly 55a, b and are enabled to provide gripping action by pressure supplied from an air cylinder (not shown).

Referring now to FIG. 7(b), there is illustrated the precision conveyor 106 which is driven by drive motor assembly 110 at a rate sufficient to index and transfer one oriented surgical needle per ¾ second (3/4 needle/sec) to the automatic swaging machine 200. A similar drive motor assembly 112 is provided for driving the indexing conveyors 102, 104. As will be explained in detail below, each drive motor assembly 110, 112 is interfaced with and operates under the control of the control system 114 to pause the indexing motion to enable the pick-up and transfer of a needle from the indexing conveyor to the precision conveyor.

Figure 9:
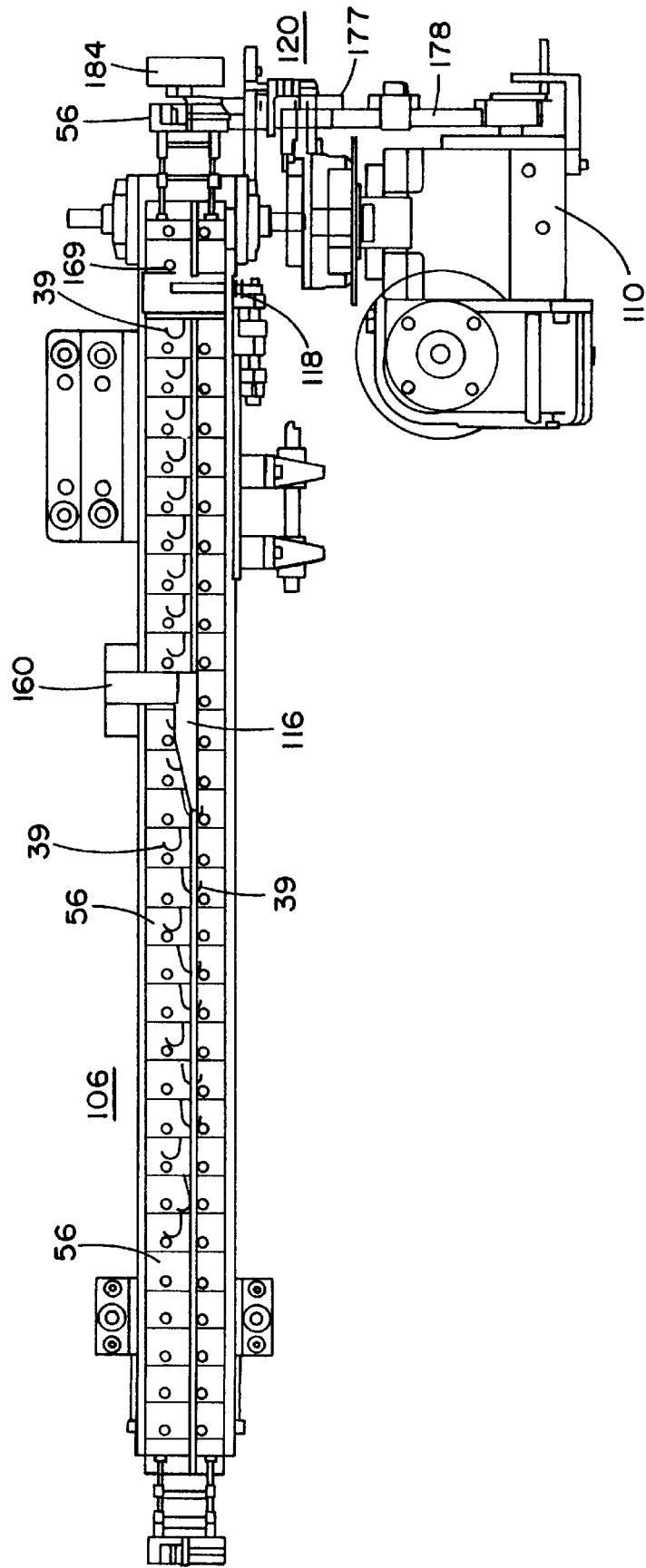
FIG. 9 is a top view of the precision conveyor and illustrates the conveyor, the needle plow mechanism, the needle pre-positioning mechanism, the moveable hard stop and the multi-axis gripper and where the conveyor is shown carrying needles that have been positioned thereon.

FIG. 9 illustrates in detail the precision conveyor 106 and the plurality of engagement boats 56 located thereon for engaging respective individual surgical needles 39. Motion of the precision conveyor 106 is also paused periodically at the desired cycle rate to allow for the transfer of the needles 39 thereto from the robots 55a, b. The precision conveyor receives needles 39 with rough positioning from the robotic assemblies 55a, b, in boats 56 as will hereinafter be described in greater detail with respect to FIGS. 11(a)–(c) and 12. The needles when received in boats 56 are orientated as to point and butt end, but not orientated with respect to the direction of curvature of the needles. As further described with respect to FIG. 13, a needle plow mechanism 156 is provided to orient the curvature of the needles. A needle pre-positioner 164 is also provided to provide prepositioning of the butt end of each needle as will be hereinafter described with respect to FIGS. 14(a) and 14(b). The needles are finally precisely positioned by the moveable hard stop mechanism 120 and will be described in greater detail in FIGS. 15(a) and 15(b). The individual needles are then removed and held for swaging to a suture by a multi-axis gripper 184, which gripper is described in greater detail in FIG. 18.

In the preferred embodiment, the control system 114 includes a programmable logic controller (PLC) that is in digital communication with the Adept® robot controllers and the vision tracking system components to control the infeed system.

As shown in FIG. 7(b), the vision tracking system comprises a camera assembly 124 having two video cameras 126 and 128, one located overhead each respective illuminated platform portion, 130a and 130b, for its indexing conveyor 102. As will be explained in detail below, the video images of the needles obtained from each camera 126, 128 are bit-mapped or suitably digitized and transmitted via suitable transmission media, such as communication lines 132a, b shown in FIG. 7(b), to the remotely located control system computer 114 where a Vision Control task processes the video images and inputs the data to each robot 55a, b via communication line 134. Preferably, the conveyors 102 and 104 are translucent and are backlit at the respective portions 130a, b and 54a, b so that a sharp video image may be obtained by the overhead camera assembly for processing.

It is understood that for descriptive purposes, only two video cameras 126, 128 corresponding to the two illuminated platforms 130a, 130b are shown in FIG. 7(b). However, the automatic needle singulation and transfer station includes a second set of video cameras (not shown) corresponding to illuminated platforms 54a and 54b for conveyor 104 so that, as mentioned above, binary images of needles on conveyor 104 may be obtained while the robots are picking and placing needles from conveyor 102. The redundancy designed into this system ensures that there will be no momentary shortage of needles fed to the swaging station 200 and that maximum throughput of oriented needles for input to the swaging station is achieved.

In the event the state of robotics technology improves, and as the robot assemblies achieve greater degrees of movement at faster speeds, the second set of cameras and a second robot assembly may no longer be required. Furthermore, a robotic assembly of sufficient speed and precision may be able to pick up randomly deposited needles from a moving conveyor and place them directly in an oriented position at the swaging station.

In the preferred embodiment, each camera 126, 128 is mounted approximately one (1) meter above each backlit indexing conveyor 102, 104 and utilizes an electrically controlled telephoto lens with a focal distance ranging from 10 mm to 140 mm that may be changed with suitable adaptors. Suitable lens controllers are used to establish lighting/iris, focus, and field of view for each camera lens, and, are interfaced with the Adept® controller via an RS-232 link.

A further component of the control system for the needle sorting and infeed apparatus includes a Supervisory Control and Data Acquisition Node hereinafter SCADA node) which is used to oversee and direct the infeed system. This node interfaces with each of the Adept® controllers via discrete RS-232 links which are used to download data information, such as needle parameters, error messages, and status messages, to the Adept® controllers during run-time. The SCADA node may comprise a personal computer or such suitable device, running commercially available FIXD-MACS® software. Serial communication is used to exchange the needle parameters entered at the FIX/DMACS "Adept® Setup" screen during a needle changeover procedure which is used to inform the infeed system of the size and type of needles to be processed. After an operator enters the needle parameters and initiates a changeover, the FIX/DMACS Node will transmit these parameters to the robot controller(s).

Figure 10:
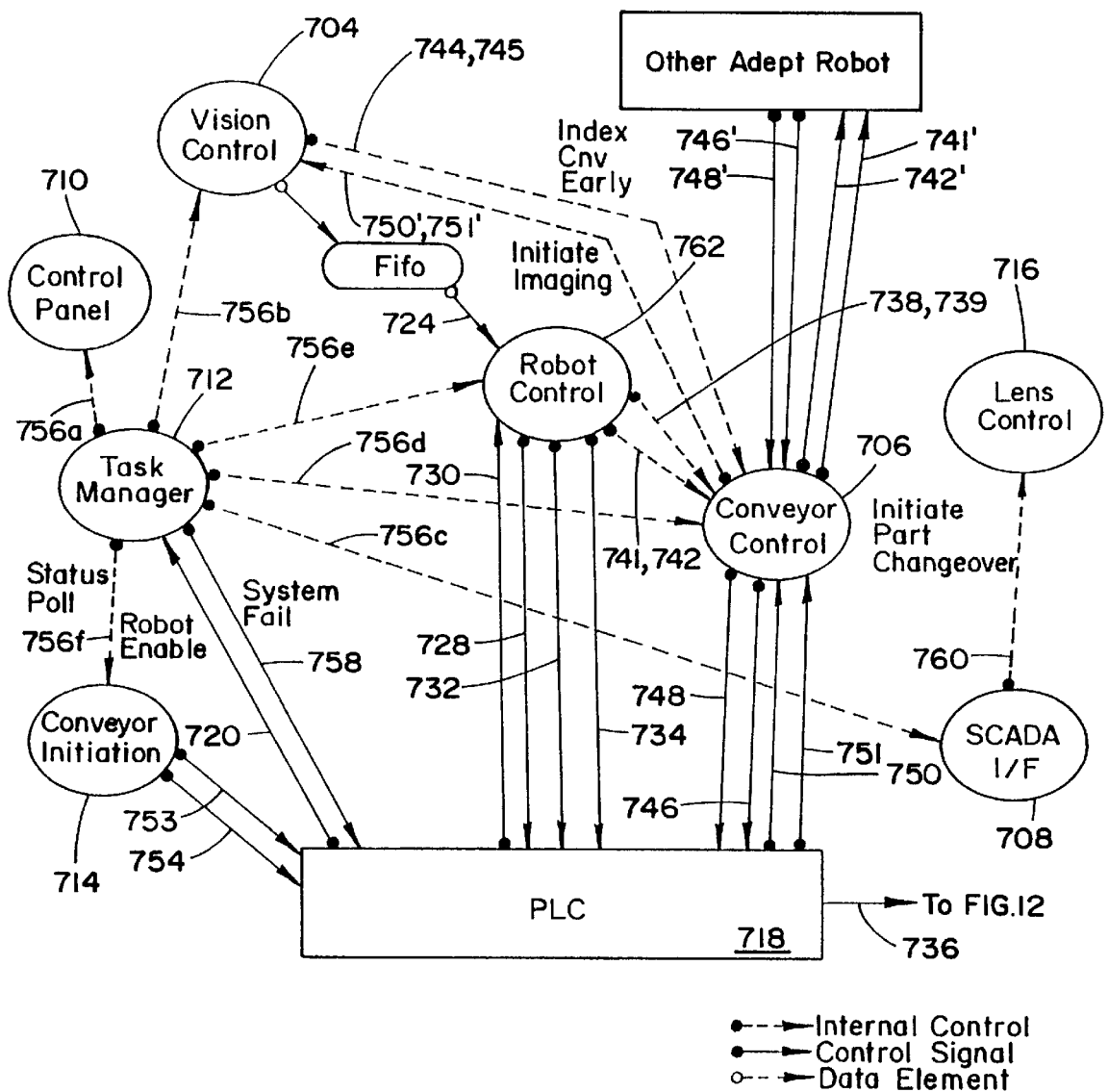
FIG. 10 is schematic representation of the control and data flow for each of the control tasks of the needle sorting apparatus of the present invention.

The robotic/vision control system 114 of the automatic needle singulation and transfer station 50 comprises individual computer software programs, each associated with a particular task to be performed by the needle sorting and infeed system 600 and executed under the control of the PLC 718. As shown in FIG. 10, the software architecture for controlling the needle sorting apparatus of the automatic needle singulation and transfer station performs eight (8) main tasks: a Robot Control task 702; a Vision Control task 704; a Conveyor Indexing Control task 706; a SCADA Node Interface task 708; A Control Panel task 710; a Task Manager 712; a Conveyor Initiation task 714; and, a Lens Control task 716. Of these eight tasks mentioned above, the first six are active during the needle infeed steady state operation as will be explained below. FIG. 10 additionally shows the data flow among the tasks and the signals which initiate the tasks. It is understood that the software language used in the preferred embodiment, is Adept's V/V+ language, which supports both vision and robotic control in a multitasking environment. Each of the tasks will be generally described below with respect to FIG. 10. A more detailed description of the following tasks can be found in commonly owned, copending U.S. application Ser. No. 09/019,138 entitled "Control System for an Automatic Needle-Suture Assembly and Packaging Machine," which is incorporated herein by its reference.

It should be understood to those skilled in the art that each robot assembly, controllers, and camera vision tracking system requires careful calibration and configuration procedures for the infeed system to properly function. For instance, each robot assembly requires that joint positions be set and joint limits be configured to ensure that the robots avoid structural damage when enabled. Furthermore, a camera-to-robot calibration is required so that the vision system may accurately compute the positional coordinates of the needle so that the robot may move to the pick position. This procedure provides a translation matrix between the camera's field-of-view and each robot base position.

The PLC 718 is responsible for initially powering the robot controllers and robots. A robot calibration procedure may be initiated after power-up to move the robot joints to known "home" positions to synchronize the digital encoders (not shown).

The process of starting the PLC 718, robot controllers, and conveyors 102, 104 and 106 is time-critical. From the robot controller perspective, when a ROBOT ENABLE signal 720 is raised by PLC 718, it begins its normal cycle by executing the Robot Control Task 702, the Vision Control Task 704, the Conveyor Indexing Control Task 706, and the Conveyor Initiation Task 714; which initiates the movement of conveyor 102, waits approximately up to two (2) seconds, and then initiates the movement of second conveyor 104 as will be described in detail below. The PLC simultaneously raises the ROBOT ENABLE signal on the other Adept robot. Under this scenario, the PLC 718 integrates the startup of the Bulk Feeding Device System, the Indexing Conveyors, and swaging machine with the raising of the ROBOT ENABLE signal 720. As will be explained in further detail below, when the ROBOT ENABLE signal goes low, the Adept robot halts its standard processing and responds to requests from the SCADA node.

Robot Control Task

There is a single Robot Control task associated with each Adept® controller for each robot assembly 55a, b although only one is indicated as element 702 in FIG. 10. The control system software for the Robot Control task 702 manages the respective robot assembly 55a or 55b as a resource, reads a FIFO buffer 722 of identified needle locations which are produced by and input from the Vision Control Task 704, interfaces with the programmable logic controller (PLC) 718 of control system 114 for needle placement handshaking, and, initiates the indexing of the conveyor belts 102, 104.

Figure 12:
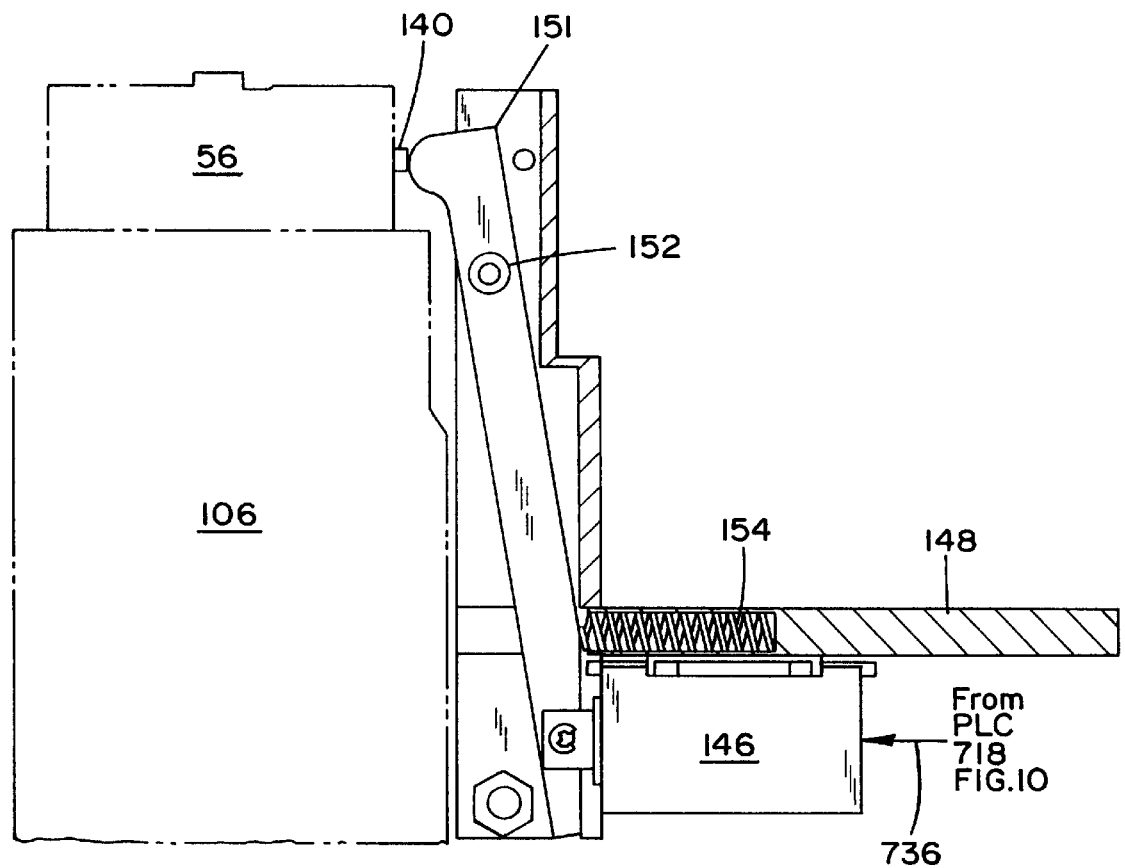
FIG. 12 is a side view of the robot load solenoid that actuates the jaws of the precision conveyor boat.

The steady state operation of the Robot Control task 702 for each robot assembly 55a, (55b) is as follows:

First, the respective robot controller continuously polls its input FIFO 722 via data line 724 to obtain positional coordinate data for the identified needle locations on a respective translucent conveyor 102 or 104. The data for the needle locations are provided to the FIFO buffer from the Vision Control task 704 via respective data lines 726 as will be explained in further detail below. When an acceptable (recognizable) needle position is entered into the FIFO buffer 722, the robot controller will remove the needle position from the buffer and direct the robot gripper arm 108a, (108b) to move to that location on the conveyor belt. Next, for each recognized needle, the Robot Control task 702 will signal the robot gripper 108a, (108b) to close on the needle barrel portion 41 and to depart from the conveyor to an approach location proximate the precision conveyor 106. The robot control task then generates a NEEDLE IN GRIPPER signal 728 to the PLC as indicated and waits for a response from the PLC 718. As shown in FIG. 12, when the PLC receives a Robot task generated NEEDLE IN GRIPPER signal 728, the PLC 718 will generate a SAFE TO PLACE signal 730 for receipt by each of the robots 55a, b. The purpose of the SAFE TO PLACE signal 730 is to inform the respective robot assembly 55a, b that a needle may be placed onto a precision conveyor boat 56 of conveyor 106. As a response to the receipt of the SAFE TO PLACE signal 730, the Robot Control task 702 will generate a DON'T INDEX PRECISION CONVEYOR signal 732 for receipt by the PLC 718 immediately before it places the needle on the precision conveyor 106. While this signal remains high, for e.g., at a logic "1" state, the Adept® robot 55a or 55b will attempt to place a needle onto a boat 56 of precision conveyor 106. This involves initiating the engagement jaws 136, 137 of the precision conveyor engagement boat 56 to retract to allow the placement of the needle therebetween, as will be explained below. Once the movement of the robot has settled and a needle is placed, the Robot task 702 will generate a NEEDLE PLACE COMPLETE signal 734 for receipt by the PLC 718 and, the PLC will generate a suitable control signal 736 to enable the engagement jaws of the precision conveyor engagement boat 56 to engage the needle. In the preferred embodiment, the dwell time of the NEEDLE PLACE COMPLETE signal 734 is approximately 48–64 milliseconds. After activating this signal, the robot assembly 55a, b will hold the needle in place for the same time period. (48–64 msec.) Immediately thereafter, the robot will open its grippers and move back to its approach location away from the engagement boat 56. Finally, the DON'T INDEX PRECISION CONVEYOR signal 732 is removed indicating that it is now clear for the precision conveyor 106 to index which is performed at the command of the PLC 718.

As a safety interlock for conveyor index initiation, the Robot Control Task 702 will signal the Conveyor Indexing Control Task 706 with an internal control respective LAST PICK signal 738, 739 indicating that the robot assembly, 55a or 55b, has picked up the last needle from the current conveyor as indicated in FIG. 10. If the maximum number of needles expected per current camera field-of-view (hereinafter "FOV") is not picked from the respective current infeed conveyor belt 102, (104), the Robot Control Task 702 will request the Conveyor Control task 706 to index that conveyor belt "early" via the INDEX CONVEYOR 1 EARLY or the INDEX CONVEYOR 2 EARLY signals 741,742 as shown in FIG. 12. Since all signals affecting the motion of the conveyors are routed through the Conveyor Control task 706, this task will generate a corresponding INDEX CONVEYOR 1 EARLY, signal 741 ' or INDEX CONVEYOR 2 EARLY, signal 742', for receipt by the other adept robot. If during normal operation a Robot Control Task receives either Index Conveyor 1 Early or the Index Conveyor 2 Early signal, it will flush the contents of its FIFO buffer 722 and continue as if the last needle has been picked from the conveyor.

The control software must take into account the floating 16–32 ms duration of a digital output based on the time slicing of V/V+. This will affect the calculation for minimum time required for placement in conjunction with setting and resetting the Don't Index Precision conveyor signal 732.

The Robot Control Task 702 performs error recovery on two type of errors. These errors are grouped as indexing errors and gross errors. As in all other tasks, gross errors cause the Task Manager 712 error recovery to respond and stop the Robot Control Task immediately. An indexing error occurs if a robot is waiting for a needle to be placed in its parts FIFO and both conveyor belts have not indexed within an appropriate amount of time. The Robot Control Task 702 recovers from this type of error by requesting the other robot to index early via signals INDEX CONVEYOR 1 EARLY and INDEX CONVEYOR 2 EARLY signals 741,742 respectively. This forces both vision/robot control systems to flush the contents of its current parts FIFO and index the conveyor belts.

Conveyor Indexing Control Task

The Conveyor Indexing Control Task 706 initiates the indexing of each respective translucent indexing conveyor 102,104 and the task is initiated by the Conveyor Initiation task 714. All signals affecting the motion of the conveyors are routed through the Conveyor Control task 706.

As shown in FIG. 10, the first step of the Conveyor Indexing Control task 706 is to check for the LAST PICK signal 738,739 internally generated from the Robot Control Task 702 and indicating that the last needle pick-up from the respective infeed translucent conveyor 102,104 has been completed by one of the Adept® robots 55a,b. Alternatively, the Conveyor Indexing Control task 706 awaits for the INDEX CONVEYOR EARLY (1 and 2) signals 744,745 internally generated from the Vision Control task 704 when no needles are recognized in the current camera FOV. As a result of receiving the LAST PICK signals 738,739 from the robot task, the Conveyor Control task will generate a corresponding INDEX CONVEYOR 1 signal 746, or, an INDEX CONVEYOR 2 signal 748, for receipt by the PLC 718. It is understood that each Adept® robot controller must request the PLC 718 to index a translucent indexing conveyor 102(104) after picking up the last needle from the respective conveyor. Therefore, the other Adept® robot must generate its corresponding INDEX CONVEYOR 1 (or INDEX CONVEYOR 2) signal for receipt by the PLC before it can command the current translucent conveyor 102, (104) to index. As a result of receiving the INDEX CONVEYOR 1 EARLY, signal 741' or INDEX CONVEYOR 2 EARLY, signal 742' from the Conveyor Control task 706 indicating that the maximum number of needles have not been picked up or that there are no or insufficient needles in the respective camera's FOV, the other Adept robot will generate a corresponding CONVEYOR 1 INDEXED EARLY signal 746', or CONVEYOR 2 INDEXED EARLY signal 748' for receipt by the Conveyor Control task 706, as shown in FIG. 12. These signals will cause the corresponding conveyor 102(104) to abort processing and initiate indexing of the belt.

After receipt of both INDEX CONVEYOR 1 or INDEX CONVEYOR 2 signals 746,748 from each of the robot assemblies, the PLC 718 commands the translucent indexing conveyor 102 to index and generates a corresponding CONVEYOR 1 SETTLED signal 750 or, a CONVEYOR 2 SETTLED signal 751 for receipt by the Conveyor Control Task 706. Note that the CONVEYOR 1 SETTLED signal 750 and the CONVEYOR 2 SETTLED signal 751 are raised approximately 2 seconds after the PLC has been requested by the robot control task 702 to index conveyor 102, (104). The Conveyor Control Task 706 then informs the Vision Control task 704 to begin needle imaging upon receipt of internal control signals 750',751' that correspond to the respective CONVEYOR 1 SETTLED and the CONVEYOR 2 SETTLED signals 750,751. Once the indexing conveyor 102 (104) has been indexed and the corresponding CONVEYOR SETTLED signal 750,751 has been received, the Vision Control Task 704 may begin needle recognition in the corresponding cameras's FOV. Specifically, as will be explained below, the cameras 126,128 above conveyor 102, 104 each take a snapshot of the respective field of views at respective illuminated portions 130a,b of the translucent conveyor and the Vision Control task 704 will control the processing of the image to make a determination of whether a recognizable needle is present each camera's field of view.

At this point, a distinction must be made between the mere presence or detection of a needle in the field of view and the presence of a "recognizable" needle. A needle may be present, but, for a variety of reasons, the Vision Task 704 may not be able to determine its positional coordinates until the camera vision parameters are changed by the execution of an auto-imaging algorithm which automatically adjusts the iris and vision system lighting parameters of each camera so that the cameras may subsequently obtain enhanced images that may be processed. During steady state, when the vision task has already "recognized" a needle in its respective field of view, the auto-imaging algorithm is not repeated.

Details of the auto-imaging algorithm will be explained in detail below.

Vision Control Task

The vision Control Task 704 controls and processes the images taken by each of the two camera assemblies 126,128. Since the timing of the two translucent conveyors are phased, only one camera is operating at one time.

Specifically, as shown in FIG. 7(b), the Vision Control task 704 interfaces with each respective camera 126,128 to identify the needle locations of recognizable needles in that camera lens's respective field of view encompassing an area located at respective illuminated platforms 130a, 130b. The Vision Task 704 then processes the positional and orientation information of the identified needle locations and writes those locations to the Robot Task FIFO 722 via data lines 726. As mentioned above, the Vision Control task is additionally responsible for initiating an early conveyor index if no needles were imaged in a camera field of view.

As described briefly above, the Vision Control task runs each time either conveyor 102,104 completes indexing. It is initiated to begin needle recognition upon receipt of either a CONVEYOR 1 SETTLED signal 750' or CONVEYOR 2 SETTLED signal 751' which is generated by the PLC 718 and routed through the Conveyor Control task 706 each time respective translucent indexing conveyor 102,104 has ceased indexing, as commanded by the Adepts. Each CONVEYOR SETTLED signal 750,751 goes high (logic "1") approximately two (2) seconds after the PLC has been requested by the Adept® robot to index a translucent indexing conveyor. Each of the CONVEYOR SETTLED signals 1 and 2 (750,751) remain high until the PLC 718 receives the next respective INDEX CONVEYOR 1 or 2 signal 746,748 from the Adept robots.

The Vision Task 704 activates that camera which is associated with the conveyor settled signal. When activated, the camera 126,128 takes a picture of the backlit areas 130a,b of the conveyor belt 102, (104). Any image obtained is preferably converted to binary image data for subsequent digital processing. The Vision Control task 704 utilizes "vision tools" to detect acceptable needles, and places the coordinates of acceptable needle pick-up points in the FIFO buffer 722 for the Robot task. An "acceptable" needle in the backlit areas is a needle that measures within the tolerances of the needle parameters that have been previously accepted during the needle changeover procedure. The needle changeover procedure is a procedure to inform the infeed system software of the type and size of the needles in the current batch to be processed and must be executed before making needle batch changes as to be discussed below. Specified needle tolerances are for the needle radius, barrel width, angular characteristics of the needle with respect to the robots, and the calculated area as computed from the needle parameters.

Auto-Imaging Algorithm

As mentioned above, if a detected needle is unrecognizable, the auto-imaging algorithm is invoked to change the camera vision parameters. Thus, after the binary image data is processed, a determination is made as to whether the needle image is of the specified radius, whether the needle image is of the specified barrel width, whether the needle image has the specified angular characteristics, and, whether the needle image area is within the specified tolerance. If any of these criteria are out of specification, then an auto-imaging algorithm is executed which functions to take a series of pictures of the same needle image at the respective camera's field of view to thereby enhance the needle image for better needle recognition by improving the vision parameters between pictures. Thus, after each of the series of pictures is taken, the auto-imaging algorithm will automatically adjust the camera's iris and vision system lighting parameters to enable the vision system to image the needles properly within the camerals field of view. For example, when adjusting the lighting of the fields of view, certain camera vision parameters such as the gain, offset, and binary threshold may be modified. The auto-imaging algorithm is executed until a needle is recognized in each camerals field of view and is not repeated until a needle changeover is executed.

Even when the cameras of the Vision Control task 704 are adjusted, needle images may still not be imaged properly. This is because each camera's field of view utilizes a backlighting source and needles that overlap, touch with each other, or, are clipped by field of view edge boundaries will not be considered for recognition. Thus, the Vision Control task will make a determination of whether the needles overlap or touch each other, and, will determine whether the needles are too close to the edge of the field of view.

After all of the possible needles are recognized, the Vision Control task will calculate the needle pick-up coordinates of the acceptable needles and place them in the Robot Control task FIFO buffer 722 to enable the robot to pick and place the acceptable needle onto the precision conveyor. In the preferred embodiment, the maximum number of needles that can be recognized during each dwell cycle of each translucent indexing conveyor is three (3). If less than this maximum or if no needles are recognized, a robot may be signaled to index the corresponding conveyor early, causing the vision system to abort its processing as described above.

Vision Task 704 is responsible for limiting the number of needle locations written to the FIFO to three, since the Robot Control Task will pick and place a needle for every needle location passed to the FIFO 722. In the preferred embodiment, the Vision Task is limited to operate for five seconds per indexing conveyor cycle.

The Vision Control Task 704 performs error recovery on three types of errors. These errors are grouped as imaging errors, processing errors, and gross errors. The gross errors cause the Task Manager error recovery to respond and stops the Vision Control Task 704 immediately. When an imaging error occurs, the Vision Control Task 704 suspends all execution on the current FOV and requests an early index of the conveyor belt by generating either INDEX CONVEYOR 1 EARLY or INDEX CONVEYOR 2 EARLY signals 744, 745 as discussed above. Receipt of these signals causes no needles to be placed in the parts FIFO and forces both vision/robot systems to pass on the current FOV of needles. If a processing error occurs, the Vision Control Task suspends all processing on the current needle and begins processing a new needle in the same FOV if another needle is available. As a result, the Vision Task does not insert the needle into the parts FIFO.

Conveyor Initiation Task

The Conveyor Initiation Task 714 functions to initiate the Conveyor Indexing Control task 706 and is started whenever the ROBOT ENABLE signal 720 is raised from the PLC 718. Once started, this task requests an INDEX INFEED CONVEYOR 1 (102), signal 753, then waits approximately two (2) seconds, and requests an INDEX INFEED CONVEYOR 2 (104), signal 754, as shown in FIG. 11. The task 714 is then terminated and is not restarted again until the ROBOT ENABLE signal 720 is lowered and raised again.

Task Manager

The Task Manager 712 initializes the software and hardware I/O signals, the global variables, and the vision/robot system tasks. Once the vision/robot system tasks are running, the task manager monitors the integrity and status of each task currently running and the resources that are controlled by these tasks. The status poll signals 756a–756f are indicated in FIG. 12. The resources are the robot, communication ports, and the I/O signal lines. The Task Manager reports any errors to the PLC, via the SYSTEM FAIL signal 758, and the SCADA node, via the SCADA Node Interface Task 708. The SYSTEM FAIL signal 758 is generated whenever a robot (as detected by the Task Manager) has recognized a gross error which prevents it from continuing operation. This signal is active-low and remains low until the Adept robot is reset. Thus, the PLC must lower the ROBOT ENABLE signal 720 immediately upon receiving this signal.

For gross errors occurring with the vision/robot control software, the Task Manager 712 is utilized to detect and recover from these errors by continuously polling the status and integrity of all steady-state tasks and resources during program execution. If it is determined that a gross error has occurred, the SYSTEM FAIL signal 758 will be raised to the PLC 718 and all tasks except the SCADA Node Interface Task, the Control Panel Task and the Task Manager will be stopped. A code indicating the reason for the last unrecoverable error will be available to the SCADA Node through the SCADA Node Interface Task. In some cases, an error message will be displayed in the Monitor Window of the Adept robot controller. After the SYSTEM FAIL signal is raised, the Task Manager will attempt to correct any problems detected on the robot and notify the operator through the Monitor Window. In most cases, the operator will only need to raise the ROBOT ENABLE signal 720 again to reset the vision/robot control software.

Control Panel Task

The Control Panel Task 710 presents a mouse controlled panel that allows an operator to access various software "debugging" utilities, to access diagnostics utilities, to control the speed of the robot, and to select new positions that the robot will move to for picking and placing needles. Also, the Control Panel Task allows the operator to stop the vision/robot system tasks from executing.

SCADA Node Interface Task

The SCADA Node Interface task 708 polls the SCADA Node RS-232 interface for messages from the SCADA node. The task will act as slave to SCADA Node requests for Adept and camera set-up procedures necessitated by product changeovers. These requests are valid only when the ROBOT ENABLE signal 720 is deactivated.

Lens Control Task

The Lens Control Task 716 is initiated only when the SCADA node requests a new product to be introduced to the vision system and is executed only as an off-line process. The Lens Control Task 716 accepts the new needle parameters and adjusts the field-of-view size for both cameras to accommodate the new product size. The zoom, focus, and iris lenses are affected by this new product introduction, as well as internal vision system parameters, such as gain, binary threshold, and offset, used for imaging. Once the cameras are adjusted, the task is suspended until another new product is introduced to the vision/robot system.

Product Changeover

Prior to enabling the robots to begin the needle infeed process, a Needle Changeover procedure is invoked to inform the Vision and Robot Control tasks of the control system software of the type and size of the needles to be processed. This needle changeover procedure must be completed before making needle batch changes. If a changeover is not completed before the first needle batch run after power-up, an error message will be displayed at the FIX/DMACS (SCADA Node) screen when the robots are enabled and the robots will not run. If a changeover is not completed between different needle batch runs, the vision tasks will not identify any needle being run.

Essentially, an operator of the system enters the needle parameters in appropriate units, e.g., millimeters and degrees at the FIX/DMACS screen of the SCADA task 708 through data lines 760. Such needle parameters for use by the Vision tasks include, the needle radius and the radius tolerance, acceptable needle angles and their tolerances, and, the needle width and the width tolerance.

In addition to inputting needle change parameters for the vision tasks, initial camera set-up parameters associated with the particular batch of needles to be processed are also input through the SCADA Node for use by the system. The software utilizes the information provided by the user via the SCADA Node to automatically adjust the lens for the correct field-of-view size, focus, and zoom parameters prior to enabling the robots.

The Precision Conveyor

Figure 11A:
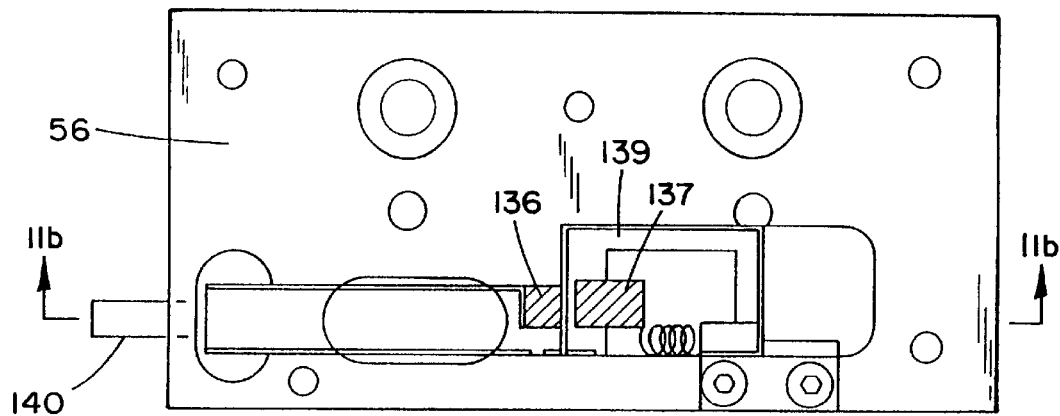
FIG. 11(a) is a detailed view of the precision conveyor boat having jaws for engaging and retaining an oriented needle for subsequent swaging.
Figure 11B:
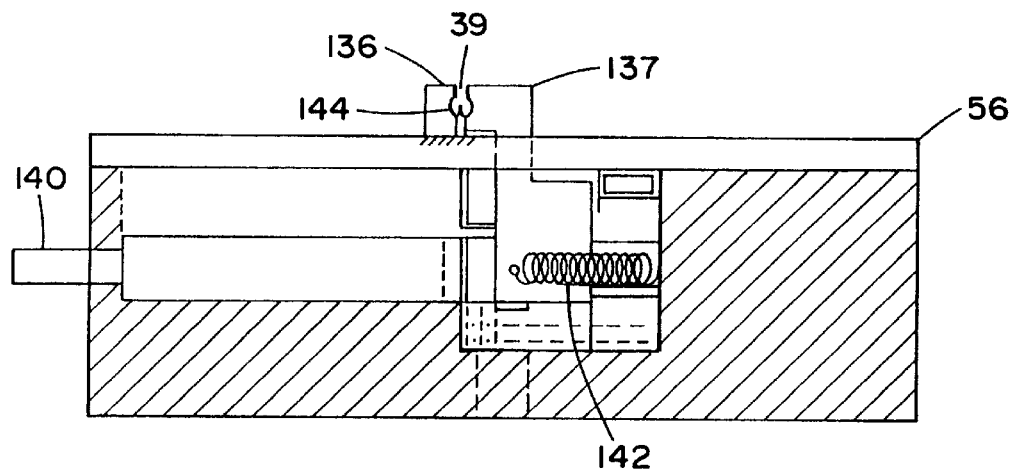
Figure 11C:
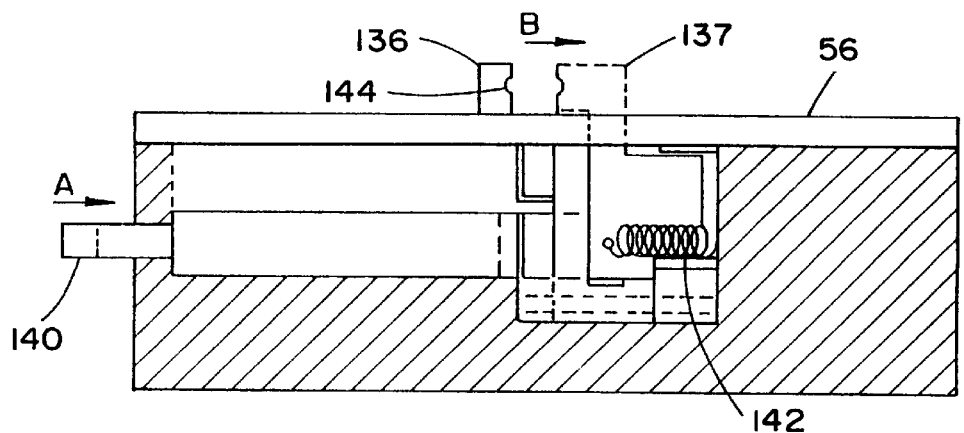
FIG. 11(c) is a detailed view of the precision conveyor boat with movable jaw extended for placement of needle oriented for automatic swaging.

FIGS. 11(a)–11(c) illustrate the precision conveyor boat 56 to which each needle 39 is transferred. Each boat is preferably provided with a pair of jaws; one jaw 136 being fixedly mounted, and the second jaw 137 being slidable within pocket 139. In operation, a push rod 140 is pressed in the direction of the arrow "A" shown in FIG. 11(c) to compress spring 142 which retracts the position of the movable jaw 137 in the direction indicated by the arrow "B" to allow for placement of needle 39 within the notch 144 of both jaws. Normally, spring 142 is biased as shown in FIG. 11(b) to maintain movable jaw 137 in its engaged position for retaining a needle 39 in the notch 144. It should be understood that any type of releasable engaging mechanism may be provided for releasably retaining a needle 39 on conveyor boat 56, provided that each needle be correctly oriented on its respective boat for subsequent swaging to take place.

FIG. 12 illustrates a robot load solenoid mechanism 146 that is activated by signal line 736 from the PLC 718 each time a needle 39 is being transferred to a precision conveyor boat 56 as described above. The robot load solenoid 146 may be mounted to the precision conveyor by an appropriate mounting plate 148. A sensor mounted on the precision conveyor, is provided to sense the proximity of the precision conveyor boat 56. At such time a conveyor boat is dwelled for transference of a needle 39 thereto, a release arm 151 of the robot load solenoid is actuated by solenoid 146 to pivot about pin 152 to depress push rod 140 and retract the movable jaw 137 to the position illustrated in FIG. 11(c). The robot arm 151 then positions the needle 39 between the jaws 136,137 of conveyor boat 56 for engagement thereof. The release arm 151 is then retracted by spring 154 as the conveyor boat 56 resumes movement.

For automatic swaging to take place at the swaging station 200 it is necessary that the needle be precisely positioned within the notch 144 of engagement jaws 136,137 of the boat 56. This is because the multi-axis gripper generally indicated at step 616 in the system flow chart of FIG. 5, must receive a precisely positioned needle for a suture to be placed within the suture receiving end 43 of needle 39. To ensure that each needle is uniformly oriented for transference to the multi-axis gripper of the automatic swaging station, a needle orientation device ("plow") 156 is provided as shown in FIG. 13(a) to orient each needle while engaged between jaws 136,137 on conveyor boat 56. The plow comprises an elongated arcuate blade 158 protruding from a mounting bracket 160 as best shown in FIGS. 13(a) and 13(b). In the preferred embodiment shown in FIG. 13(c), the plow is fixedly mounted at one end 162 of the precision conveyor 106 to enable arcuate blade 158 to scoop needle 39 positioned on the conveyor boat 56 while in forward motion. After contact is made, the arcuate portion 41 of the needle 39 is lifted and rolls over the arcuate blade 158 of the plow 156 as shown in FIGS. 13(c) through 13(e). Provision of the plow 156 ensures that each needle conveyed to the suture swaging station is oriented in the same direction.

Figure 14A:
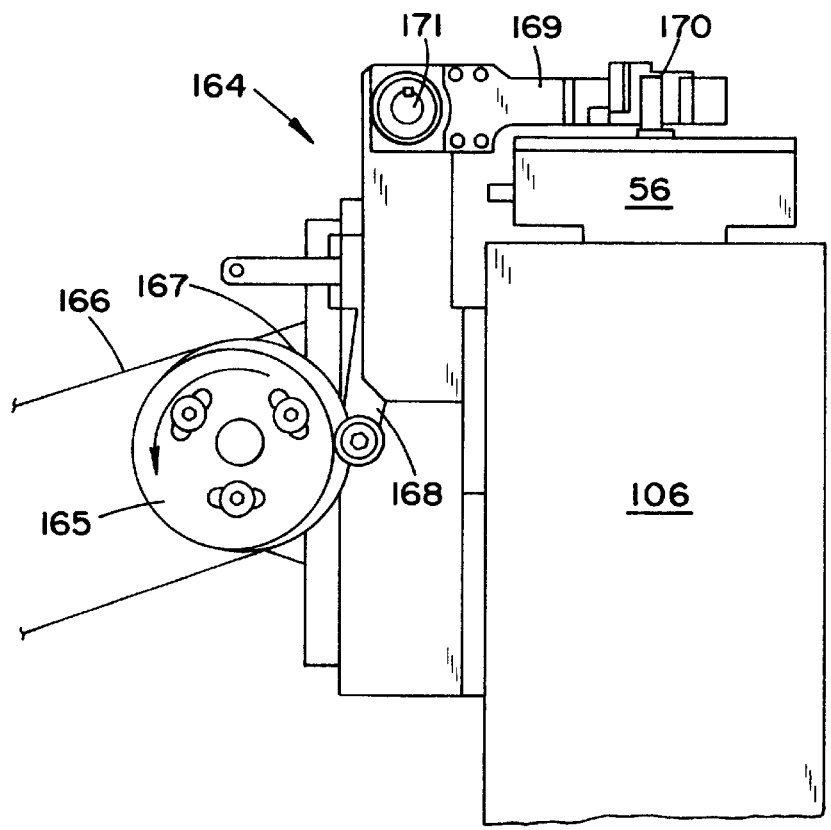
FIG. 14(a) is a side view of the needle pre-positioning assembly which further orients the needle within the engagement jaws of conveyor boat.
Figure 14B:
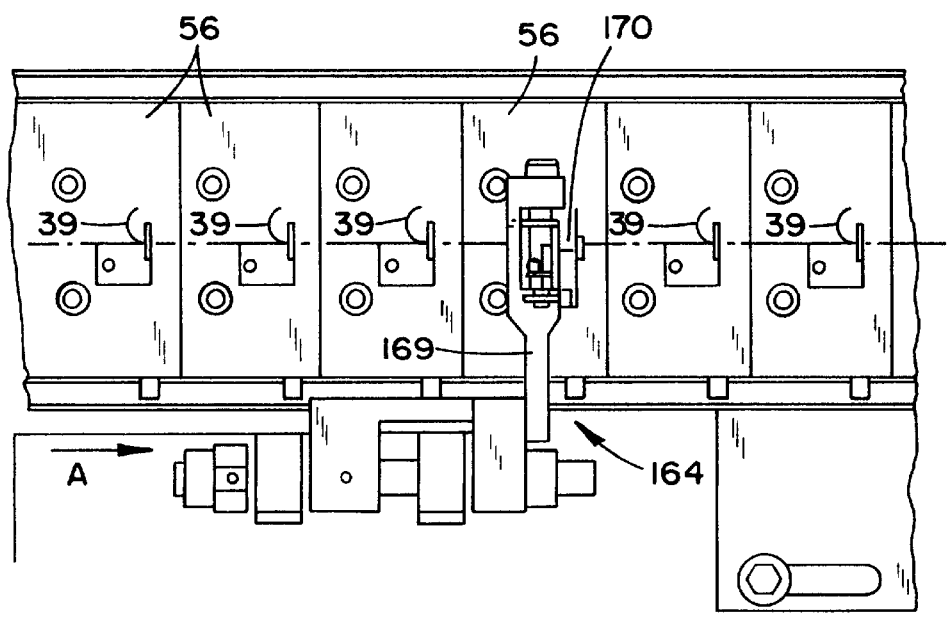
FIG. 14(b) is a top plan view of the needle pre-positioning assembly for further orienting the needle within the engagement jaws of conveyor boat.

Another mechanism is provided for further orienting the needle upon the precision conveyor boat is the needle pre-positioning assembly 164 illustrated in FIG. 14(a) and 14(b). The pre-positioning assembly 164 comprises a pulley 165 operable by a drive motor (not shown) and timing belt 166 for rotating a cam 167 as shown in FIG. 14(a). Cam follower 168 is provided for actuating arm 169 to reciprocate from a first position above the engagement jaws 136, 137 of conveyor boat 56, to a position that enables blade 170 of arm 169 to bear upon the butt end 43 of needle 39 while the precision conveyor boat 56 is conveyed in the forward direction as indicated by the arrow A in FIG. 14(b). Impeding the forward motion of the needle 39 by blade 170 forces the needle to move within engagement jaws 136,137 of the conveyor boat 56 so that the engagement jaws 136,137 engage the needle at a precise location, for e.g., its barrel portion 41. Note that the cam 167, as driven by timing belt 166, is designed so that the arm stop 169 reciprocates in a timed relation with the forward motion of the boat 56 as dictated by the Robot Control tasks 702 and PLC 718, so that each needle in each conveyor boat 56 is further pre-positioned and oriented. After the needle is oriented, the arm stop 169 is reciprocated to its position above the conveyor boat 56 to await the next needle for further orientation in the manner heretofore described.

Precise Positioning and the Moveable Hard Stop Assembly

Figure 15A:
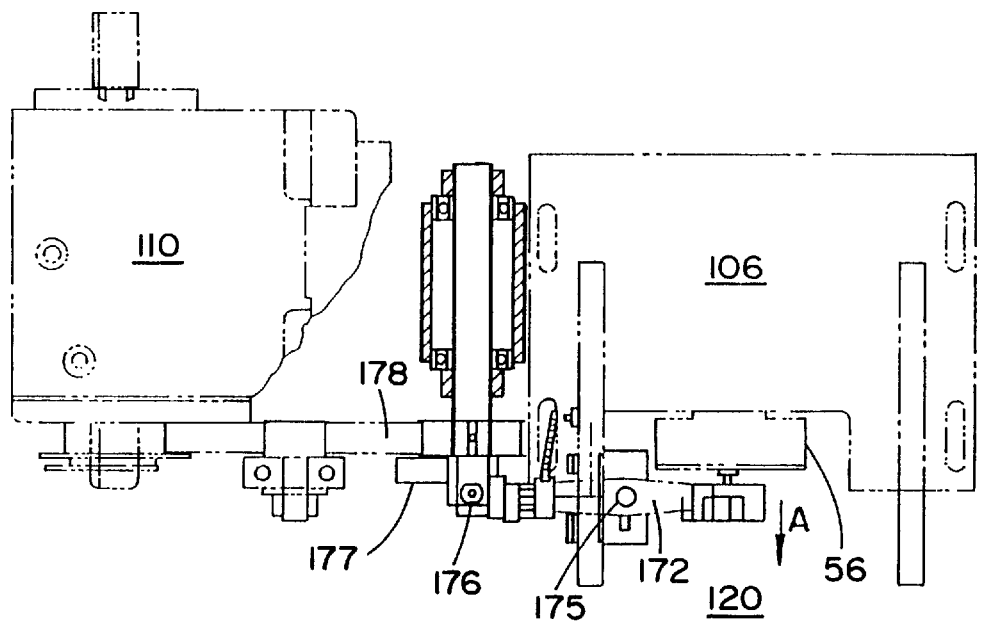
FIG. 15(a) is a plan view of the moveable hard stop assembly for final positioning of the needle in conveyor boat.
Figure 15B:
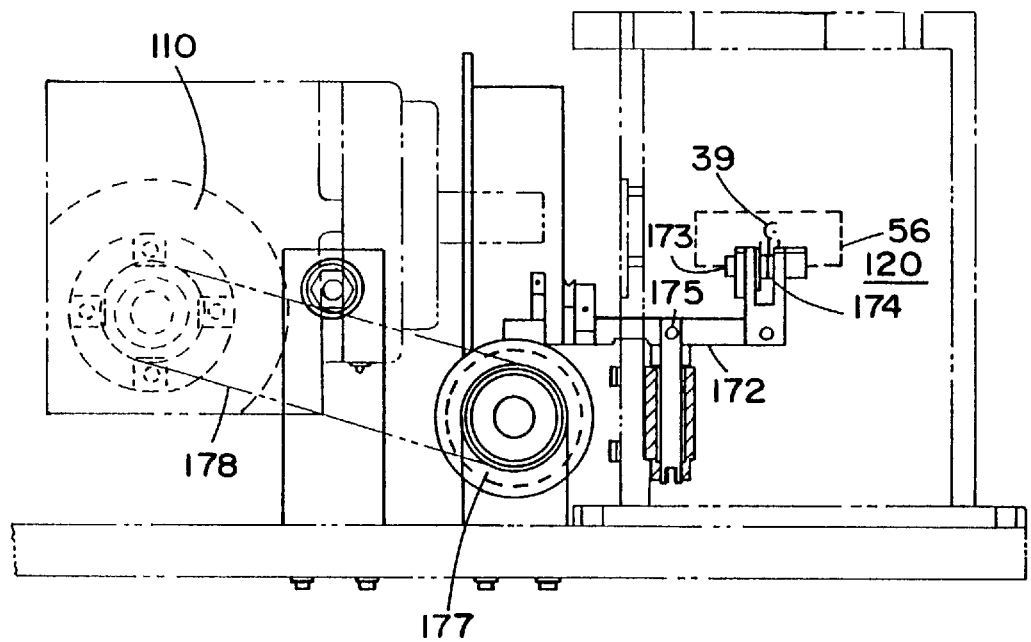
FIG. 15(b) is a front elevation view of the moveable hard stop assembly illustrated in FIG. 15(a)
Figure 17A:
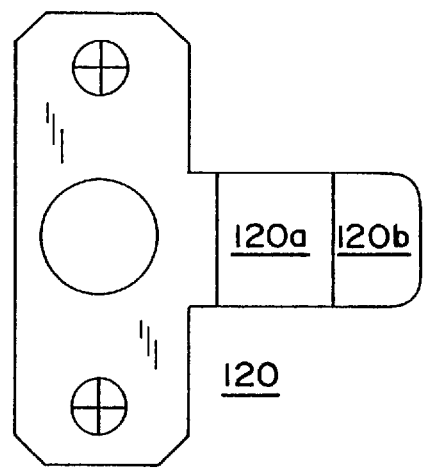
FIG. 17(a) is a top plan view of the hard stop used by the moveable hard stop assembly.
Figure 17B:
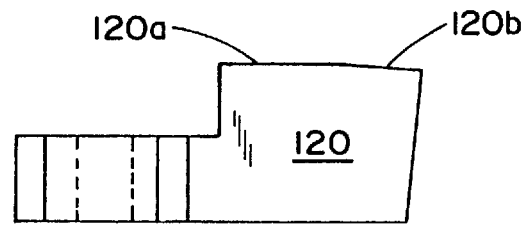
FIG. 17(b) is a side elevation view of the hard stop illustrated in FIG. 17(b)

After the needle 39 has been plow oriented in the conveyor boat 70 and pre-positioned as previously described with respect to FIGS. 13(a–e) and 14(a–b), it is conveyed to a precision positioning station for precise placement before hand-off to the automatic swaging system 200. The precise positioning station and a moveable hard stop assembly 120 is illustrated in FIGS. 15(a) and 15(b) where FIG. 15(a) is a top or plan view of the apparatus and FIG. 15(b) is an elevation end view of the apparatus. The hard stop assembly 120 illustrated in FIGS. 15a and 15b is the mechanism used for executing a hard stop of the needle conveyed in conveyor boat 56 when the boat has reached the end of its destination at the hand-off point for the needle swaging station 200. The hard stop 120 (illustrated in FIGS. 17(a) and 17(b) provides a precise positioning surface for the needle in boat 56. Typically, the hard stop 120 provides positioning within an accuracy of 0.001 inches of a denoted reference position subsequently used for swaging. The hard stop of the present invention differs from the knife blade stop described with respect to the previous generation machines inasmuch as the knife blade stop in the parent application was a fixed stop mechanism whereas the apparatus illustrated in FIGS. 15a and 15b is a moveable stop mechanism. The moveable stop assembly 120 is reciprocated out of the way to provide clearance for the conveyor boat 56 as it continues its downward travel to return to the opposite end of the conveyor.

As the conveyor boat 56 reaches its final position as illustrated in FIG. 15(a) the moveable hard stop 120 is reciprocated inwardly towards the precision conveyor to receive the butt end of the needle 44 on needle face 120a as illustrated in FIG. 17(a),(b). As the boat 56 arrives at its final location, the gripping jaws 201,202 (illustrated in FIGS. 31(a)–31(f)) of the swage device arrive on the opposite side of the needle hard stop 120. The needle is thus restrained during handoff against downward movement by the needle face 120a of hard stop 120, from side-to-side movement by the jaws 136, 137 of the conveyor boat 56 against rearward motion by the conveyor boat 56 and against forward motion by the face of multi-axis gripper on the swage machine which is to receive the needle. The multi-axis gripper has three gripping pins 180, 181, and 182 which engage the needle to maintain position and orientation after the transfer is complete. After the jaws 136, 137 are opened and gripping pin 182 of the multi-axis gripper is closed, the hard stop 120 is reciprocated in the direction of the arrow A in FIG. 15a to provide clearance for movement of jaws 137,137 on boat 56 and for movement of the butt end of the needle as it is moved out of position by the multi-axis gripper. To provide further clearance for the butt end of the needle, and to avoid dislodging it from its precise position, the trailing face of the hard stop 120 is tapered as illustrated at 120b in FIG. 17(b).

The hard stop 120 is spring mounted in a pivot arm 172 by means of a pivot pin 173 and a coil spring 174 which maintains the position of the stop, but provides breakaway capability for the stop in the event of misalignment of the precision conveyor. The breakaway prevents any damage to the conveyor boat 56 from the hard stop 120 in the event of any malfunction of the device. The pivot arm 172 is pivoted about pivot point 175 by means of a guide roller 176 and a face cam 177 which is rotated by an extended drive shaft from the Camco drive motor 110 through belt drive assembly 178.

Figure 16:
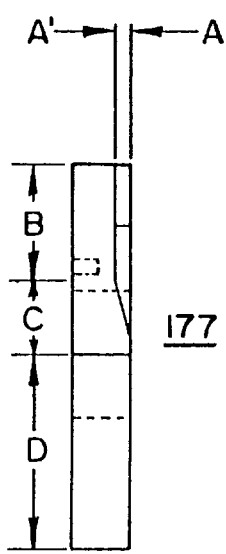
FIG. 16 is a side view of the face cam plate used by the moveable hard stop assembly to retract the hard stop after transfer of the precisely positioned needle.

The face cam 177 is illustrated in FIG. 16(c) and provides for reciprocal movement of the hard stop mechanism of approximately ⅛ of an inch during each dwell period. The cam surface is illustrated with A—A' being the reciprocal distance, dwell period B, being the retracted dwell period, dwell period D being the engaged dwell period, and C being one of the transition periods. The pivot arm 172 is pulled into engagement with the face cam by means of a tension spring 179. As the face cam 177 is rotated, the hard stop is held in its engagement position for approximately 195° of rotation of the face cam and held in its retracted position for approximately 120° of travel with transition periods therebetween. The ratios of belt drive 178 are chosen to provide one cycle of rotation for the face cam 177 for each step advance of the conveyor boat 56.

Multi-Axis Gripper

Referring now to FIG. 18, the multi-axis gripper 184 of the present invention receives the needle from the precision conveyor 106 and moveable hard stop mechanism 120, and transports the needle through the swage operation 200 in which a suture is automatically inserted into the barrel end of the needle, and the metal of the needle swaged about the suture. As can be appreciated, when the opening in the barrel is only 0.0106 and the suture diameter is 0.0088, a high degree of precision handling is required, particularly so when the insertion and swage operation need to be completed in less than 0.5 seconds in order to maintain an 80 needle per minute cycle rate. The multi-axis gripper 184 also transports the needle through the pull test station 400 in which the suture bond is tested and to the packaging area 500, where the armed suture (needle and suture) is automatically packaged.

Figure 18A:
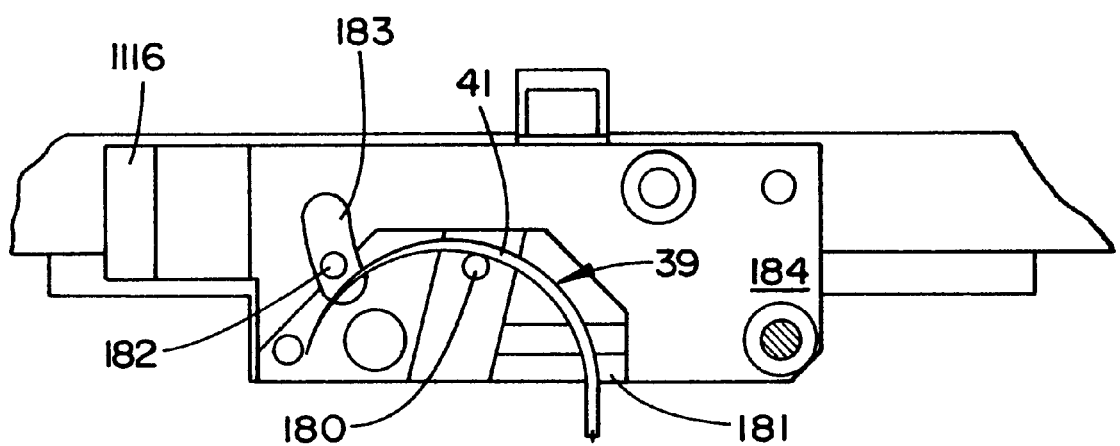
FIG. 18(a) is an elevation view of the multi-axis gripper of the present invention.

As illustrated in FIG. 18a, the gripper portion of the multi-axis gripper is illustrated, with three needle gripping pins 180,181,182, that extend outward from the gripper to engage a portion of the needle 39 therein. Pins 180 and 181 are fixed and pin 182 is reciprocable along channel 183 to grip the needle 39 in a three point gripping engagement. The moveable hard stop 120 provides a precise positioning point for the butt end of the needle 39, and the pins 180, 181 of the multi-axis gripper provide precise arcuate placement for the needle. It is important to note that the multi-axis gripper pin configuration can accommodate different size and arc needles while maintaining their precise positioning.

Figure 18B:
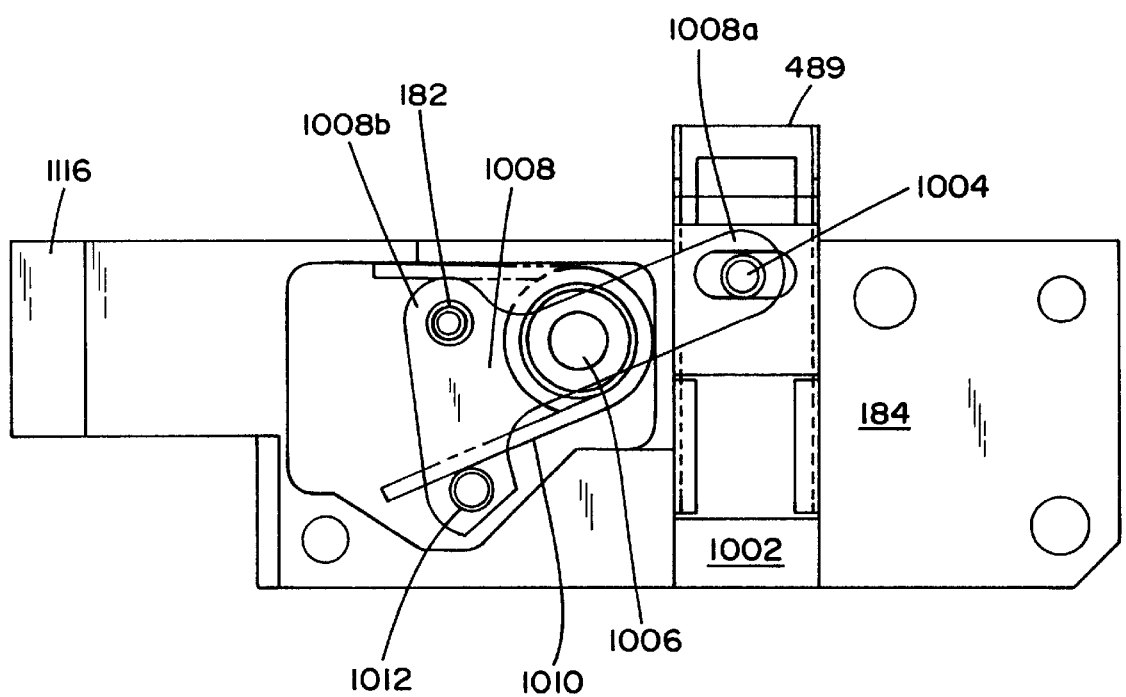
Figure 18C:
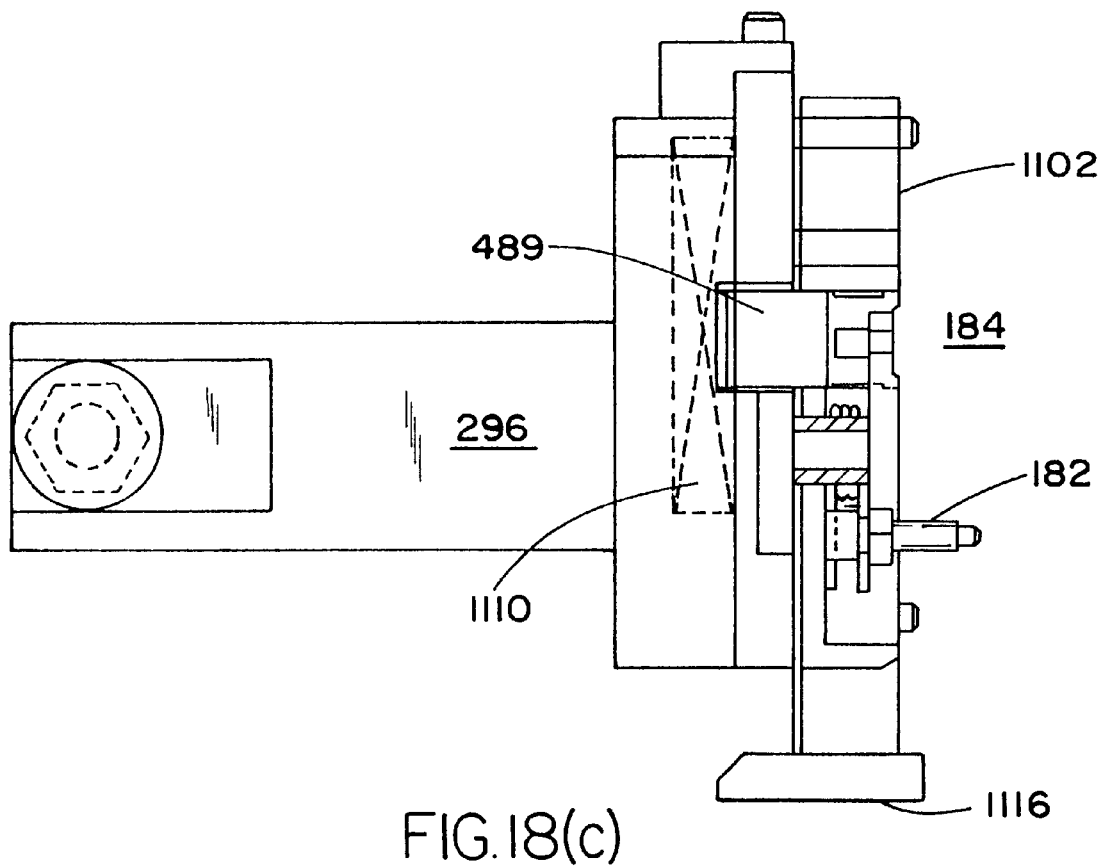
FIG. 18(c) is top plan view of the multi-axis gripper and slide assembly used in the present invention, illustrating in dotted lines the various operating components thereof.
Figure 18D:
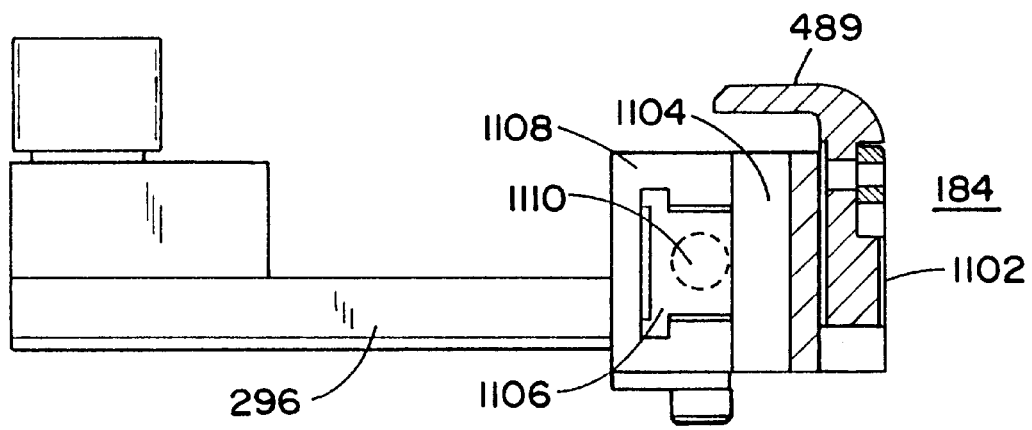
FIG. 18(d) is partially cross-sectioned side view of the multi-axis gripper and slide assembly illustrated in FIG. 18(c).

As illustrated in FIG. 18b, plunger 489 resides and translates within bore 1002. Lever 1008 rotates about a first pivot pin 1006 and is rotatably and slidably connected to the plunger 489 about a second pivot pin 1004 at a first end 1008a of lever 1008. At a second end 1008b of lever 1008 is affixed pin 182 which also rotates about the first pivot pin 1006. The lever 1008, and thus pin 182 is biased in the closed position by spring 1010 which urges against stop 1012. When the plunger 489 is depressed, it translates within bore 1002 which causes the lever 1008 to rotate about the first pivot pin 1006. This in turn opens pin 182 against the biasing force of spring 1010 to release the needle 39 engaged therein.

In operation, a plurality of multi-axis grippers are employed, each of which grips a single needle for swaging, pull-testing and packaging. Referring to FIGS. 9, 15(a) and 18, as the multi-axis gripper is moved into position, the pin 182 is opened and the gripper is reciprocated towards the needle so that open pins are presented on each side of the needle. The jaws 136,137 of the precision conveyor boat are then opened, and during transfer, the needle rests on the moveable hard stop 120. Pin 182 of the multi-axis gripper is then closed to grip the needle and the moveable hard stop is reciprocated out of engagement with the needle, and away from the jaws 136,137 of the precision conveyor to allow the precision conveyor to advance the next needle into the needle transfer position.

Suture Drawing and Cutting

Simultaneously with the positioning and transfer of the surgical needles to the multi-axis gripper on the swage dial, predetermined lengths of suture are being drawn, tipped and cut by the suture drawing and cutting station 300, as indicated in steps 18–24 of FIGS. 3(a) and 3(b).

FIG. 19 illustrates a front elevational view of one designed embodiment of a servo tower 300, and shows the suture path therethrough. Suture 42 is pulled off one end of a supply roll 302 mounted to one side of the servo tower, through the center of an annular guide disc 304, and into a mechanical tensioner 306. The mechanical tensioner 306 can comprise a stationary guide frame 308 and a pivotally mounted guide frame 310, pivotally mounted about a pin 312 at the lower end of the stationary guide frame. Each of the stationary guide frame and the pivotally mounted guide frame has a series of spaced guide elements, each with a central guide aperture therein, which are alternately interleaved, such that the spaced guide elements of the pivotally mounted guide frame alternate with the spaced guide elements of the stationary guide frame. The pivotally mounted guide frame 310 is spring biased about the mounting pin 312 to rotate the top thereof away from the top of the stationary guide frame, such that the suture extending between the alternating stationary guide frame elements and the pivoted guide frame elements is placed under tension while being pulled therethrough.

The suture then extends to and is wrapped twice around a tension roller 314 which is mounted on one end of a torque motor 316, which applies a given tension to the suture 42 as it is pulled through the servo tower by the first and second gripper assemblies 232, 230. Each different suture size and material should have a different tension applied thereto as it is drawn through the apparatus. The torque motor 316 provides a different tension force for each different suture size and type, and the specific tension force(in grams per volt to be applied by the torque motor) is downloaded from a computer program at each suture batch changeover. The proper tension is important for several operations described herein, and is particularly important for the cutter assembly to operate while providing a clean neat cut without a broom effect.

The suture then extends to an out-of-suture sensor positioned at 317, and then through a pair of opposed rollers 318, 320 of a knot detector. One of the pair of rollers is 318 mounted on one end of a lever arm 322, and if a knot travels between the pair of opposed rollers, it pushes the lever arm away, and the movement of the lever arm is detected by a photodetector 324. The suture 42 then travels around an idler roller 326 to change direction, to a further idler roller 328 to change direction again, from which the suture 42 extends vertically downwardly through a heated tipping assembly 330, which heats and ultimately stiffens a small length of the suture, at which the suture is subsequently cut and the cut tip is inserted into and swaged to a needle. The suture 42 then extends downwardly from the tipping assembly to a large idler roller 332 mounted near the bottom of the machine having an appropriately 7 inch diameter, at which the suture reverses direction and travels vertically upwardly to the first and second gripper assemblies 228, 229, only one of which (229) is visible in FIG. 19, the suture cutter assembly 334 and a suture swaging station 200.

FIG. 22 is a schematic illustration of the different positions in the servo tower including, from the bottom, the large idler roller 322, the bottom servo gripper position 338, the position 340 of the cutting blade, the home position 342 of the servo gripper, and the final insertion position 344 of the servo gripper. During the insertion operation, the cut suture end is guided by a funnel shaped aperture 203 in a funnel element 213 into the aperture in the end of a needle, after which a moving anvil 202 is moved relative to a stationary anvil 201, of a swage die, to swage and attach the needle to the suture.

In this embodiment, after initialization, one gripper assembly will be in a home position, 2.000" below the face of the swage die mounting surface, allowing a 2.0301" movement from the home position to an insert position. A proximity switch is located on each tower at 2.000' below the face of the swage die mounting surface to set the home position during an initialization procedure.

Assuming that the machine is being initially set up to cut a desired length of suture, the cutter assembly 334 will be moved to a predetermined vertical position in the swaging machine by operation of the handcrank 494. This is done by aligning a pointer for the cutter assembly with a vertical scale positioned on the side of the swaging machine at 335, similar to the vertical scale 354 shown in FIGS. 19 and 20 for the tipping assembly.

During operation, assume that the lower gripper assembly has just moved up to the home position. At the home position, the gripper assembly stops and waits a predetermined time, during which a needle is preclamped in an insertion position in the swaging station 200, and then moves to the insert position. The following operations are then performed substantially simultaneously. The bottom gripper assembly closes, a tipping operation is performed simultaneously at the tipping assembly 330, and the swage die is simultaneously actuated to swage the needle end around the suture, attaching it thereto. Thereafter, the cutting assembly 334 is activated, cutting in the tipped area to cut the suture to the given length. Thereafter, the upper gripper assembly opens, and the assembly returns to the bottom position, and simultaneously therewith the lower gripper assembly moves up to the home position, and the cycle is then repeated.

After removal of the swaged needle and attached suture length from the apparatus, it is subjected to a sterilization operation, during which the suture length incurs some shrinkage. Accordingly, the cut lengths of suture must be cut to lengths slightly longer than their desired(or label) final lengths to compensate for such shrinkage.

The following table gives, for silk suture, in the left column the commercial(or label) suture length, in the middle column the low servo position of the low gripper assembly below the face of the swage die mounting surface, and in the right column the cut length of suture prior to shrinkage. VICRYL shrinkage during sterilization is approximately 3% of the table values for silk.

| | |
|---|---|
| 18" servo - 16.51 | allowed for 18.380" |
| 27" servo - 25.51 | allowed for 27.380" |
| 30" servo - 28.51 | allowed for 30.380" |
| 36" servo - 34.51 | allowed for 36.380" |

As described above, after heating of a predetermined length of suture at the tipping assembly, the suture must cool to allow setting and hardening of the suture material prior to cutting of the suture at the hardened length and insertion of the cut stiffened end into a needle. This cooling of the suture is provided in this embodiment by allowing a discrete number of machine cutting cycles to occur between tipping of the suture and cutting of the suture. This is provided by allowing a predetermined long length of suture travel between the tipping assembly and the cutter assembly. Hence, the suture tipping assembly 330 is positioned near the top of the servo tower, and after heating thereat, the suture travels to the bottom of the machine, around the large idler roller 332 thereat, and then back upwardly to the cutter assembly 334. The large diameter of the idler roller 332, relative to the other idler rollers 326, 328, is provided because the small length of suture which has been heated at the tipping assembly 330, has begun to harden and set by the time the heated section reaches the large idler roller. The large diameter thereof facilitates the suture to travel therearound without picking up a permanent curved set from the large idler roller, as it is desirable for the suture to be straight, without any curve, when it is subsequently cut and inserted into a needle. The idler rollers 326 and 328 typically have a 0.5 inch diameter, whereas the large diameter roller 332 has a diameter preferably greater than 6.0 inches, approximately 7.0 inches in one embodiment.

The operation of the machine depends upon a discrete whole number of machine cutting operations to be performed between the tipping and cutting operations. Accordingly, for each different length of cut suture, the tipping assembly 330 must be positioned at a different predetermined position within the machine for the tipped section of suture to be precisely and correctly positioned at the cutter assembly 334 after a given number of machine cycles.

The following table gives in its columns, proceeding from left to right, the label suture length, the actual cut suture length, the number of machine cycles or increments provided between tipping and cutting, the total travel length of the suture between tipping and cutting, the tipping assembly vertical position above the table top, and the tipping assembly scale pointer position above the table top (explained in greater detail hereinbelow).

| SUTURE LENGTH | | INCRE- | | ABOVE TABLE TOP | |
|---|---|---|---|---|---|
| LABEL | ACTUAL | MENTS | TOTAL | TIPPER C | POINTER |
| 18 IN. | 19 IN. | 6 | 114 IN. | 27.64 IN. | 25.89 IN. |
| 27 IN. | 28 IN. | 4 | 112 IN. | 25.64 IN. | 23.89 IN. |
| 30 IN. | 31 IN. | 4 | 124 IN. | 37.64 IN. | 35.89 IN. |
| 36 IN. | 36.25 IN. | 3 | 108.75 IN | 22.39 IN. | 20.64 IN. |

Figure 20:
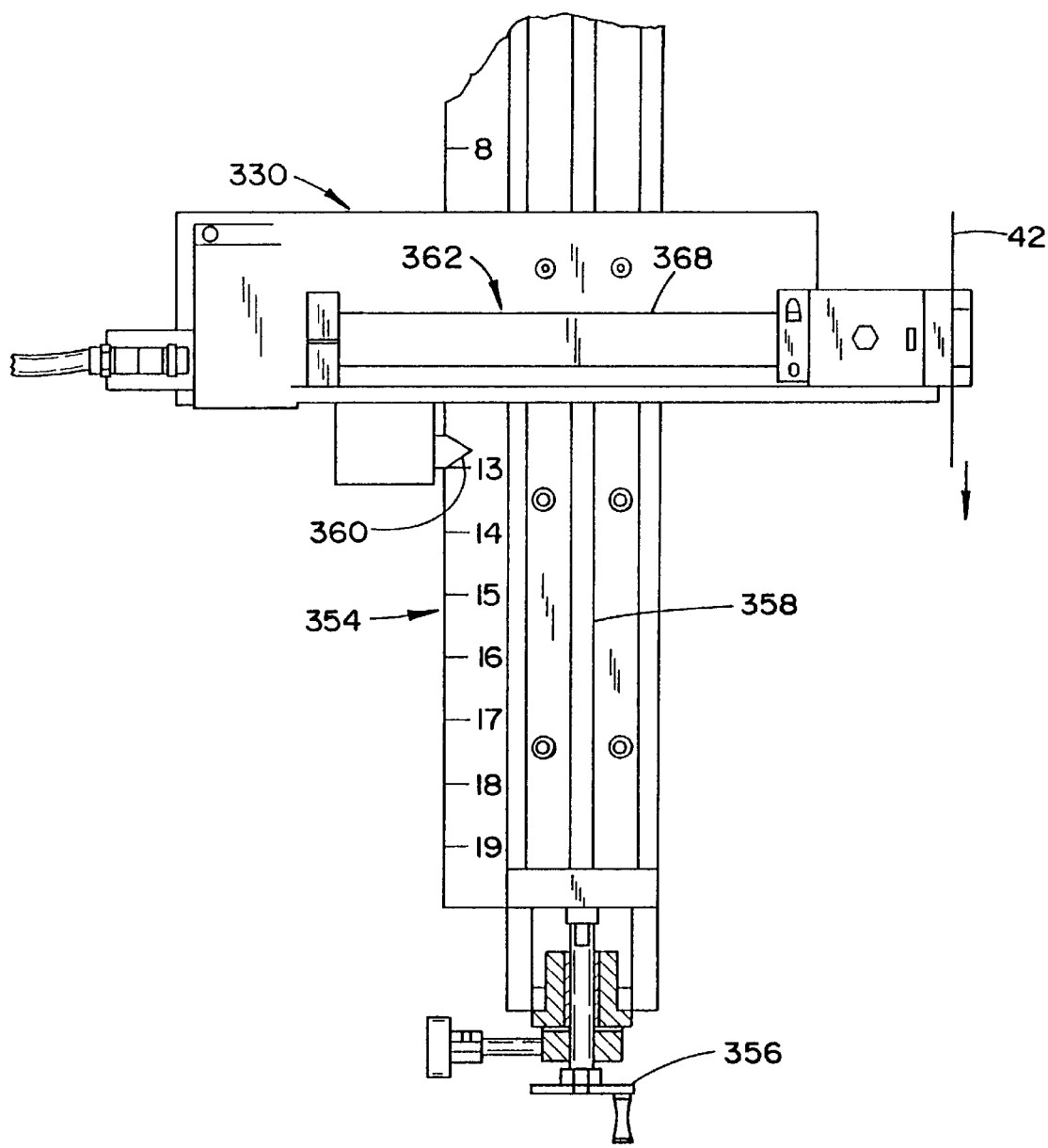
FIG. 20 illustrates an enlarged front elevational view of the suture tipping assembly at which a small length of the suture is heated to stiffen the suture material after subsequent cooling thereof, and also illustrates the adjustable movement thereof along a vertical scale provided adjacent to the tipping assembly.

FIG. 20 illustrates an enlarged front elevational view of the suture tipping assembly at which a small length of the suture is heated to stiffen the suture material after subsequent cooling thereof, in preparation for cutting a given length of the suture and inserting the lead cut end of the suture into the end of a needle for swaging thereto. FIG. 20 illustrates the movement of the tipping assembly 330 along a vertical scale 354 provided adjacent to the tipping assembly 330. The vertical position of the tipping assembly in the machine is adjustable by a handcrank 356 and precision leadscrew 358, similar to the positioning mechanism for the cutter assembly as described hereinabove. As the handcrank is rotated, the vertical position of the tipping assembly 330 in the machine is changed, and is precisely positioned by reading a pointer 360 attached to the tipping assembly on the scale 354. A chart is provided for the machine which gives, for each desired length of suture, the appropriate position for pointer 360 of the tipper assembly 330 on the vertical scale 354, and a similar position for the cutter mechanism 334 on the vertical scale 335.

In this embodiment, the position of the cutting mechanism along the drawing axis is adjustable to provide several different lengths of cut suture. For each different cutting position of the cutting mechanism, the tipping mechanism is adjustably positioned at a different predetermined position in the apparatus to provide for the tipped section of suture to be precisely positioned at the cutter mechanism after a discrete number of machine cycles.

In an alternative embodiment which does not have this infinite adjustment feature, several standard lengths of suture are accommodated by several standard positions which are fixed in the machine by pins which secure the cutter mechanism to the machine frame by pin receiving holes in the machine at the standard positions. For example, the cutter mechanism might be moved to a position for cutting 18" sutures and be secured to the frame by the placement pins being inserted into the pin receiving holes in the machine for 18" sutures. The cutter mechanism might also be moved to positions for cutting 27", 30", or 36" sutures by moving the placement pins to the pin receiving holes in the machine provided for those length sutures. Each different position can have a separate proximity switch provided therefor, which indicates the cutting mechanism position to the controller, which then downloads the appropriate servo gripper bottom position. The appropriate tipping mechanism position is known for each different cutter mechanism position.

Figure 21:
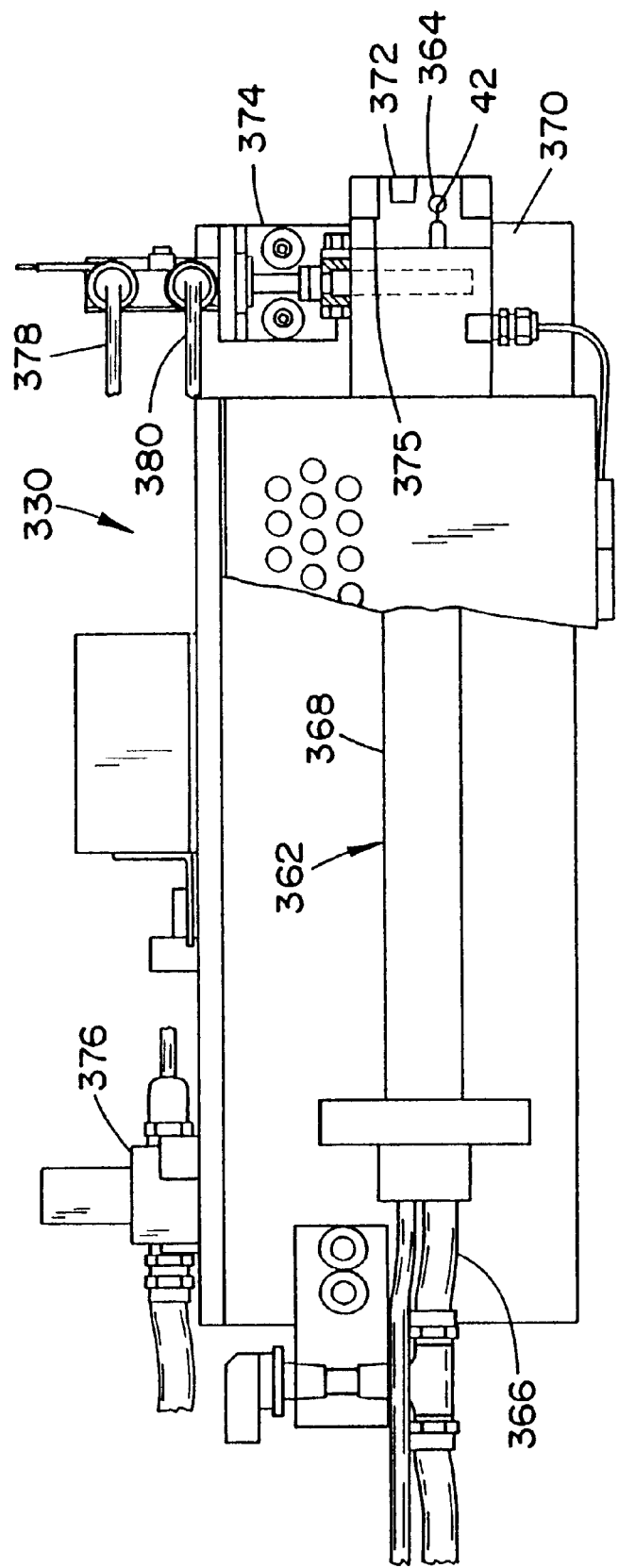
FIG. 21 is an enlarged top plan view of the tipping assembly shown in FIGS. 19 and 20, and illustrates further details of the flow of heated air through the tipping assembly and its control to selectively heat and tip a small length of the suture.

FIGS. 20 and 21 illustrate the heater 362 in the tipping assembly 330 and the vertical movement of the suture 42 down (front view, FIG. 20) and through (top view, FIG. 21) a suture tipping aperture 364, FIG. 21, positioned on the right side of the tipping assembly. FIG. 21 illustrates further details of the flow of heated air through the tipping assembly and its control to selectively heat and tip the suture. As described previously, the tipping assembly 330 is mounted near the top of the machine so that it takes a discrete number of machine cycles for the suture to reach the cut position. This gives the tipped area time to cool down before the cutting and insertion operations. The tipping assembly operates by flowing air supplied at a regulated pressure through an inlet air duct 366 at a regulated flow rate, in one embodiment 195 CFH (Cubic Feet per Hour), over a heater coil mounted within an outer heater casing 368. Air is supplied to a flowmeter at a regulated pressure required to maintain 195 CFH of air flowing over the heater coil. A thermocouple 370 is positioned in the air flow at the discharge end of the heater casing 368, to monitor and control the air temperature through a controller in a programmable logic controller (PLC). The tipping assembly 330 is operated at various temperatures between 200° F. and 550° F. depending upon the particular suture material to be run. The particular temperature is a down loaded parameter from an operating program at each suture batch changeover. The tipping assembly guides the suture and provides a 2.000" long heating aperture 364 for the tipping length.

The constant flow of heated air at the outlet of 368 flows either 1) through the heating aperture 364 in which the suture 42 is intermittently stopped and positioned during a tipping operation, or 2) alternatively the heated air is dumped into the surrounding atmosphere through a diverter channel 372, FIG. 21. The flow of hot air is controlled by an air cylinder 374, under control of a solenoid 376, which controls the flow of actuating air through air tubes 378, 380. The air cylinder 374 controls the position of a retractable slide element having a flow aperture therein which is selectively positioned in front of either 1) a channel into the heating aperture 364 or 2) the diverter channel 372, depending upon the position of the slider element which is controlled by an air cylinder.

As an example, the following control parameters have been established for heat tipping of Braided VICRYL sutures sizes 1, 0, 2/0, 3/0 and 4/0.

The suture tension refers to the tension force in grams which the tension roller 314 and torque motor 316 apply to the suture as it is being drawn through the machine by the grippers.

| Suture Size | Tipping Text +/− 25 deg. | Tipping Time +/− 25 Ms | Suture Tension +/− 25 Grams |
|---|---|---|---|
| 4/0 | 375 F. | 380 | 275 |
| 3/0 | 395 F. | 380 | 275 |
| 2/0 | 410 F. | 380 | 275 |
| 0 | 425 F. | 380 | 275 |
| 1 | 435 F. | 380 | 275 |

As a further example, the following control parameters have been established for suture tension and heat tipping of silk sutures sizes 2/0, 3/0 and 4/0. In the following table the left column lists commercial needle types, the next column needle sizes, the next column suture sizes, the next column suture tension in grams applied by the tension roller 314, the next column tipping dwell time, the next column tipping heated air flow in standard cubic feet per minute, and the right column suture tipping temperature.

SILK SUTURE AND TIPPING PARAMETERS

| Needle type | Wire Size (0.000") | Suture Size | Suture Tension (grams) | Tipping Dwell (seconds) | Tipping Air Flow (SCFM) | Tipping Temperature (° F.) |
|---|---|---|---|---|---|---|
| Tolerance | N/A | N/A | (±10 grams) | (±0.020) | (±5) | (±15) |
| CT-1 | 39 | 2–0 | 275 | 0.380 | 190 | 300 |
| CT-2 | 39 | 2–0 | 275 | 0.380 | 190 | 300 |
| SH | 26 | 2–0 | 275 | 0.380 | 190 | 300 |
| SH | 24 | 3–0 | 275 | 0.380 | 190 | 300 |
| SH | 22 | 4–0 | 275 | 0.380 | 190 | 300 |
| SH-1 | 22 | 3–0 | 275 | 0.380 | 190 | 300 |
| SH-1 | 18 | 4–0 | 275 | 0.380 | 190 | 300 |

The previous tables are for braided VICRYL suture and silk suture, and similar tables could be developed for other suture materials such as Ethibond (braided polyester) and monofilament and braided nylon.

Figure 23:
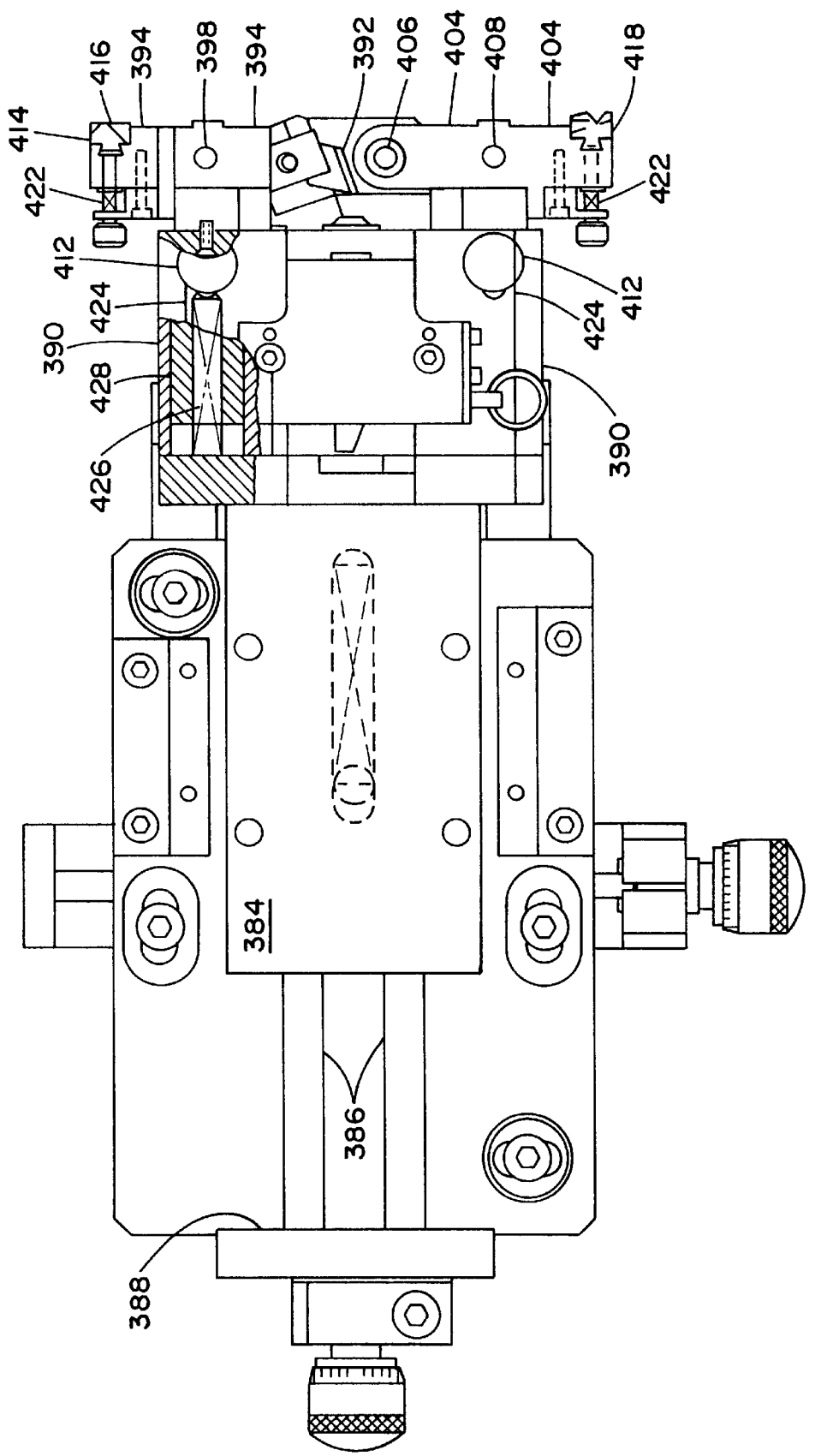
FIG. 23 illustrates a top plan view of a cutter assembly pursuant to the present invention, shown in a retracted position.
Figure 24:
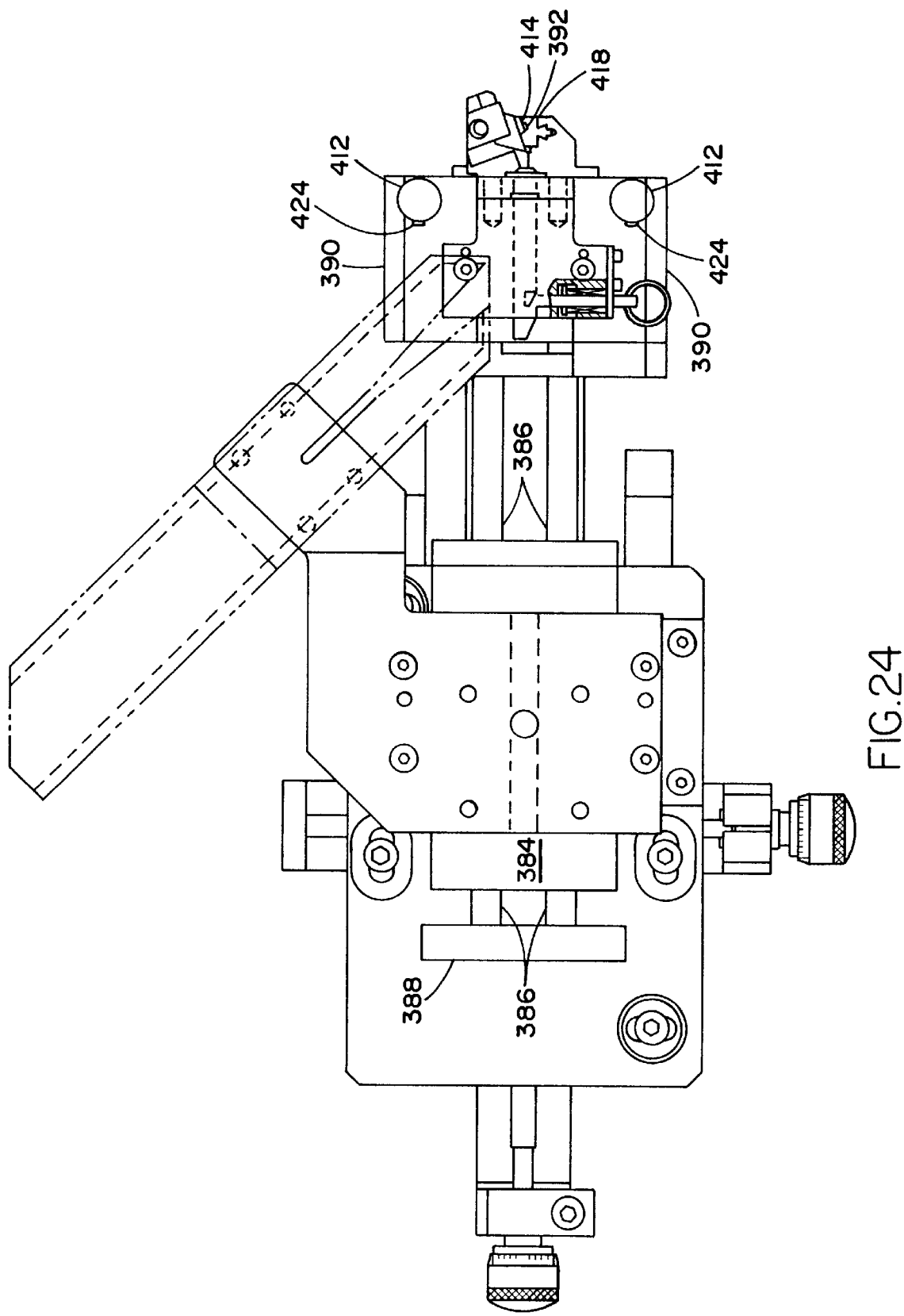
FIG. 24 is a top plan view of the cutter assembly of FIG. 23, shown in an extended cutting position.
Figure 25:
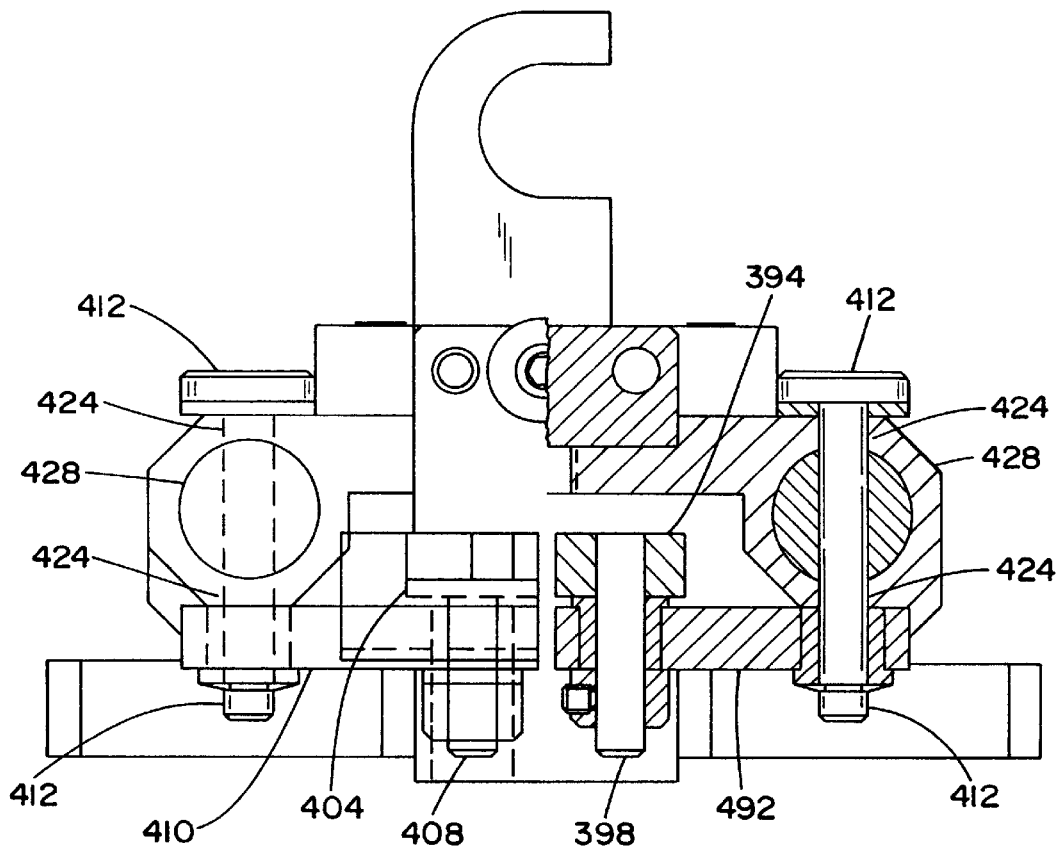
FIG. 25 is a front elevational view of the cutter assembly of FIGS. 23 and 24, and illustrates further details of the drive mechanisms for the cutter assembly.

FIG. 23 illustrates a top plan view of a cutter assembly pursuant to the present invention, shown in a retracted position. FIG. 24 is a top plan view of the cutter assembly of FIG. 23, shown in an extended cutting position. FIG. 25 is a front elevational view, similar to that of FIG. 19, partly in section, of the cutter assembly 334 of FIGS. 23 and 24, and illustrates further details of the drive mechanisms for the cutter assembly.

The cutter assembly is actuated by an air cylinder 384 which during a cutting operation drives a slide mechanism (blade overtravel block) 386 from the retracted position of FIG. 23 to the extended position of FIG. 24. The air cylinder 384 mounts two drive rods 386 which extend therethrough and which the air cylinder translates back and forth to extend and retract the cutter assembly. A transverse bar 388 connects the two drive rods 386 at their ends remote from the cutter mechanism. The other ends of the two drive rods 386 are connected to the slide mechanism (blade overtravel block) 390, on which the knife blade 392 is mounted by a suitable mounting structure for movement therewith.

Referring to FIGS. 23, 24 and 25, a first locator arm 394 is pivoted about a first stationary pin (not visible in FIG. 23 but similar to 406) at its inner end, and is pivotally mounted by a drive pin 398 to a first link arm 400 near its middle portion. Likewise, a second opposed locator arm 404 is pivoted about a second stationary pin 406 at its inner end, and is pivotally mounted by a drive pin 408 to a second link arm 410 near its middle portion. The second ends of the first and second link arms 400, 410 are secured to overtravel pins 412 which are mounted to the blade overtravel block 390, as illustrated in FIG. 25.

During operation, as the blade overtravel block 390 is driven by the air cylinder 384 to the extended position, the first and second link arms 492, 410 are pulled by the overtravel pins 412, which in turn pull the drive pins 398, 408 of the first and second locator arms 394, 404. This causes the first and second locator arms 394, 404 to rotate from the open position of FIG. 23 to the closed position of FIG. 24, and causes the first and second link arms to rotate to the position shown in FIGS. 24 and 25. The first locator arm 394 has a first insert 414 removably positioned at its end having a convex V shape 416, and the second locator arm 404 has a second insert 418 removably positioned at its end having a concave V shape 420. When the first and second link arms are rotated together as shown in FIG. 24, the convex V insert 416 clamps against the concave V insert 418 to secure the suture therebetween at the points of the Vs. The inserts are removable, and also secured in place, by set screws 422 in the link arms.

The overtravel pins 412 are not mounted fixedly to the overtravel block 386, but are mounted in elongated slots 424 in the overtravel block 390, and are mounted against spring 426 loaded pistons 428. After the locator arms 394,404 clamp against each other, further movement of the overtravel block 390 causes the overtravel pins 412 to compress the spring 426 loaded pistons 428 and translate in their slots 424.

During a cutting operation, as the air cylinder 384 drives the blade overtravel block 390 to the right from the retracted position of FIG. 23 to the extended position of FIG. 24, the first link arm 492 and locator arm 394 are driven in clockwise rotations as viewed in FIGS. 23 and 24, and the second link arm 410 and locator arm 404 are driven in counterclockwise rotations as viewed in FIGS. 23 and 24. They are driven until the convex V insert 416 positioned at the distant end of the first locator arm 394 is seated into the concave V insert 418 positioned at the end of the second locator arm 404 to assume the position of FIG. 24, with the suture positioned and clamped between the points of the Vs of the inserts. The knife blade 392 is mounted on and is also driven to the right by the blade overtravel block 390 to assume the position shown in FIG. 24. Further movement to the right by the blade overtravel block 390 causes a compression of the springs 426 positioned behind the pistons 428, such that the inserts 416, 418 and clamped suture are now stationary. However, further movement to the right by the blade overtravel block causes the knife blade 392 to continue to translate to the right relative to the then-stationary positioning inserts 416, 418 and to sever the suture held therebetween. The cutting blade 392 translates along the side surfaces of the inserts, as best illustrated in FIG. 26, and cuts the suture.

Figure 26:
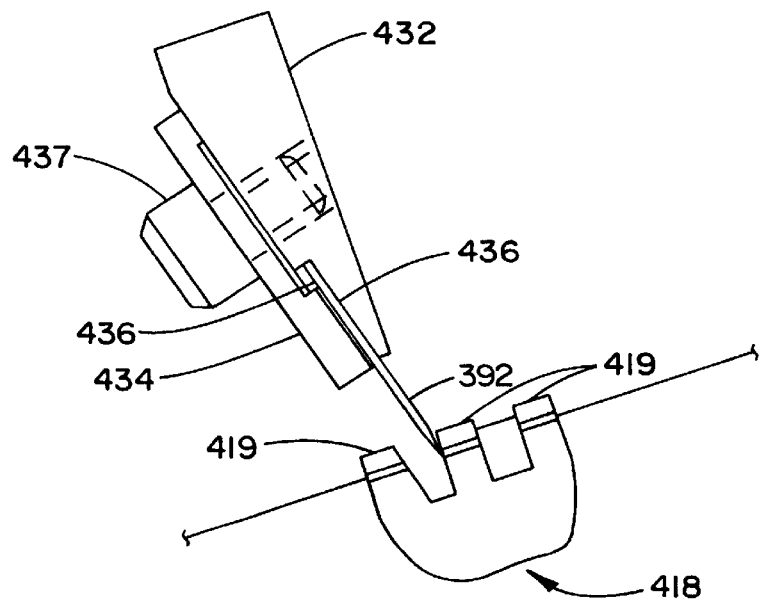
FIG. 26 is an enlarged end view of the knife blade in its mounting position relative to one edge of the concave V insert and also illustrates further details of the concave V insert.

FIG. 26 illustrates a side profile of the concave V 418 insert which has three separate concave V arms 419 to position the suture. The convex V insert has three similar separate convex V arms, and the knife blade slides adjacent to the center V arms, as shown in FIG. 26, to cut the suture. FIG. 26 also illustrates the knife blade 392 which is seated in a positioning slot 436 between a blade mounting structure 432 and a removable blade cap 434 which is secured to the blade mounting structure 432 by a removable screw 437.

The suture drawing, tipping and cutting is more completely described in U.S.S.N. 08/804,477, U.S.S.N. 08/803,573, and U.S.S.N. 08/804,478, all of which are entitled "Suture Cutting System," the disclosures of which are incorporated herein by reference thereto.

The Swage Dial Drive Assembly

Figure 27A:
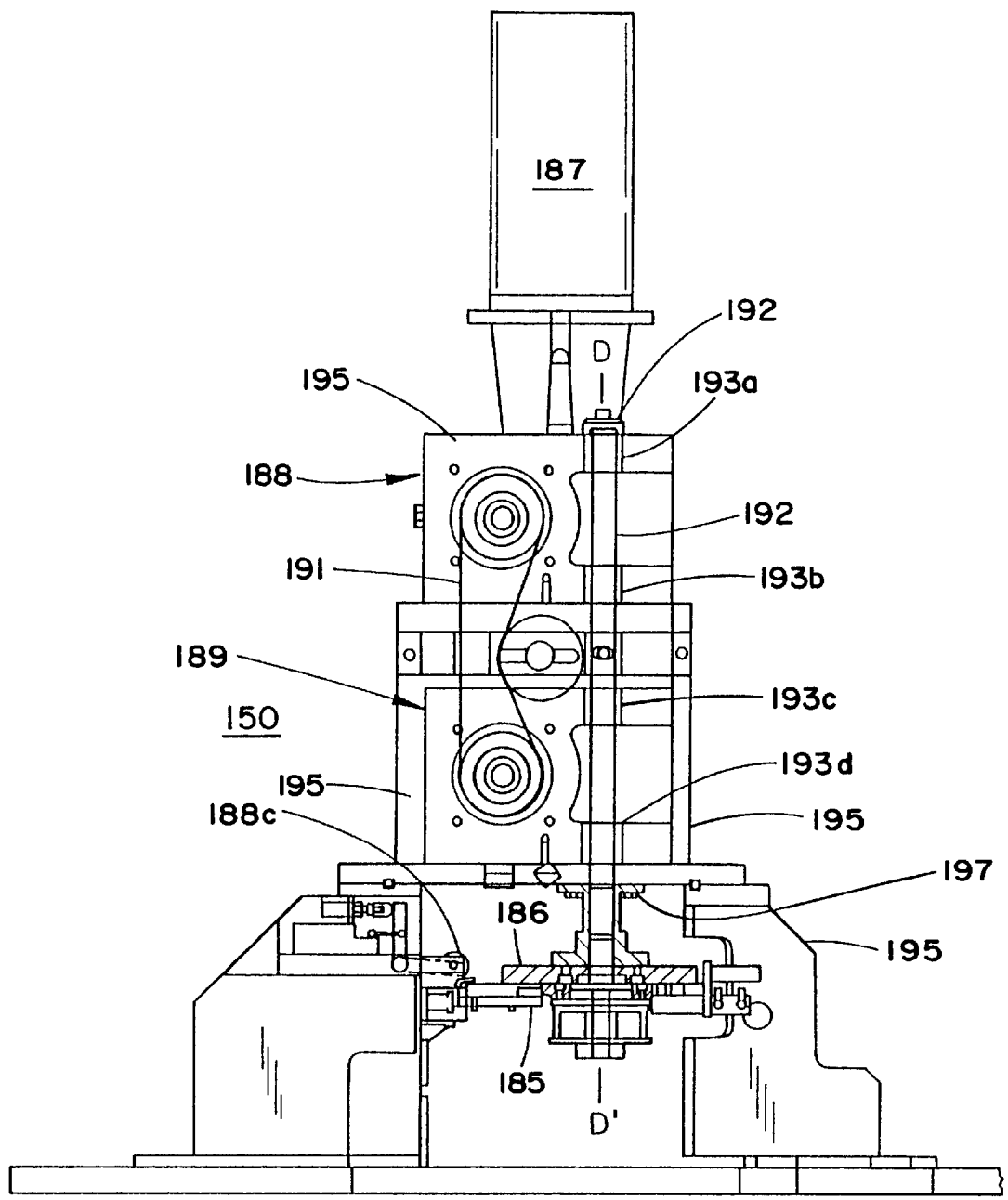
FIG. 27(a) is an elevation view of a portion the apparatus illustrating the drive for the cam dial and swage dial of the present invention.
Figure 27B:
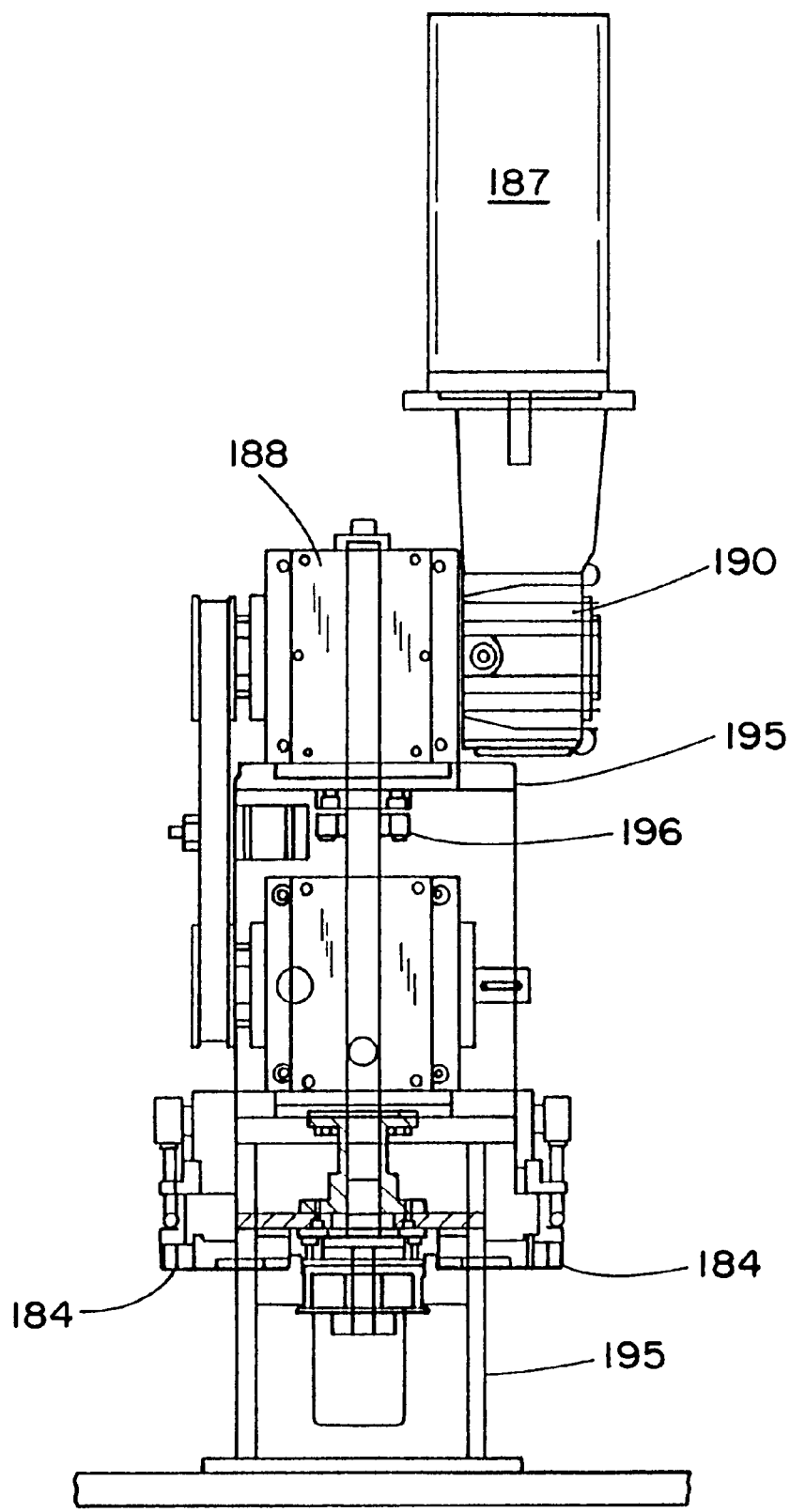
FIG. 27(b) is a side view of the drive for the swage dial illustrated in the elevation view of FIG. 27(a).

The drive assembly for the swage dial 150 is illustrated in FIGS. 27(a) and 27(b). As illustrated in FIG. 27(a), the swage dial assembly 150 includes a swage dial 185 and a cam dial assembly 186 both of which are independently driven by the drive means of the present invention. A drive motor 187 drives both of these dials through a first indexing drive transmission 188 and a second indexing drive transmission 189 through a 90° reduction transmission 190 and are coupled together with a timing belt 191. The indexing drive assemblies 188,189 are "CAMCO" Indexer Drivers Model 35ORGD 4H24-180 with a 10 to 1 reduction in transmission 190 and an oscillation motion for the cam dial assembly 186. The first indexing CAMCO drive includes 180° of drive and 180° of dwell for every revolution of the transmission drive 190 which results in a 90° drive dwell cycle for the first indexing drive 188. The first indexing drive 188 drives shaft 192 about a single drive axis D—D' illustrated in FIGS. 27–28. It is journalled for rotation in bearings 193*a,b,c*, and d and is secured in place by drive cap 194 and a compression drive collar 196 which is connected to the output of the first indexing drive 188. A modular frame assembly 195 supports each of the drive elements about the central drive axis D—D'.

The second indexing drive 189 also includes 180° of drive, a second 60° of drive, a 30° dwell, a 60° drive and a 30° dwell for each revolution of the input drive from belt means 191, and the indexing drive 189 is phased with the drive and dwell cycles of the first drive 188. During each dwell period of the swage dial 185, the cam dial assembly 186 is held in a dwell position and then rotated to enable radial reciprocation of the multi-axis grippers with respect to the swage dial 185.

Figure 28:
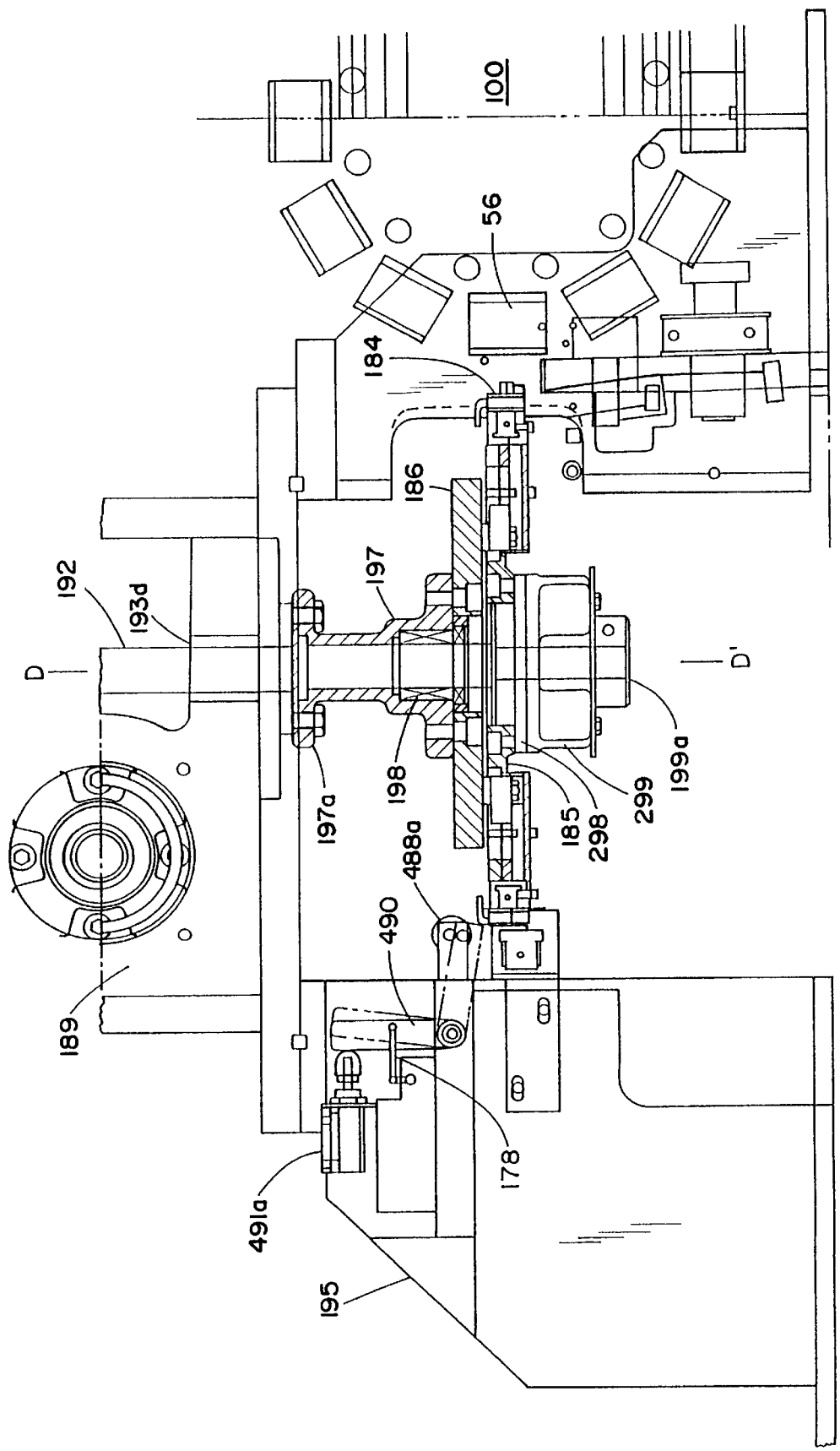
FIG. 28 is a detailed and partially cross section view of the drive for the swage dial taken along section lines "A"—"A" in FIG. 27(a) which illustrates a multi-axis gripper ready to reciprocate outwardly to receive an oriented surgical needle from a precision conveyor.

The cam dial assembly 186 is mounted on an annular drive collar 197 which connects the output of the second indexing drive 189 to the cam dial plate 186 as more fully illustrated in FIG. 28. The annular drive 197 is journalled for rotation on drive shaft 192 by means of needle bearings 198 to provide a single drive access D—D' for rotation of the swage dial assembly 150. The annular drive collar provides suspension support and rotational drive for the cam dial assembly 186. The use of this annular collar also separates the cam dial and swage dial from the drive apparatus and enables operator workspace for alignment of the apparatus and for part changes when necessary. The annular drive collar 197 is bolted to the output drive flange of the indexing drive 189 as shown at 197(*a*).

The swage dial 185 is mounted for rotation on a ball detent clutch 199*a* which is fixably attached to shaft 192 and enables breakaway rotation between clutch drive plates 298 and 299 in the event of a catastrophic jam. The clutch 199 and shaft 192 also provide suspension support and rotational drive for the swage dial 185.

The annular cam drive 197 is bolted to the output of the second indexing drive 189 as illustrated at 197*a* and thus provides for both suspension support and rotation of the cam dial assembly 186. Likewise, the breakaway clutch 199 provides physical support and rotational drive for the swage dial 185 by virtue of its fixed mounting on shaft 192 at 199*a*.

The Swage Dial

Figure 29B:
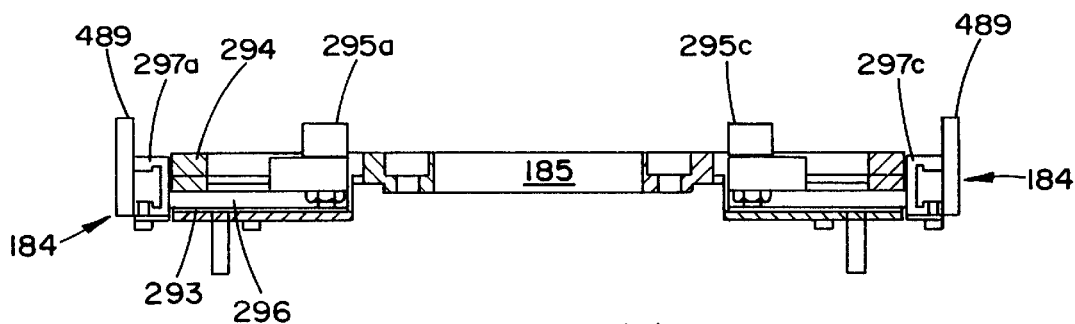
FIG. 29(b) is cross-sectional view of the four station swage dial assembly showing two multi-axis grippers in a retracted position.
Figure 29C:
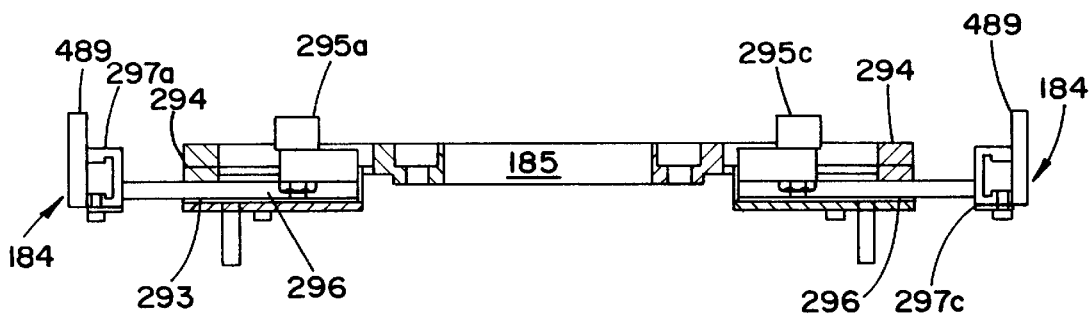
FIG. 29(c) is cross-sectional view of the four station swage dial assembly showing two multi-axis grippers in an extended position.
Figure 30A:
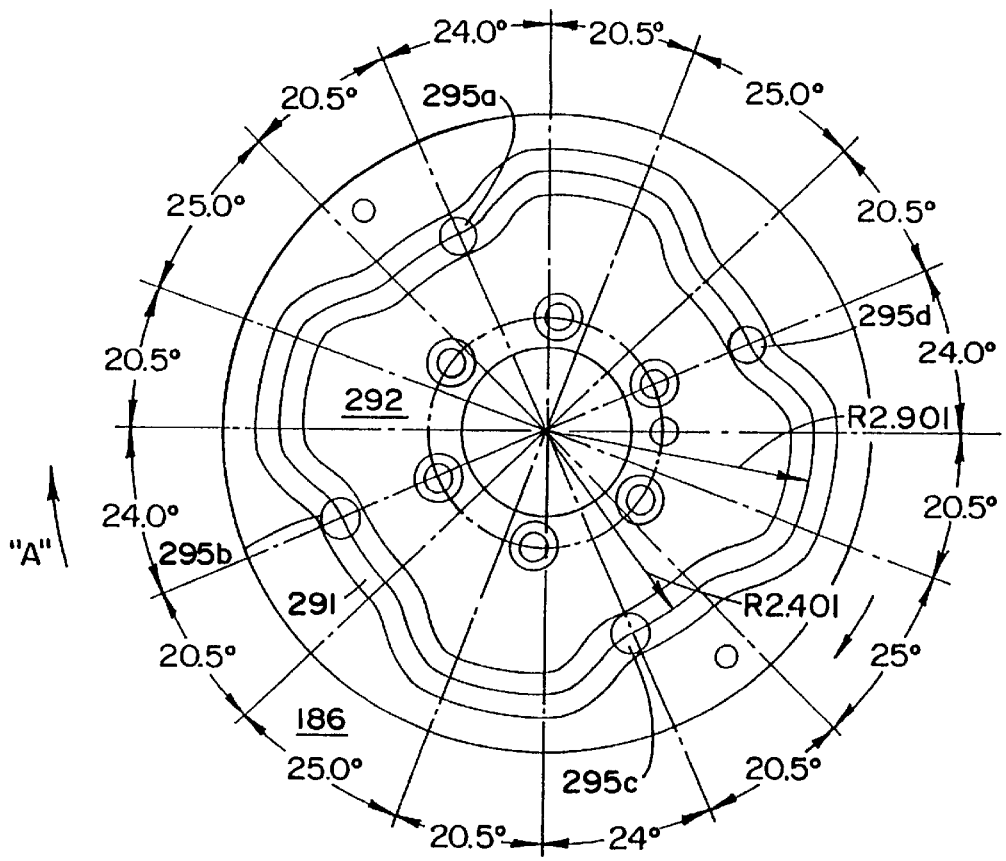
FIG. 30(a) is detailed top view of the cam dial assembly having cam dial plate with a cam follower in a retracted position within a cam track.
Figure 30B:
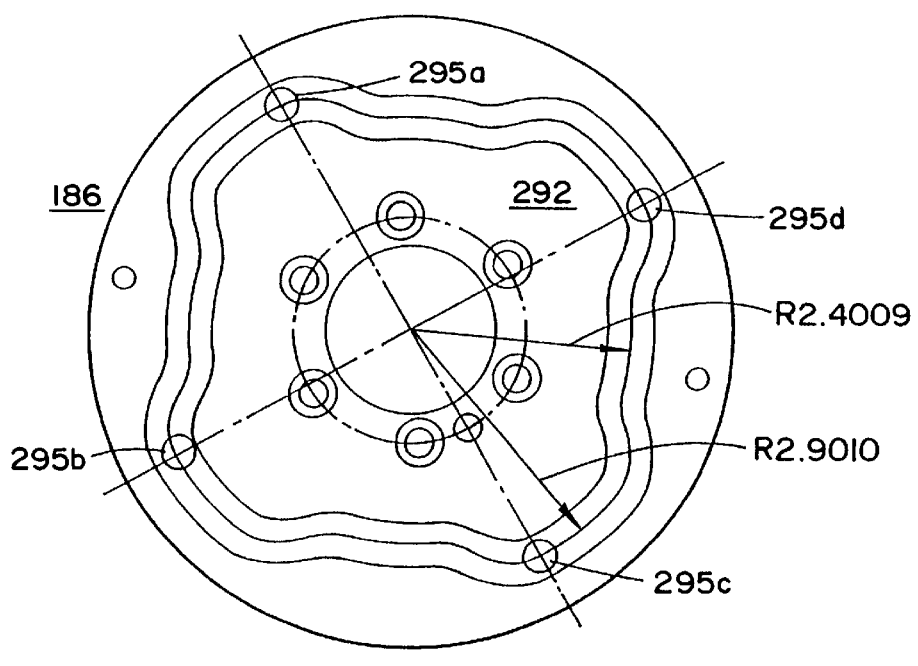
FIG. 30(b) is top view of the cam dial plate showing a cam follower in an extended position within the cam track.

The process for extending each multi-axis gripper 184 for needle processing at each of the stations 100, 200, 400, and 500 will now be explained. As shown in FIGS. 29(*a*), 29(*b*) and 29(*c*), each multi-axis gripper 184 is connected to a reciprocating carriage 297 and a cam slide 296. Cam followers 295(*a*),(*b*),(*c*) and (*d*) are mounted to a cam slide 296 at one end thereof with the multi-axis gripper at the other end. Cam slide 296 is slidable within stationary guides 294,293 and is adapted for reciprocal movement when the cam follower 295 is actuated. In the preferred embodiment shown in FIG. 30(*a*), cam followers 295(*a*)–(*d*) are rollers that fit within the cam track of a rotatable cam dial assembly 186. Cam dial assembly 186 is shown in FIG. 30(*a*) as comprising a cam dial plate 292 having a continuous cam track 291 which receives cam followers 295(*a*)–(*d*) attached to multi-axis grippers 184*a,b,c*, and 184*d*, respectively. Each cam follower 295 is positioned within the cam track at each station for movement therein.

As illustrated in FIG. 30(*a*), cam dial 292 is positioned above swage dial 185 and mounted coaxial therewith. The cam dial 292 is rotatable about a central axis and controlled by a separate rotary indexing transmission as described previously so that it may rotate separately from the swage dial plate 185. The cam dial is driven in multiple drive and dwell cycles as previously explained, and the degrees of each phase are diagrammatically illustrated in FIG. 30(*a*). FIG. 30(*a*) also shows cam followers 295*a–d* in a first retracted position within the cam track 291. When the dials are in this position, each of the reciprocating carriages and consequently multi-axis grippers 184 are in their retracted position as shown in FIGS. 29(*a*) and 29(*b*) discussed above. To extend the multi-axis grippers 184 in place at their respective stations, the cam dial plate 292 is rotated in the clockwise direction with respect to the swage dial plate 185, as indicated by the arrow A in FIG. 30(*a*), for approximately 25–45 degrees, forcing cam followers 295*a–d* in its cam track 291 to move toward the periphery of the dial as shown in FIG. 30(*b*). Consequently, each of the cam slides 296, reciprocating carriages 297*a*, and the multi-axis grippers 184 move to the extended position as shown in FIG. 29(*c*). To move back to its retracted position, the cam dial plate 292 is rotated in the counter clockwise direction with respect to the swage dial plate 185 for approximately 20 to 30 degrees, forcing cam followers 295*a–d* in the cam track 292 to move to their retracted position (FIG. 30(*a*)). Consequently, the cam slide 296, reciprocating carriage 297*a*, and the multi-axis gripper 184 move back to the retracted position as shown in FIG. 29(*b*) and discussed above.

It should be understood that when cam dial plate 292 rotates with respect to swage dial 185, each multi-axis gripper 184 is either extended or retracted by the cam track. Thus, the system is designed so that all processes performed at each station occur simultaneously and for approximately the same duration of time when the multi-axis grippers are in their extended position, for e.g., for needle pick-up, for needle swaging, for needle pull-testing, or needle packaging.

When the multi-axis gripper 184 is retracted, the needle engaged thereby may then be indexed to a different station for further processing. To index the needle to another station, both swage dial plate 185 and cam dial plate 292 are rotated together for approximately 90 degrees to position the multi-axis gripper at the next station. For example, when the cam dial plate 292 and the swage dial plate 185 are simultaneously rotated 90 degrees counterclockwise in FIG. 29, the gripper 184 that had received the needle at station 100 is now indexed to station 200 for swaging a suture thereto. Similarly, after swaging, the cam dial plate 292 and the swage dial plate 185 are simultaneously rotated counterclockwise so that the armed needle at station 200 is indexed to the pull-testing station 400 for pull-testing thereof. The operations performed concurrently at each station about the swage dial increases throughput to provide an output of pull-tested armed surgical needles at a rate of approximately 80 per minute in the preferred embodiment.

FIG. 29(*a*) also illustrate roller cam surface 1100 which acts on the multi-axis gripper. Each of the multi-axis grippers 184 is mounted for linear movement with respect to the cam slide 296 by means of an off-set slide assembly, the details of which will be explained as with respect to FIGS. 18(*c*) and (*d*). As indicated therein, the housing 1102 of the multi-axis gripper 184 is mounted on a mounting block 1104 and slide 1106, where slide 1106 is spring biased to a home position during reciprocation within slide carriage 1108 by spring member 1110. This second reciprocal movement is transverse to the reciprocal movement imparted by cam slide 296.

Referring to FIGS. 31(*a*) and 31(*c*)–(*f*) roller cam 1100 is used to provide the compound offset movement of the multi-axis gripper as it is reciprocated outwardly by the swage dial cam plate 186. FIG. 29(*a*) illustrates a typical positioning for the off-set drive used to drive cam roller 1100 at the precise positioning station 100. Roller cam 1100 is mounted on a linear slide 1112, which is driven by an air motor 1114, mounted on the swage dial frame. FIG. 29(*a*) also illustrates the relative motions of the multi-axis gripper 184, with arrow A indicating the off-set movement, arrow B indicating the reciprocal movement which results in the radial reciprocation of the multi-axis gripper 184 to 184*a* in FIG. 29(*a*), and arrow C indicating the rotary motion of the swage dial 185.

Needle Swaging Station

The swaging operation taking place at the swaging station will now be described. FIGS. 31*a*–31*f* illustrate the multi-axis needle gripper 184 and swaging and suture alignment dies shown in various stages of the suture insertion and needle swaging sequence. This sequence, and the interaction of the dies in relation to each other, the needle and the insertion of the suture accomplish the insert and swage function with minimal parts and simple motions.

Figure 31A:
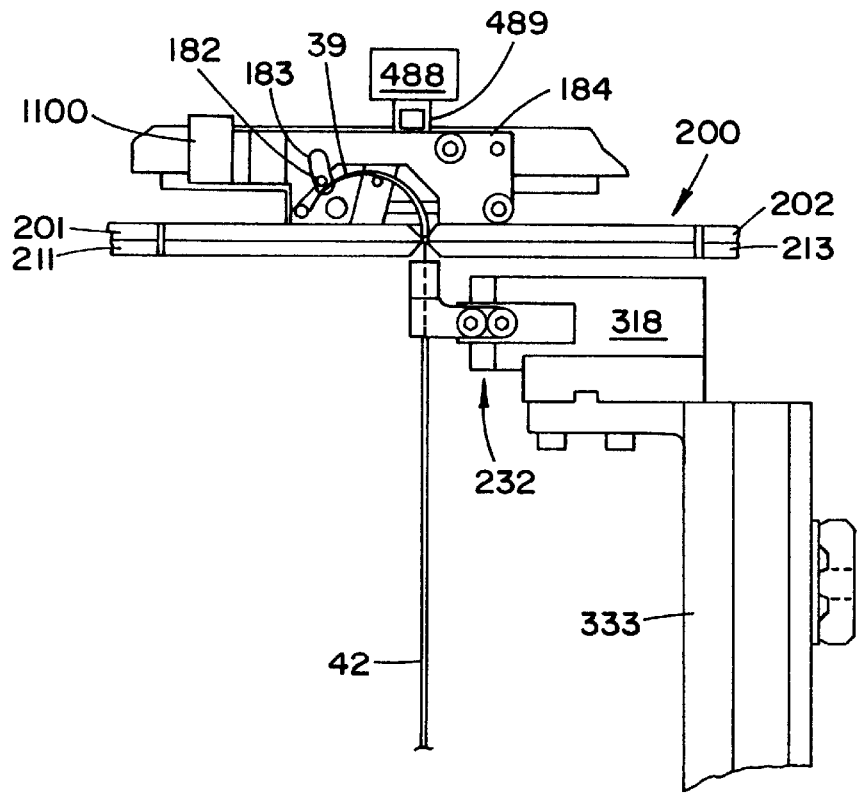
FIG. 31(a) is a detailed view of the gripper shown inserting the suture tip within the confines of the suture receiving end of the surgical needle.
Figure 31B:
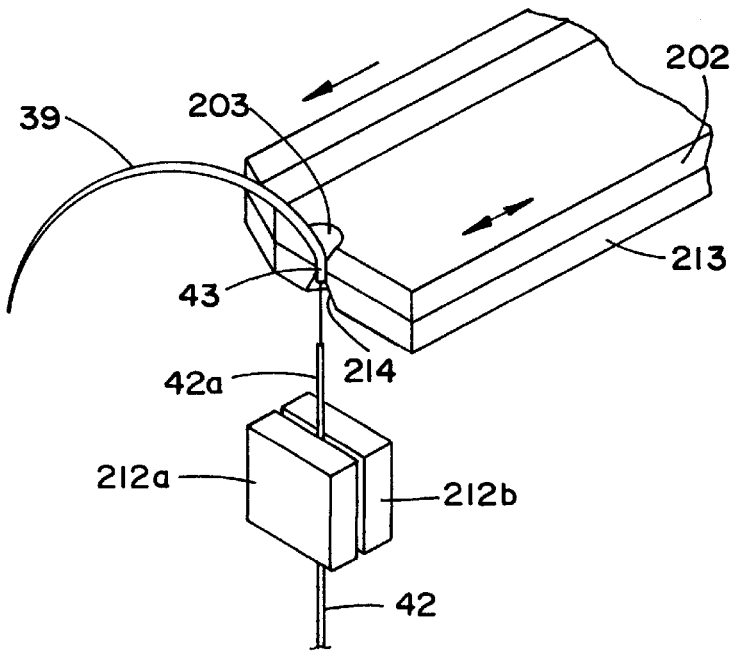
FIGS. 31(b)–31(f) illustrate the multi-axis gripper and swaging and suture alignment dies shown in various stages of the suture insertion and needle swaging sequence.
Figure 32A:
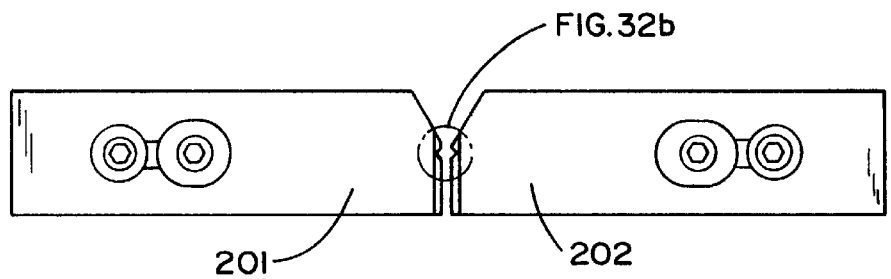
FIG. 32(a) is a detailed top view of the swage dies of the swaging assembly showing the recesses formed in the swage die opening located therebetween.
Figure 33B:
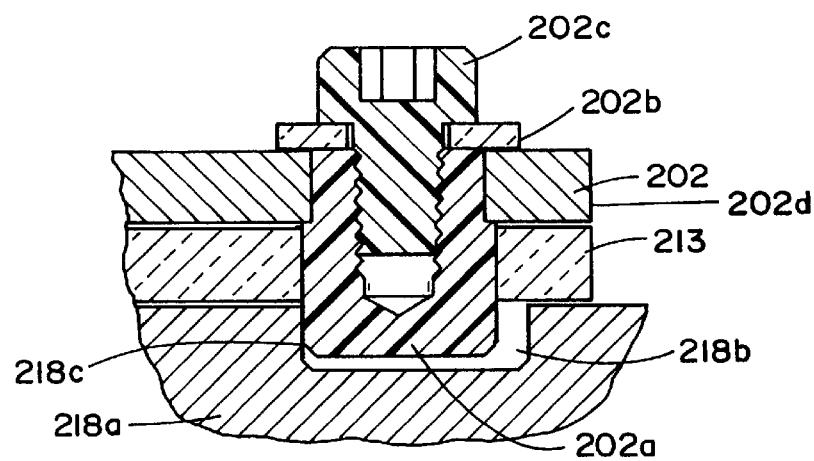
FIG. 33(b) is a detailed view of the swage stop mechanism for the swage assembly.
Figure 32B:
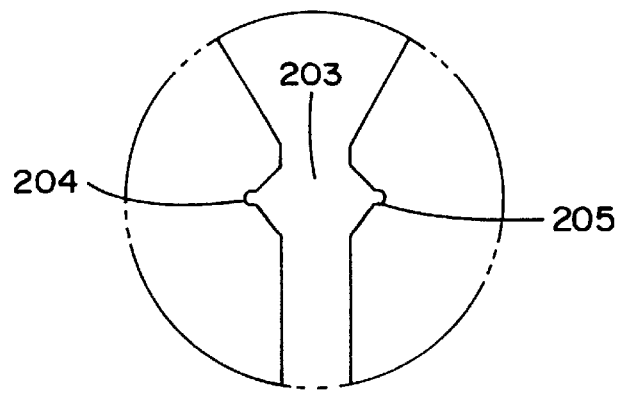
FIG. 32(b) is an enlarged view of the swage die opening shown encircled in FIG. 32(a)
Figure 33A:
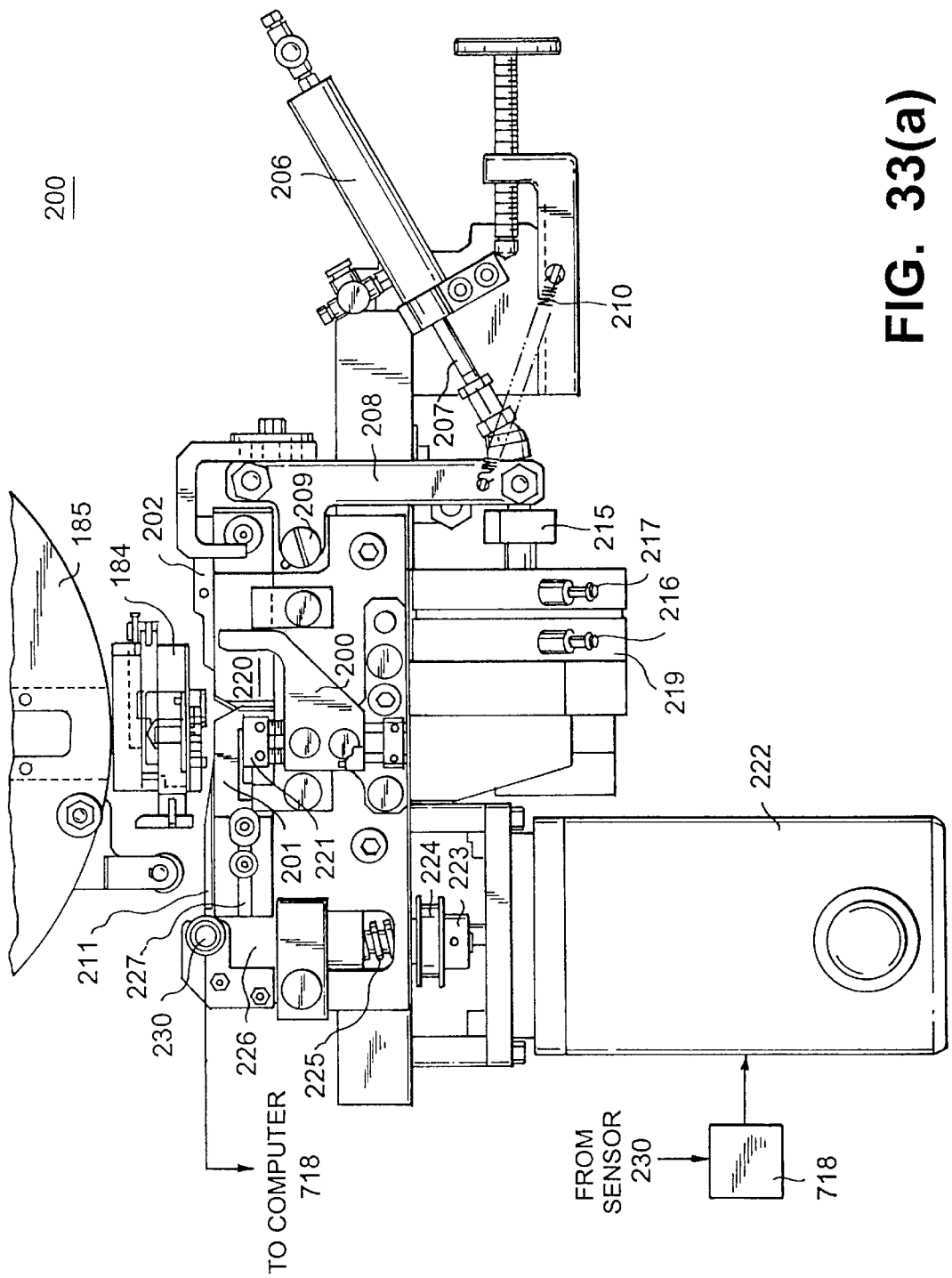
FIG. 33(a) is a top view of the swage assembly of the present invention with the multi-axis gripper indexed thereat.

After conveying the needle to swaging assembly 200 shown in FIG. 33*a* and 33*b*, the multi-axis gripper 184 is radially extended from the swage dial in the manner described above to position the suture receiving end 43 of needle 39 between the funnel shaped die opening formed at the ends of two swage dies 201, 202, as shown in FIG. 31*a*, and the partial perspective view of FIG. 31*b*. As will be explained, swage die 201 is fixed in position, and swage die 202 is movable laterally toward the fixed swage die 201, as indicated by the arrow, to accomplish swaging of the suture receiving end of a needle placed therebetween. A funnel shaped die opening 203 having an exit diameter slightly larger than the diameter of the suture receiving end 43 of the needle 39 is formed when the two swage dies 201, 202 are positioned adjacent each other, as shown in FIGS. 31*e* and 31*f*. In the preferred embodiment shown in FIGS. 32*a* and 32*b*, the ends of each of the swage dies 201, 202 are provided with recesses 204, 205, respectively, so that the metal deformation that occurs as a result of the swaging of the needle 39 does not result in metal flash or spurs at the suture receiving end 43 of the needle. Note that different sets of swage dies may be provided, depending upon the size (diameters) of the needles and sutures to be swaged.

To precisely position the suture receiving end 43 of needle 39 between the swage die opening 203 formed at the ends of two swaging dies 201, 202, the movable swage die 202 is temporarily moved apart. In the illustration of the swaging assembly 200 shown in FIG. 33*a*, swage die 202 is moved apart from the fixed swage die 201 by actuating air cylinder 206 to provide a force to cylinder rod 207 to enable swage die operating lever 208 to pivot about screw 209 and pull movable swage die 202 a predetermined distance away from the fixed swage die 201. In the preferred embodiment, lever 208 is biased by spring 210 so that the movable swage die 202 will return toward the fixed swage die by the spring restoring force when the pressure provided by the air cylinder 206 is terminated.

Figure 31C:
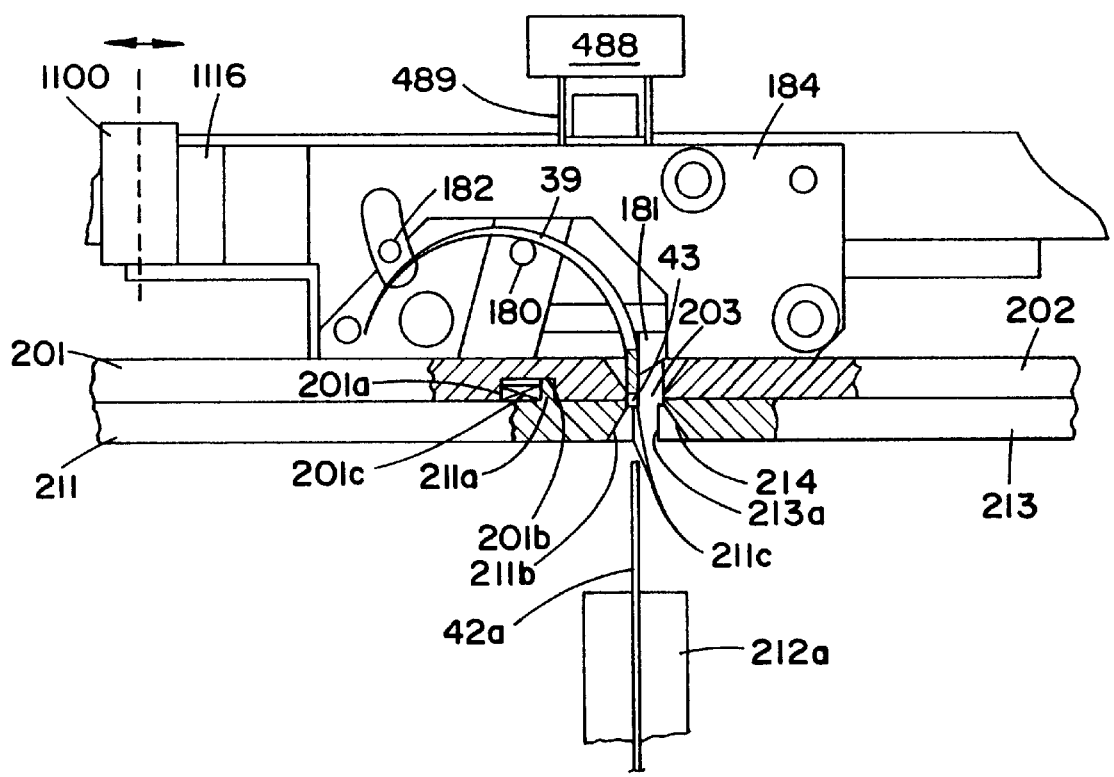

FIG. 31*c* shows die 201 in its fixed position, and movable die 202 in its spaced apart position prior to receiving the surgical needle 39 presented by multi-axis gripper 184. Suture alignment die 211, containing suture guide funnel half 211*b* is positioned under swage die 201, and free to slide laterally within limits. Alignment die 211 has a tang 211*a* that protrudes into cavity 201*a* formed within swage die 201. Compression spring 201*c* bears against the back wall of cavity 201*a* and tang 211*a* such that funnel die 211 slides forward until it is constrained by cavity wall 201*b*. In this position, it is forward of the center axis defined by the suture receiving end of the needle, and serves as a shelf 211*c* that helps assure suture receiving end 43 of needle 39 is in position for swaging. In this stage of the cycle, the parts are not positioned for suture insertion, and suture clap 212*a* gripping suture 42 and stiffened end 42*a*, are in dwell. Suture alignment die 213, containing funnel half 214, is fastened to swage die 202 by suitable fastening means described in detail below, and travels with it to the open position shown.

Figure 31D:
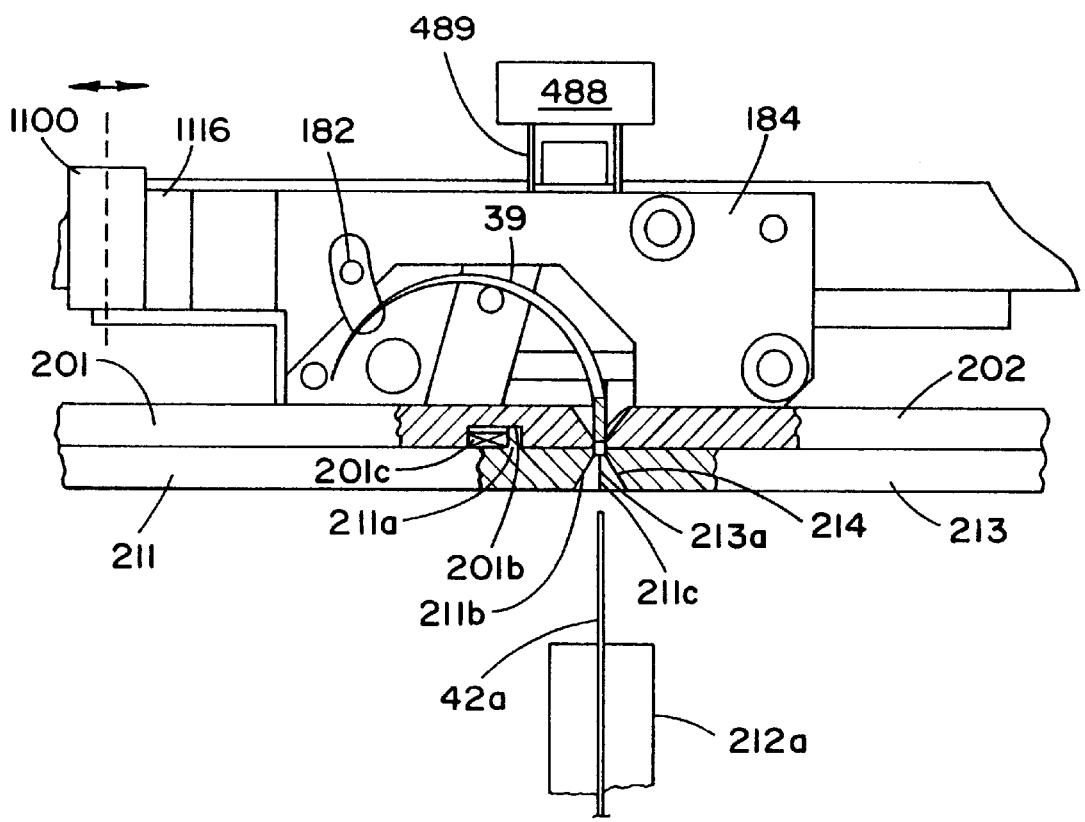
Figure 31E:
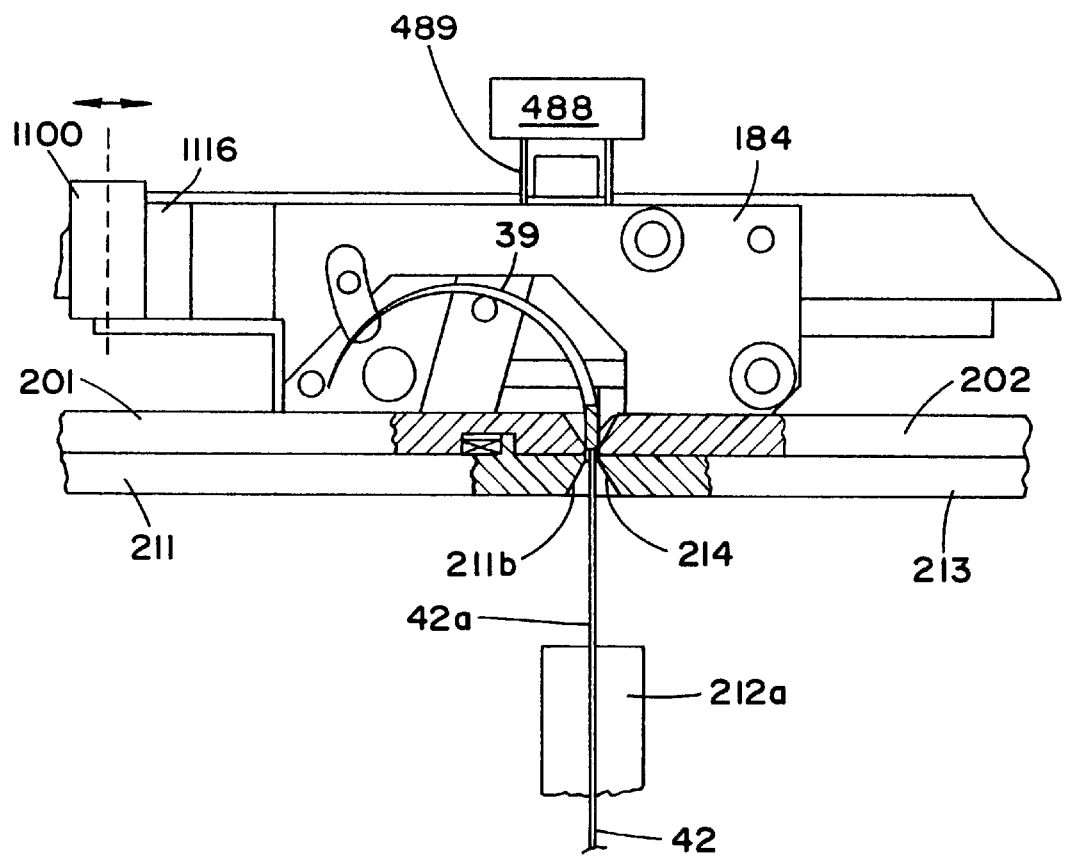
Figure 31F:
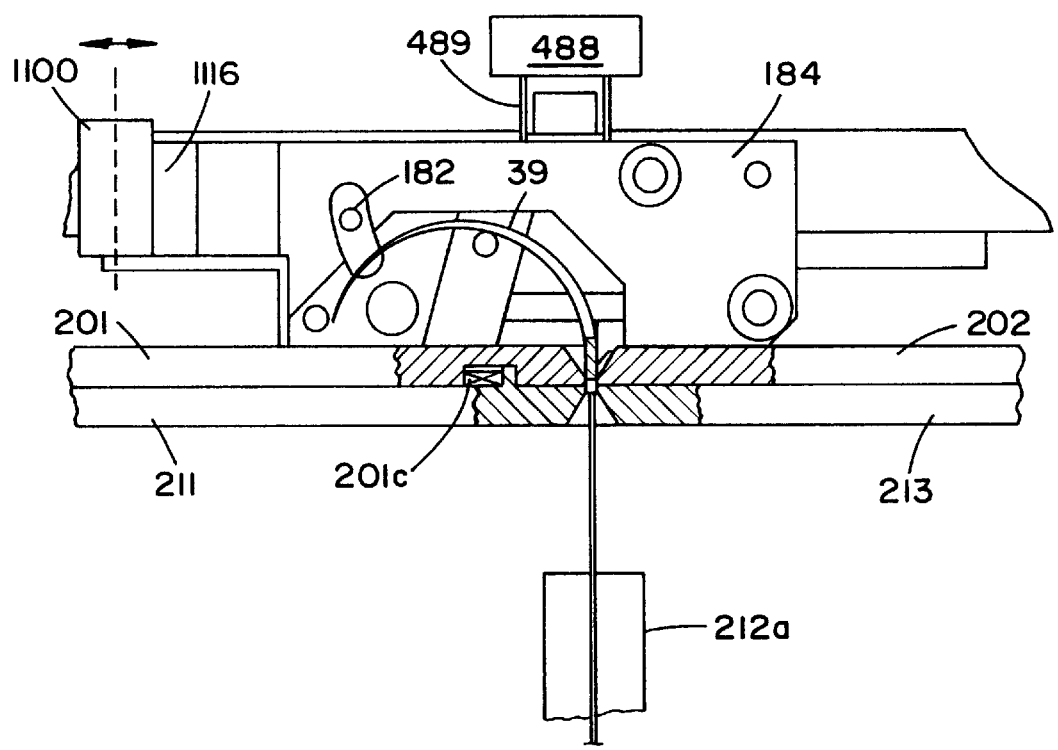

While the swage dies are apart, the multi-axis gripper 184 is extended to position the suture receiving end 43 of needle 39 within the opening 203, as shown in FIG. 31*c* and FIG. 33*a*. After positioning the suture receiving opening 43 of needle 39 at the swage die opening 203, the swage die 202 and suture alignment die 213 are moved toward needle 39 with the resilient spring force present in spring 210 (FIG. 33*a*) that is sufficient to enable the die 202 to grip and locate the suture receiving end 43 precisely against fixed swage die 201 without deforming the cavity of the suture receiving opening 43 formed therein. Concurrently, needle retaining pin 182 in multi-axis gripper 184 is raised by downward external force on plunger 489, as described above, thereby releasing the needle so that its position is determined by the grip of swaging dies 201 and 202. The motion of dies 213 and 202 cause the face 213*a* of suture alignment die 213 to come in contact with the corresponding face 211*c* of suture alignment die 211. The resilient force causing this motion is forceful enough to compress spring 201*c* and move funnel die 211*b* to the left, such that tang 211*a* is no longer in contact with cavity wall 201*b*. Dimensioning of dies 202 and 213 is such that this motion results in the formation of two funnel halves 211*b* and 214 defining a smooth conical shape that is coaxial with the suture receiving end 43 of needle 39. FIG. 31*d* shows the suture receiving end 43 being gripped by the swage dies 201, 202 prior to suture insertion. Note that the exit diameter of the conically shaped funnel guide formed of funnel halves 211*b* and 214 is preferably equal to or greater than the diameter of the suture tipped end 42*a* and smaller than the diameter of the suture receiving end 43 of the needle 39, as shown in FIG. 31*e*, so that the tipped end 42*a* of the suture strand may be easily inserted therein.

FIG. 31*e* shows suture gripper 212*a* moved vertically to the insertion position, which causes stiffened suture end 42*a* to enter funnel 211*b* and 214, and be guided into the suture receiving cavity 43 of needle 39 axially aligned therewith. Once the strand is inserted into the suture receiving end 43 of the needle (step 23), as discussed above, the automatic swaging of the suture receiving cavity occurs. In the preferred embodiment of the swaging assembly 200 shown in FIG. 33*a*, a pneumatic air cylinder 219 provides air pressure to actuate cam 215 that bears on lever 208 to thrust movable swage die 202 toward the fixed swage die to accomplish the swaging of the suture receiving end of the needle placed therebetween. Air pressure is supplied to the swage cylinder 219 via ports 216, 217 under the control of the control system computer 114.

FIG. 31*f* shows the completed swage stroke. The swage die 202 has been driven to a fixed stop by the swage cylinder, which exerted sufficient force to deform the suture receiving end 43 of needle 39. As deformation takes place, suture alignment die 213 further displaces funnel die 211, causing additional compression of spring 201*c*. In the preferred embodiment, the movable swage die 202 comes to an automatic stop by a swage stop mechanism herein described.

As shown in FIG. 33b, movable swage die 202 and suture alignment die 213 are mechanically held coincident to each other by shouldered post 202a, the smaller diameter of which is a light press fit into the mating hold die 202. Cap screw 202c with washer 202b retain the post in die 202. The larger diameter of post 202a, below die 202, extends through a light press fit hole in funnel die 213, so that the right hand swage and funnel dies are linked to move together laterally during the swaging cycle. The lower portion of shouldered post 202a extends through funnel die 213 into groove 218b, which is cross milled into swage assembly frame 218a. When the swage stroke is performed, the swage cylinder drives this die assembly to the left until it is positively stopped by the lower portion of post 202a, striking wall 218c of groove 218b. This stalls air cylinder 219, so that the stroke of the movable right hand die assembly shown is always the same for repeating cycles of the machine.

In an alternative embodiment, both swage dies 201, 202 may be movable towards each other to accomplish swaging. Furthermore, an adjustable swage stop mechanism for changing the swage stroke distance of one of the movable dies may be provided to further control the swaging pressure applied to the suture receiving opening and obviate the need for a fine-tuning positioning adjustment for a fixed swage die.

As shown in the top view of FIG. 33a, a needle fence assembly 220 is provided to ensure that the needle 39 does not tip or become misaligned when the end 43 of the relaxed needle is positioned between the swage dies. The needle fence assembly 220 comprises a needle fence plate 221 whose distance from the tapered swage die opening 203 is adjustable depending upon the size of the surgical needle to be swaged.

In the preferred embodiment, the degree of swage compression imparted on the needle and resulting strength of grip by the needle on the suture is adjusted by precise positioning of the fixed die 201. As shown in FIG. 33a, servomotor 222 drives pulley 223 via timing belt 224, which rotates the swage adjust screw 225. The pitch of the swage adjust screw 225 is selected to move sliding wedge 226 a small distance. The swage die 201 has a complementary ramp angle 227 at the opposite end, which bears on the wedge 226 to retract or advance the position of the swage die 201 a precise distance proportional to the movement of the sliding wedge. Thus, the rotation of the swage adjust screw 225 and motion of the sliding wedge 226 results in transverse movement of the swage die 201 to thereby finely adjust its fixed position. For example, when a larger suture is to be swaged to a needle, the position of the fixed die 201 may be moved further away from the suture drawing axis so as to provide the desired amount of deformation when the swaging pressure is applied to the needle by the movable swage die 202. In the preferred embodiment shown in FIG. 33a, the control system computer 114 will send the approximate signals to automatically direct the servomotor 222 to adjust the position of the swage adjust screw 225, and hence, the position of the fixed die 201, in accordance with the pull-out test values of the needle-suture bond as measured by automatic pull-test system, as explained in further detail below. Specifically, appropriate control signals may be generated to direct the servomotor 222 to adjust the rotational position of the swage adjust screw 225 in accordance with stored statistical results of the pull-testing occurring at the pull-test station. Automatic pull-testing of the armed needle is desirable to ensure that the upstream swaging dies are optimally positioned to avoid over-swaging the needle-suture bond and, hence, preventing the likelihood of clip-off and to avoid under-swaging the needle-suture bond to prevent the chance of pull-out.

After swaging of the needle, the movable die 202 is again retracted by air cylinder 219, and the pin 182 of the multi-axis gripper 184 is actuated to engage the armed needle in the manner described above. Subsequently, the multi-axis gripper 184 is retracted (step 29) to its position along the swage dial 150 for subsequent indexing to the pull-test station 400 for further processing (steps 31–33).

Immediately after the short stroke of the right or top gripper 228, and after the swage cycle, a new suture length is positioned for swaging in that the left gripper 229 secures the suture strand, and the suture material 42 is cut by the cutter assembly 334 in the manner described above and as indicated in step 24 in FIG. 3b. As shown in FIG. 19, the cutter assembly 334 is positioned slightly about the left gripper 229 so that the indefinite length suture strand 42 will be gripped when the swaged strand is cut. Thus, the left gripper 229 is now gripping the suture material 42 with a tipped end 42a, and it now becomes the lead gripper.

The cycle continues at the swaging station with the new lead gripper vertically drawing the material 42 along the height of the drawing tower 300 to position the next strand to be cut for insertion within the surgical needle. The process of advancing suture material 42 by alternating grippers at each cycle eliminates the recycle or return time for retaining the gripper to the original position.

Referring to FIG. 31(a), after the needle has been swaged to the suture, the multi-axis gripper 184 closes pin 182 on needle barrel end 43 as the drive roller 488 is reciprocated out of engagement with plunger 489. Simultaneously therewith, the moveable swage plate 202 is retracted to enable movement of needle 39 by the multi-axis gripper 184. Before the swage dial 185 is rotated, the offset drive cam roller 1100 is again advanced to bear against cam plate 1116 and provide egress of the needle 39 from the swage die cavity in fixed swage plate 201. Once the multi-axis gripper 184 and needle 39 have cleared the fixed swage plate 201, the cam dial assembly 186 is rotated advancing cam rollers 295 inwardly to retract the multi-axis grippers 184 in a radial direction and enable rotation of the swage dial 185. Swage dial 185 then rotates the needle and suture assembly to the pull test station 400 for testing.

Automatic Pull Test Station

The automatic pull-test station 400 that provides automatic pull-testing of a surgical needle and suture assembly is shown generally in FIGS. 34 through 37. As illustrated in FIG. 34 the automatic pull-test assembly 400 generally comprises a load cell mounting assembly 430 for mounting a load cell 435 which responds to loading of a V-plate needle arm 439 which receives the armed needle 39 from the multi-axis gripper 184. A needle release cam roller 488 is provided for relaxing the armed needle from the grip of the multi-axis gripper 184. A pull-test fence assembly 440 is provided to prevent the armed needle 39 from tipping over or becoming misaligned when the armed needle is relaxed.

The suture gripping assembly 470 includes two pairs of retractable grippers 425a,b and 426a,b for gripping the suture during the pull-tests. Grippers 425a,b are operatively connected to the weighted slide block assembly 472 for performing non-destructive pull-tests as will be described with respect to FIGS. 35 and 37. Two separate pneumatic cylinders are used to drive grippers 426a,b for destructive pull-tests.

A detailed description of each of these assemblies and their interaction will be explained in detail hereinbelow.

As shown in FIG. 34, a surgical needle 39 with attached suture is retained by a multi-axis gripper 184 and, in the manner described above, is indexed to the automatic pull test station 400 by the rotary swage dial 150 to the position illustrated in FIG. 34. To position the armed needle 39 in the load cell 435, the multi-axis gripper 184 is extended from the swage dial 150 from center load "A" to center load "B" so that the end portion 44 of needle 39 is positioned above a corresponding receiving V-plate arm 436(a) of the load cell assembly 430 as shown in FIG. 34.

Figure 36A:
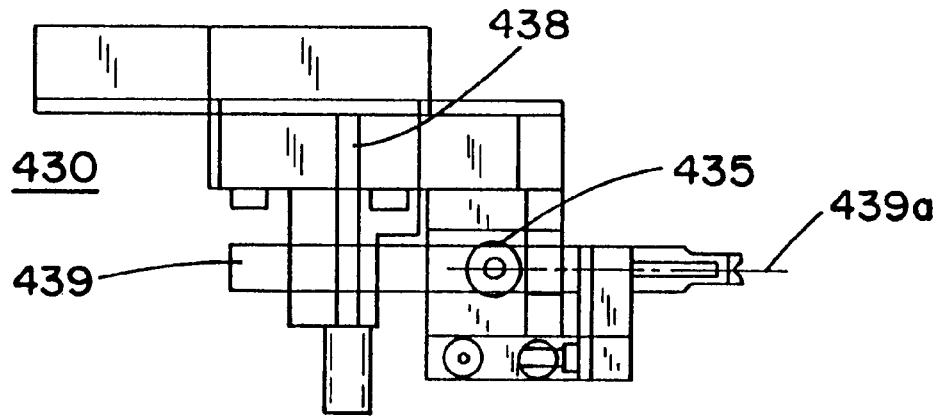
FIG. 36(a) is a plan view of the load cell assembly of the present invention, illustrating the v-plate needle arm.

FIG. 36(a) illustrates a top view of the load cell assembly 430 with load cell 435 mounted thereon. In the preferred embodiment, load cell 435 is loaded by a pivotally mounted V-plate needle arm 439 having a thin needle supporting blade 439(a) for supporting the suture receiving end portion 44 of various size surgical needles with the suture material 42 depending therefrom. Different V-plate arms may be provided for different needle suture combinations which accommodate larger and smaller sutures having diameters of approximately 0.009 to 0.017+/−0.001 inches. Depending upon the batch of surgical needles currently being pull tested, the appropriate V-plate needle arm 439 will be positioned to receive the needle from the multi-axis gripper.

Non-destructive pull testing of the armed surgical needle 39 is accomplished as follows:

After positioning the multi-axis gripper 184 in the extended position as heretofore described, grippers 425a,b of suture gripping assembly 470 are closed from an open position to grip the suture strand slightly below the V-plate needle arm 439 of load cell assembly 430 as shown in FIG. 38. A single pneumatic actuator 472 (illustrated in FIG. 35(a)) is provided for opening and closing gripper arms 425a,b and the cylinder is controlled by a control system program resident in control system computer 114 as explained in further detail in copending patent application U.S.S.N. 08/804,476 entitled "Production, Tooling and Quality Control System" assigned to the same assignee of the present invention, the disclosure of which is incorporated herein by reference thereto.

Figure 35A:
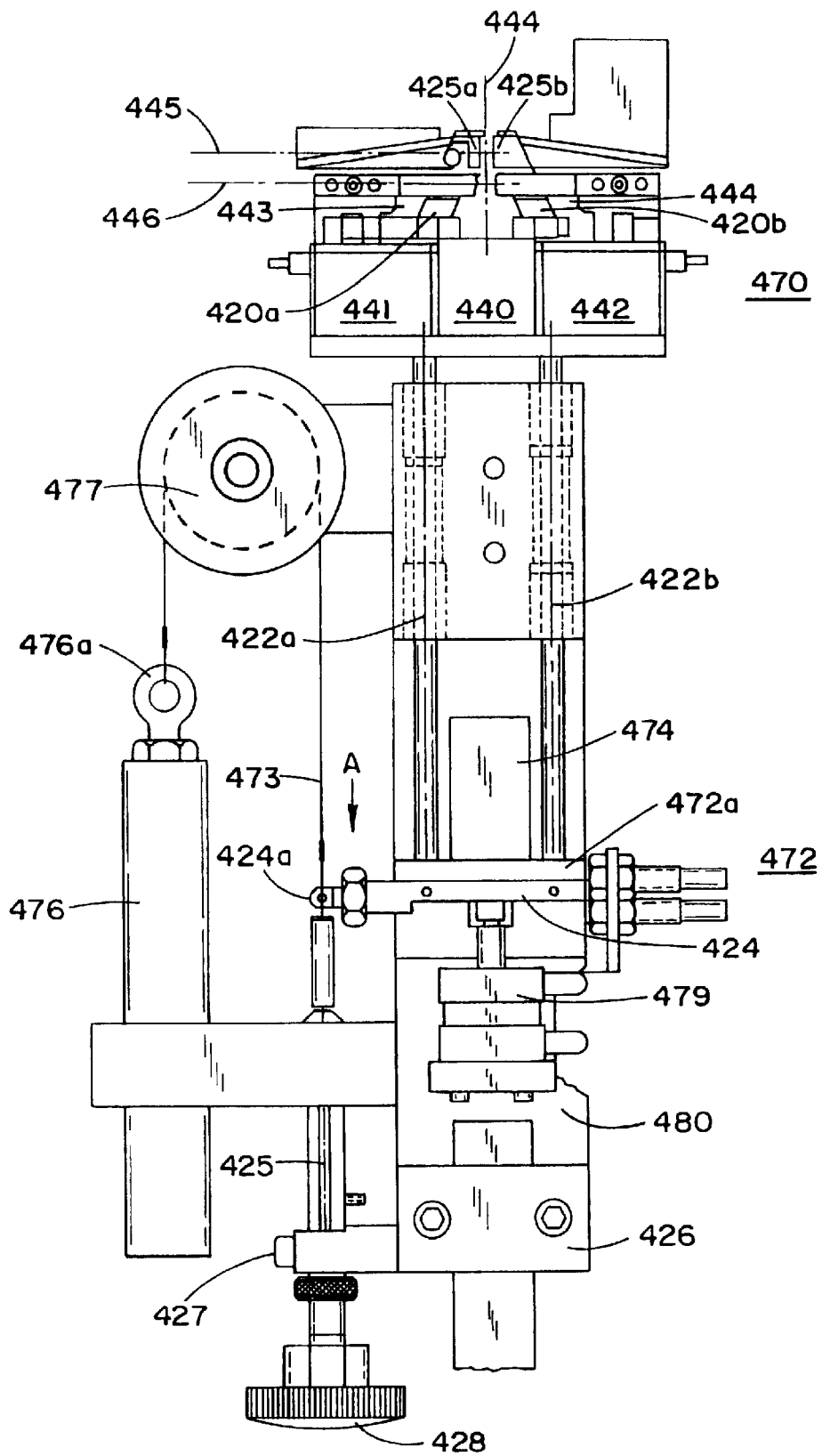
FIG. 35(a) is a front elevation view of the pull test assembly illustrating the gripper assembly and the slide block assembly.
Figure 35B:
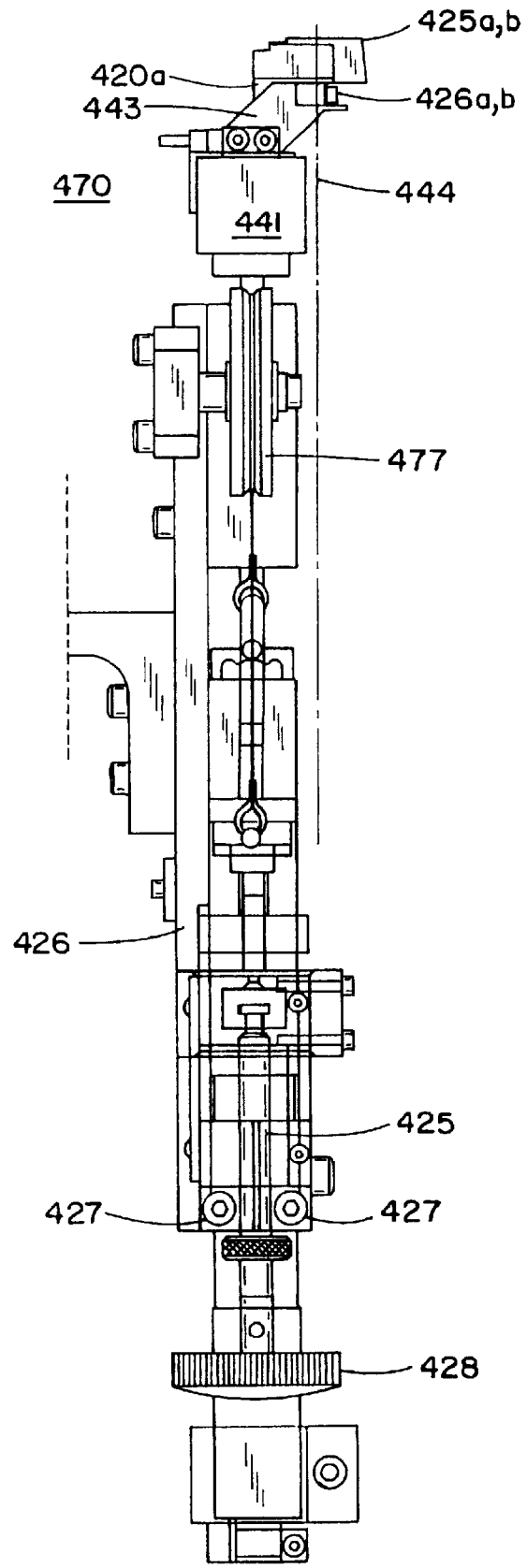
FIG. 35(b) is a side elevation view of the pull test assembly of FIG. 35(a) illustrating the gripper assembly and the slide block assembly.

FIGS. 35(a) and 35(b) illustrate the slide block assembly 472 that is composed of slide rods 422a,b and a lower slide block 472a which reciprocates vertically on the slide rods 422 a,b. Slide block 472a includes a load balancing plate 424 upon which air cylinders 474, 479, apply respective upward and downward forces depending upon the type of pull-test that is to be performed. As shown in FIG. 27, air cylinder 479 is shown in an extended position providing an upward force that supports the load balance plate 424 and consequently maintains slide block 472a of slide assembly 472 at a fixed vertical position.

Slide block 472a is counterweighted to a net zero weight by appropriately sized counterweight 476 that is attached to the load balance plate at 424(a) and acts through cable 473, around pulley 477, and to attachment point 476a. This counterweight 476 acts to balance the net load on slide block 472a to a neutral position. An adjustable net downward force of 2 to 30 oz. is provided by an adjustable spring tension device 425, which is more clearly illustrated in FIG. 37. One end of spring tension device 425 is mounted to fixed position on the frame 426 by a mounting bolts 427. The other end of spring tension device 425 is attached to the load balancing plate 424 at 424a and exerts an adjustable downward loading between the load balance plate 424 and the fixed frame member 426. This adjustable download tension is normally offset by air motor 479 which drives the lower slide block 424 upward to a home position.

The amount of spring tension applied during a non-destructive pull-test can be varied from 2 to 30 oz. by rotation of a knob (not shown) on shaft 428 and the effective pull test loading is indicated by pointer 429 on scale 430.

To accomplish the non-destructive pull test, air cylinder 479, mounted on sub frame 480 and controlled by system computer 114, is relaxed from its extended position (FIG. 35(a)) supporting the load balance plate 424. This removes the upward force on load balancing plate 424 as shown in FIG. 35(a), to thereby impose the selected spring tension net weight of 2 to 30 ounces downwardly on slide block 472a and through slide rods 422 a,b to the gripper assembly 470 and the gripper jaws 425a,b to pull downwardly on the suture attached to swage needle 39, in the direction of arrow "A". The accuracy of this system is enhanced because slide block 472 is suspended on slide rods 422a,b which are mounted in low friction ball bushings, pressed into frame member 471, thereby imposing minimal mechanical drag on the system.

Note in FIG. 34, that the fixed slide block frame 426 is positioned parallel to the axis 444 of the suture depending from the needle 39, and is located a distance away from the axis corresponding to the length of the offset arms 420a,b of gripper jaws 425a,b.

Simultaneous with or momentarily before the slide assembly 472 is released, the needle release cam roller 488 is actuated to enable multi-axis gripper 184 to disengage its grip on the armed needle 39. Releasing the armed needle from the grip of the gripper 184 is necessary to ensure that it is firmly positioned on the V-plate needle supporting blade at 439(a). Moreover, to provide an accurate pull-test, the needle must be released so that there is no existing upward force that would cause false results.

As shown in FIGS. 28 and 34, the needle release cam roller assembly comprises needle release solenoid 491a that is actuated to rotate pivotal lever arm 490. Pivotal lever arm 490 pivots about pin 490(a) to depress plunger 489 of the multi-axis gripper 184 as previously described with respect to FIGS. 31(a–d). Depressing plunger 489 opens pin 182 to release the needle 39 engaged therein.

Referring to FIG. 34, to prevent the needle 39 from becoming misaligned or from tipping over after the multi-axis gripper 184 releases its grip on the needle, a needle fence assembly 440 is provided. As shown in FIG. 34, the needle fence assembly 440 includes vertical fence plate 442 which can be adjusted to lie a needle's diameter away from the face of gripper 184, and thereby retains the needle in an upright position for the test. Adjusting the lateral positioning of the vertical fence plate 442 is accomplished by rotating lead screws 443 (shown in FIG. 34) to advance or retract the fence for an appropriate distance. In the preferred embodiment, the configuration of the face of the vertical needle fence plate 442 (not shown) may be changed to accommodate the configurations of different size needles.

The controlled release of the minimum pull-test is of short duration, preferably ranging in milliseconds. If the test is successful, i.e., the suture meets the minimum pull-test requirements, the needle is re-gripped by the multi-axis gripper 184 by deactuating the needle release solenoid 176(a) which retracts the cam roller 488 and releases the downward force on plunger 489. The suture gripper jaws 425a,b are then retracted to their open position to release their grip on the suture as controlled by the control system. Subsequently, the multi-axis gripper 184 is retracted and the rotary swage dial 150 and rotated to convey the armed needle downstream for automated packaging at 500.

Figure 39:
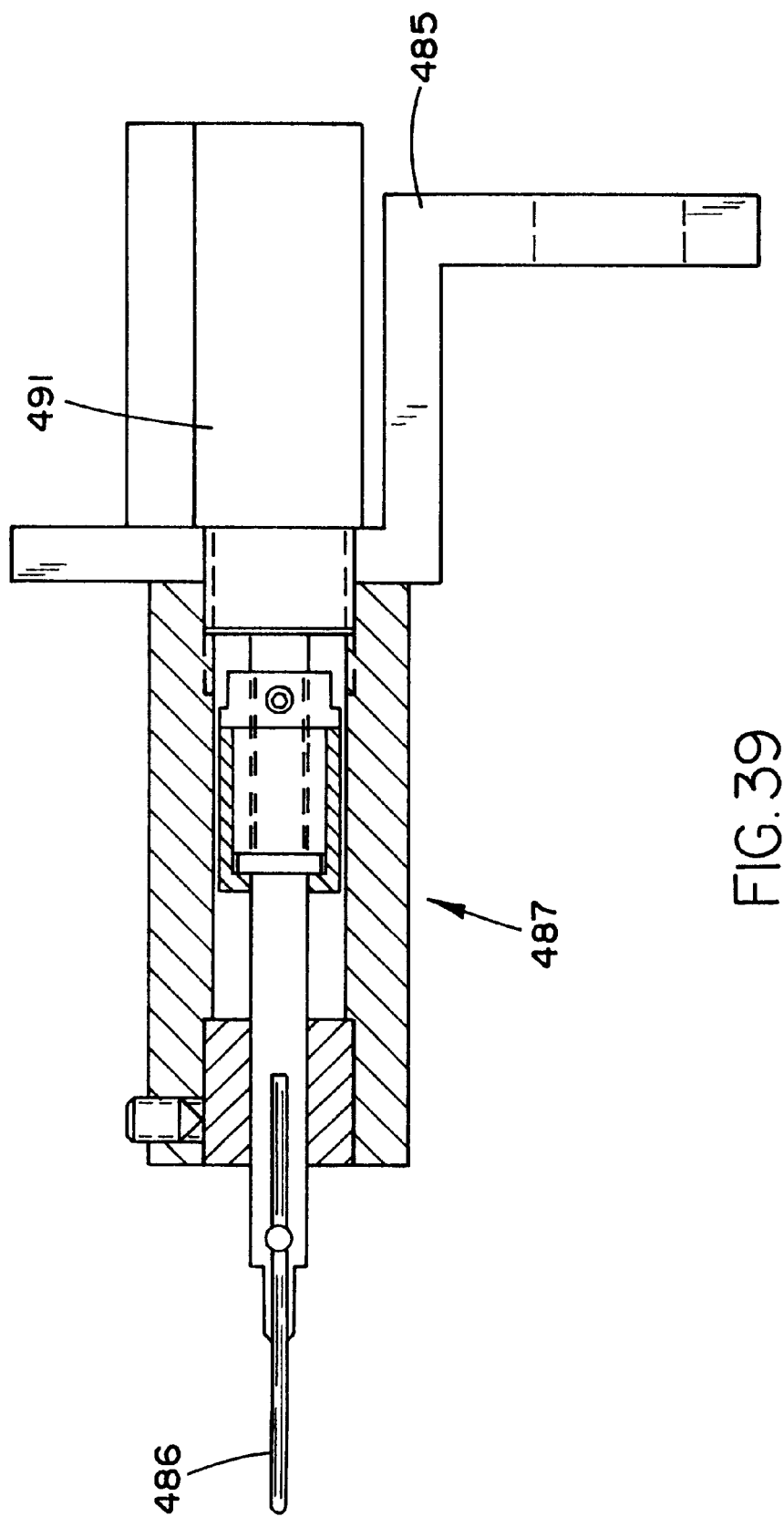
FIG. 39 is a partially cross sectioned top view of the needle stripper assembly used in the present invention.

If the suture fails the minimum pull-test, i.e., if the suture is dislodged from the surgical needle 39 as a result of the non-destructive test, the control system computer 114 is flagged so that the disarmed needle 39 will be ejected at the pull-test station. The dislodged suture strand will be drawn into a vacuum assembly (not shown) and the needle 39 will be ejected by a needle stripper assembly 487, shown generally in FIG. 22(a) and in detail in FIG. 39. As shown in FIG. 39, needle stripper solenoid 491 will be actuated by a control signal output from the control system computer 114 to extend needle stripper pin 486 to a space between the needle 39 and the face of the multi-axis gripper 184. Thus, when the needle is in its relaxed state on the multi-axis gripper 184 and the minimum pull-test fails, the needle stripper pin 486 is extended to remove the needle from the multi-axis gripper 184. The needle stripper assembly 487 is mounted to the swage dial assembly by mounting bracket 485. The needle will fall and be collected by appropriate collection means (not shown) located at the pull-test station.

After the pull test, whether successful or unsuccessful, the apparatus prepares for the next armed needle to be pull-tested. Slide block assembly 472 and retracted gripper jaws are pushed back up with respect to the fixed slide mount frame 426 to the home position by an appropriate upward force supplied by the air cylinder 479 as controlled by the control system computer 114. At this time, another data signal may be sent for storage in a database maintained by the control system computer that indicates that the pull-test performed on the particular needle 39 was either successful or unsuccessful, together with a data signal which represents the loading on load cell 435. A signal flag may also be sent which indicates that a needle suture assembly is being conveyed downstream for bundling thereof.

Figure 36B:
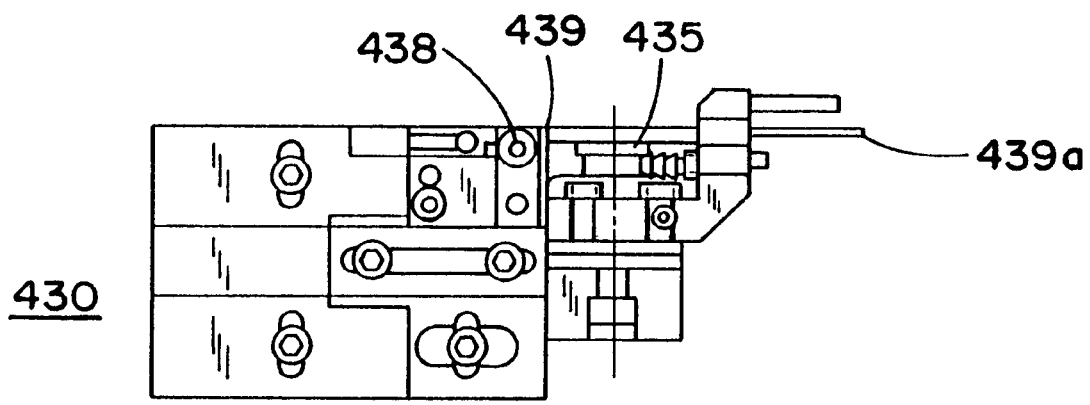
FIG. 36(b) is an elevation view of the load cell assembly of the present invention, illustrating the v-plate needle arm.
Figure 37:
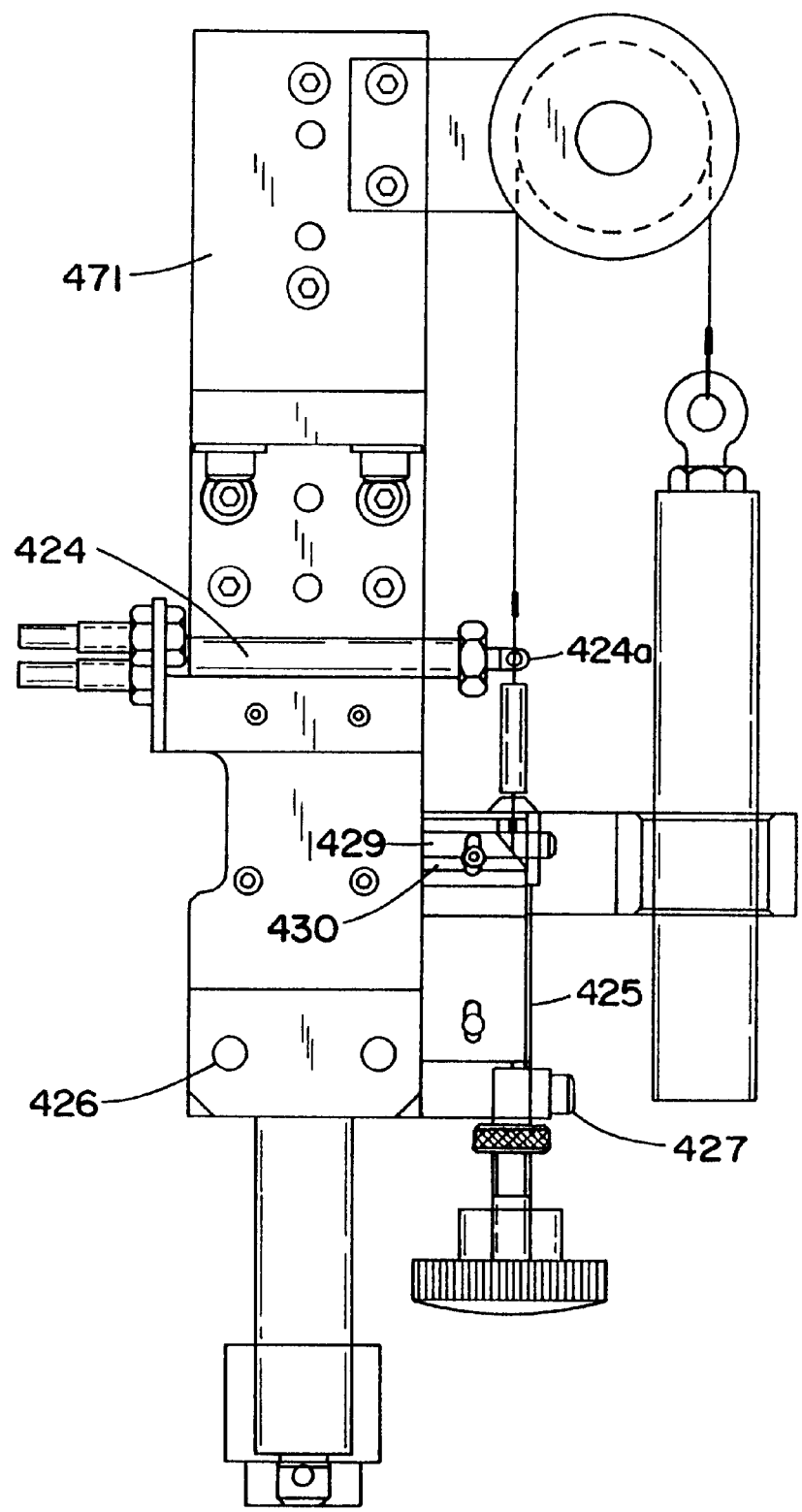
FIG. 37 is a rear elevation view of the pull test assembly illustrating the spring tension assembly used for non-destructive pull tests.

In the preferred embodiment of the invention, the load cell 435, illustrated in FIGS. 34 and 36(a) 36(b) is a piezoelectric transducer that measures the force applied by the slide block assembly to the needle-suture assembly 39. The force is received by the V-plate needle arm at 439(a), and transmitted to load cell 435 mounted underneath the v-plate arm 436 by virtue of the pivotal mounting of the v-plate needle arm on bolt 438. This single point mount enables an easy parts change for needle v-plate arm when different needle or suture sizes call for a different opening at 439(a). The transducer load cell 435 may be interfaced with the control system computer 114 by conventional means, and, in the preferred embodiment, is a 25 lb. transducer manufactured by Techniques Co. (Model No. MDB-25PH). The forces applied to the suture 39 and measured by the load cell transducer 435 during the destructive pull-testing may be stored for statistical purposes or for real-time monitoring during a swage die setup routine that may take place when a new batch of surgical needles are to be swaged. For instance, if the non-destructive pull-tests fail and the force measured by the transducer 435 is determined to be at the low end of a predetermined range, then the control system computer 114 will acknowledge this and send appropriate signals to the upstream swaging assembly described previously causing the fixed swaging die 201 to be advanced an incremental amount toward the moveable swage die 202, resulting in subsequent swages being stronger. Likewise, if the non-destructive pull-test passes, i.e., the forces measured by the transducer are determined to be between a minimum and maximum load, then no die adjustment need be made.

As previously mentioned, the automatic pull-test assembly 400 is used to perform a minimum pull-test upon every armed surgical needle indexed thereto prior to automatic packaging thereof. A destructive pull-testing of the armed surgical needle is performed at a parts change set up and at every nth needle indexed thereafter. The purpose of performing a destructive pull-test is to set the swage dies located at the upstream swaging station for correct maximum swage pull-out value. This is by necessity a destructive test, and the test frequency, which is programmable, is set high enough to maintain control of the operation, but low enough to avoid excessive product waste. In the preferred embodiment, this frequency may be set at every 50th needle, but could be every 75th or 100th needle.

Another purpose of the destructive pull test is to aid in installing a new swage die set during a changeover procedure, which is a procedure that is used to prepare the needle swaging apparatus (swage dies) for processing a new batch of needles when they are of a different size from a previously processed batch. Contrary to the non-destructive pull-test described above, the pull-test apparatus is programmed for 100% destructive test of a swaged needle, while the swaging assembly is operating and feeding the armed needles to the pull-test station. The die adjustment system at the upstream swaging assembly will receive a signal from the computer 114 transducer load cell 435, at each machine cycle, and quickly perform a correct adjustment of the swage dies.

Destructive test pull-out values are recorded in the system computer 114 and are used to compute statistical process control information which is fed back to the machine operator through display screens.

Destructive pull testing of the armed surgical needle 39 is accomplished similarly as described herein above with respect to the minimum pull test, but with a second pair of gripper jaws 426a,b and destructive test air cylinder 474. However, the fundamental difference between the tests is a fixed mechanical stroke that is always strong enough to pull the suture out of the needle. This destructive stroke replaces the variable 2 to 30 ounce force of the minimum pull test routine.

As shown in FIG. 35(a), a second air cylinder 474 located opposite air cylinder 479 is programmed to provide a fixed stroke against load balancing plate 424 from the home position shown in FIG. 28(a). This results in a downward vertical displacement of lower slide block assembly 472 from the position shown in FIG. 35(a). This also results in a downward force upon slide rods 472(a) and (b), which moves the gripper assembly 470 downwardly, including gripper jaws 426 a,b and the suture gripped therein, in the direction of the arrow "A" as shown in FIG. 35(a). The air pressure supplied to cylinder 474 is set high enough to always pull the suture out of needle 39. This stroke is limited by the bottom portion of slide assembly 472 striking the top of stationary frame 426. The destructive pull test jaws 426a,b are serrated on their gripping surface, as shown in FIG. 35(a) to ensure a positive non-slip grip on the suture during the destruct cycle. Further, the destruct gripper jaws 426 a,b are driven by a pair of air cylinders 441,442 through angled offset arms 443,444.

The axis of reciprocation for each of the sets of jaws is illustrated in FIG. 35(a), with the axis for the non-destruct gripper at 445, and the axis of reciprocation for the destructive gripper jaws illustrated in FIG. 35(a) at 446.

The force necessary to accomplish the destructive pull-test is measured by the piezoelectric load cell transducer 435 as discussed above, and data representing this force is sent to the control computer 114. If it is determined by the process control algorithm (described below) that the destructive pull-test forces as measured by the transducer load cell are lower than a predetermined range of pull-test values, the control system computer 114 will send out appropriate control signals to increase the swaging die stroke applied when swaging the suture to the needle at the upstream swaging station. If it is determined that the destructive pull-test forces as measured by the transducer load cell are higher than the predetermined range, the control system computer 114 will send out appropriate control signals to the upstream swaging assembly to move a fixed swage die a small incremental distance away from the moveable swage jaw, thereby decreasing the swaging pressure applied when swaging the suture to the needle.

Since the destructive pull-test necessarily results in the suture becoming dislodged from the needle 39, the needle 39 is again removed from the grip of the multi-axis gripper 184 by the needle stripper pin 486(*a*) as described above. Subsequently, the gripper jaws 426a,b are retracted to their open positions and air cylinder 479 provides the upward force to restore the gripping assembly 470 and slide block assembly 472 back to their normal position in preparation for the next pull-test.

Automated Packaging Station

The automated packaging station 500 will now be described with reference to FIGS. 40–71 and described in greater detail in copending application, Ser. No. 09/020,084, the disclosure of which is incorporated herein by reference.

Figure 40:
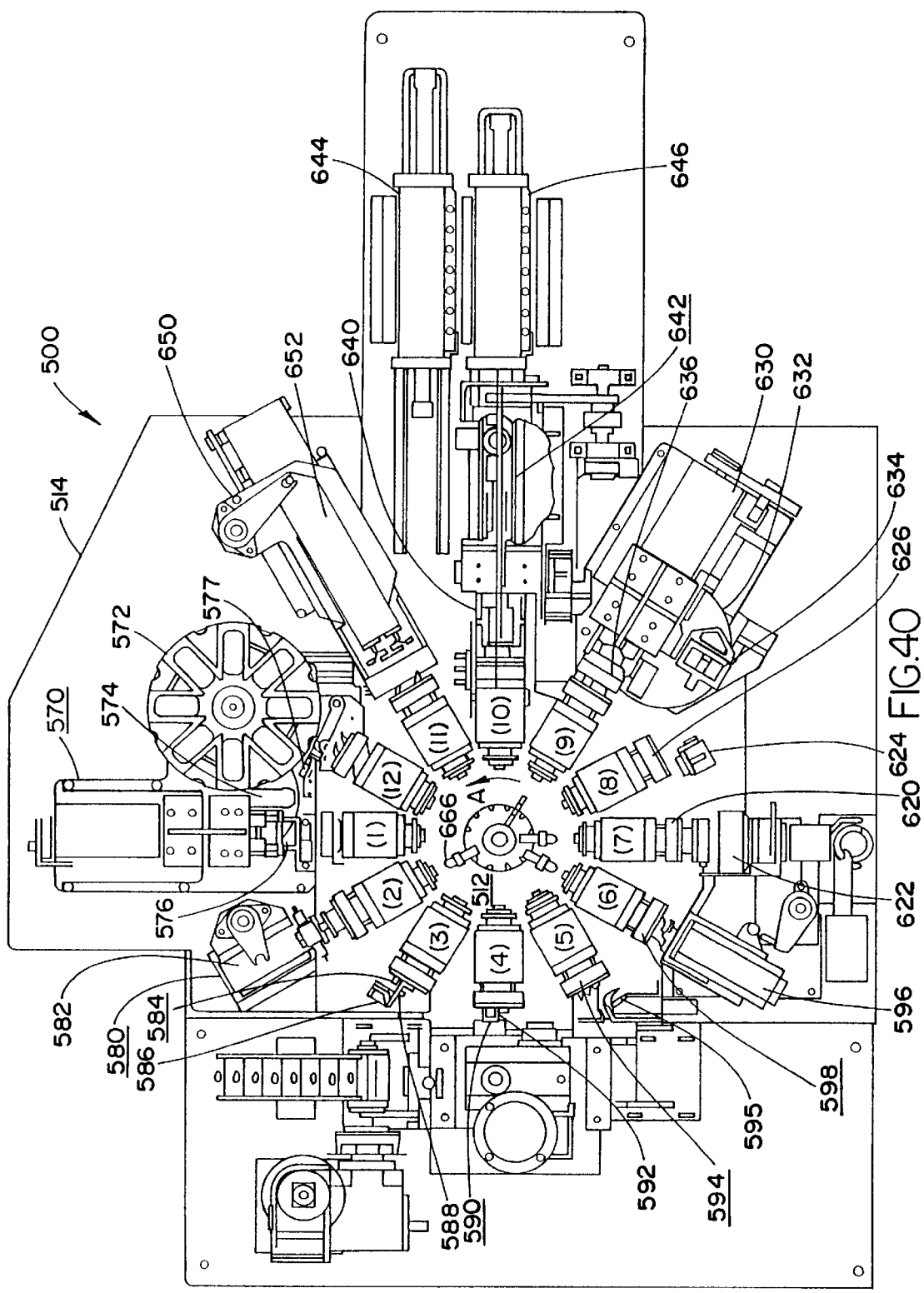
FIG. 40 illustrates generally diagrammatically, a plan view of the automated packaging station for the automated packaging of individual surgical needles and attached sutures, pursuant to the present invention.
Figure 41:
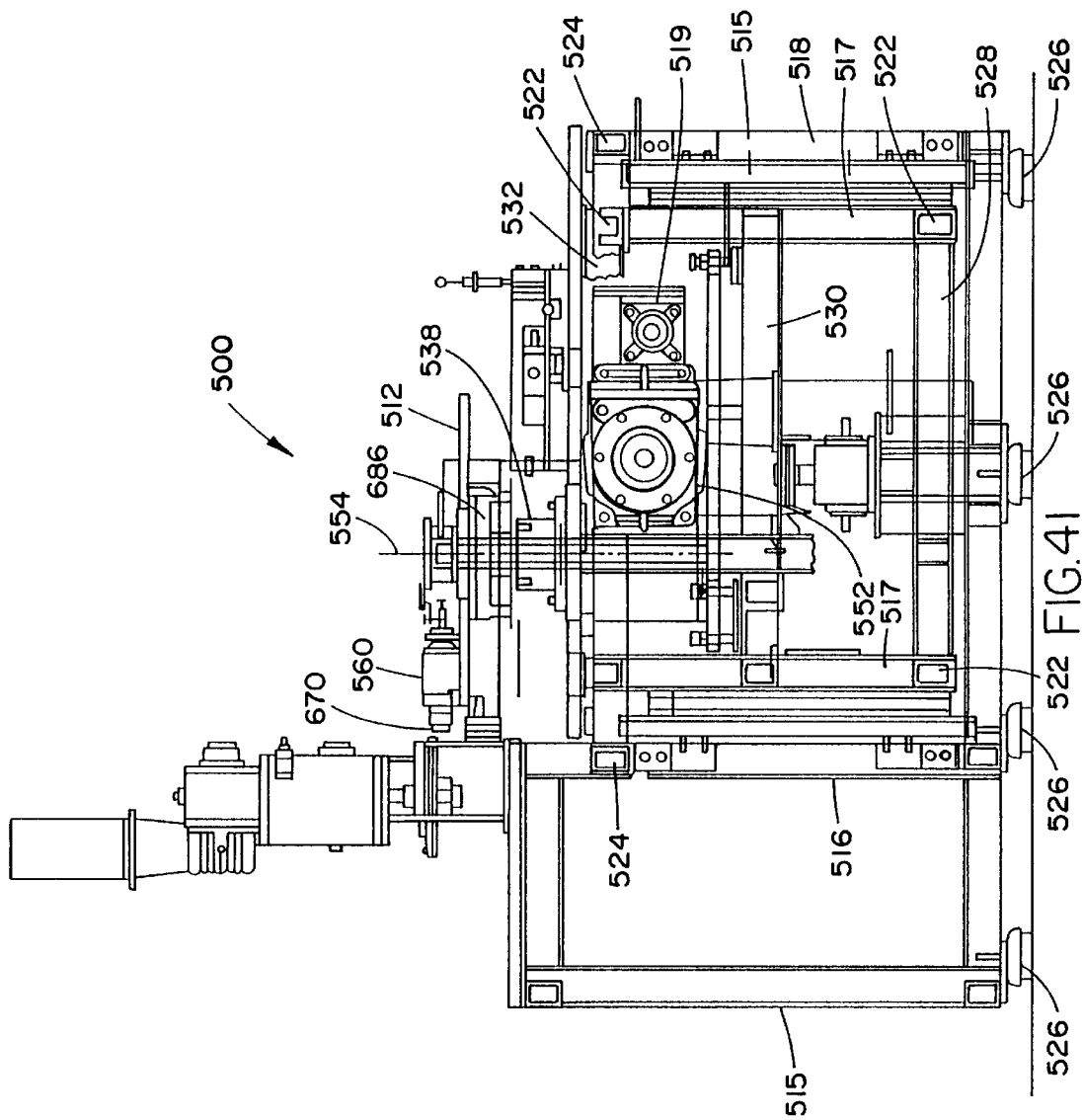
FIG. 41 illustrates a side elevational view of the machine frame for the packaging station illustrated in FIG. 40.
Figure 42:
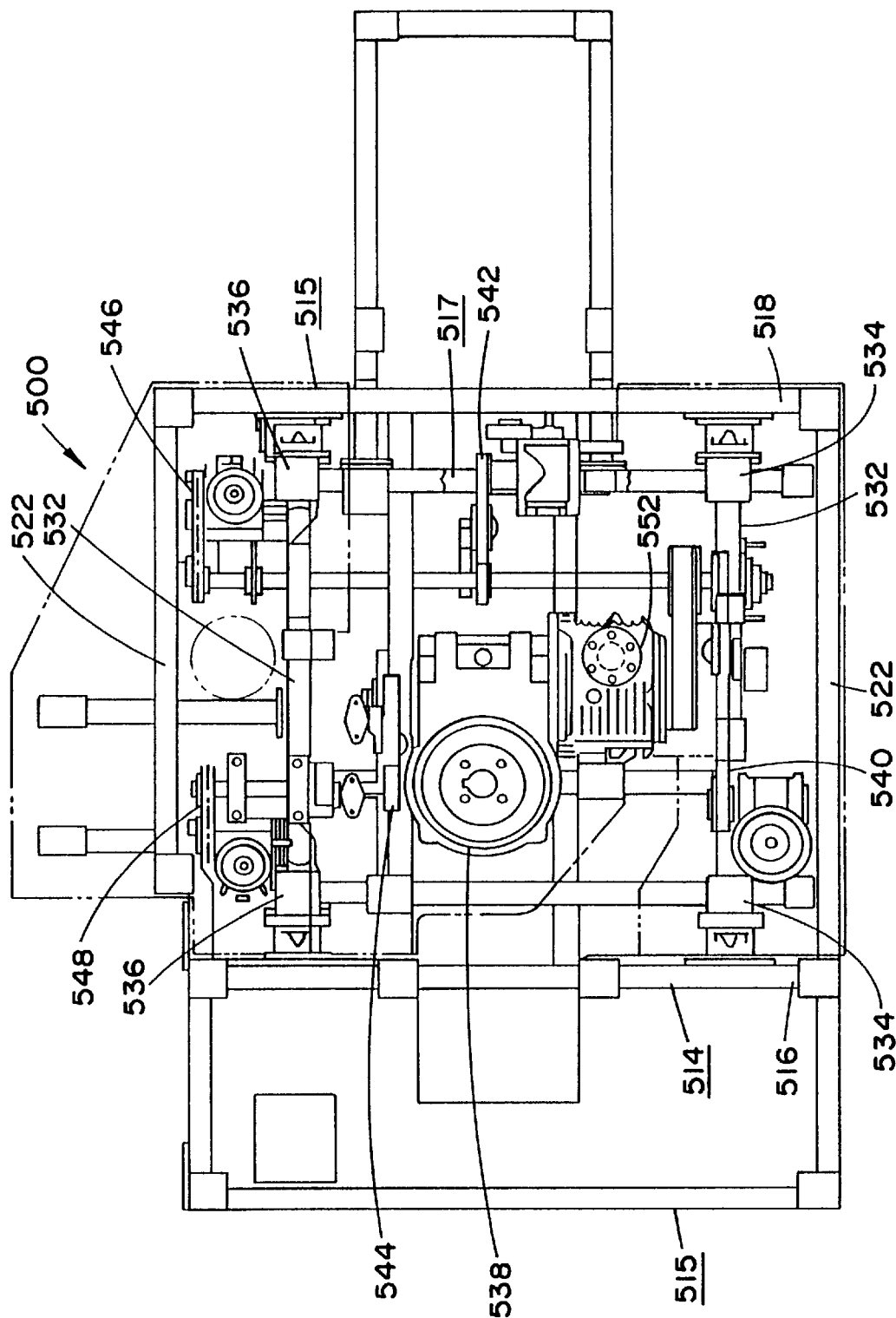
FIG. 42 illustrates a top plan view of the machine frame of FIG. 41.

Referring now in more specific detail to the drawings, FIGS. 40 through 42 illustrate, in a generally diagrammatic plan view, the automated needle and suture packaging machine 500 pursuant to the invention. The machine 500 comprises a rotary turret or turntable 512 which is essentially a packaging dial supported on an essentially stationary machine frame structure 514. The rigid frame structure 514, as illustrated in FIGS. 41 and 42, basically includes structural uprights 516 and 518, which are interconnected by horizontal beams 520, 522, 524, with the entire frame structure 514 adapted to be supported on a floor through the intermediary of adjustable leveling footings 526. The frame structure 514 comprises an outer stationary frame arrangement 515, and an inner vertically adjustable frame arrangement 517 comprising horizontal beams 528, 530 and 532, and vertical beams 534, 536 interconnected therewith supporting the turntable 512 for vertical adjustment relative to the stationary machine frame components. The vertical adjustment of the frame arrangement 517 is provided for by a central servo motor actuated jack screw 538, which also concurrently effectuates the vertical adjustment of all of the operative packaging devices at the various workstations of the machine so as to accommodate the packaging of a wide range of differently sized surgical needles without the necessity for modifying any machine components.

As illustrated in FIGS. 48*a* through 48*f* differently sized surgical needles, identified by symbols RB-1, SH-1, SH, CT-1, CTX and CT by way of example, may be introduced into basically identical packaging trays 45, and which also indicates the different adjustments of the packaging machine above a fixed reference line of the swage dial apparatus 185 and the swage table 195 from which the surgical needles and attached sutures are transferred by the multi-axis gripper 184 to the tray 45 mounted on tool nest 560 of the packaging station 500.

In order to adapt the packaging station 500 to the differently sized surgical needles which are to be packaged in essentially identically-sized packaging trays 45, the latter of which may accommodate a wide range of needle sizes without having to have the suture package modified, the turntable 512 and the tool nests 560 which are mounted thereon, including the various workstation components, are adapted to be adjustable in elevation relative to the multi-axis grippers 184 so as to compensate for changes in needle size, without having to modify the functioning of the packaging station 500 or the need to replace any of the structural components of the machine at the various workstations.

As indicated in the drawing FIG. 41, the machine frame 514 includes the stationary frame portion 515, which is essentially immovably supported on a suitable level support surface or floor. Arranged within the stationary support arrangement of the frame portion 515 for the packaging station 500 is the frame portion 517 which is movable relative to stationary frame portion 515, and is adapted to be vertically adjusted through the intermediary of the jack screw arrangement 538 which is connected to turntable 512, and enables the height of the latter to be adjusted in correlation with the particular size of surgical needle which is to be transferred into the tray 45.

The elevational adjustability of the movable frame 517 and, resultingly, that of the turntable 12 and tool nests 560 may be preprogrammed or otherwise determined and controlled by the operating personnel for the packaging station 500. This ability to vertically adjust the movable frame 517, and thereby the operating height of the turntable 512 and tool nests 560 which are mounted thereon, imparts a versatility to the machine which renders it readily applicable to the packaging of a wide range of surgical needle sizes.

Arranged within the frame structure are the various belt drives 540, 542, 544, 546 and 548 and operating drive components 550 for the machine, and the vacuum-generating systems 552 employed in the packaging cycles for the suture packages. The turntable 512 is oriented in a horizontal plane, and through the intermediary of a program-controlled drive installation, is rotatable in an indexing or incrementally angular advance about a central vertical axis 554. In this instance, during operation of the machine, the turntable 512 is rotated in a counter-clockwise direction when viewed from above, as represented by arrow A, so as to be advanced in 30° increments.

The rotary turret or turntable 512 is essentially constituted of a circular disk-shaped member or packaging dial which has a plurality of tool nests 560 mounted thereon. The tool nests 560 are mounted in a circumferentially uniformly spaced array on the upper surface of the package dial or rotary turret 512, and with each tool nest 560 having an outer end projecting radially outwardly of the peripheral edge of the turret or dial 512.

In this particular construction of the packaging machine 500, by way of example, twelve (12) tool nests 560 are arranged at uniformly distributed annular spacings of 30° from each other about the circumference of the dial or rotary turret 512.

In essence, as mentioned hereinbelow, the rotary turret or turntable 512 of the packaging machine 500 is adapted to be indexed forwardly in an angularly incremental or indexed rotational advance, each such incremental advance comprising one-twelfth of the 360° circumferential rotation of the turntable, or basically 30°, along the direction of rotation identified by arrow A in FIG. 40, such that the tool nests 60 which are each adapted to mount a suture tray or package are designed to be advanced in sequence to a number of successive workstations; designated herein as workstations (1) through (12), which are stationarily evenly spaced about the periphery of the rotary turret 512, as illustrated in FIG. 40 of the drawings.

The successive workstations which collectively constitute the automated machine 500 for the packaging of surgical needles and attached sutures are essentially briefly described as follows; viewed in the direction of rotation of arrow A:

(1) A first workstation 570 relates to the operative aspect of empty suture package trays being successively separated from the bottom of stacks of trays contained in a rotary carousel 572 to be transferred onto a rotationally indexed plate 574 under the action of a vacuum, and thereafter picked up and transferred by a cam-controlled robotic pivot arm structure 576 to successive tool nests 560 so as to be retained thereon while being conveyed by the rotary turret or dial 512 to subsequent workstations, as set forth hereinbelow.

At workstation 570 (1), wherein empty suture package trays or bases are applied onto the tool nests 60 of the automated packaging station 500, reference may be specifically had to FIGS. 49 through 54 of the drawings.

Figure 49:
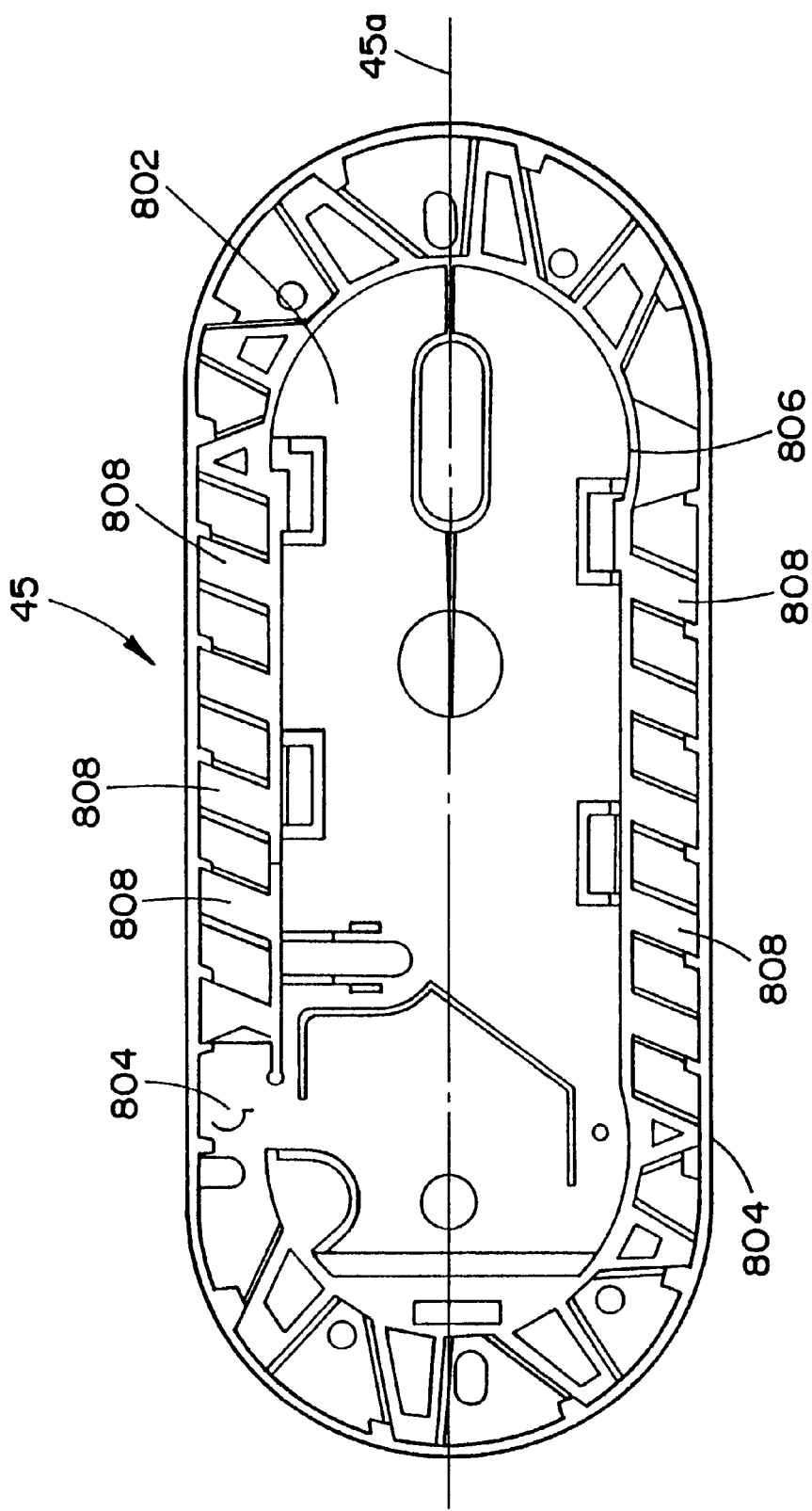
FIG. 49 illustrates a packaging tray for the packaging of an individual surgical needle and attached suture.

The suture package tray 45, as shown in FIG. 49 of the drawings, is essentially constituted of molded plastic material, and includes a planar base 802 with parallel sides and semi-circular rounded ends. A vertical wall 804 extends about the perimeter of the tray, while inwardly spaced thereof is a second vertical wall 806 having radially outwardly extending fingers 808 which are flexible at the upper edge reaching close to the outer wall 804 so as to define a hollow channel structure. Apertures and surgical needle engaging structure is molded into the tray, as more specifically disclosed in copending U.S. patent application Ser. No. 08/521,978; filed Aug. 31, 1995, the disclosure of which is incorporated herein by reference, and which is commonly assigned to the assignee of this application.

Figure 53:
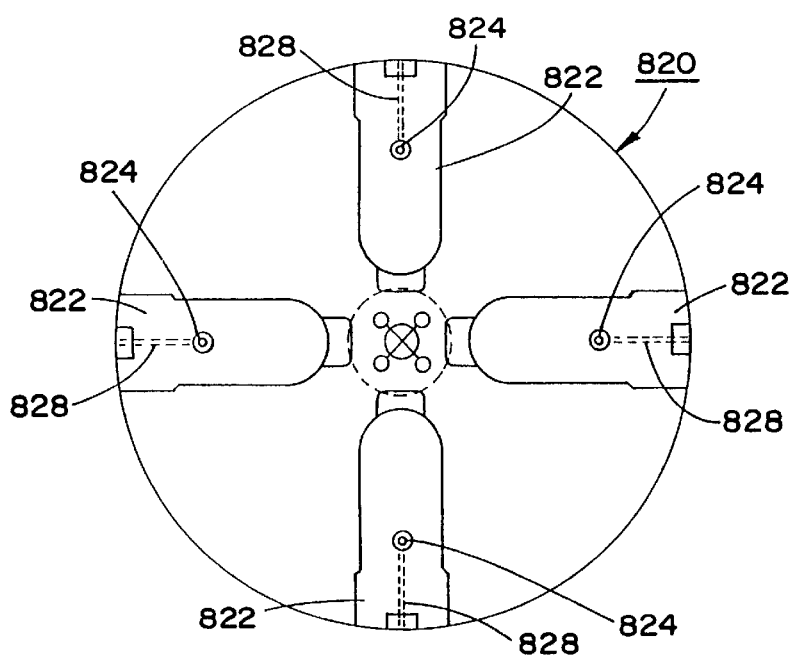
FIGS. 53 and 54 illustrate, respectively, plan and side views, shown partly in section, of the rotatable plate member for separating trays from the carousel of FIG. 52.
Figure 54:
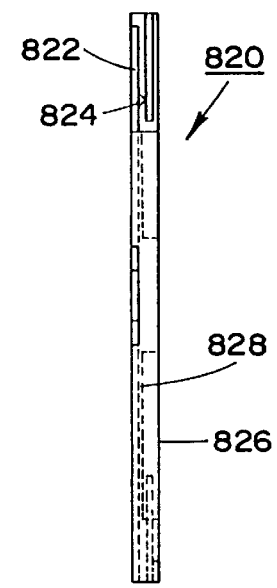
Figure 55:
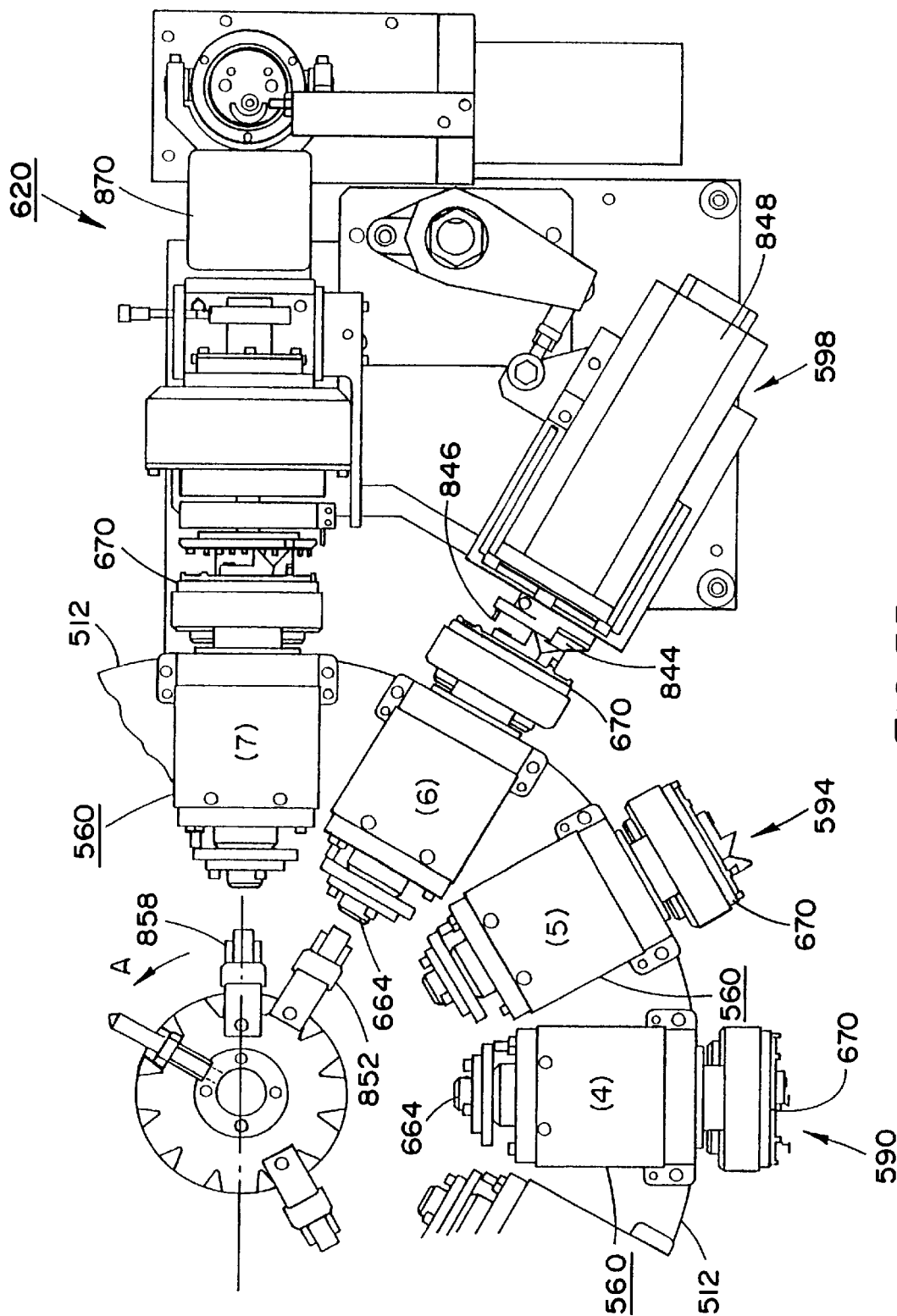
FIG. 55 illustrates a top plan view of the suture winding stations of the packaging station.
Figure 59:
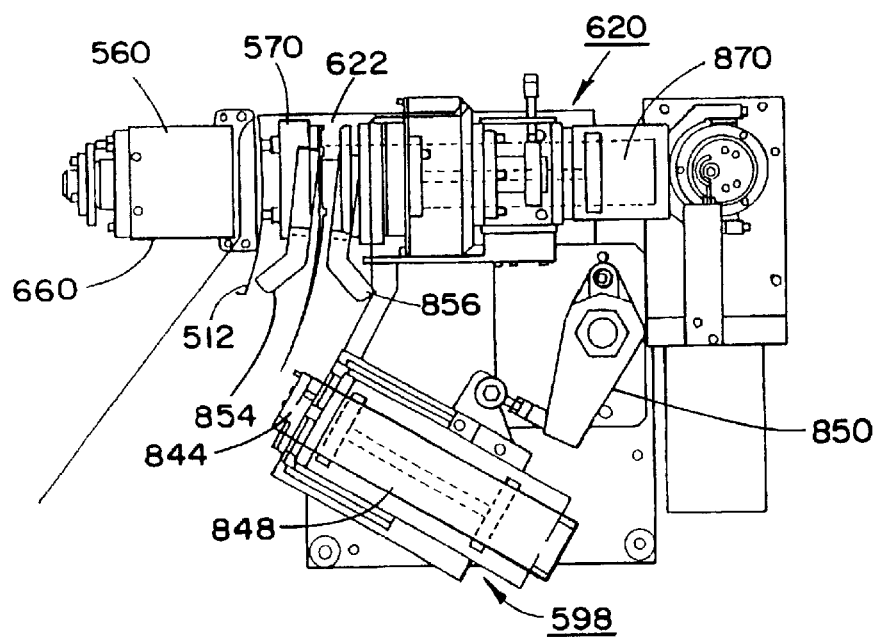
FIG. 59 illustrates a top plan view of the winding stations.

In essence, arranged adjacent the rotary dial or turntable 512, the latter of which is supported on the vertically adjustable frame arrangement 517, as shown in FIGS. 41 and 42, and which dial 512 mounts twelve tool nests 560 in uniform circumferentially spaced relationship, so as to enable the rapid provision of successive tool nests 560 with trays 45 having a shape as shown in FIG. 49; is the tray-loading installation 810. The installation, which is also supported on the adjustable frame structure 517, includes the rotatable carousel 572 which has eight (8) vertical chutes 812 arranged in an adjoining spoke-like annular array about a vertical control shaft 814. Each chute 812 is adapted to hold a vertical stack of superimposed empty package trays 45, as shown in the drawings. The carousel 572 is adapted to be rotatably indexed about shaft 84 through the intermediary of a suitable drive mechanism 816 whereby one of the chutes at any one time, which is filled with a stack of the trays 45, is adapted to have the open bottom end thereof located in close proximity above-the upper surface 818 of a circular or disc-like plate 820. The plate 820 is arranged beneath the lower end of the carousel 572 with a surface portion thereof extending below the bottom end of the chute 812 of the carousel which is most closely adjacent thereto. The circular rotary plate 820, as shown in FIGS. 53 and 54 has four radially extending depressions or recesses 822, each being of a depth essentially corresponding to the height of the vertical wall 804 and peripheral shape of the package tray 45, and with each recess 822 being at a 90° angular spacing relative to an adjacent recess. Each recess 822 has an aperture 824 in its bottom surface 826 communicating with a passageway 828 leading to a controllable vacuum generating arrangement within the packaging station 500.

Between the chute 812 and the disc-like plate 820 is a single multi-tray buffer area 823 containing a buffer stack of trays 45. After a chute 812 is empty, the buffer area 823 allows time for the next chute 812 of the rotatable carosel 572 to be indexed into position without stopping the machine. Therefore, trays 45 can be continuously fed into the disc-like plate 820 from the buffer stack of trays 45 without interrputing the packaging process.

When one of the recesses 822 of the rotary plate 820 is in alignment with the bottom of buffer area 823 containg the buffer stack of trays 45, a bottommost tray 45 of the buffer stack is sliced off or separated from the remaining buffer stack of trays and deposited in the recess 824 located therebeneath under the effect of a vacuum which is applied to the bottom surface 826 of the recess 824.

Figure 50:
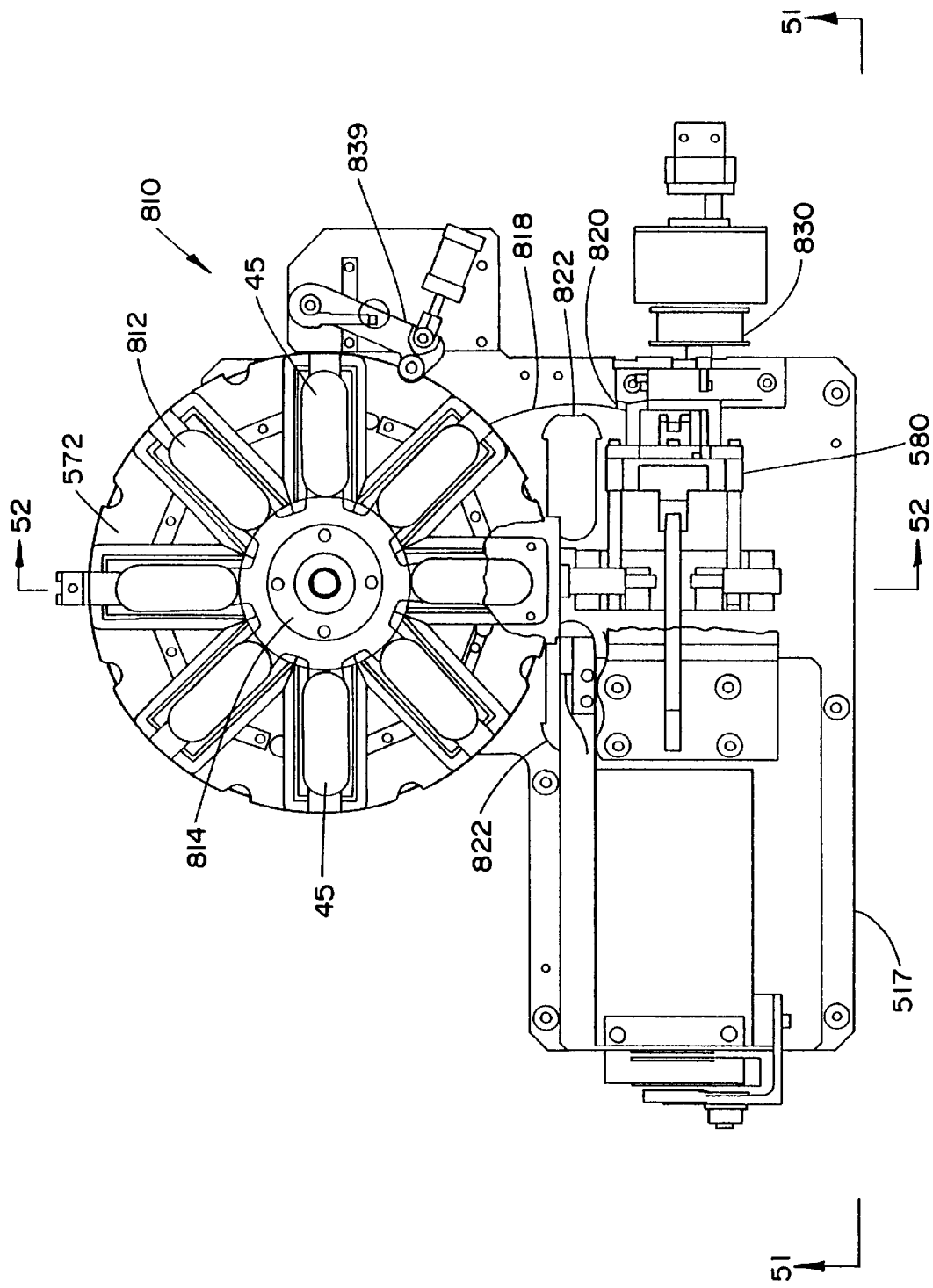
FIG. 50 illustrates a top plan view of the carousel and robotic pivot-arm arrangement of the tray loading and feeding workstation of the packaging station.
Figure 51:
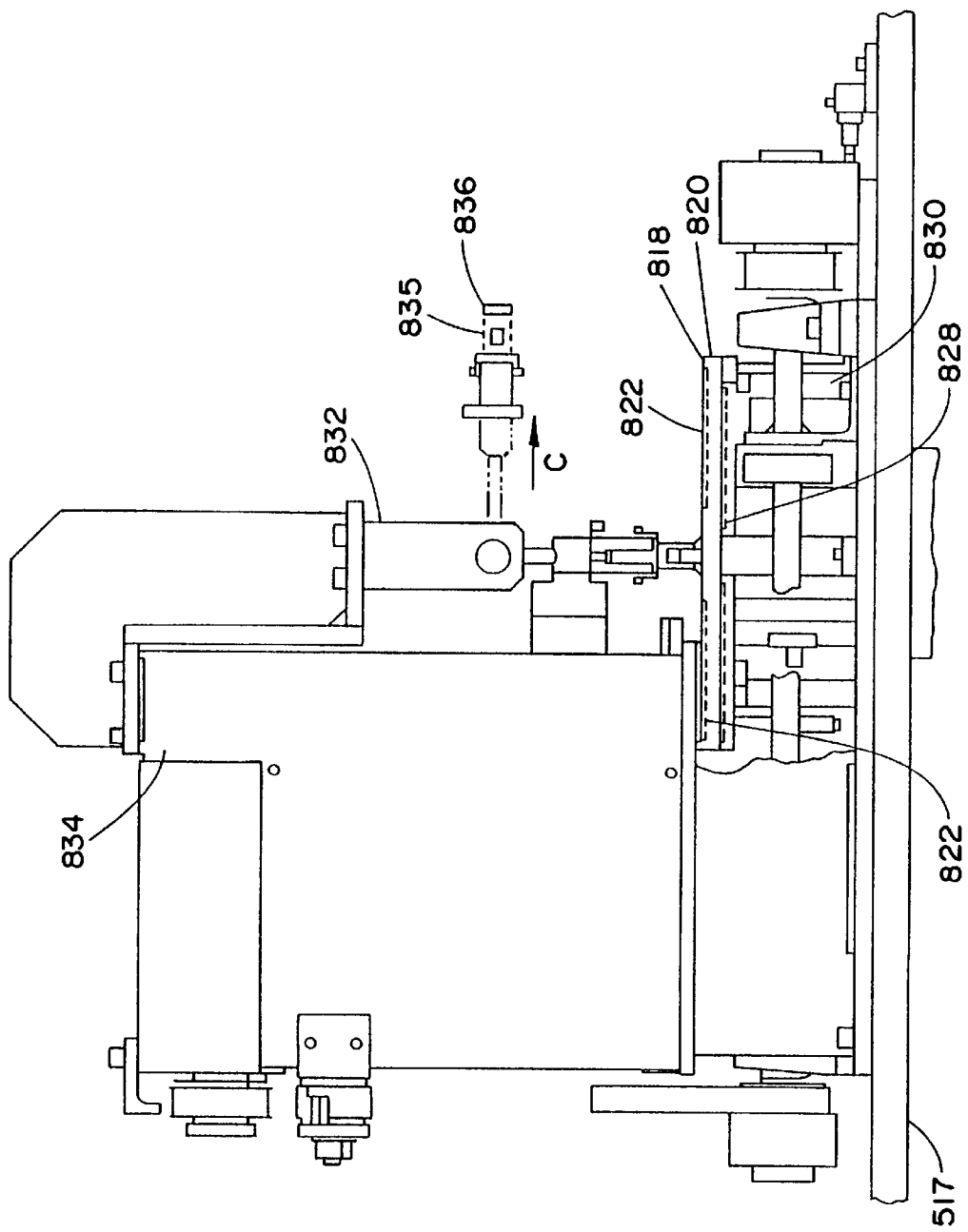
FIG. 51 illustrates an elevational side view taken along line 51—51 in FIG. 50.
Figure 52:
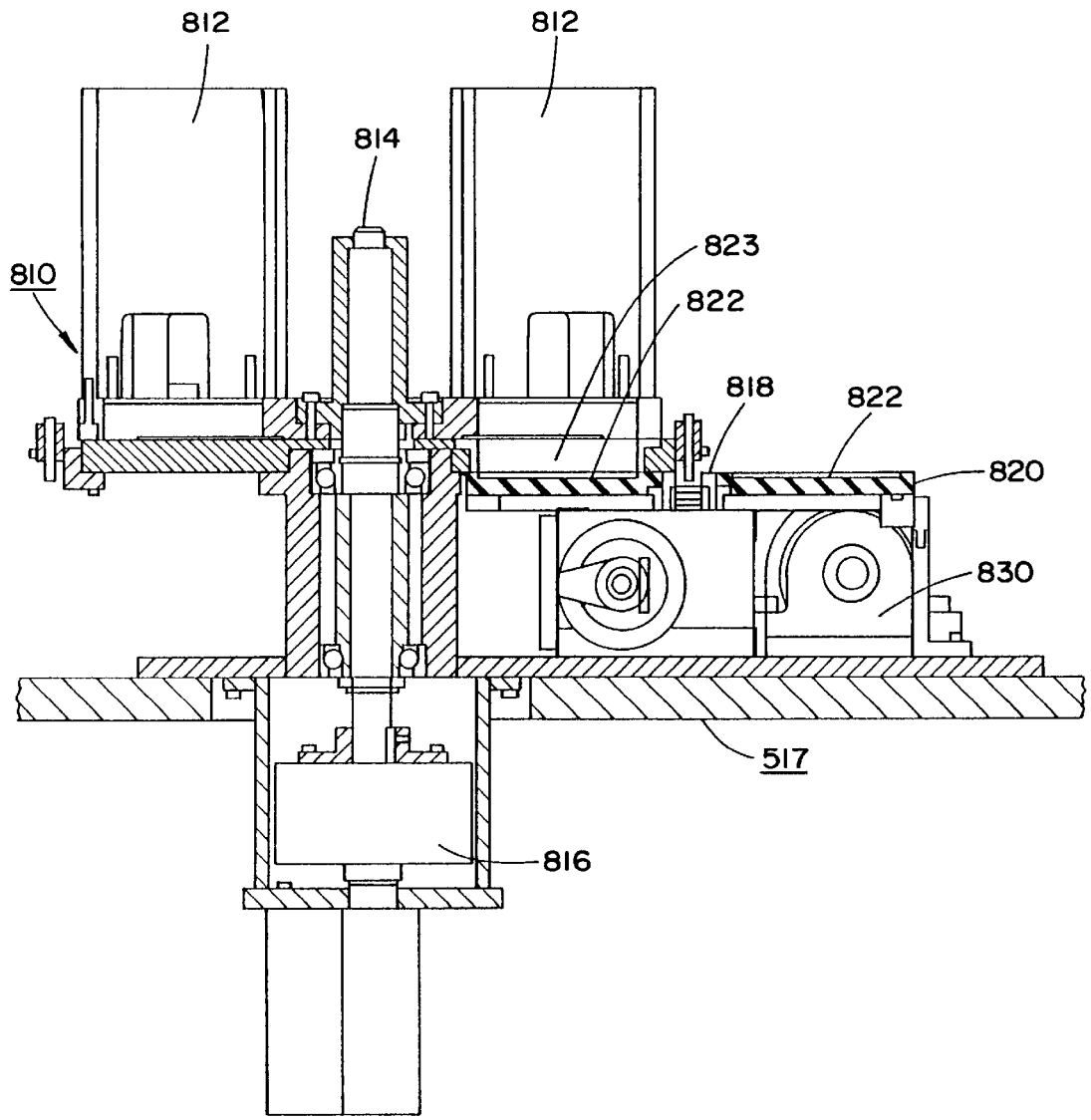
FIG. 52 illustrates, on an enlarged scale, a sectional view taken along line 52—52 in FIG. 50.

As the plate 820 is rotatably indexed forwardly by means of a drive unit 830, each successive recess 822 has a successive bottommost tray 45 deposited therein from the buffer stack of trays 45 which is in superimposed alignment therewith. As the plate 820 continues its indexed rotation, a robotic or cam-controlled pivot arm 832 mounted in housing structure 834, as shown in FIGS. 50 and 51, has a gripper attachment 835 located at a forward end 836 depending downwardly so as to contact the tray 45 located in recess 822 on plate 820. The vacuum is released in the recess 822, and the gripper atttachment 835 grasps the tray 45. The pivot arm 832 is then pivoted upwardly into a horizontal orientation, as shown in FIG. 51, and then extended forwardly along arrow C to cause the bottom surface of the tray 45 carried thereon to come into contact with the tray-receiving surface on the vertical plate element 670 of a therewith aligned tool nest 560 on the rotary turntable 512.

Thereupon, the gripper attachment 835 releases the tray 45, while a vacuum is applied to plate element 670 to resultingly cause the tray 45 to be assumed and retained thereon. The pivot arm 832 is then retracted and pivoted downwardly, as shown in FIG. 51, so as to engage a successive tray 45 positioned in the next recess 822 in the plate 820, and thereafter, in synchronism with the forwardly indexed rotation of the turntable 512 in a direction of arrow A, repeat the foregoing cycle of positioning trays 45 on the plate elements 670 of successive tool nests 560 coming into operative alignment with the robotic pivot arm structure 832.

As the chute 812 of the carousel 572 which is located above plate 820 empties of trays 45, upon the last remaining tray 45 of the stack of trays in that chute 812 being transferred to the rotary plate 820, the carousel 572 is rotatably indexed forwardly by an indexing mechanism 839 to the next or adjacent tray-filled chute 812, so as to now have that tray-filled chute 812 arranged in superposed alignment with the rotary plate 820 and to enable the uninterrupted continuing supplying of empty trays 45 to the recesses 822 in rotary plate 820, and thereafter through the intermediary of the repetitive cycles of operation of robotic pivot arm member 832 to the tool nests 560 on the turntable 512 of the automated packaging station 500. The empty chutes 812 on the carousel 572 may be manually refilled with new stacks of package trays 45, as required.

Thereafter, the tool nest 560 with the tray 45 retained under a vacuum on the radially outwardly facing surface the plate element 670, which is at a generally horizontal orientation of the longitudinal axis 45*a* of the tray 45 defined by the walls 804, with the vacuum being generated in the installation through vacuum plenum 686 communicating with plate element 670 through the dial 512 and housing 660, is then advanced to workstation 580 at (2) through the indexed advance of the turntable 512 (a rotation of 30° in the direction of arrow A).

(2) At this workstation 580, to which the respective tool nest 560 supporting the empty tray thereon has been advanced by the rotational advance of the turntable 512 mounting the tool nest; in effect, indexed 30° forwardly; operative slide-controlled pivot structure 582 engages a plate element on the outer end of the tool nest 560 which supports the empty tray under a vacuum, and rotates the plate element and tray counterclockwise within the vertical plane thereof about a horizontal radial axis of the tool nest 560 through an angle of approximately sixteen and one-half (16.5°) degrees so as to be in appropriate angular orientation relative to a horizontal axis for facilitating the subsequent insertion and retention of a surgical needle and attached suture into the tray.

(3) This workstation 584 provides for a sensor 586 which is mounted stationarily on a bracket arrangement 588 and faces the tool nest 560 so as to be able to check for the presence of an empty tray on the tool nest. The sensor 586 is suitably aimed at a black spot present on the packaging tooling nest, and in the absence of a tray being positioned thereon, enables deactivating the forward advance of the turntable 512 and concurrently may emit a signal to alert personnel regarding the missing tray.

(4) The next workstation 590 along the rotational path of motion of the turntable in the direction of arrow A, provides gripper mechanism 592 for inserting a single surgical needle and a therewith attached suture into the suture tray which has been indexed forwardly by the rotary turret 512 so as to be located in operative alignment with the needle-feed mechanism. The needles are conveyed by a mechanism so as to be mounted on suitable clamping or needle "park" structure constituting an integral portion of the tray. Vacuum-controlled suture capture and tensioning devices which are located below each tool nest 560, become operative at this workstation to capture and tension the suture portions depending outwardly and downwardly of the tray mounting the surgical needle.

(5) At this workstation 594, a stationary sensor 595 located radially outwardly of the turntable 512 may be utilized to ascertain the presence of a surgical needle and attached suture having been properly introduced into the tray at the previous workstation 590.

(6) A first tray winding mechanism 596 at this workstation 598 engages the plate element on the tool nest supporting the tray, while the suture capture and tensioning device ensures that the suture portion depending outwardly and downwardly from the tray is maintained under tension by a vacuum-operated tensioning device associated therewith, with the tray being rotated counterclockwise within its vertical plane through approximately 163.5°, to assume a horizontal orientation which is 180° inverse 6 its original orientation on the tool nest 560 at workstation (1), and with the remaining length of the suture being tensioned by the vacuum device externally of the tray.

Referring now to FIGS. 40 and 55–60 in the which the first tray winding mechanism is shown in more detail. At the first winding workstation 598 (6) in the direction of rotation of the turntable 512 along arrow A downstream of the needle transfer workstation 590 (4) where a surgical needle and attached suture were introduced into the package tray 45 by a suitable transfer mechanism, operating structure 596 as detailed hereinbelow, imparts a pivoting displacement to the packaging tray 45. Concurrently, a vacuum-operated clamping unit 840 capturing the suture and vacuum nozzle 842 for tensioning the portion or length of the suture depending outwardly of tray 45 maintain their function, as described in copending application Ser. No. 09/019,674, the disclosure of which is incorporated herein by reference. In this connection, the vacuum-operated unit engages the suture until the latter is to be fully wound into the package tray 45 while concurrently the plurality of vacuum nozzles imparts tension to the suture so as to prevent the suture from snagging during the process of being wound into the package tray 45 at the second winding station 620(7).

Figure 57:
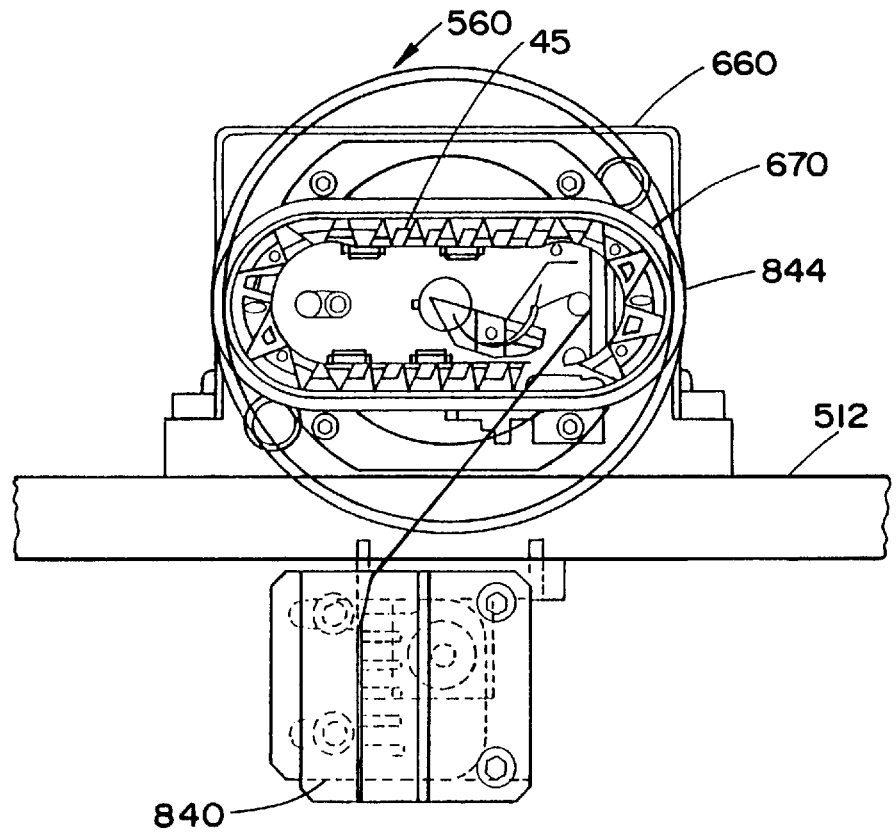
FIG. 57 and 58 illustrate, respectively, front and side views of a tool nest mounting a packaging tray and suture vacuum capture and clamping unit.

At the first winding workstation 598 (6), a winder head 844 of the winding apparatus 596 includes pin structure 846 which upon advance of slide bracket 848 towards the tool nest 560, engages the support plate 670 on the tool nest 560 on which the packaging tray 45 is mounted, this advance being caused by a pivot arm element 850, and drive means (not shown) imparts rotation thereto counterclockwise through an angle of approximately 163.5°. This, in effect, inverts the longitudinal orientation of the package tray 45 about is axis 45*a* and of the needle contained therein, while orienting the longitudinal tray axis horizontally as shown in FIG. 57, it previously having been imparted an angular counterclockwise tilt of about 16.5° to facilitate the insertion into the tray 45 of the surgical needle and attached suture at the needle transfer workstation 590 (4). The apparatus for effecting the foregoing initial winding includes the rotatable winder head 844 which intermittently advances by means of slide bracket 848 which is activated by pivot arm element 850 towards and through pin 846 into engagement with the tool nest 560 so as to be able to impart rotation to the tray 45, and then retracts after having rotated the tool nest plate member 670 and the package tray 45 mounted thereon through the above-mentioned angle of 163.5°. In this connection, the shaft 664 in the tool nest 560 has been released by the air motor in the tool nest housing 660 so as facilitate rotation thereof and axial movement into contact with a cam 852 mounted on turntable 512. This allows the plate member 670 to rotate with the winder head 844, and upon completion of rotation, the air motor in housing 660 of the tool nest 560 is deactivated so as to cause the shaft 664 to retract, and pins in the housing secure the plate member 670 in its rotated position.

(7) At a subsequent workstation 620, a further winding mechanism 622 engages the tool nest 560 and the tray mounted thereon, and imparts rapid rotation to the tray so as to enable tray structure engaging portions of the mechanism to introduce and completely wind the entire remaining length of the suture into a peripheral groove extending about the confines of the tray.

Figure 58:
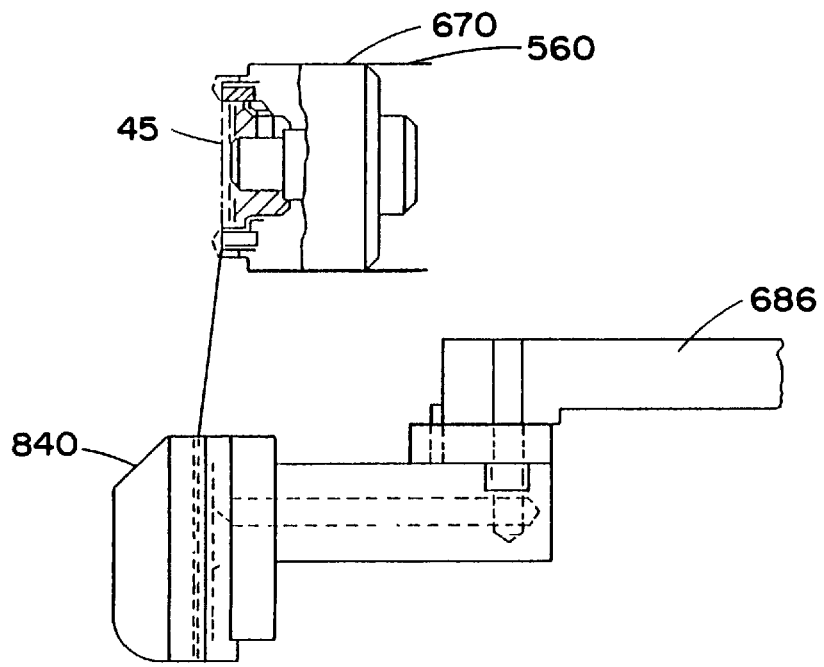
Figure 60:
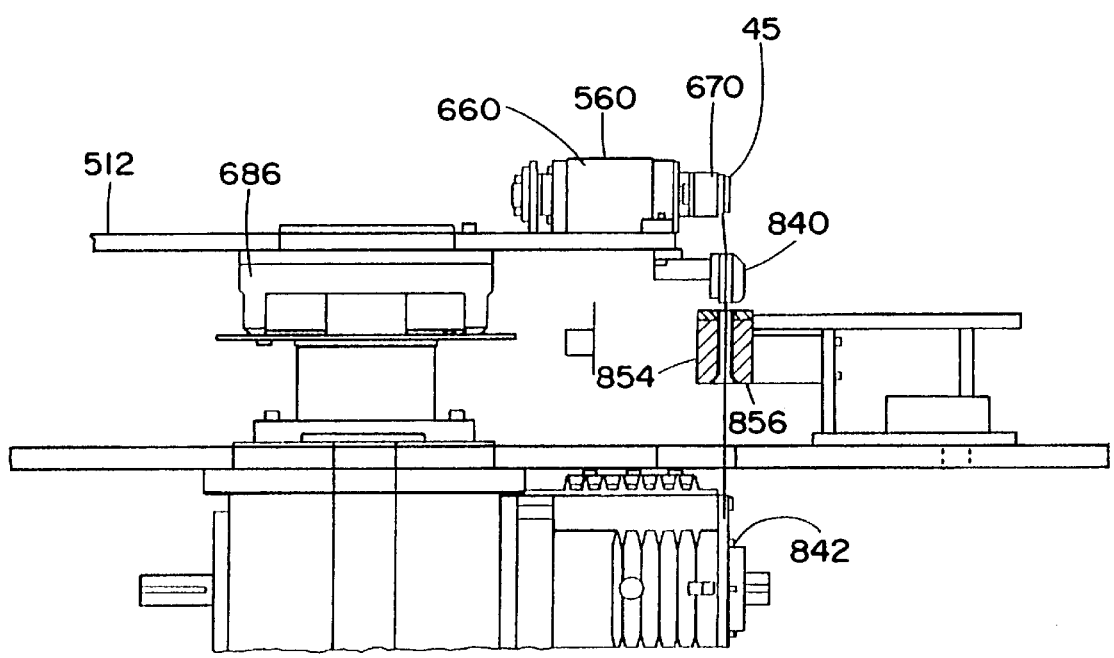
FIG. 60 illustrates a side view of the vacuum tensioning arrangements for the suture.
Figure 61:
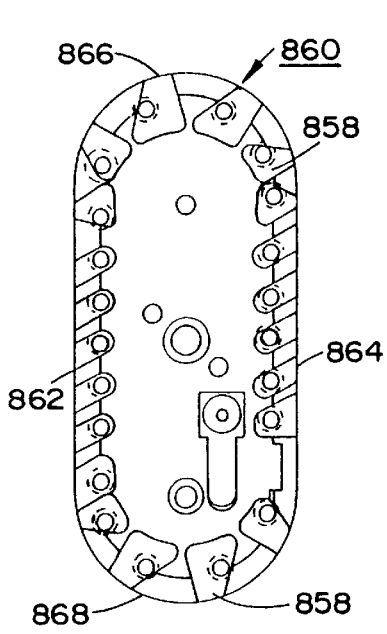
FIG. 61, 62 and 63 illustrate, respectively front, side and rear views of a winding head for winding the sutures into the trays.
Figure 62:
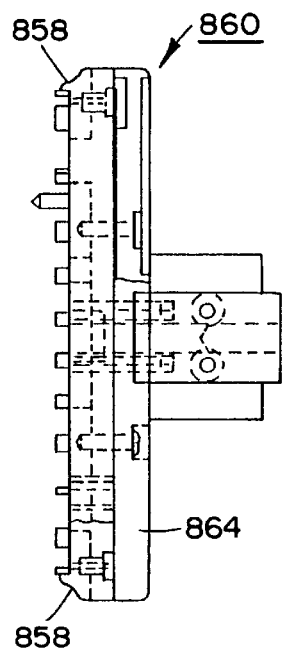
Figure 63:
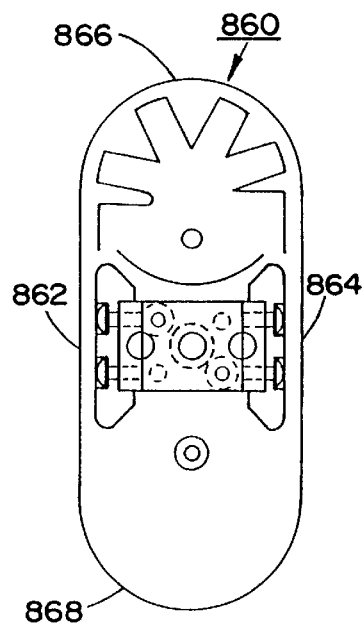
Figure 64:
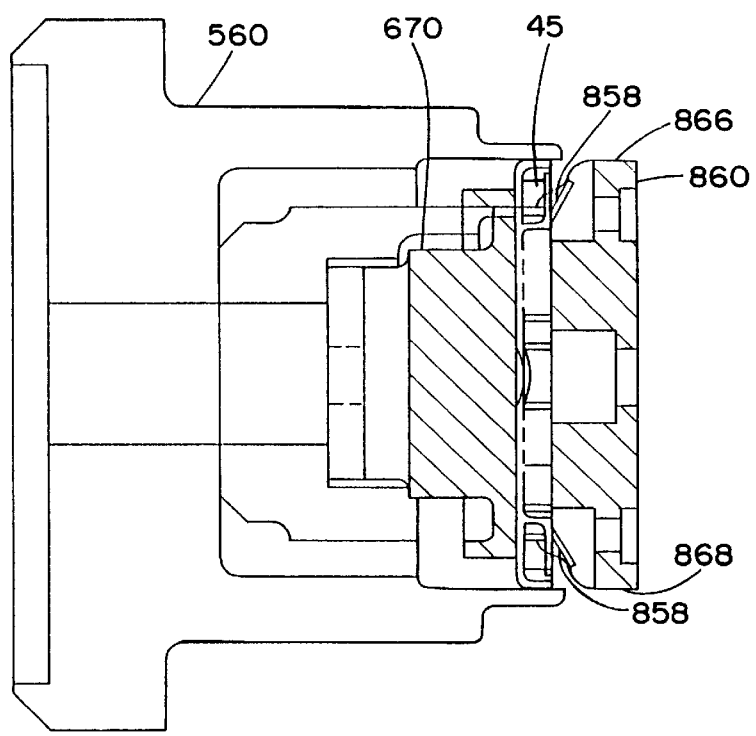
FIG. 64 illustrates a sectional view of the winding head in operative engagement with a packaging tray for winding sutures into the tray.

After the tray 45 is oriented at station (6), the invertedly oriented package tray 45, as shown in FIGS. 57 and 58, is advanced by turntable 512 to the second winding station (7), with a portion of the suture still depending downwardly and being engaged by the vacuum clamping unit 840 and tensioned by the vacuum nozzles or fingers 842, and is guided between vacuum guide plate elements 854, 856 below the clamping unit 840. The shaft 664 in tool nest housing 660 is released, as in the instance of the first winding workstation, and retracted to contact cam 856 on dial 512, as described above, to allow plate 670 to rotate with the tray 45. Lifting surfaces 858 on winder head 860, the latter of which, as shown in FIGS. 61 to 64, has a shape with longitudinal straight sides 862, 864 and convex ends 866, 868, and which is mounted on winder 622, is adapted to cooperatively engage finger structure extending over the peripheral channel in the tray 45. Accordingly, during rotation of the plate member 670 and tray 45 on the tool 560, the raised fingers of the tray 45 will allow for guiding the suture into the peripheral tray channel. A so-called "zipper" winding mechanism of this type is described in copending application Ser. No. 08/521,978 the disclosure of which is incorporated herein by reference. This winding rotation of the winder 622 is imparted by means of a drive 870 which rotates the package tray 45 at a high rate of speed over a plurality of rotations commensurate with the length of the particular suture portion extending therefrom, so as to cause the entire length of suture to be wound in one or more circumferential windings into the peripheral channel formed in the package tray 45.

Figure 56:
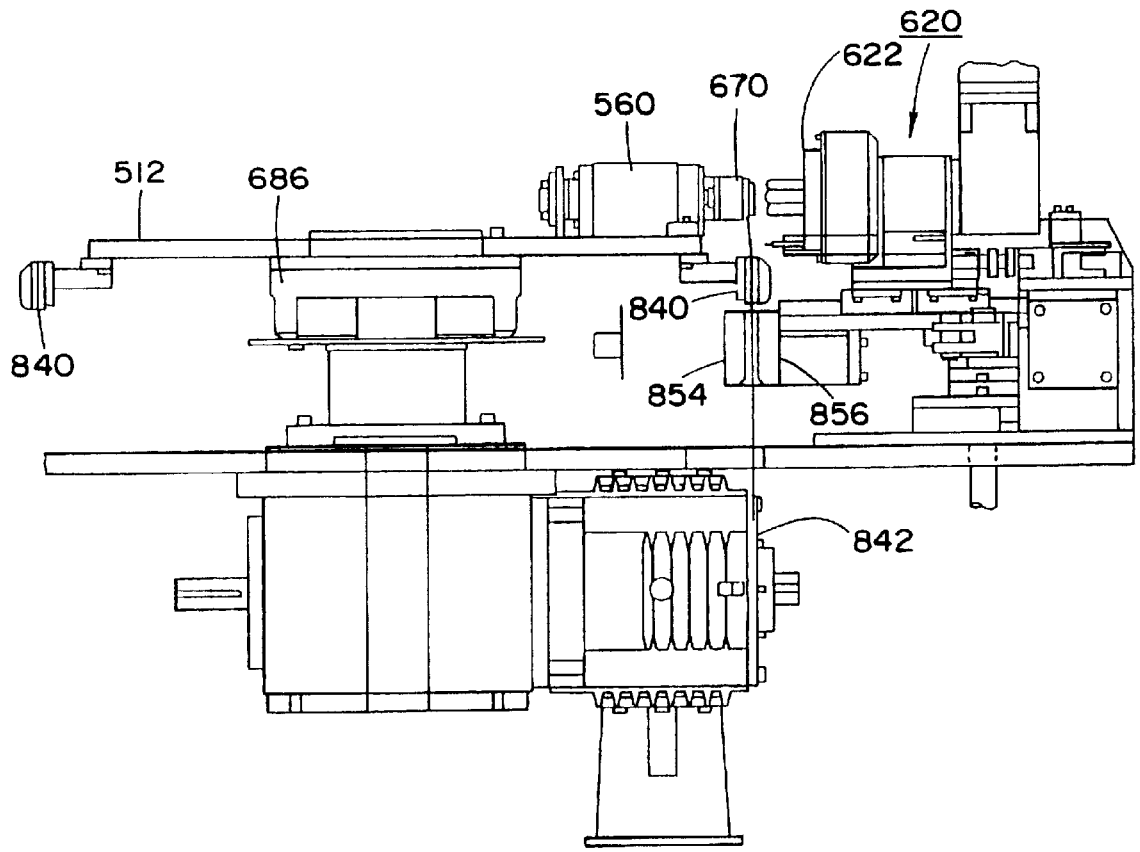
FIG. 56 illustrates a generally diagrammatic side view of the winding stations of FIG. 55.
Figure 56A:
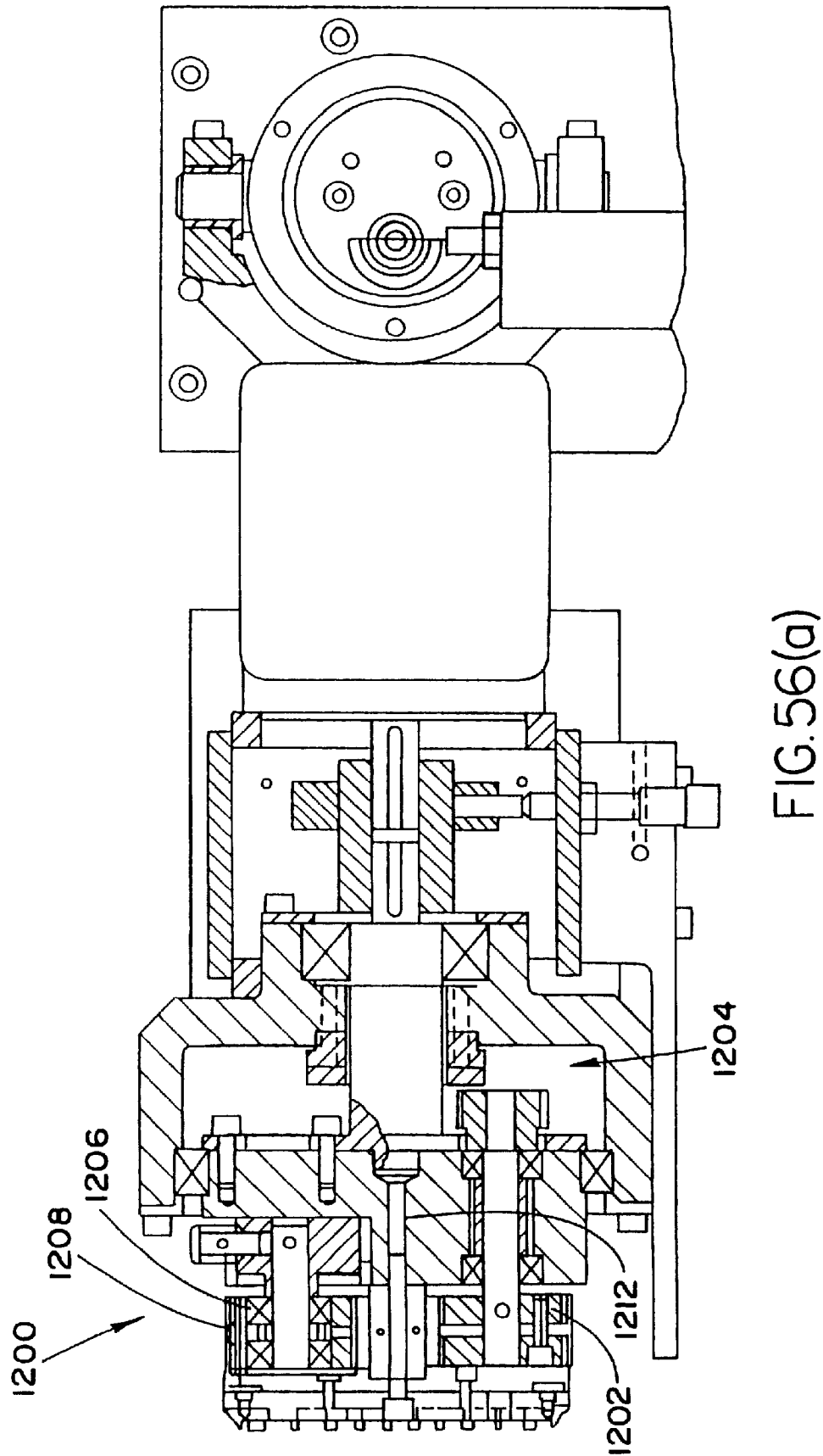
FIG. 56a illustrates a partial sectional view of the suture winding arrangement showing the planetary gearing system.
Figure 56B:
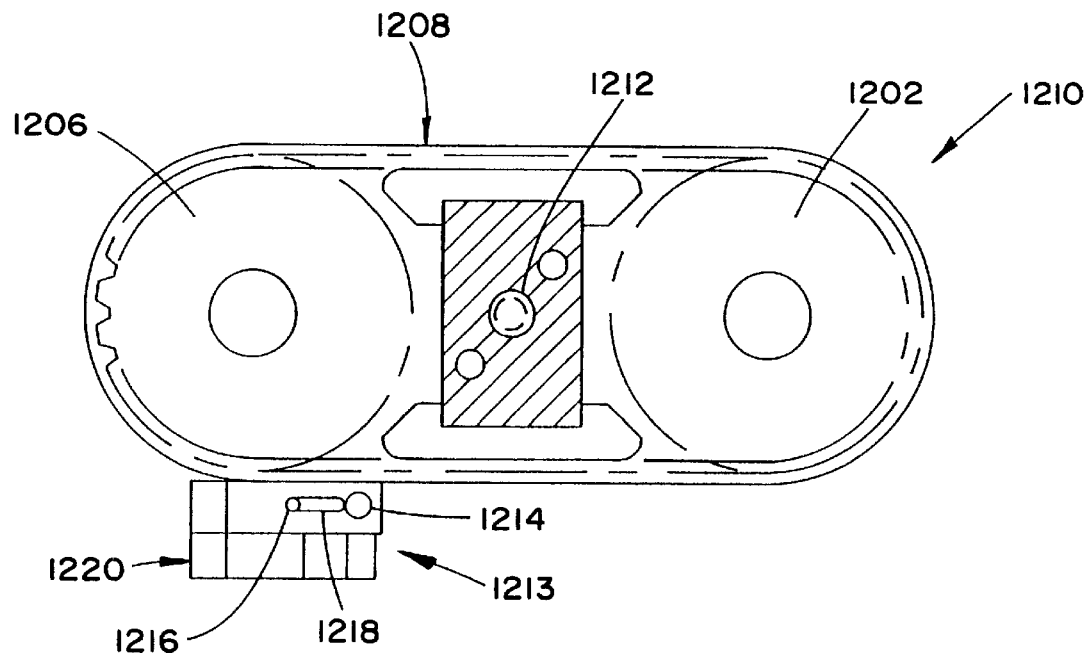
FIGS. 56b and 56c illustrate front and top views, respectively, of the planetary gear sub-assembly.
Figure 56C:
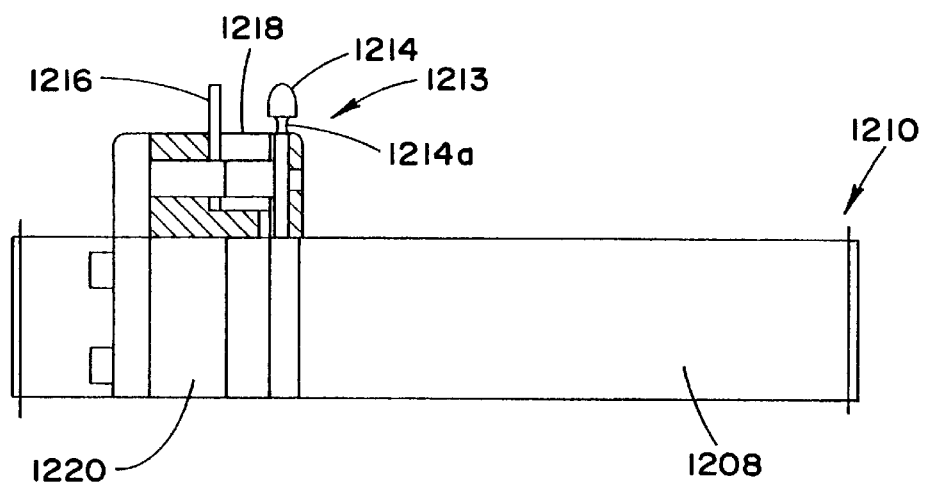

To maintain the suture's position while the winding head 860 is being rotated, a counter-rotating planetary gear system 1200 is employed. Referring to FIGS. 56*a* through 56*c*, the plantary gear system 1200 is shown in greater detail. The planetary gear system 1200 comprises a driven gear 1202 which is driven in an opposite direction to the winding head 860 through the winding head motor by a suitable gearing system 1204. The driven gear 1202 in turn drives idler gear 1206 by way of pully belt 1208 meshably connected thereto. The driven gear 1202, idler gear 1206, and pulley belt form a sub-assembly 1210 shown in FIGS. 56*b* and 56*c*, which freely rotates about a central shaft 1212. Thus, the planetary gear sub-assembly 1210 rotates in an opposite direction to the winding head 860 about the same central axis. Attached to the pulley 1208 is a suture guide assembly 1213 comprising a fixed pin 1214 having a notch 1214*a* for location of the suture, and a movable pin 1216 which moves in a slot 1218. The movable pin 1216 moves into engagement with the stationary pin 1214 to clamp the suture therebetween by the application of air pressure acting on a piston (not shown) connected thereto. Application of a vacuum to the same piston retracts the movable pin 1216.

Before winding the suture, the suture is clamped by both the clamping unit 840 and the suture guide assembly 1213 which defines the suture's path during winding. This defined path is maintained during rotation of the winding head 860 because the planetary gear system 1200 maintains the suture guide assembly 1213 at a fixed point by way of its counter rotation with respect to the winding head 860.

Thereafter, the winder head 860 is retracted from the tool nest 560, the shaft 664 is released from contact with the cam 858 by deactivating the air motor in housing 660, and and the movable pin 1216 of the suture guide assembly 1213 is retracted, resultingly locking the plate element 670 in predetermined horizontally extending position.

(8) A stationary sensor 624 at this workstation 626 is located radially outwardly of the turntable 512, and is adapted to ascertain the positioning of the surgical needle in the tray.

(9) This workstation 630 provides apparatus for the application and attachment of a cover or label to the tray containing the surgical needle and attached suture to produce or complete suture to produce a complete suture package. A rotatably indexed disc-like plate 632 includes a plurality of equidistantly circumferentially spaced cover-receiving areas, these being rotated below a vertical stack 634 of covers or labels such that, under the action of a vacuum, the bottommost covers of the stack are sequentially sliced off or separated and deposited into a respective area of the plate under the influence of the vacuum present therebeneath, and thereafter rotated into radial alignment with a tool nest 560 mounting the tray containing the surgical needle and attached wound suture. A cam-controlled robotic pivot arm structure 636 lifts the cover from the plate, while a subsequent area receives a further cover from the stack for transfer onto a following tray, and pivots upwardly and extends horizontally forwardly so as to position the cover into latching engagement with the tray, thereby forming the completed suture package.

(10) A robotic pivotable gripper arm 640 removes the completed package from the tool nest 560 at this subsequent workstation 642, and swings downwardly so as to deposit the completed suture package into receiving bins or compartments within elongated tray members 644 whereby upon a certain amount of trays being deposited to fill the tray member the latter is indexed to align a further empty compartment of a tray member with the tool nests. The tray member having the various filled compartments is then conveyed to a storage unit 646 and replaced automatically by another empty tray member.

Referring back to FIG. 6, the packaging tray 45 is shown with the cover 46 having been applied thereto so as to produce a complete suture package 47 having a single needle and attached suture arranged therein. The cover 46 extends over only a portion of the packaging tray area so as to afford visual inspection of the contents of the suture package and to permit withdrawal of the needle and attached suture without having to remove the cover. Interengageable latching structure 48, such as cut-outs and flaps, formed on the cover and package tray ensure their latched engagement upon application of the cover 46 to the packaging tray 45. The cover surface 49 may be provided with suitable printing whereby the cover, in essence, also constitutes a label for the suture package.

Referring now more specifically to the description of the suture package unloading workstation 642 (10), reference may be had to drawing FIGS. 65 through 71. Basically, the components of the workstation 642 are supported on a stationary horizontal platform 872. The major components, as detailed hereinbelow are a robotic arm arrangement 874; elongate parallel movable racks comprising compartmented trays 876 each possessing a plurality of compartments 878, which are adapted to each receive and stack a predetermined quantity of completed suture packages 47 which have been removed in succession by means of the robotic arm arrangement 874 from tool nests 560 on the turntable 512 of the packaging station 500.

The compartmented trays 876 are each mounted so as to be slidable along parallel supports 880, 882 radially extending into proximity with and below the turntable 512 of the packaging station.

Figure 65:
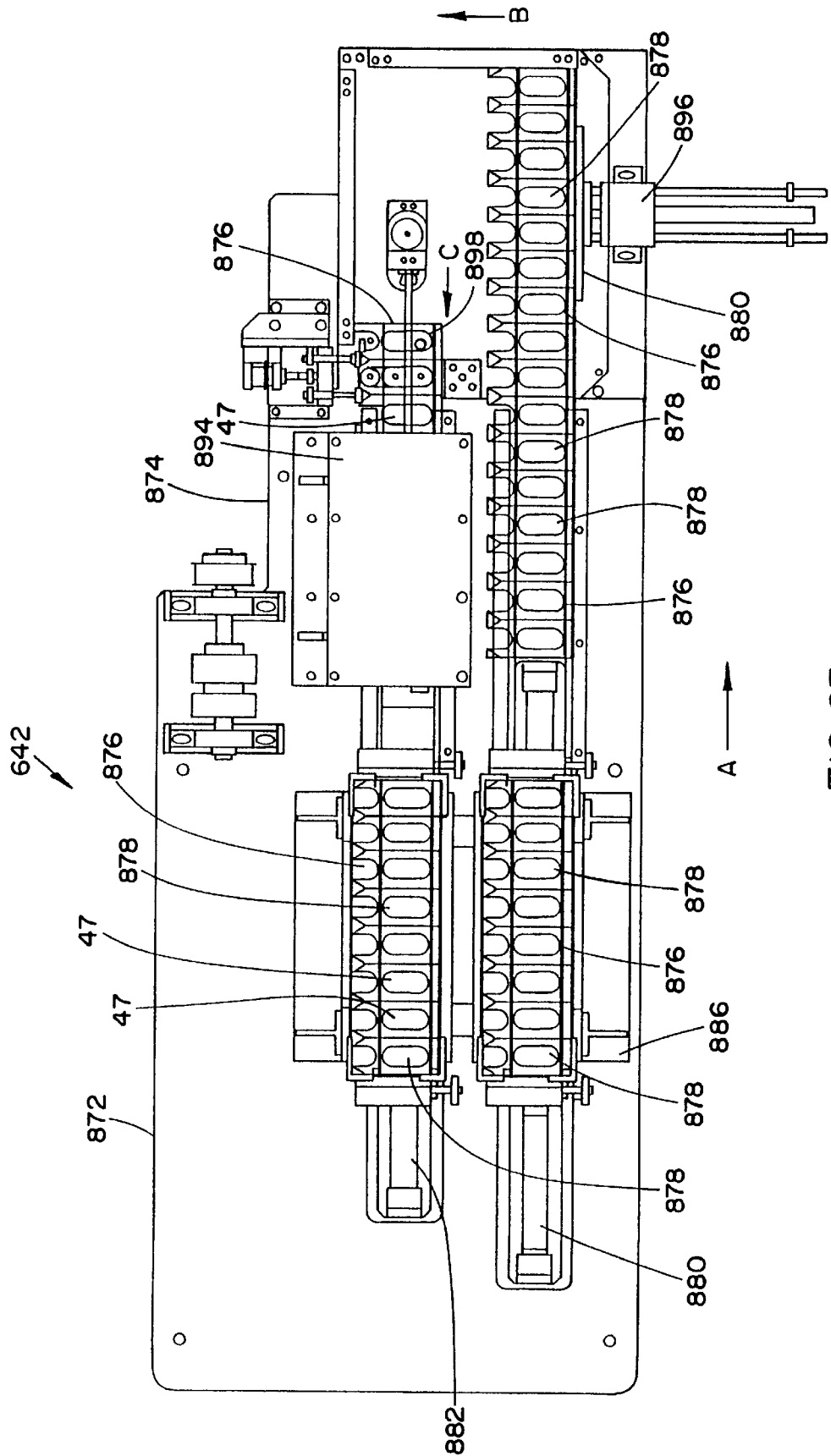
FIG. 65 illustrates a diagrammatic plan view of the suture package unloading arrangement.
Figure 66:
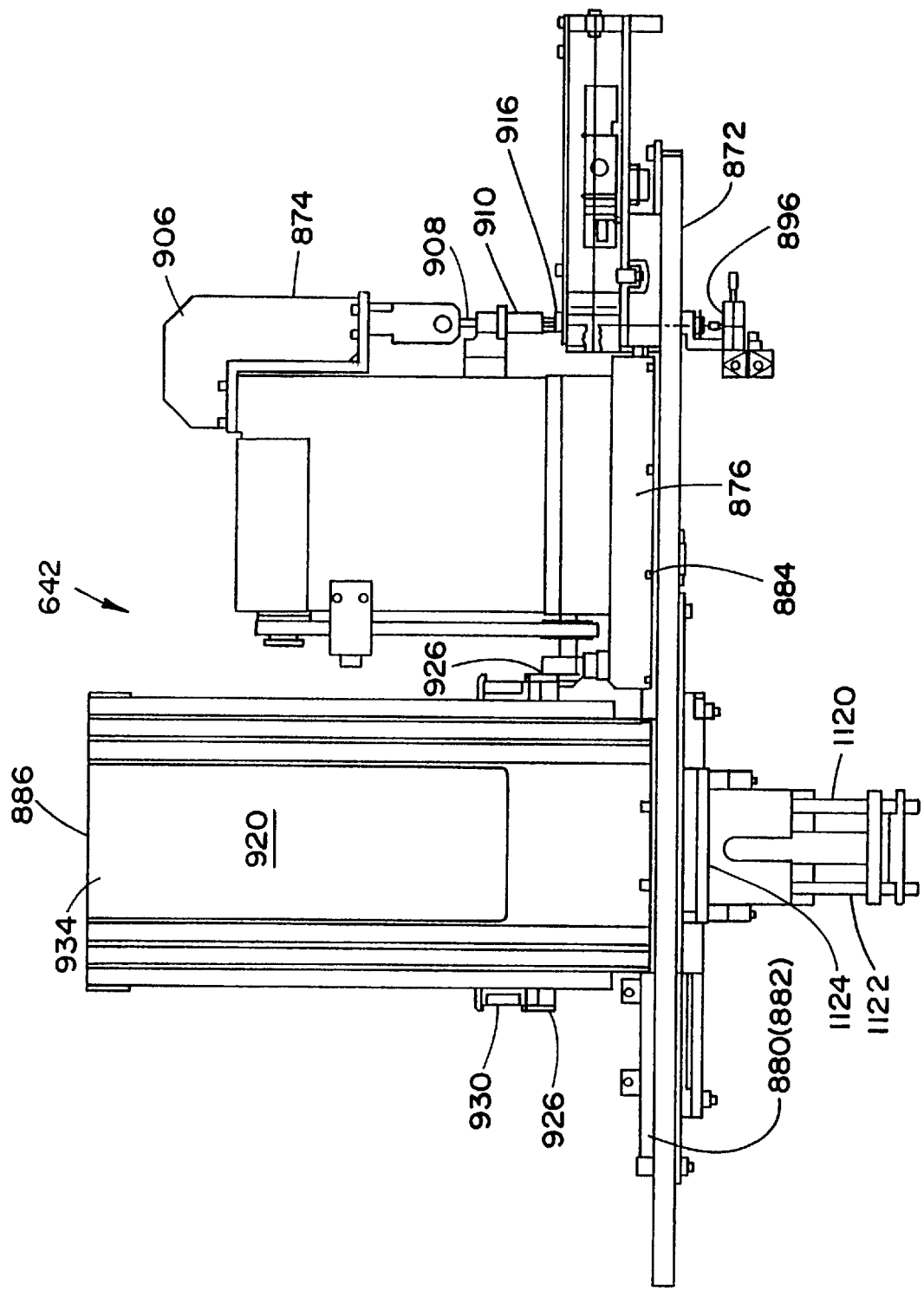
FIG. 66 illustrates a side elevational view of the suture package unloading arrangement of FIG. 65.
Figure 69:
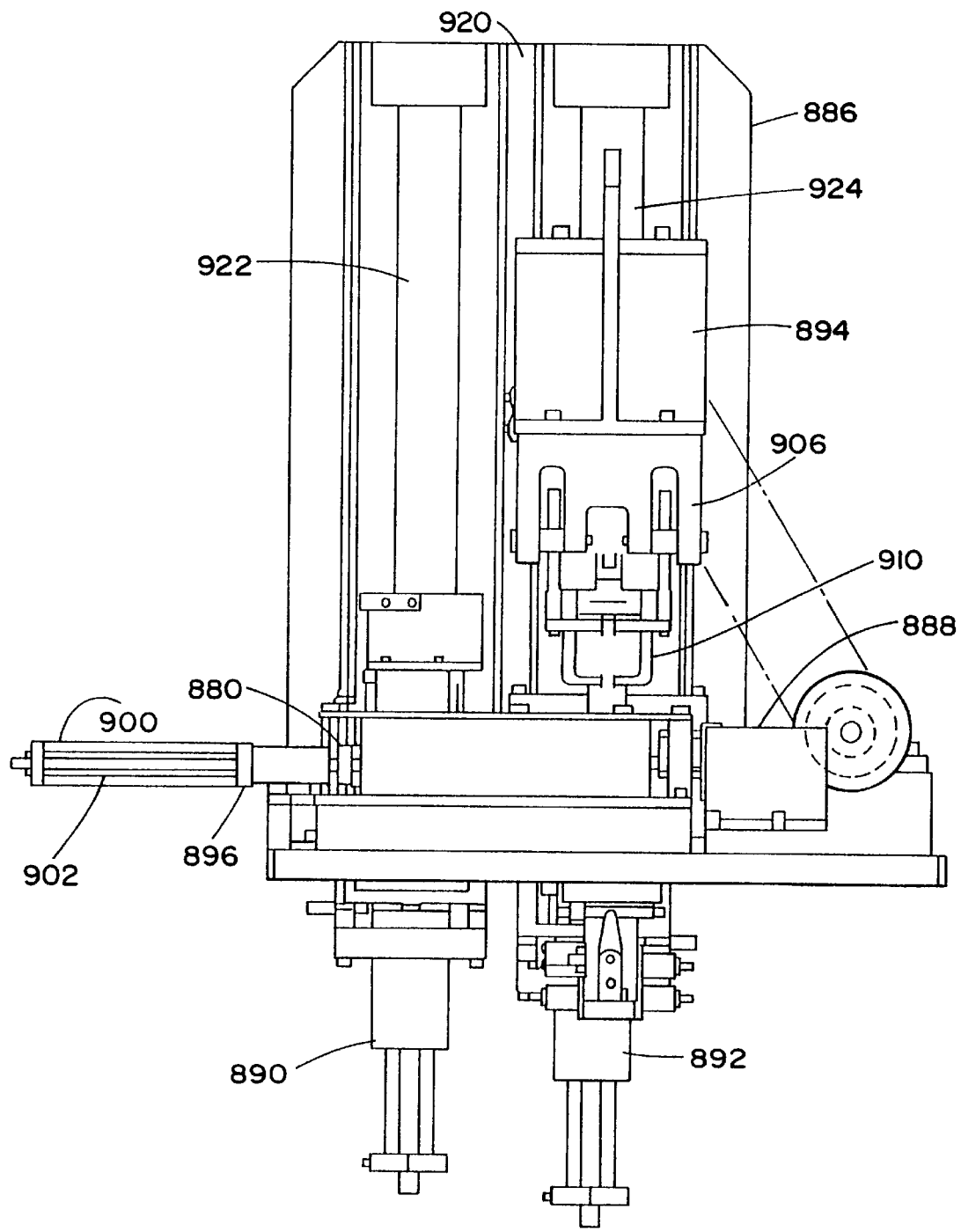
FIG. 69 illustrates a front end view of the arrangement of FIG. 66.
Figure 70:
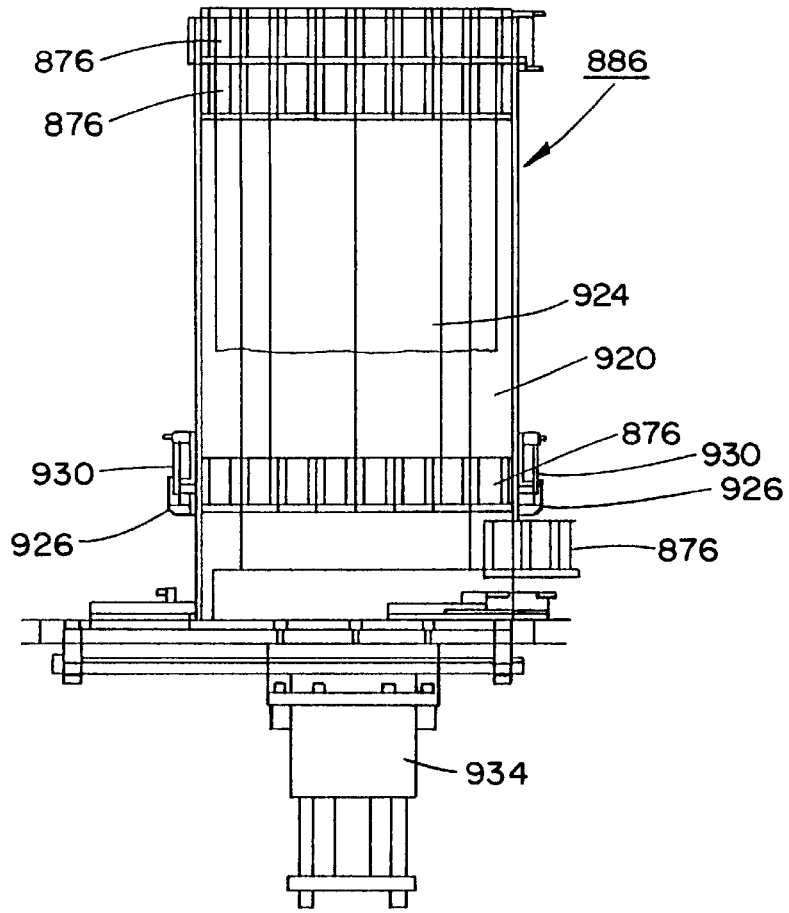
FIG. 70 illustrates, generally diagrammatically, a side elevational view of a storage housing portion of the arrangement of FIG. 66.
Figure 71:
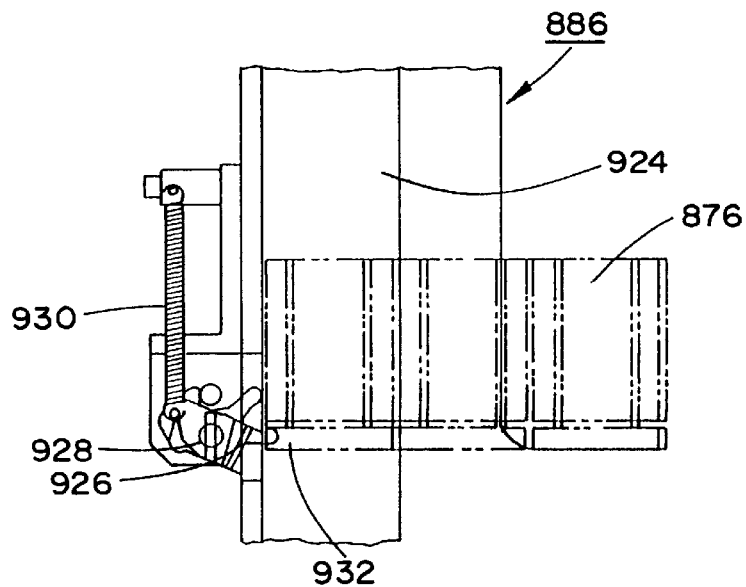
FIG. 71 illustrates, generally diagrammatically, a fragmentary segment of the storage housing portion of FIG. 70, showing a detail of the lifting device for compartmented trays containing suture packages.

As can be ascertained from the drawing FIGS. 65 and 66, each compartmented tray 876 is movable along its longitudinal axis by means of tray-engaging elements 884 spaced along the bottom of each of the supports 880, 882. The slidable support 880 is adapted to convey empty of the compartmented trays 876 towards the turntable 512. The slidable support 882, conversely, is adapted to index compartmented trays beneath the robotic arm arrangement 874 for filling the compartments 878 with stacks of suture packages 47 and then conveying the suture package-filled compartmented trays away from the turntable 512 for stacking in a storage 886 through the intermediary of an elevator mechanism 888. As shown in FIG. 69, the longitudinal or axial conveyance of slidable support 880 is implemented by a drive unit 890, whereas the indexing motion and conveyance of slidable support 882 is carried out through an indexing and drive unit 892 which is located below the platform 872.

Referring more specifically to FIGS. 66 through 69, the robotic arm arrangement 874 is located above the slidable support 882 and includes a housing 894 straddling the support 882, with the housing being arranged intermediate the compartmented tray storage 886 and the turntable 512 of the packaging station 500, in effect along the path of axial movement or travel of the compartmented trays 876 which are being filled with suture packages 47 and transported to the storage 886.

In essence, a continuous sequence of empty compartmented trays 876 are adapted to be advanced forwardly along a path of travel towards turntable 512 as shown by arrow A in FIG. 66 so that a forwardmost compartmented tray is in position adjacent a pusher plate 880 of drive mechanism 896 for displacing the forwardmost compartmented tray 876 laterally in the direction of arrow B. When a compartmented tray 876 has its most rearward compartment 898 located in alignment with the robotic pivot arm arrangement 874, the compartment is successively supplied with a predetermined quantity of suture packages 47; i.e. such as ten (10) packages. At that point, the compartmented tray is indexed in the direction of arrow C by a distance of one compartment 898 so as to enable the following compartment to be filled with suture packages 47. This sequence is repeated until all of the compartments have been filled with suture packages, whereupon the filled compartmented tray is advanced towards the storage 886, as described hereinbelow. At that time, the forwardmost compartmented tray 876 on the slidable support 880 is laterally displaced by the pusher plate 894 which slides along support rods 900, 902 adjacent a piston unit 904 of the drive mechanism 896 so as to locate the rearwardmost compartment 898 thereof below the robotic pivot arm arrangement 874. Thereupon, the filing cycle for the compartmented tray 876 is repeated as heretofore, while a successive empty compartmented tray 876 is advanced forwardly along arrow A so as to positioned adjacent the retracted pusher plate 880.

Reverting to the construction of the robotic pivot arm arrangement 874, the housing 894 incorporates driving mechanism (not shown) located in housing portion 906 having a depending arm 908 with a pivotable arm device 910 for conveying suture packages 47 from therewith aligned tool nests 560 into the compartments 898 of the compartmented trays 876.

Figure 68:
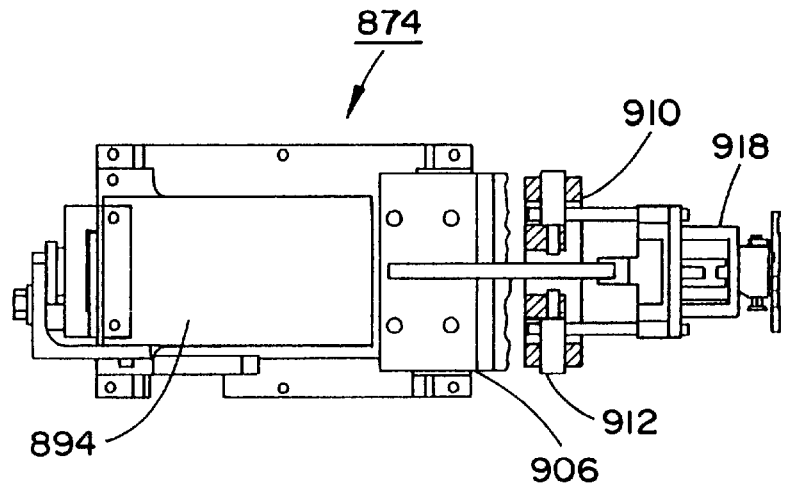
FIG. 68 illustrates a top plan view of the robotic pivot arm portion of FIG. 67, shown with the pivot arm in the horizontally upward pivoted position.
Figure 67:
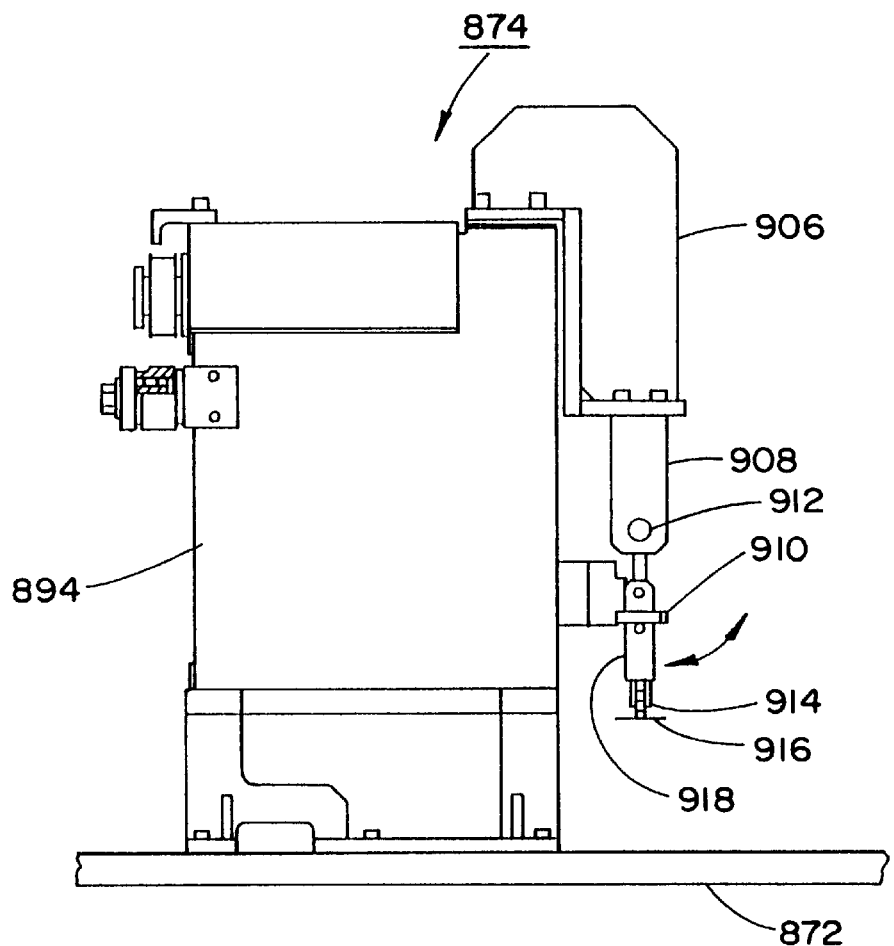
FIG. 67 illustrates a side elevational view of the robotic pivot arm portion of the arrangement of FIG. 66.

The robotic pivot arm arrangement 874 has pivot arm device hinged for swinging and axial movements at hinge point 912 so as to be oriented downwardly, as shown in FIGS. 66 and 67 for depositing suture packages 47 into the compartments of the compartmented trays 876, or extended horizontally for reciprocation, as shown in FIG. 68. During that horizontally oriented axial reciprocatory movement, the pivot arm device is adapted to remove suture trays 47 from the plate element 670 on a therewith aligned tool nest 560. The free or distal end 914 of the pivot arm device 910 includes a gripper attachment 916. Upon a suture package 47 being arranged on the tool nest 560 which is located at this workstation of the turntable 512, the arm 918 is horizontally oriented and extended towards the tool nest 560 so as to have the gripper attachment 916 contact the suture package. While the vacuum retaining the suture package 47 on the tool nest 560 is concurrently released, the suture package 47 is withdrawn from the tool nest 560 by the pivot arm 918.

The pivot arm 918, with the suture package 47 grasped by the gripper attachment 916 is then retracted and pivoted downwardly, as shown in FIGS. 66 and 67, whereupon the gripper releases the suture package 47 so as to enable the suture package 47 to drop into a compartment 898 located therebeneath. The turntable 512 is concurrently indexed forwardly, as shown in FIG. 40, so as to permit a successive tool nest 560 mounting a completed suture package 47 to be positioned at the package unloading workstation, and the pivot arm 918, which has already released the previous suture package 47 is swung upwardly into its horizontal position and extended forwardly so as to contact the suture package 47 located on that tool nest 560, and the gripper arrangement 916 while the vacuum in tool nest 560 is released as heretofore. Then, as previously, the pivot arm is retracted, swung downwardly and the gripper released so as to enable the suture package 47 to drop into the compartment 898 therebelow in superposition on the previous suture package or, alternatively, if the compartment is full and the compartmented tray 876 has been indexed forwardly by one compartment in the direction B, to cause the suture package to drop into an empty compartment.

Referring more specifically to FIGS. 65 through 70, the filled compartmented trays 876 each of which; for example, may have a series of eight compartments 898 each having ten suture packages 47 stacked therein, are successively conveyed by slidable support 882 to a position below the storage 886. The storage 886 consists of an open housing structure 920 having two adjacently arranged vertically-extending chutes 922, 924, one of which is adapted to have empty compartmented trays 876 stacked therein, and the other receives filled compartmented trays 876. The housing structure 920 has a lifting arrangement 922 connected therewith, which may be a pneumatic cylinder and push rods 1120, 1122 connected to a push plate 1124 as shown in FIG. 66, which raises the compartmented trays 876 in sequence, as diagrammatically illustrated in FIGS. 70 and 71. In that instance, pivotable fingers 926 which swing about pivot points 928 under the biasing action of tension springs 930, and which are connected to slidable frame elements 932 operated by a lift or hoisting drive 934, hold the filled compartmented trays 876 in position after elevation so as to facilitate further trays to be positioned therebelow. The stacks of filled compartmented trays 876 may then be manually removed from the open side 936 of housing structure 970; in effect, from chute 924, and empty trays 874 inserted into adjacent chute 922 so as to be lowered onto slidable support 880.

(11) In the event of a suture package being defective, such as having a cover lacking or misplaced, and the resultant package has accordingly not been removed at the preceding package unloading workstation 642; at this workstation 650 a reciprocating arm structure 652 has a gripper head which engages and removes the rejected packages from the tool nests, and deposits them onto a conveyor belt 654 for conveyance to a suitable waste disposal site.

(12) A sensor 577 at the final workstation on the packaging machine 500 checks for the presence of a package that may not have been removed at stations (10) and (11). This is a further safegard built into the packaging machine 500 to ensure that the tool nest at station (1) is empty and ready to accept an empty package tray.

As shown in FIGS. 43 through 45, each tool nest 560 includes a housing 660 which is fixedly mounted on the upper surface 662 of the rotary turret 512. Each housing 662 includes a horizontal radially extending central through bore having a shaft 664 rotatably journalled therein. The shaft 664 is normally secured against rotation within housing 660; however, at predetermined workstations of the machine, the shaft 664 may be released by means of a locting pin 661 so as to be rotatable and axially radially inwardly movable within housing 660 against stationary cam structure 663 mounted centrally on the rotary turret or dial 512 for regulating the rotational displacement which may be imparted to the shaft 664, as discussed hereinbelow in more specific detail.

The radially outwardly facing structure 668 of a plate element 670, which is fixedly secured to the radially outer end of shaft 664, is adapted for supporting suture package components, and particularly the package trays which are utilized in the production of surgical needle and attached suture-containing packages.

In essence, the radially outer structure of the tool nest housing 660 for mounting suture trays includes the plate element 670 which comprises an elongate vertically oriented plate member 672 having generally parallel opposite sides 674 and convexly rounded opposite ends 676 so as to be generally in conformance with the peripheral shape of a package tray. An external planar surface on the plate member 672 includes protruding perimeter or rim structure 678 for seating engagement therein of a suture tray, with the plate member 672 being fixedly secured to the radially outer end of the shaft 664 so as to be adapted for rotation therewith. Extending forwardly from the external planar surface of the rotatable plate member 672 of the tool nest 560 are protuberances or guide pins 580 which are intended to align the package tray thereon for appropriate positioning on the plate member 572, with the tray adapted to be retained thereon through the application of a vacuum to the exterior plate member surface through passageways communicating with a vacuum source connected thereto through the tool nest housing 660.

Figure 46:
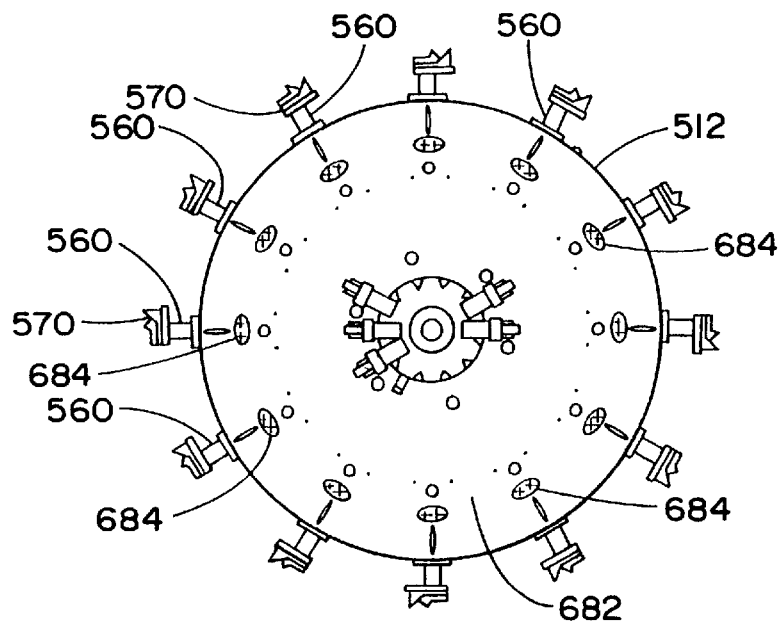
FIG. 46 illustrates a bottom view of the dial or turntable mounting the tool nests, showing vacuum ports for communicating the tool nests with vacuum-generating source means.
Figure 47:
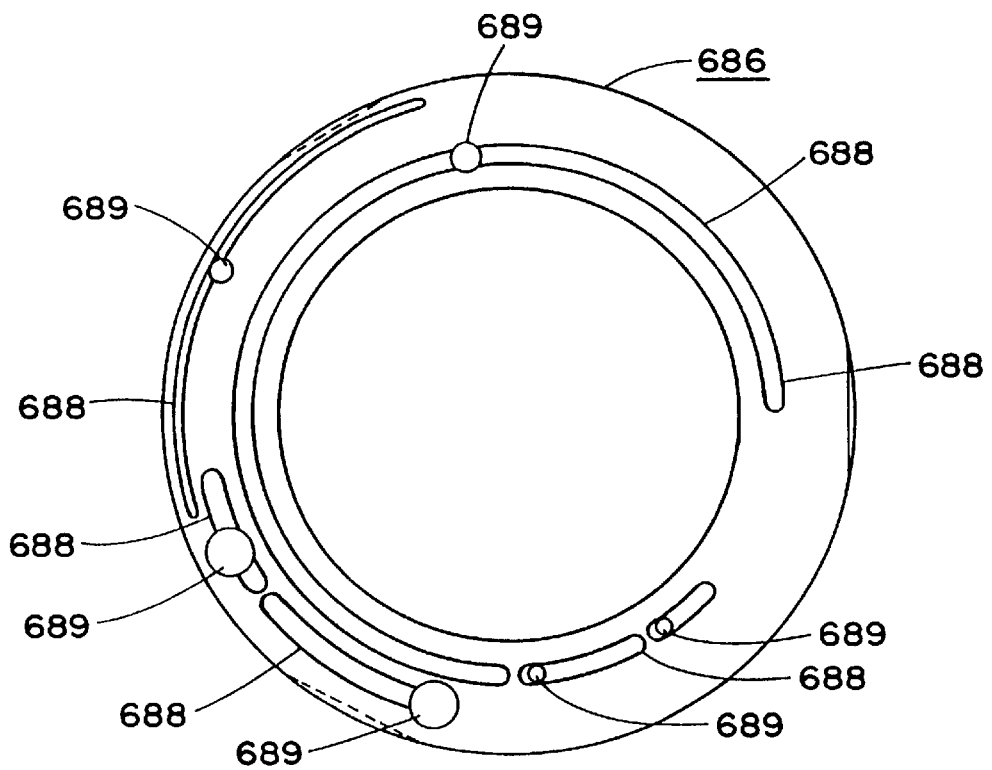
FIG. 47 illustrates a vacuum plenum for supplying the tool nests with controlled vacuum conditions.
Figure 48:
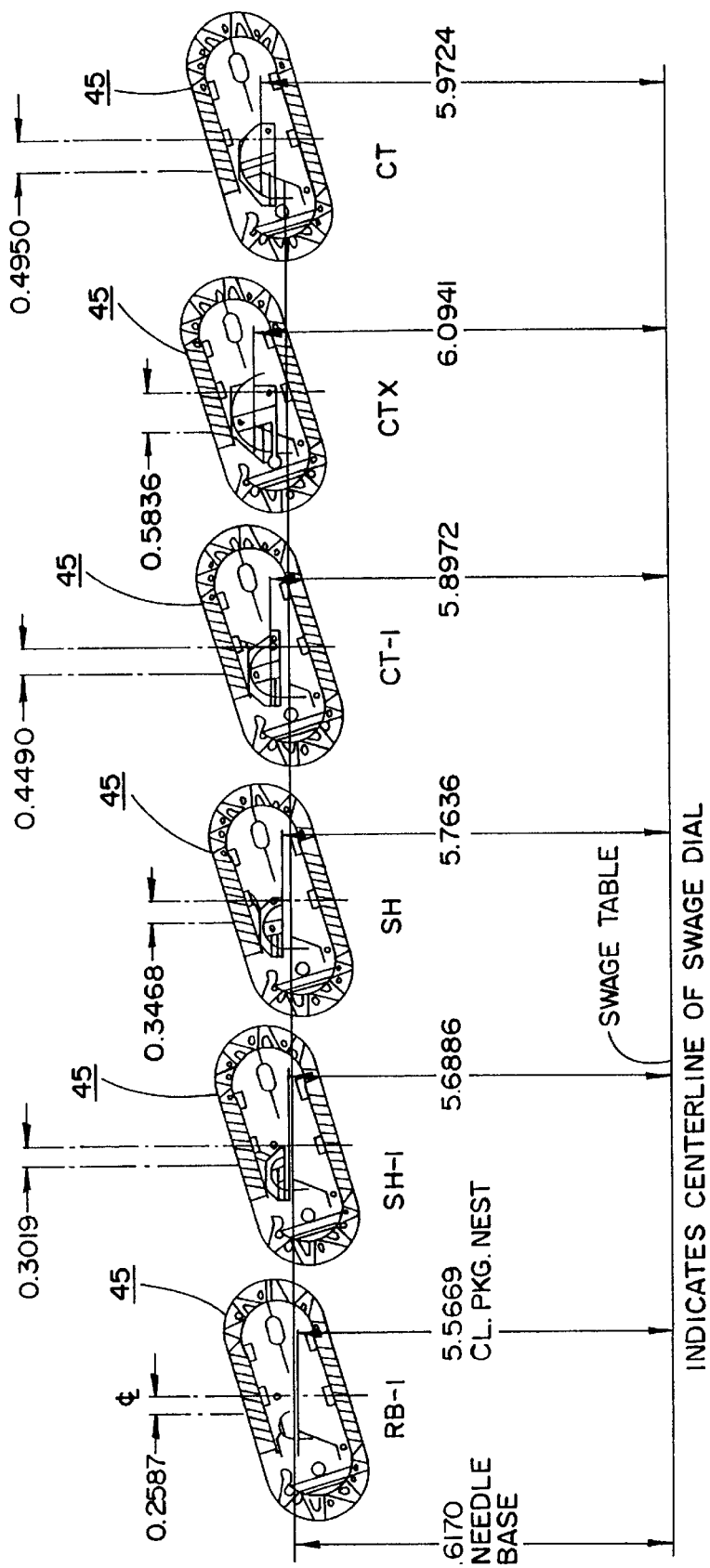
FIGS. 48a through 48f illustrate the positioning values for differently sized surgical needles by the multi-axis grippers and the swage table.

The vacuum passageways extend through the lower surface 682 of the dial or turntable 512, as shown in FIG. 46, which includes a plurality of apertures 684 each communicating with, respectively, passageways leading to an associated tool nest 560. The vacuum is supplied to the apertures 684 in a selective controlled mode through the intermediary of a stationary vacuum plenum 686 arranged below the dial 512, as shown in FIG. 41 of the drawings. The plenum 686, as shown in FIG. 47, includes outlet slots 688 and ports 689 for applying or closing a vacuum to respective tool nests 560 in accordance with the rotational positions of the dial 512 with the aperture or ports 684 in the lower surface 682 being in communication with the vacuum plenum outlet slots or ports.

Although this invention has been shown and described with respect to detailed embodiments thereof, it will be understood by those skilled in the art that various changes in form and detail thereof may be made without departing from the spirit and scope of the claimed invention.

What is claimed is:

1. An automated swage wind and packaging machine for attaching a suture to a surgical needle having a suture receiving opening formed therein and automatically packaging said needle and suture, said machine comprising:
    (a) an automatic needle sorting and infeed station for singulating and precisely positioning said surgical needles for subsequent swaging, said station individually singulating a single needle from a bulk supply and depositing a single needle upon a first conveyor means; computer control imaging means for obtaining and processing a digital image of said needle to obtain positional and orientation data for each of said singulated and imaged needles on said first conveyor means; and transfer means for removing said needle from said first conveyor means in accordance with its individual positional and orientation data and transferring said needle to a second precision conveyor for conveyance to a subsequent swaging station;
    (b) a suture cutting station for automatically cutting an indefinite length of suture material to a definite length and automatically inserting said suture into said suture receiving opening formed in said surgical needle;
    (c) a swage station for swaging said surgical needle to close said suture receiving opening about a free end of said suture to secure said suture thereto and form therefrom a needle and suture assembly; and
    (d) a needle packaging station having a suture winding arrangement for the automated individual packaging of said needle and suture assembly to produce a suture package, wherein said packaging station includes means for automatically winding said suture within the confines of a tray and attaching a cover to said tray so as to constitute said suture package, said packaging station having at least one tool nest for supporting said tray, and means for imparting a forwarding motion to said tool nest and said tray supported thereon for indexed advance to a plurality of workstations stationarily arranged proximate the path of advancing movement of said at least one tool nest; said suture winding arrangement comprising;
        (i) a first workstation including means for imparting a preterminal rotational movement to the tray which has a surgical needle retained therein with an attached suture having a portion extending outwardly and downwardly from said tray; and
        ii) a second workstation including means for imparting rapid rotational movement to said previously rotated tray so as to completely wind said depending suture portion into the confines of said tray;
    whereby unsorted needles and an indefinite length of suture material are automatically formed into a plurality of oriented surgical needle and suture assemblies and sequentially packaged with a single assembly in a single package tray.

2. The automated swage wind and packaging machine as claimed in claim 1 wherein said automatic needle sorting and infeed station further includes means for singulating each of said needles prior to deposition upon said first conveyor means, each of said singulated needles being deposited upon said first conveyor means in a spaced apart relation.

3. The automated swage wind and packaging machine as claimed in claim 1 wherein said transfer means includes one or more robot means each robot means having a gripper means for picking up needles from said first conveyor means, and placing said needles upon said second conveyance means.

4. The automated swage wind and packaging machine as claimed in claim 1 wherein said second conveyance means includes one or more engagement devices for gripping a respective needle, said transfer means placing each said needle in a respective engagement device.

5. The automated swage wind and packaging machine as claimed in claim 1 wherein said computer control imaging means further includes memory means for storing said positional and orientation data corresponding to said imaged needles, said transfer means including means for accessing said memory means to obtain said positional and orientation data corresponding to said imaged needles.

6. The automated swage wind and packaging machine as claimed in claim 1 wherein said computer control imaging means for obtaining and processing a digital image of said individually deposited needles includes one or more camera means, each of said one or more camera means in communication with said computer control imaging means.

7. The automated swage wind and packaging machine as claimed in claim 6 wherein each of said camera means obtains a video image of said needles upon said first conveyor means at each of respective said one or more predetermined locations within a field-of-view of each of said one or more camera means.

8. The automated swage wind and packaging machine as claimed in claim 2 wherein said automatic needle sorting and infeed station further includes a vibrating bowl and track assembly for providing a single file output of needles to a linear discharge slide mechanism which deposits single needles at spaced positions on said first conveyor means.

9. The automated swage wind and packaging machine as claimed in claim 3 wherein said robot means is in communication with said memory means, said robot means accessing said memory means to obtain said positional and orientation data corresponding to said imaged needles.

10. The automated swage wind and packaging machine as claimed in claim 4 wherein each of said engagement devices includes a pair of engaging jaws for engaging a needle positioned therebetween by said transfer means.

11. The automated swage wind and packaging machine as claimed in claim 10 wherein each said engagement device further includes a spring means for biasing a first movable jaw of said pair of engaging jaws into engagement with a second fixed jaw of said pair of engaging jaws to retain said needle positioned therebetween.

12. The automated swage wind and packaging machine as claimed in claim 11 wherein each of said engagement devices further includes means for retracting said first movable engaging jaw from engagement with said second fixed jaw prior to positioning said needle therebetween.

13. The automated swage wind and packaging machine as claimed in claim 12 wherein said means for retracting said first movable jaw from engagement with said second fixed jaw is a push rod for pushing said first movable jaw in opposition to said bias of said spring means.

14. The automated swage wind and packaging machine as claimed in claim 4 further including a first orienting means for orienting each said needle in a uniform direction while positioned upon said second conveyance means.

15. The automated swage wind and packaging machine as claimed in claim 14 further including a second orienting means for further orienting said needle axially within said pair of engagement jaws.

16. The automated swage wind and packaging machine as claimed in claim 15 further including a third orienting means for further orienting said needle to within 0.001 inch of a desired predetermined orientation for said needle upon said second conveyance means.

17. The automated swage wind and packaging machine as claimed in claim 1, wherein rotation-imparting means at said first workstation rotates said tray so as to assume an orientation which is 180° inverted relative to the initial orientation of said tray on said at least one tool nest.

18. The automated swage wind and packaging machine as claimed in claim 17, wherein said rotation-imparting means comprises a winder head reciprocable towards and away from said tray on the support surface of said at least one tool nest, said winder head being engageable with said support surface in the forwardly extended position of the winder head; and drive means for imparting rotation to said winder head for rotating said tray.

19. The automated swage wind and packaging machine as claimed in claim 18, wherein the support surface on said at least one tool nest is fastened to a rotatable shaft extending through said at least one tool nest; means normally securing said shaft against relative rotation, said means releasing said shaft for axial movement and rotation to facilitate said winder head imparting the rotational movement to said tray and support surface.

20. The automated swage wind and packaging machine as claimed in claim 19, wherein cam structure is contacted by an opposite end of said shaft to limit the axial movement of said shaft.

21. The automated swage wind and packaging machine as claimed in claim 20, wherein said at least one tool nest includes locking pin means for locking said shaft in a predetermined rotational position responsive to deactivation of said release means so as to maintain said tray in said rotationally inverted position on said support surface.

22. The automated swage wind and packaging machine as claimed in claim 19, wherein said shaft releasing means comprises an air motor.

23. The automated swage wind and packaging machine as claimed in claim 1, wherein said rapid rotation imparting means at said second workstation comprises a winder head structure engageable with said tray and support surface for winding the extending portion of the suture into said tray.

24. The automated swage wind and packaging machine as claimed in claim 23, wherein said winder head structure at said second workstations comprises protruding means which are engageable with surface structure on said tray so as to facilitate winding of said depending suture portion into a peripheral channel formed in said tray.

25. The automated swage wind and packaging machine as claimed in claim 23, wherein said winder head structure at said second winding workstation is rotated at a high rotational speed.

26. The automated swage wind and packaging machine as claimed in claim 23, wherein the support surface on said at least one tool nest is fastened to a rotatable shaft extending through said at least one tool nest; means normally securing said shaft against relative rotation, said means releasing said shaft for axial movement and rotation to facilitate said winder head imparting the rotational movement to said tray and support surface.

27. The automated swage wind and packaging machine as claimed in claim 26, wherein cam structure is contacted by an opposite end of said structure to limit the axial movement of said shaft.

28. The automated swage wind and packaging machine as claimed in claim 27, wherein said at least one tool nest includes locking pin means for locking said shaft in a predetermined rotational position responsive to deactivation of said release means so as to maintain said tray in said rotationally inverted position on said support surface upon completing the of winding of the suture into said tray.

29. The automated swage wind and packaging machine as claimed in claim 26, wherein said shaft releasing means comprises an air motor.

30. The automated swage wind and packaging machine as claimed in claim 1, wherein suture tensioning means imparts tension to the depending suture portion prior to and during the winding of the suture into said tray.

31. The automated swage wind and packaging machine as claimed in claim 30, wherein said suture tensioning means comprises a plurality of vacuum nozzles.

32. The automated swage wind and packaging machine as claimed in claim 30, wherein further vacuum tensioning means impart tension to a trailing end of said depending suture portion until said suture is completely wound into said tray.

33. The automated swage wind and packaging machine as claimed in claim 1, wherein a plurality of said tool nests are mounted on a turntable, said workstations being spaced about the periphery of said turntable.

34. The automated swage wind and packaging machine as claimed in claim 1, further comprising an indexing means for sequentially indexing said needle suture assemblies to a pull test station located between said swaging station and said needle packaging station, said pull-test station comprising means for automatically testing swage bond strength of each said needle-suture assembly indexed thereto.

35. An automated swage wind and packaging machine for attaching a suture to a surgical needle having a suture receiving opening formed therein and automatically packaging said needle and suture, said machine comprising:
- (a) an automatic needle sorting and infeed station for singulating and precisely positioning said surgical needles for subsequent swaging;
- (b) a suture cutting station for automatically cutting an indefinite length of suture material to a definite length and automatically inserting said suture into said suture receiving opening formed in said surgical needle, the suture cutting station including;
  - (i) a tipping means for heating a predetermined small length of said suture to stiffen said small length of said suture during subsequent cooling thereof, in preparation for cutting said suture at said stiffened small length and inserting a stiffened lead cut end of said suture into an end of said needle for swaging thereto;
  - (ii) first and second gripping means for gripping said indefinite length suture and alternately drawing it along a drawing axis, said first and second gripping means being mounted for reciprocal movement on said at least one longitudinal member;
  - (iii) means for cutting said indefinite length suture at said stiffened small length to provide uniform lengths of suture, wherein said cutting means includes a retractable cutter and counter-rotating first and second locator arms which clamps the stiffened small length therebetween while said cutting element severs the clamped suture;
- (c) a swage station for swaging said surgical needle to close said suture receiving opening about a free end of said suture to secure said suture thereto and form therefrom a needle and suture assembly; and
- (d) a needle packaging station having a needle transfer arrangement for the automated packaging of a single needle having an attached suture to produce a suture package, wherein said needle packaging station includes means for automatically winding said suture within the confines of a tray and attaching a cover to said tray so as to constitute said suture package, said needle packaging station having at least one tool nest for supporting said tray, and means for imparting a forwarding motion to said tool nest and said tray supported thereon for indexed advance to a plurality of workstations stationarily arranged proximate the path of advancing movement of said at least one tool nest; said needle packaging station having means for adjusting the elevation of said at least one tool nest relative to the needle swage station so as to accommodate the transferring of differently sized surgical needles into said tray without substantially modifying any components of the machine;

whereby unsorted needles and an indefinite length of suture material are automatically formed into a plurality of oriented surgical needle and suture assemblies and sequentially packaged with a single assembly in a single package tray.

36. The automated swage wind and packaging machine as claimed in claim 35, wherein the tipping means is adjustably positioned at different positions in the apparatus.

37. The automated swage wind and packaging machine as claimed in claim 36, wherein the position of the tipping means in the apparatus is adjustable by a handcrank and precision leadscrew, such that as the handcrank is rotated, the position of the tipping means in the machine is changed.

38. The automated swage wind and packaging machine as claimed in claim 37, wherein the tipping means includes a pointer positioned adjacent to a linear measurement scale stationarily positioned in the apparatus, such that the position of the tipping means is precisely controlled by aligning the pointer with a specified reading on the linear measurement scale.

39. The automated swage wind and packaging machine as claimed in claim 36, wherein the tipping means includes a pointer positioned adjacent to a linear measurement scale stationarily positioned in the apparatus, such that the position of the tipping means is precisely controlled by aligning the pointer with a specified reading on the linear measurement scale.

40. The automated swage wind and packaging machine as claimed in claim 35, including means for directing a constant flow of heated air to flow either through a heating aperture in which the suture is intermittently stopped during a tipping operation, or through a diverter channel to dump the heated air into the surrounding atmosphere.

41. The automated swage wind and packaging machine as claimed in claim 40, wherein the flow of hot air is controlled by a retractable slide element having a flow aperture therein which is selectively positioned in front of either an inlet to the heating aperture or to the diverter channel.

42. The automated swage wind and packaging machine as claimed in claim 41, wherein a thermocouple is positioned in the air flow at the discharge end of the heater to monitor and control the air temperature through a controller in a programmable logic controller.

43. The automated swage wind and packaging machine as claimed in claim 42, wherein said tipping means is operated at different temperatures between 200° F. and 550° F. depending upon the particular suture material being run, and the particular temperature is a downloaded parameter from an operating program at each suture batch changeover.

44. The automated swage wind and packaging machine as claimed in claim 35, wherein a thermocouple is positioned in the air flow at the discharge end of the heater, to monitor and control the air temperature through a controller in a programmable logic controller.

45. The automated swage wind and packaging machine as claimed in claim 35, wherein said tipping means is operated at different temperatures between 200° F. and 550° F. depending upon the particular suture material being run, and the particular temperature is a downloaded parameter from an operating program at each suture batch changeover.

46. The automated swage wind and packaging machine as claimed in claim 35, wherein the suture extends to and is wrapped around a tension roller which is mounted on one end of a torque motor, which applies a given tension to the suture as it is pulled through the apparatus by the first and second gripping means.

47. The automated swage wind and packaging machine as claimed in claim 46, wherein each different suture size and material has a different tension applied thereto by the torque motor as it is drawn through the apparatus.

48. The automated swage wind and packaging machine as claimed in claim 47, wherein the suture is wrapped around the tension roller a multiple number of times.

49. The automated swage wind and packaging machine as claimed in claim 48, wherein the suture is wrapped around the tension roller twice.

50. The automated swage wind and packaging machine as claimed in claim 35, wherein said elevation adjusting means comprise servo motor actuated jack screw lifting means for adjusting the elevational positions of said at least one tool nest relative to said needle transfer means.

51. The automated swage wind and packaging machine as claimed in claim 50, wherein a turntable mounts a plurality of said tool nests in peripherally spaced relationship for indexed advance to successive of said workstations, said jack screw lifting means being connected to said turntable for adjusting the elevation thereof.

52. The automated swage wind and packaging machine as claimed in claim 51, wherein said workstations about said turntable are mounted on a stationary frame of said machine, said turntable being supported on a vertically movable frame located within said stationary frame of said machine.

53. The automated swage wind and packaging machine as claimed in claim 35, further comprising an indexing means for sequentially indexing said needle suture assemblies to a pull test station located between said swaging station and said needle packaging station, said pull-test station comprising means for automatically testing swage bond strength of each said needle-suture assembly indexed thereto.

54. An automated swage wind and packaging machine for attaching a suture to a surgical needle having a suture receiving opening formed therein and automatically packaging said needle and suture, said machine comprising:
   (a) an automatic needle sorting and infeed station for singulating and precisely positioning said surgical needles for subsequent swaging;
   (b) a suture cutting station for automatically cutting an indefinite length of suture material to a definite length and automatically inserting said suture into said suture receiving opening formed in said surgical needle;
   (c) a swage station at a third predetermined location for swaging said surgical needle to close said suture receiving opening about a free end of said suture to secure said suture thereto and form therefrom a needle and suture assembly; and
   (d) a needle packaging station having a package feed arrangement for the automated packaging of a single needle having an attached suture to produce a suture package, wherein said needle packaging station includes means for automatically winding said suture within the confines of a tray and attaching a cover to said tray so as to constitute said suture package, said needle packaging station having at least one tool nest for supporting said tray, and means for imparting a forwarding motion to said tool nest and said tray supported thereon for indexed advance to a plurality of workstations stationarily arranged proximate the path of advancing movement of said at least one tool nest, said package feed arrangement comprising a first workstation including means for mounting an empty said tray on a support surface located on said at least one tool nest, said means comprising means for stacking a supply of said empty trays; a rotary plate arranged beneath said tray stacking means, said rotary plate being adapted to receive an individual one of said trays from the bottom of said stacking means; means for indexing said rotary plate forwardly at predetermined angular increments; and robotic means for engaging said tray on said rotary plate and transferring said tray to the support surface on said one tool nest;
   whereby unsorted needles and an indefinite length of suture material are automatically formed into a plurality of oriented surgical needle and suture assemblies and sequentially packaged with a single assembly in a single package tray.

55. The automated swage wind and packaging machine as claimed in claim 54 wherein said swage station includes first and second swaging die means, said first swaging die means having an end thereof defining a portion of a swage die opening, and said second swaging die means having an end thereof defining another portion of said swage die opening, wherein said second swaging die means is positioned next to said first swaging die means to form a swage die opening for receiving said needle.

56. The automated swage wind and packaging machine as claimed in claim 55, wherein said first swaging die means is fixed in position and said second swaging die means is laterally movable toward and away from said first fixed swage die means.

57. The automated swage wind and packaging machine as claimed in claim 56 wherein said swaging means includes means for moving said second swage die means laterally away from said first swage die means prior to positioning said needle within said swage die opening.

58. The automated swage wind and packaging machine as claimed in claim 57, wherein said moving means further moves said second swage die means toward said first swage die means to grip said needle placed therebetween.

59. The automated swage wind and packaging machine as claimed in claim 58 wherein said moving means includes spring biasing means to provide a force sufficient to move said second swage die toward said first swage die to grip the needle without deforming said suture receiving opening of said needle positioned at said swage die opening.

60. The automated swage wind and packaging machine as claimed in claim 59, wherein said moving means includes an air cylinder means for supplying adequate force to thrust said movable swage die means toward said first swage die means to accomplish swaging of said needle gripped therebetween.

61. The automated swage wind and packaging machine as claimed in claim 60, wherein said second swage die means is thrust towards said first die means for a swaging stroke of a predetermined distance to accomplish said swaging.

62. The automated swage wind and packaging machine as claimed in claim 61, wherein said moving means includes stop means for terminating the motion of said second swage die means during said swaging stroke.

63. The automated swage wind and packaging machine as claimed in claim 62 wherein said jaws are opened to a non-engaging position for relaxing said surgical needle in said swage die opening after gripping but before swaging thereof.

64. The automated swage wind and packaging machine as claimed in claim 63, wherein said swaging means further includes a fence for maintaining the position of said needle within said swage die opening during the swaging thereof.

65. The automated swage wind and packaging machine as claimed in claim 64 wherein said swaging means further includes means for adjusting the position of said first swaging die means to change the amount of swage deformation occurring to said suture receiving opening during swaging thereof.

66. The automated swage wind and packaging machine as claimed in claim 65 wherein said first fixed swaging die means includes a wedge follower located at one end thereof, said means for changing the position of said first fixed swaging die means including a wedge assembly positioned to move transverse to said wedge follower to laterally move said wedge follower and said first fixed swaging die means in accordance with transverse movement of said wedge assembly.

67. The automated swage wind and packaging machine as claimed in claim 66 wherein said transverse movement of said wedge assembly is controllable by a servomotor means for rotating a swage adjust screw of a predetermined pitch, said rotation of said swage adjust screw being translated into linear motion of said wedge assembly.

68. The automated swage wind and packaging machine as claimed in claim 67 wherein said computer control means determines and controls the optimum positioning of said first swaging die means to avoid over-swaging and underswaging said needle.

69. The automated swage wind and packaging machine as claimed in claim 54, wherein said tray stacking means comprises an open-bottomed chute having a vertical stack of said trays arranged therein, said rotary plate being horizontal and extending closely below the bottom of said chute so as to receive the bottommost tray therefrom on an upper surface of said rotary plate.

70. The automated swage wind and packaging machine as claimed in claim 69, wherein said rotary plate is in communication with a vacuum-generating source for imparting a vacuum to the upper surface of said rotary plate to retain said tray thereon during at least the indexing advance of said rotary plate.

71. The automated swage wind and packaging machine as claimed in claim 54, wherein said robotic means comprises pivotable arm structure having tray-engaging means for lifting said tray from said rotary plate and transferring said tray to the support surface on said at least one tool nest.

72. The automated swage wind and packaging machine as claimed in claim 71, wherein said rotary plate communicates with a vacuum-generating source for imparting a vacuum thereto for retaining said tray on said plate, said vacuum being released upon said tray-engaging means contacting said tray, and a vacuum in said tray-engaging means retaining said tray thereon to facilitate transporting said tray to the support surface on said at least one tool nest.

73. The automated swage wind and packaging machine as claimed in claim 72, wherein upon said tray-engaging means mounting said tray on the support surface of said at least one tool nest, said vacuum in said tray-engaging means is released and a vacuum concurrently applied to the support surface of said at least one tool nest so as to retain said tray thereon.

74. The automated swage wind and packaging machine as claimed in claim 54, wherein a carousel comprises a plurality of said chutes in a circular rotatable arrangement whereby upon a chute being emptied of said trays, an adjacent tray-filled chute is rotated into position above said rotary plate to facilitate the supplying of trays to said rotary plate.

75. The automated swage wind and packaging machine as claimed in claim 54, wherein said robotic means comprises a cam-controlled robotic pivot arm adapted to swing between a vertical orientation to a horizontal and forward motion for transferring said tray from said rotary plate to said support surface on said at least one tool nest.

76. The automated swage wind and packaging machine as claimed in claim 54, wherein a second workstation includes means for imparting a predetermined angular displacement to said tray and support surface on said at least one tool nest mounting said tray to facilitate subsequent insertion of a surgical needle into said tray.

77. The automated swage wind and packaging machine as claimed in claim 76, wherein said means for imparting said angular displacement comprises structure for engageable contact with said support surface.

78. The automated swage wind and packaging machine as claimed in claim 77, wherein said structure comprises a slidable element having contact means for engaging said support surface, and pivot arm means for imparting movement to said contact means towards said support surface to impart said angular displacement thereto.

79. The automated swage wind and packaging machine as claimed in claim 76, wherein said support surface on said at least one tool nest is fastened to a rotatable shaft extending through said at least one tool nest; means normally securing said shaft from relative rotation, said means releasing said shaft for axial movement and rotation in said at least one tool nest to facilitate said angular displacement means to impart said angular displacement to said tray and support surface.

80. The automated swage wind and packaging machine as claimed in claim 79, wherein cam structure is contacted by an opposite end of said shaft to limit the axial movement of said shaft.

81. The automated swage wind and packaging machine as claimed in claim 54, wherein said at least one tool nest includes locking pin means for locking said tray and support surface in said angularly displaced position.

82. The automated swage wind and packaging machine as claimed in claim 76, wherein said angular displacement of said tray and support surface on said at least one tool nest subtends an angle of about 16.5° with a horizontal axis of said tray.

83. The automated swage wind and packaging machine as claimed in claim 54, wherein a plurality of said tool nests are mounted on a turntable, said workstations being spaced about said turntable.

84. The automated swage wind and packaging machine as claimed in claim 54, further comprising an indexing means for sequentially indexing said needle suture assemblies to a pull test station located between said swaging station and said needle packaging station, said pull-test station comprising means for automatically testing swage bond strength of each said needle-suture assembly indexed thereto.

* * * * *